(12) United States Patent
Yu et al.

(10) Patent No.: US 7,378,418 B2
(45) Date of Patent: *May 27, 2008

(54) AZABICYCLIC HETEROCYCLES AS CANNABINOID RECEPTOR MODULATORS

(75) Inventors: Guixue Yu, Princeton Junction, NJ (US); William R. Ewing, Yardley, PA (US); Amarendra B. Mikkilineni, Easton, PA (US); Annapurna Pendri, Glastonbury, CT (US); Philip M. Sher, Plainsboro, NJ (US); Samuel Gerritz, Guilford, CT (US); Bruce A. Ellsworth, Princeton, NJ (US); Gang Wu, Princeton, NJ (US); Yanting Huang, Pennington, NJ (US); Chongqing Sun, East Windsor, NJ (US); Natesan Murugesan, Princeton Junction, NJ (US); Zhengxiang Gu, Princeton, NJ (US); Ying Wang, Princeton, NJ (US); Doree Sitkoff, Dresher, PA (US); Stephen R. Johnson, Erdenheim, PA (US); Ximao Wu, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 189 days.

This patent is subject to a terminal disclaimer.

(21) Appl. No.: 11/016,135

(22) Filed: Dec. 17, 2004

(65) Prior Publication Data
US 2005/0143381 A1    Jun. 30, 2005

Related U.S. Application Data

(60) Provisional application No. 60/531,451, filed on Dec. 19, 2003.

(51) Int. Cl.
| C07D 487/04 | (2006.01) |
| A61K 31/4162 | (2006.01) |
| A61P 3/04 | (2006.01) |
| A61P 43/00 | (2006.01) |

(52) U.S. Cl. ........................... 514/248; 544/236
(58) Field of Classification Search ............... 544/236; 514/248
See application file for complete search history.

(56) References Cited

U.S. PATENT DOCUMENTS

| 4,515,791 A * | 5/1985 | Allen et al. ........... 514/248 |
| 6,610,694 B1 | 8/2003 | Kawano et al. |
| 2004/0063580 A1 | 4/2004 | Kuragano et al. |

FOREIGN PATENT DOCUMENTS

| EP | 1 120 418 | 8/2001 |
| GB | 1 568 398 | 5/1980 |
| WO | WO 00/20417 | 4/2000 |
| WO | WO 02/38562 | 5/2002 |
| WO | WO 2004/074259 | 9/2004 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition,vol. 1, 1004-1010, 1996.*
Petrocellis et al., British Journal of Pharmacology, 141, 765-774.*
Black, Curr. Opin.. Investig. Drugs 5(4): 389-394, 2004.*
U.S. Appl. No. 11/016,198, filed Dec. 17, 2004, Yu et al.
U.S. Appl. No. 11/015,876, filed Dec. 17, 2004, Ewing et al.
Deeb A. et al., "Studies on Polyazaindenes Synthesis of Several New Condensed Pyridazine Derivatives", Collect. Czech. Chem. Commun., vol. 55 (11), pp. 2795-2799, 1990.
Patent Abstracts of Japan, vol. 010, No. 287 (C-375), Sep. 30, 1986 & JP 61 106576 (Nippon Soda Co. Ltd), May 24, 1986, Abstract; Claim 1, Table 1.
Database Beilstein, Beilstein Crossfire Iristitut Zur Foerderung Der Chemischen Wissenschaften; BRN 6750837 1994, XP002327081, abstract & Tarzia, G., et al., Benzodiazepine receptor ligands. Synthesis and preliminary pharmacological evaluation of 2-aminoalkyl-8-chloro- and 2-aryl-1,2,4-triazolo[3,4-a]phthalazine-3(2H)-ones. Farmaco (Societa Chimica Italiana: 1989) Jan. 1989, vol. 44, No. 1, (Jan. 1989), pp. 17-28, ISSN: 0014-827X.
Database Beilstein, Beilstein Crossfire Institut Zur Foerderung Der Chemischen Wissenschaften; BRN 9575107 2004, XP002327082, abstract & Wasfy, A.A.F., Journal Chem Res Miniprint, vol. 8, 2003, pp. 835-846.

* cited by examiner

*Primary Examiner*—Venkataraman Balasubram
(74) *Attorney, Agent, or Firm*—Rosemary M. Miano; Maureen S. Gibbons

(57) ABSTRACT

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I:

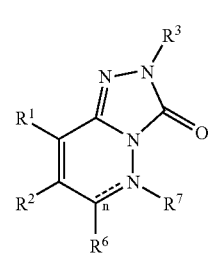

including all prodrugs, pharmaceutically acceptable salts and stereoisomers, $R^1$, $R^2$, $R^3$, $R^6$, $R^7$, m and n are described herein.

31 Claims, No Drawings

AZABICYCLIC HETEROCYCLES AS CANNABINOID RECEPTOR MODULATORS

RELATED APPLICATION

This application claims priority benefit under Title 35 § 119(e) of U.S. Provisional Application No. 60/531,451, filed Dec. 19, 2003, the contents of which are herein incorporated by reference.

BACKGROUND OF THE INVENTION

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I

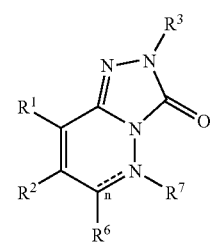

including all prodrugs, pharmaceutically acceptable salts and stereoisomers, $R^1$, $R^2$, $R^3$, $R^6$, $R^7$ and n are described herein:

Definitions

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carboxamido, carbonyl, alkenyl, alkynyl, nitro, amino, alkoxy, aryloxy, arylalkyloxy, heteroaryloxy, amido, $-OC(O)NR^8R^9$, $-OC(O)R^8$, $-OPO_3H$, $-OSO_3H$, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chains of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chains of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

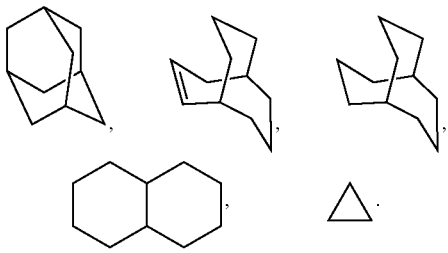

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

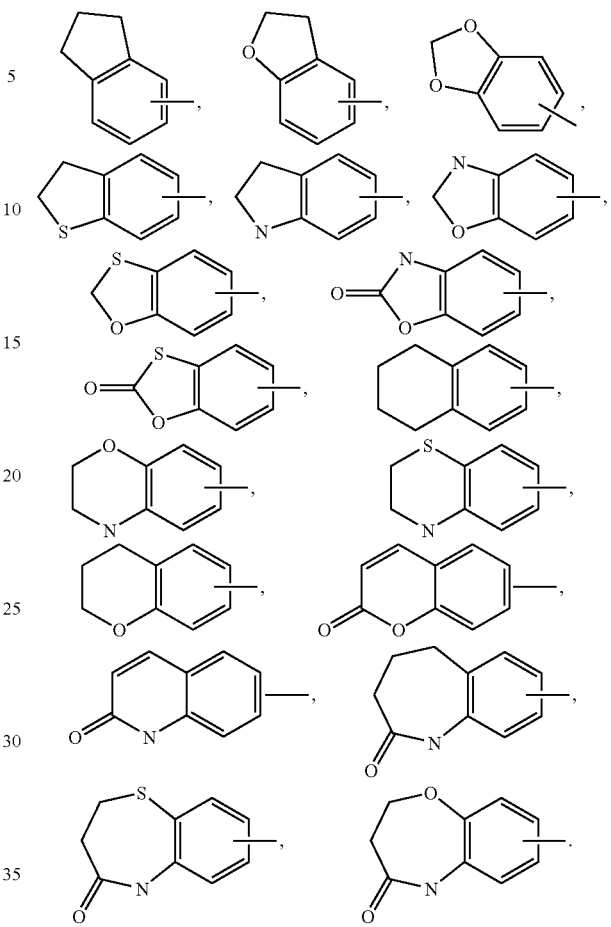

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the*

Literature 1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

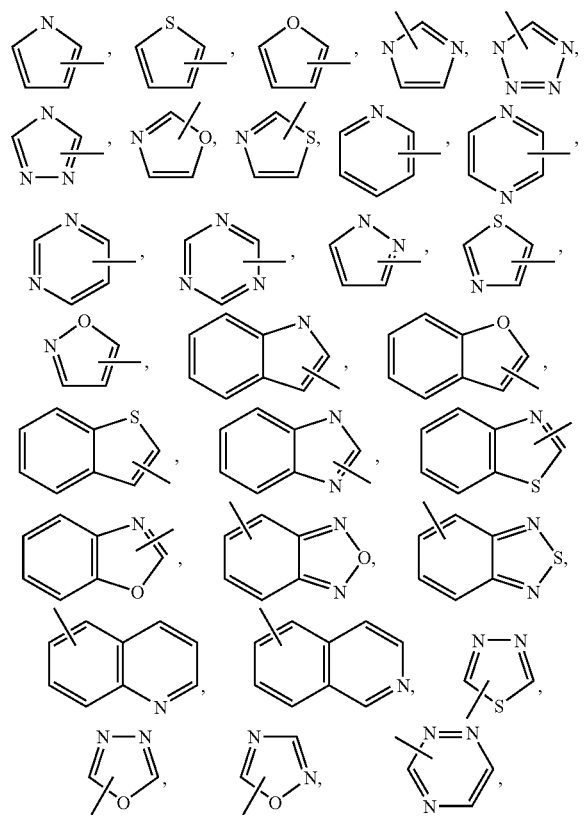

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a —CH$_2$— group.

The term "nitro," as used herein, refers to a —NO$_2$ group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$-C$_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of formula I with an open valence for further substitution wherein such substitution can, upon biotransformation, generate a compound of formula I. Examples of such functional groups of bioactive metabolites include, but are not limited to, —OH, —NH or functional groups wherein the hydrogen can be replaced with a functional group such as —PO$_3$H$_2$ for example, which, upon biotransformation generates an —OH or —NH functional group of a compound of formula I.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. Prodrug esters may also include—but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as—but not limited to—favorable aqueous solubility or in vivo exposure to the bioactive component formula I.

The term "prodrug" as employed herein includes functionalization of bioactive amine- or hydroxyl-containing compounds of formula I to form alkyl-, acyl-, sulfonyl-, phosphoryl-, or carbohydrate-substituted derivatives. Such derivatives are formed by reacting compounds of formula I with alkylating-, acylating-, sulfonylating-, or phosphorylating reagents employing procedures known to those skilled in the art. Alkylation of amines of formula I may result in—but are not limited to—derivatives that include spacer units to other prodrug moieties such as substituted alkyoxymethyl-, acyloxymethyl-, phosphoryloxymethyl-, or sulfonyloxymethyl-groups. Alkylation of amines of formula I may result in the generation of quarternary amine salts that act in vivo to provide the bioactive agent (i.e., the compound of formula I).

Preferred prodrugs consist of a compound of formula I where a pendant hydroxyl is phosphorylated to generate a phosphate derivative. Such a prodrug may also include a spacer group between the compound of formula I and the phosphate group, such as a methyleneoxy-group. Methods to generate such a prodrug from a compound of formula I are known to those skilled in the art, and are listed in the references below.

Preferred prodrugs also consist of a compound of formula I where a pendant amine, such as a pyridine group, is alkylated with a group, such as methyl, to form a quarternary ammonium ion salt. Methods to generate such a prodrug from a compound of formula I are known to those skilled in the art, and are listed in the references below.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985);

*A Textbook of Drug Design and Development*, P. Krogsgaard-Larson and H. Bundgaard, eds. Ch 5, pgs 113-191 (Harwood Academic Publishers, 1991).

*Hydrolysis in Drug and Prodrug Metabolism*, B. Testa and J. M. Mayer, (Verlag Helvetica Chimica Acta AG, Zurich, Switzerland; Wiley-VCH, Weinheim, Federal Republic of Germany, 2003)

Ettmayer, P.; Amidon, G. L.; Clement, B.; Testa, B. "Lessons Learned from Marketed and Investigational Prodrugs" *J. Med. Chem.* 2004, 47 (10), 2393-2404.

Davidsen, S. K. et al. "N-(Acyloxyalkyl)pyridinium Salts as Soluble Prodrugs of a Potent Platelet Activating Factor Antagonist" *J. Med. Chem.* 1994, 37 (26), 4423-4429.

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

Abbreviations

The following abbreviations are employed in the Schemes, Examples and elsewhere herein:
Ac=acetyl
AcOH=acetic acid
Boc=tert-butoxycarbonyl
DCM=dichloromethane
DIPEA=N,N-diisopropylehtylamine
DMF=N,N-dimethylformamide
EDAC=1-(3-Dimethylaminopropyl)-3-ethylcarbodiimide hydrochloride
EtOAc=ethyl acetate Et₃N=triethylamine
Et₂O=diethyl ether
HOBt=1-hydroxybenzotriazole hydrate
HPLC=high performance liquid chromatography
LAH=lithium aluminum hydride
MeOH=methanol
MS or Mass Spec=mass spectrometry
NaOH=sodium hydroxide
PG=protecting group
RT=room temperature
TFA=trifluoroacetic acid
THF=tetrahydrofuran
min=minute(s)
h=hour(s)
L=liter
mL=milliliter
μL=microliter
g=gram(s)
mg=milligram(s)
mol=moles
mmol=millimole(s)
nM=nanomolar Compounds of the present invention may be prepared by procedures illustrated in the accompanying schemes.

Methods of Preparation

The compounds of the present invention may be prepared by methods such as those illustrated in the following Scheme 1 to 9. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, $R^1$, $R^2$, $R^3$, $R^6$ and $R^7$ are as described for a compound of formula I.

The following are the definitions of symbols used throughout Schemes 1 to 9:

PG suitable nitrogen protecting group, exemplified by benzyl, methoxymethyl—[MOM], benzyloxymethyl—[BOM], 2-(trimethylsilyl)ethoxymethyl—[SEM], methoxyethoxymethyl—[MEM], or t-butyl groups;

EE $S_n2$ or $S_n1$ leaving group exemplified by halogen (Cl, Br, I) and sulfonates (—OSO₂-aryl (e.g., —OSO₂Ph or —OSO₂PhCH₃), or —OSO₂-alkyl (e.g., —OSO₂CH₃ or —OSO₂CF₃));

MM boronate ester or boronic acid, or trialkylstannane; or metal atom such as zinc, magnesium or lithium as part of an organometallic compound used as an intermediate for transition metal mediated coupling reactions.

SCHEME 1

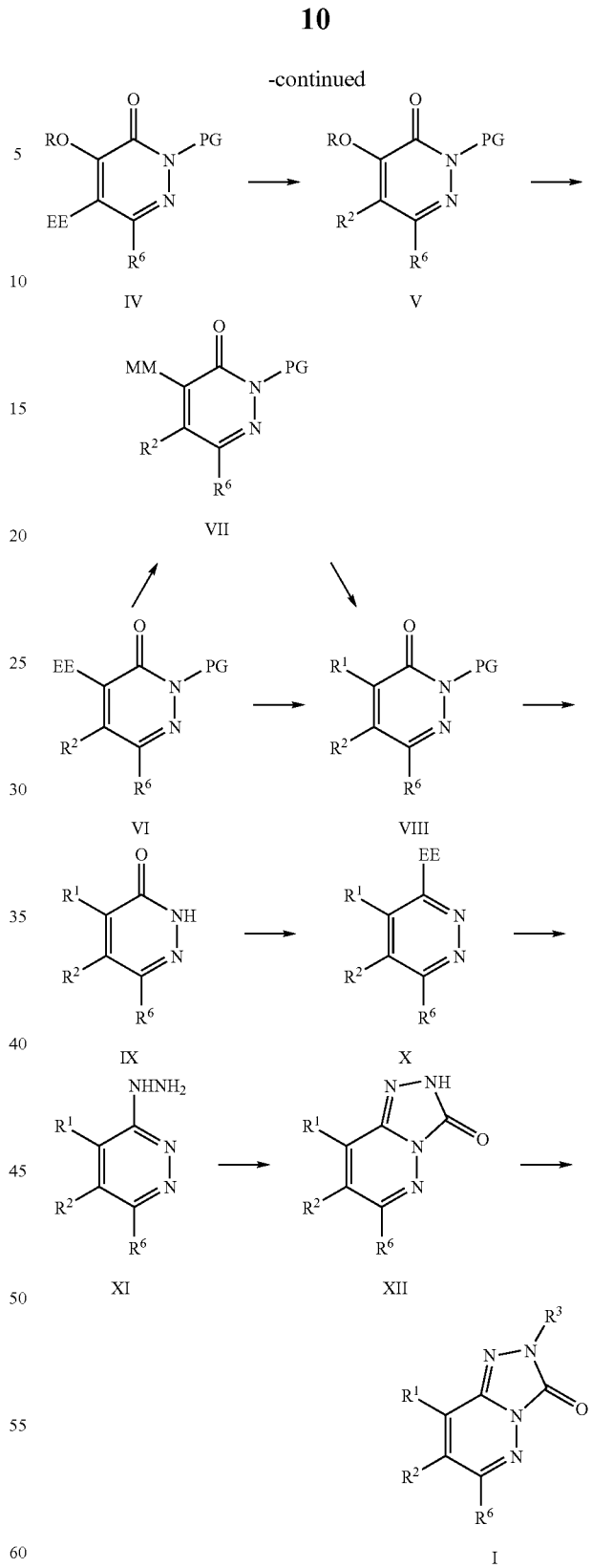

Compounds of formula II are either commercially available or available by means known to one skilled in the art. Compounds of formula III can be prepared by reacting compounds of formula II with an appropriate protecting group such as benzyl bromide. Exemplary nitrogen protecting groups and methods of protecting the nitrogen are similar to those for protecting amines, such as those described in T. W. Greene and P. G. M. Wuts, *Protecting Groups in Organic Synthesis*, John Wiley & Sons, Inc, New York, 1991. Preferred nitrogen protecting groups are benzyl, tert-butyl, methoxymethyl (MOM), methoxyethoxymethyl (MEM), and 2-(trimethylsilyl)ethoxymethyl (SEM) groups.

Compounds of formula IV may be prepared from compounds of formula III via selective displacement of the leaving group (EE) by the conjugate base of an appropriate alcohol, RO-M, wherein R is alkyl or benzyl, and M is a metalloid such as Li, Na, Mg (halide) and the like in solvents such as dioxane. Similar reactions have been described in the literature (Riedl, Z. et. al. Tetrahedron, 2002, 5645-5650).

Compounds of formula V can be prepared by the reactions of compounds of formula IV with activated $R^2$, such as activated by boronic acids, tin, Grignard reagents, Zinc, Cu, etc in the presence of an appropriate catalyst if needed such as $Pd(PPh_3)_4$. Compounds of formula V may also be prepared from a compound of formula IV via displacement of the leaving group (EE) by the conjugate base of a compound $R^2$—H, wherein $R^2$ is as previously defined, using a base in an inert solvent. Exemplary bases include sodium carbonate, potassium carbonate, cesium carbonate, sodium hydride, potassium hydride, or alkyl lithiums.

Compounds of formula VI, where EE=Cl, can be prepared by reacting compounds of formula V with a chlorinating agent such as $POCl_3$ in an inert solvent such as toluene at elevated temperature.

Compounds of formula VII, where MM is a metal or a borate ester, may be prepared via lithiation of a compound of formula VI wherein EE is hydrogen or a halogen (chloro, bromo, iodo), and reacting the resulting aryl lithium with an appropriate borate derivative or with reagents such as tri-alkyltin halide.

Compounds of formula VIII can be prepared by the reactions of compounds of formula VI with activated $R^1$, such as activated by boronic acids, tin, Grignard reagents, Zinc, Cu, etc in the presence of an appropriate catalyst if needed such as $Pd(PPh_3)_4$. Compounds of formula VIII may also be prepared from a compound of formula VI via displacement of the leaving group (EE) by the conjugate base of a compound $R^1$—H, wherein $R^1$ is as previously defined, using a base in an inert solvent.

Compounds of formula VIII can also be prepared by a palladium or nickel catalyzed coupling of a compound of formula VII wherein MM is a borate ester with an appropriately activated $R^1$ such as halide or mesylate. When MM is a metal atom such as tin, zinc, magnesium, and lithium, similar cross-coupling reactions can be performed using activated $R^1$ such as halide or borate esters with an appropriate catalyst such as tetrakis(triphenylphosphine)palladium(0) and dichlorobis(triphenylphosphine)nickel(II).

Compounds of formula IX can be prepared by removing the protecting group (PG) in compound VIII under acidic (e.g. TFA for t-butyl or Boc-), basic (e.g. NaOH for amide), catalytic hydrogenation (for benzyl-), or Lewis acid (e.g. $AlCl_3$ for benzyl) conditions.

Compounds of formula X can be prepared by reacting compounds of formula IX with a chlorinating agent such as $POCl_3$ in an inert solvent such as toluene at elevated temperature.

Compounds of formula XI can be prepared by reacting compounds of formula X with hydrazine in an inert solvent such as pyridine at elevated temperature.

Compounds of formula XII can be prepared by reacting compounds of formula XI with a carbonylating agent such as carbonyldiimidazole, phosgene, triphosgene or urea in an inert solvent such as tetrahydrofuran.

Compounds of formula I can be prepared by reacting compounds of formula XII with $R^3$—X (X is a leaving group such as F, Cl, Br, I, —OMs, —OTos), or epoxides at elevated temperatures. I can also be prepared by reacting compounds of formula XII with $R^3$—OH under Mitsunobu conditions.

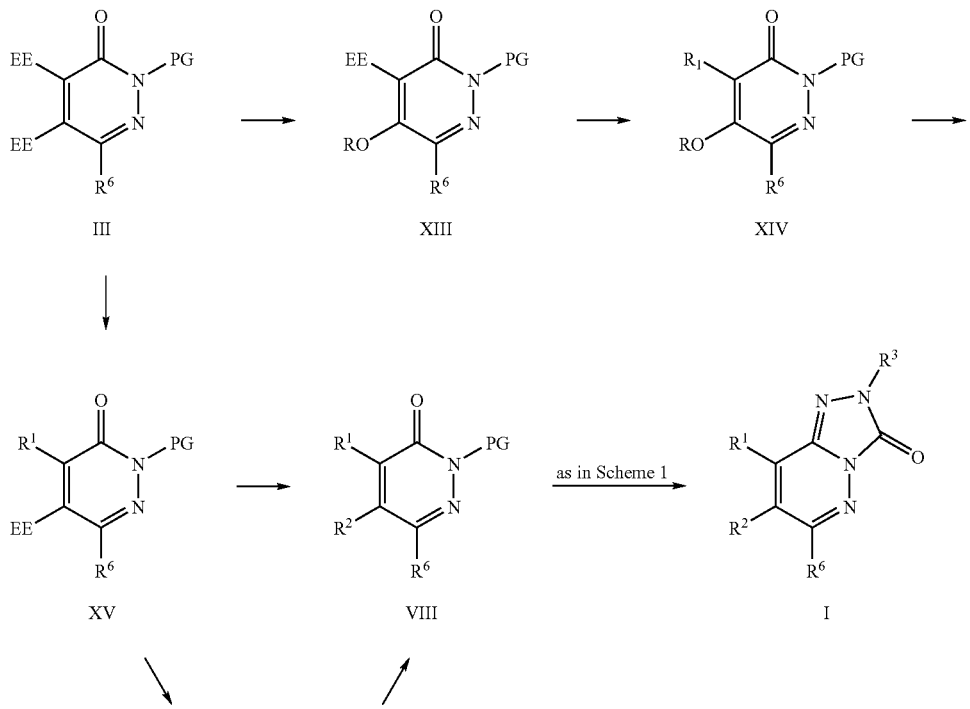

SCHEME 2

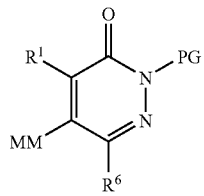

XVI

As illustrated in Scheme 2, compounds of formula XIII may be prepared from compounds of formula III via selective displacement of the leaving group (EE) by the conjugate base of an appropriate alcohol, RO-M, wherein R is alkyl or benzyl, and M is a metal such as Li, Na, Mg(halide) and the like in solvents such as methanol. Such selective displacements, for example when EE=Cl, has been reported in the literature. (Riedl, Z. et. al. Tetrahedron, 2002, 5645-5650).

Compounds of formula XIV can be prepared by the reactions of compounds of formula XIII with activated $R^1$, such as activated by boronic acids, tin, Grignard reagents, Zinc, Cu, etc in the presence of an appropriate catalyst if needed such as $Pd(PPh_3)_4$. Compounds of formula XIV may also be prepared from a compound of formula XIII via displacement of the leaving group (EE) by the conjugate base of a compound $R^1$—H, wherein $R^1$ is as previously defined, using a base in an inert solvent.

Compounds of formula XV, where EE=Cl, can be prepared by reacting compounds of formula XIV with a chlorinating agent such as $POCl_3$ in an inert solvent such as toluene at elevated temperature. Alternatively, compounds of formula XV, where EE=Cl, can also be prepared by the reactions of compounds of formula III with activated $R^1$, such as activated by boronic acids, tin, Grignard reagents, Zinc, Cu, etc in the presence of an appropriate catalyst if needed such as $Pd(PPh_3)_4$.

Compounds of formula XVI, where MM is a metal or a borate ester, may be prepared via lithiation of a compound of formula XV wherein EE is hydrogen or a halogen (chloro, bromo, iodo), and reacting the resulting aryl lithium with an appropriate borate derivative or with reagents such as trialkyltin halide.

Compounds of formula VIII can be prepared by the reactions of compounds of formula XV with activated $R^2$, such as activated by boronic acids, tin, Grignard reagents, Zinc, Cu, etc in the presence of an appropriate catalyst if needed such as $Pd(PPh_3)_4$. Compounds of formula VIII may also be prepared from a compound of formula XV via displacement of the leaving group (EE) by the conjugate base of a compound $R^2$—H, wherein $R^2$ is as previously defined, using a base in an inert solvent.

Compounds of formula VIII can also be prepared by a palladium or nickel catalyzed coupling of a compound of formula XVI wherein MM is a borate ester with an appropriately activated $R^2$ such as halide or mesylate. When MM is a metal atom such as tin, zinc, magnesium, and lithium, similar cross-coupling reactions can be performed using activated $R^2$ such as halide or borate esters with an appropriate catalyst such as tetrakis(triphenylphosphine)palladium(0) and dichlorobis(triphenylphosphine)nickel(II).

Compounds of formula I may be prepared from a compound of formula VIII as described in Scheme 1.

SCHEME 3

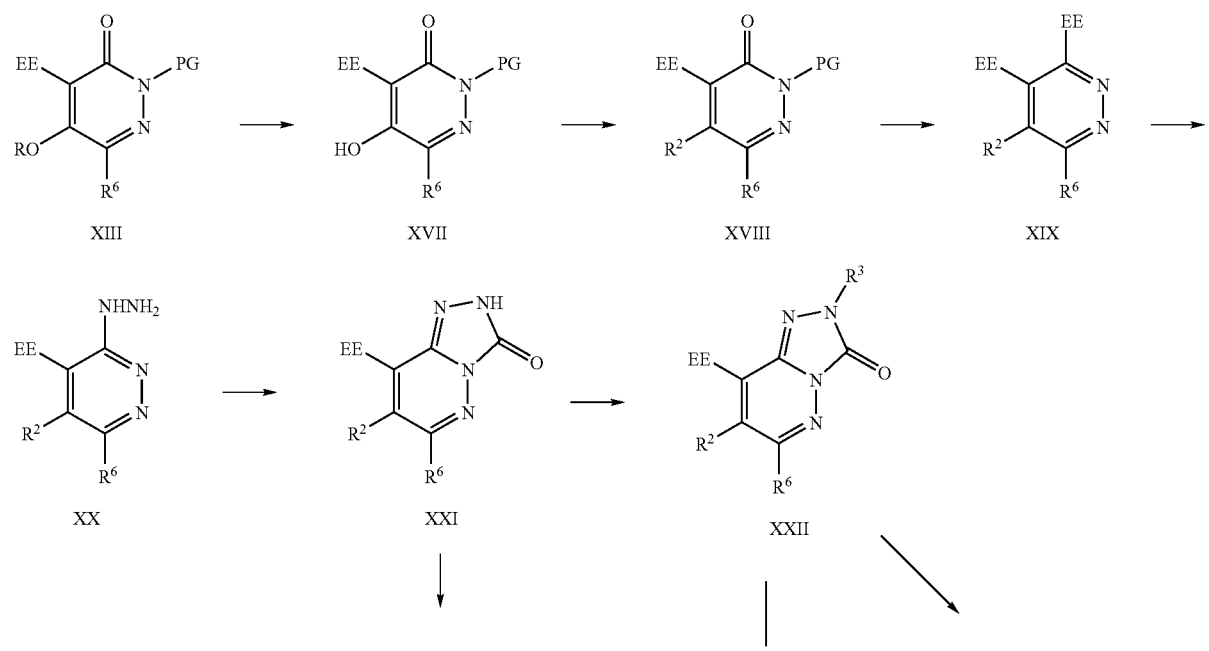

-continued

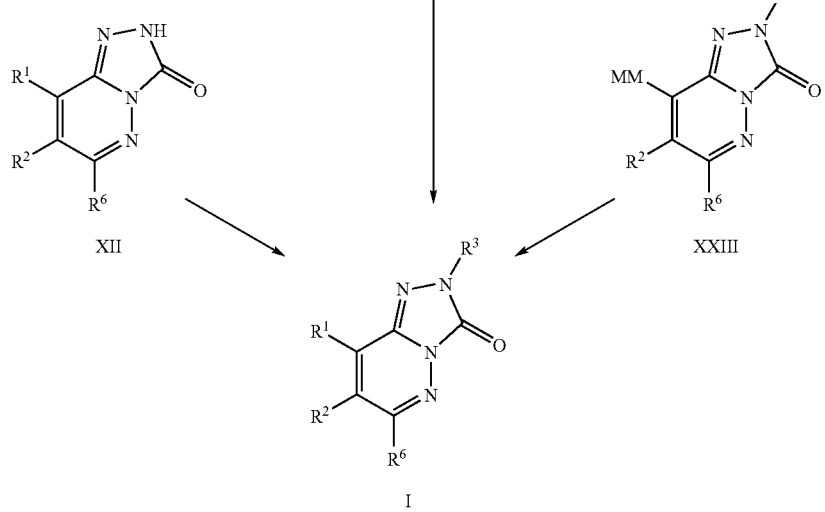

As illustrated in Scheme 3, compounds of formula XVII may be prepared from a compound of formula XIII (from Scheme 2) via displacement of the R group (R=alkyl) using bases such as sodium hydroxide in a suitable solvent such as water. The hydroxyl group in XVII can be activated by reacting with reagents such as trifluromethane sulfonic anhydride in the presence of a suitable base such as triethylamine. This activated moiety can then be selectively coupled with activated $R^2$, such as activated by boronic acids, tin, Grignard reagents, Zinc, Cu, etc in the presence of an appropriate catalyst if needed such as $Pd(PPh_3)_4$ to provide compounds XVIII.

Compounds of formual XIX can alos be made by treatment of compounds of Formula V with $POCl_3$ at elevated temperatures.

Compounds of formula XIX can be prepared from compounds XVIII in a two step sequence: (a) by removing the protecting group (PG) in compound XVIII under acidic (e.g. TFA for t-butyl or Boc-), basic (e.g. NaOH for amide), catalytic hydrogenation (for benzyl-), or Lewis acid (e.g. $AlCl_3$ for benzyl) conditions, followed by (b) reacting the resulting intermediate with a chlorinating agent such as $POCl_3$ in an inert solvent such as toluene at elevated temperature. In certain instances, direct treatment of XVIII with chlorinating agents such as $POCl_3$ at higher temperature may provide compounds of formula XIX in one step from XVIII.

Compounds of formula XX can be prepared by reacting compounds of formula XIX with hydrazine in selected solvents such as isobutanol.

Compounds of formula XXI can be prepared by reacting compounds of formula XX with a carbonylating agent such as carbonyldiimidazole, phosgene, triphosgene or urea in an inert solvent such as tetrahydrofuran.

Compounds of formula XXII can be prepared by reacting compounds of formula XXI with $R^3$—X (X is a leaving group such as F, Cl, Br, I, —OMs, —OTos), or epoxides at elevated temperatures. XXII can also be prepared by reacting compounds of formula XXI with $R^3$—OH under Mitsunobu conditions.

Compounds of formula I can be prepared by the reactions of compounds of formula XXII with activated $R^1$, such as activated by boronic acids, tin, Grignard reagents, Zinc, Cu, etc in the presence of an appropriate catalyst if needed such as $Pd(PPh_3)_4$. Compounds of formula I may also be prepared from a compound of formula XXII via displacement of the leaving group (EE) by the conjugate base of a compound $R^1$—H, wherein $R^1$ is as previously defined, using a base in an inert solvent.

Compounds of formula XXIII, where MM is a metal or a borate ester, may be prepared via lithiation of a compound of formula XXII wherein EE is hydrogen or a halogen (chloro, bromo, iodo), and reacting the resulting aryl lithium with an appropriate borate derivative or with reagents such as trialkyltin halide.

Compounds of formula I can also be prepared by a palladium or nickel catalyzed coupling of a compound of formula XXIII wherein MM is a borate ester with an appropriate activated $R^1$ such as halide or mesylate. When MM is a metal atom such as tin, zinc, magnesium, and lithium, similar cross-coupling reactions can be performed using activated $R^1$ such as halide or borate esters with an appropriate catalyst such as tetrakis(triphenylphosphine)palladium(0) and dichlorobis(triphenylphosphine)nickel(II).

Compounds of formula I can also be prepared from XXI in a two step sequence: (a) cross-coupling of XXI with an activated $R^1$, such as activated by boronic acids, tin, Grignard reagents, Zinc, Cu, etc in the presence of an appropriate catalyst if needed such as $Pd(PPh_3)_4$ or displacement of EE in XXI with a conjugate base of $R^1$—H, to provide compounds XII, followed by (b) reacting compounds of formula XII with $R^3$—X (X is a leaving group such as F, Cl, Br, I, —OMs, —OTos), or epoxides at elevated temperatures.

SCHEME 4

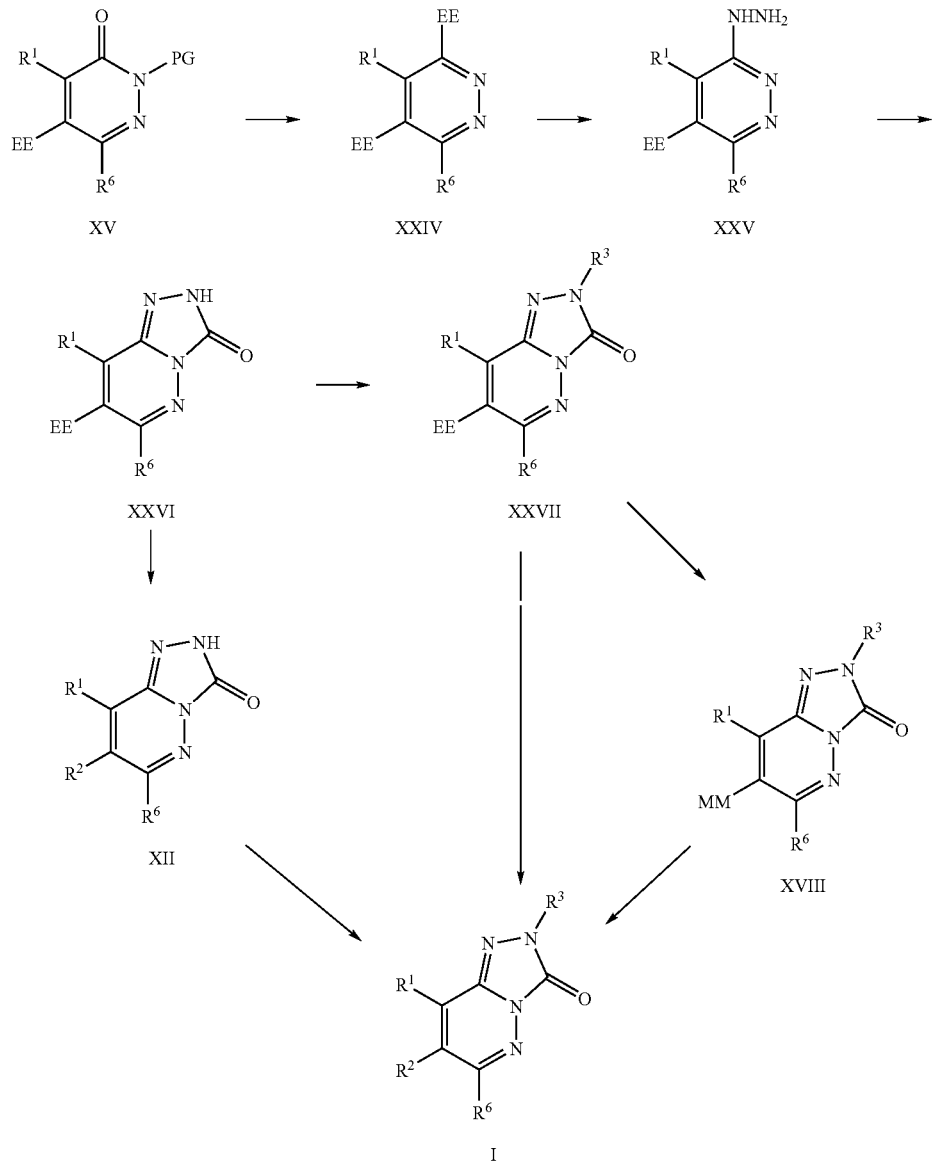

As illustrated in Scheme 4, compounds of formula XXIV can be prepared from compounds XV in a two step sequence: (a) by removing the protecting group (PG) in compound XV under acidic (e.g. TFA for t-butyl or Boc-), basic (e.g. NaOH for amide), catalytic hydrogenation (for benzyl-), or Lewis acid (e.g. AlCl$_3$ for benzyl) conditions, followed by (b) reacting the resulting intermediate with a chlorinating agent such as POCl$_3$ in an inert solvent such as toluene at elevated temperature.

Compounds of formula XXV can be prepared by reacting compounds of formula XXIV with hydrazine in selected solvents such as isobutanol.

Compounds of formula XXVI can be prepared by reacting compounds of formula XXV with a carbonylating agent such as carbonyldiimidazole, phosgene, triphosgene or urea in an inert solvent such as tetrahydrofuran.

Target compounds of formula I can be prepared from compounds of formula XXV1 by following an analogous sequence of reactions as described in Scheme 3 via intermediates XII, XXVII and XXVIII.

SCHEME 5

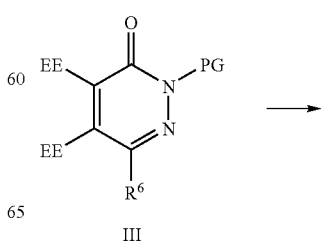

III

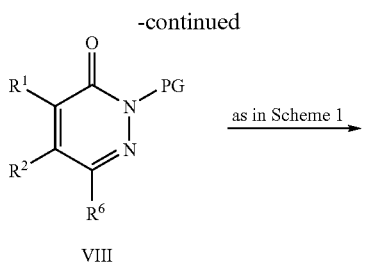

VIII with activated $R^2$, such as activated by boronic acids, tin, Grignard reagents, Zinc, Cu, etc in the presence of an appropriate catalyst if needed such as $Pd(PPh_3)_4$. Compounds of formula I can then be prepared from compounds of formula I by following an analogous sequence of reactions as described in Scheme 1.

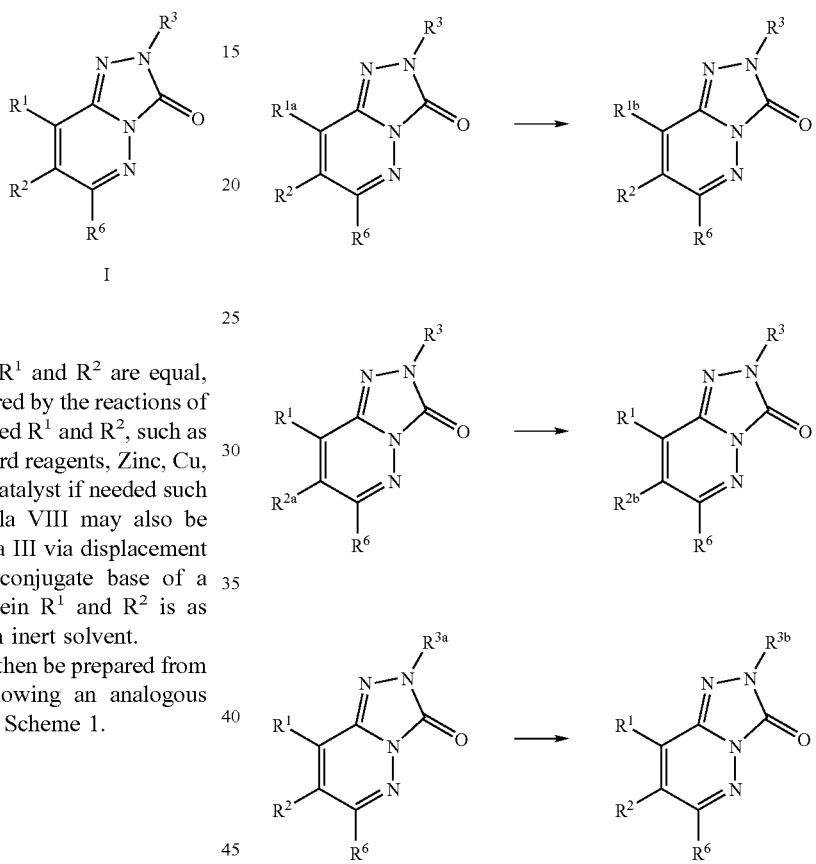

As illustrated in Scheme 5, when $R^1$ and $R^2$ are equal, compounds of formula VIII can prepared by the reactions of compounds of formula III with activated $R^1$ and $R^2$, such as activated by boronic acids, tin, Grignard reagents, Zinc, Cu, etc in the presence of an appropriate catalyst if needed such as $Pd(PPh_3)_4$. Compounds of formula VIII may also be prepared from a compound of formula III via displacement of the leaving group (EE) by the conjugate base of a compound $R^1$—H and $R^2$—H, wherein $R^1$ and $R^2$ is as previously defined, using a base in an inert solvent.

Target compounds of formula I can then be prepared from compounds of formula VIII by following an analogous sequence of reactions as described in Scheme 1.

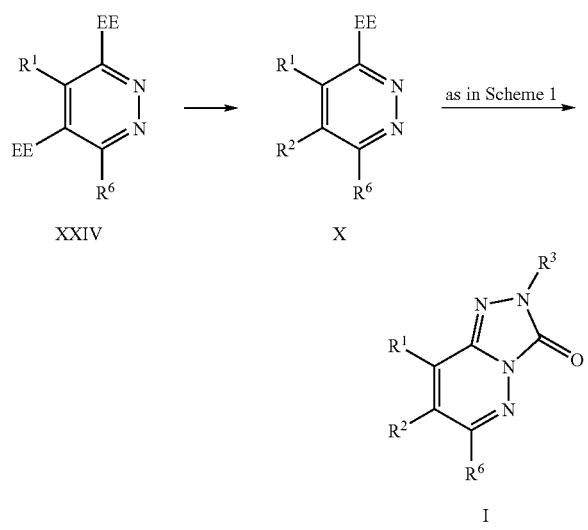

As illustrated in Scheme 6, compounds of formula X can be prepared by the reactions of compounds of formula XXIV As illustrated in Scheme 7, analogs having certain arbitrarily defined subsets of $R^1$ and $R^2$ and $R^3$ can be changed to other analogs having certain other arbitrarily defined subsets of $R^1$ and $R^2$ and $R^3$ by manipulation of the functional groups embedded in these R groups. For example, when $R^{1a}$, $R^{2a}$, $R^{3a}$ are groups such as amino, aminoaryl, aminoalkyl or aminoaryloxyl, they can be reacted with either carboxylic acids or acid chlorides or sulfonyl chlorides to provide amide or sulfonamide derivatives. Such a manipulation can also be conducted via parallel synthesis.

In addition, when $R^{1a}$, $R^{2a}$ or $R^{3a}$ are substituted with an activated group such as a halogen or boronic acid, additional metal catalyzed cross-coupling reactions may be performed to provide additional set of analogs as described by Formula I. Such a manipulation can also be conducted via parallel synthesis.

SCHEME 8

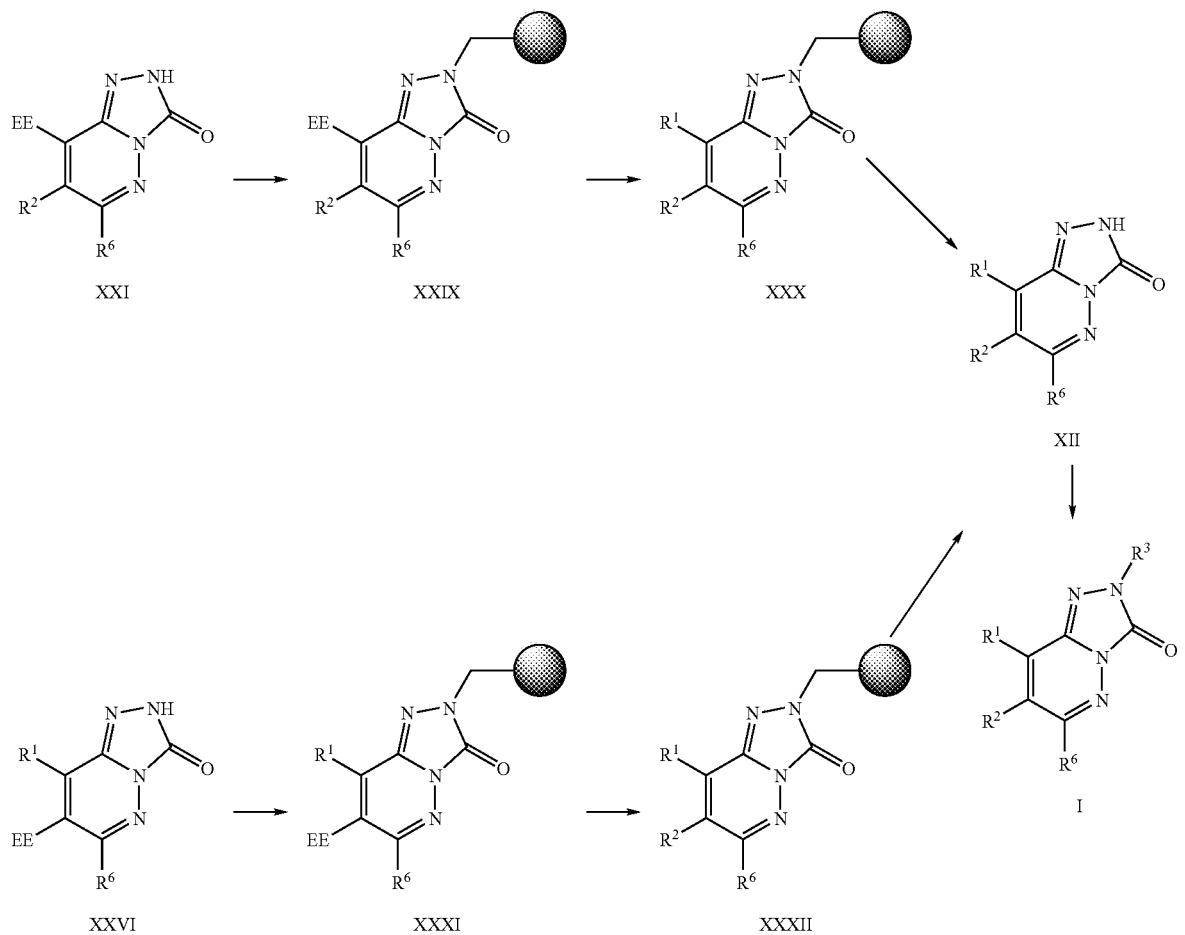

As illustrated in Scheme 8, compounds of formula I can be prepared by parallel synthesis using solid-phase synthesis. For example, compounds of formula XXI can be reacted with a polymer bound resin to provide compounds XXIX. Compounds of formula XXX can be prepared by the reactions of compounds of formula XXIX with activated $R^1$, such as activated by boronic acids, tin, Grignard reagents, Zinc, Cu, etc in the presence of an appropriate catalyst if needed such as Pd(PPh$_3$)$_4$. Removal of the poymer bound resin then provides compounds of formula XII. Compounds of formula XII can be converted to compounds of formula I as shown in Scheme 1.

Target compounds of formula I can also be prepared from compounds of formula XXVI by following an analogous sequence of reactions as described above.

SCHEME 9

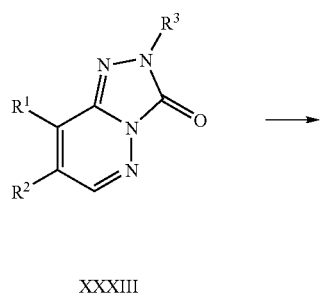

-continued

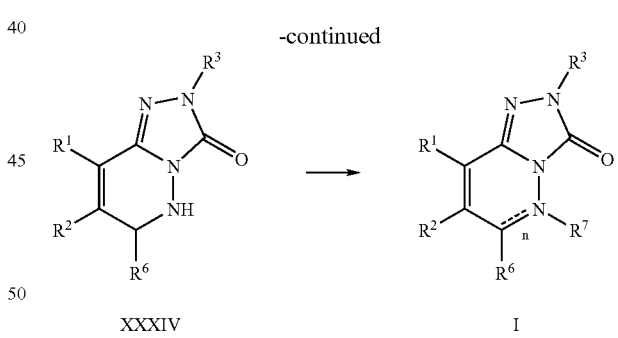

Compounds of formula XXXIII can undergo reaction with an activated $R^6$, such as $R^6$-M wherein M is a metalloid such as Li, Na, Mg(halide) and the like in solvents such as THF to give compounds of formula XXXIV, which is recognized as a subset of compounds of formula I wherein n is single bond and $R^7$ is hydrogen. A compound of formula XXXIV can be reacted with an oxidant, such as atmospheric oxygen or 2,3-dichloro-5,6-dicyanohydroquinone and the like, to give compounds of formula I wherein n is double bond and $R^7$ is absent. A compound of formula XXXIV can be reacted with an alkylating agent, such as and alkyl halide, or an acylating group, such as acetic anhydride, benzoyl chloride and the like to give compounds of formula I. A compound of formula XXXIV can be reacted with a phosphorylating reagent, such as POCl$_3$ or Cl—P(O)(OEt)$_2$ to give, upon hydrolysis, compounds of formula I. Examples of transformation of amines to phosphonamidates can be found in: Wang R. et al. *J. Med. Chem.* 2003, 46 (22), 4799-4802; Guillaume, H. A. *J. Org. Chem.* 1989, 54 (24), 5731-5736. A compound of formula XXXIV can be reacted with a sulfonylating agent, such as pyridine-SO$_3$ complex or Cl—S(O)mR$^8$, to give compounds of formula I. Examples of such transformations can be found in Tschamber, T. and Streith, *J. Heterocycles* 1990, 30 (1), 551-559; Couloigner, E., Cartier, D., Labia, R. *Bioorg. Med. Chem. Lett.* 1999, 9, 2205-2206; Tschamber, T. et al. *Heterocycles* 1985, 23 (10), 2589-2601.

Parallel synthesis may be employed in the preparation of compounds, for example, where the intermediates possess an activated reaction center: such as but not limited to, the nitrogen of the triazolone, a reactive heteroaryl chloride for Suzuki coupling chemistry or a carboxylic acid for amide coupling chemistry.

EXAMPLES

The following Examples serve to better illustrate, but not limit, some of the preferred embodiments of the invention.

Analytical HPLC and HPLC/MS Methods Employed in Characterization of Examples

Analytical HPLC was performed on Shimadzu LC10AS liquid chromatographs. Analytical HPLC/MS was performed on Shimadzu LC10AS liquid chromatographs and Waters ZMD Mass Spectrometers using the following methods:

Unless otherwise indicated, method A is used in the characterization of intermediates or final compounds of the examples listed in the experimentals or in the tables.
Method A. Linear gradient of 0 to 100% solvent B over 4 min, with 1 min hold at 100% B;
  UV visualization at 220 nm
  Column: Phenomenex Luna C18 4.6×50 mm
  Flow rate: 4 ml/min
Solvent A: 0.2% phosphoric acid, 90% water, 10% methanol
Solvent B: 0.2% phosphoric acid, 90% methanol, 10% water
Method B. Linear gradient of 0 to 100% solvent B over 8 min, with 3 min hold at 100% B;
  UV visualization at 220 nm
  Column: Phenomenex Luna C18 4.6×75 mm or Zorbax SB C18 4.6×75 mm
  Flow rate: 2.5 ml/min
Solvent A: 0.2% phosphoric acid, 90% water, 10% methanol
Solvent B: 0.2% phosphoric acid, 90% methanol, 10% water
Method C. Linear gradient of 10 to 100% solvent B over 4.0 min, with 0.5 min hold at 100% B;
  UV visualization at 220 nm
  Column: Xterra MS-C18, 4.6×50 mm
  Flow rate: 4 ml/min
Solvent A: 0.1% trifluoroacetic acid, 90% water, 10% acetonitrile
Solvent B: 0.1% trifluoroacetic acid, 10% water, 90% acetonitrile
Method D. Linear gradient of 0 to 100% solvent B over 4 min, with 1 min hold at 100% B;
  UV visualization at 220 nm
  Column: Phenomenex Luna C18 4.6×50 mm
  Flow rate: 4 ml/min
Solvent A: 0.1% trifluoroacetic acid, 90% water, 10% methanol
Solvent B: 0.1% trifluoroacetic acid, 90% methanol, 10% water
Method E. Linear gradient of 0 to 100% solvent B over 4 min, with 1 min hold at 100% B;
  UV visualization at 220 nm
  Column: Phenomenex Luna C18 4.6×50 mm
  Flow rate: 4 ml/min
Solvent A: 10 mM NH$_4$OAc, 90% water, 10% methanol
Solvent B: 10 mM NH$_4$OAc, 90% methanol, 10% water
Method F. Linear gradient of 1 to 100% solvent B over 2.35 min, with 0.5 min hold at 100% B;
  UV visualization at 220 nm
  Column: Xterra MS-C18, 2.1×50 mm
  Flow rate: 1.0 ml/min
Solvent A: 0.1% trifluoroacetic acid, 100% water
Solvent B: 0.1% trifluoroacetic acid, 100% acetonitrile
Method G. Linear gradient of 10 to 100% solvent B over 2.0 min, with 0.56 min hold at 100% B;
  UV visualization at 220 nm
  Column: Xterra MS-C18, 4.6×50 mm
  Flow rate: 1.0 ml/min
Solvent A: 10 mM NH$_4$OAc, 95% water, 5% acetonitrile
Solvent B: 10 mM NH$_4$OAc, 95% acetonitrile, 5% water NMR Employed in Characterization of Examples $^1$H NMR spectra were obtained with Bruker or JOEL fourier transform spectrometers operating at the following frequencies: $^1$H NMR: 400 MHz (Bruker), 400 MHz (JOEL), or 500 MHz (JOEL); $^{13}$C NMR: 100 MHz (Bruker), 100 MHz (JOEL) or 125 MHz (JOEL). Spectra data are reported as Chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for CD$_2$HSOCD$_3$, 3.30 ppm for CD$_2$HOD, 7.24 ppm for CHCl$_3$, 39.7 ppm for CD$_3$SOCD$_3$, 49.0 ppm for CD$_3$OD, 77.0 ppm for CDCl$_3$). All $^{13}$C NMR spectra were proton decoupled.

Example 1

Preparation of 7,8-bis(4-chlorophenyl)-[1,2,4]triazolo[4,3-b]pyridazin-3(2H)-one

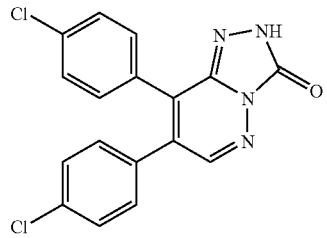

1A. Preparation of 2-Benzyl-4,5-dibromopyridazin-3(2H)-one

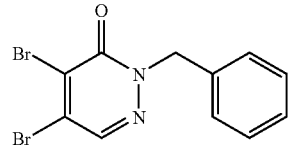

To a solution of dibromopyridazinone (50.0 g, 197.0 mmol) in DMF (200 mL) at RT was added K$_2$CO$_3$ (32.6 g, 236.4 mmol). Benzylbromide (37.0 g, 216.7 mmol) was added via a syringe. The resulting greenish suspension was stirred at RT for 6 h until all the pyridazinone was consumed as judged by HPLC. The reaction mixture was then poured into an Erlemneyer flask containing water (500 mL) with stirring. A beige colored solid formed. The suspension was stirred for 15 min at RT and then was filtered. The solid was rinsed thoroughly with water until no color was apparent in the filtrate. The solid was dried in a vacuum oven at 50° C. overnight. The title compound, 2-benzyl-4,5-dibromopyridazin-3(2H)-one, (68.0 g, 196.5 mmol) was >95 pure as judged by HPLC and was obtained as a solid. MS: M+H=343. $^1$H NMR (CDCl$_3$, 500 MHz): δ 7.80 (1H, s), 7.45 (2H, d, J=5.0 Hz), 7.29-7.36 (3H, m), 5.31 (2H, s).

1B. Preparation of 2-Benzyl-4,5-bis(4-chlorophenyl)pyridazin-3(2H)-one

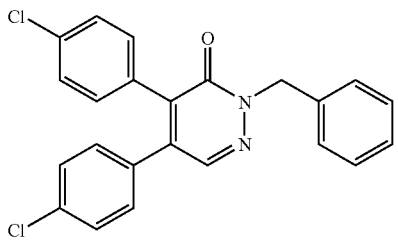

To a suspension of 2-benzyl-4,5-dibromopyridazin-3(2H)-one (40 g, 116.0 mmol) in toluene (300 mL) was added Pd(PPh$_3$)$_4$ (4.0 g, 3.5 mmol) under an atmosphere of agron. 4-Chlorophenylboronic acid (40.0 g, 255.2 mmol) was added subsequently portionwise. Under vigorous stirring, Na$_2$CO$_3$ (27.0 g, 255.2 mmol) dissolved in water (50 mL) was added to the suspension. Argon was bubbled through this suspension for 10 min. before the flask was placed in an oil bath preheated at 120° C. The reaction was refluxed for 6 h. The reaction was then allowed to cool to RT and was poured into water (500 mL). The aqueous mixture was extracted with EtOAc (3×300 mL). The combined organic layers were washed with NaOH (0.5 N, 200 mL) and water (2×500 mL). The organic layer was filtered through a silica gel pad (~50 g) in a sintered glass funnel to remove dark color impurities. Solvents were then evaporated under reduced pressure. The resultant thick syrup contained predominantly the title compound 2-benzyl-4,5-bis(4-chlorophenyl)pyridazin-3(2H)-one which could be used directly in the next reaction, 1C. MS: M+H=407. $^1$H NMR (CDCl$_3$, 500 MHz): δ 7.87 (1H, s), 7.54 (2H, d, J=5.0 Hz), 7.32-7.38 (3H, m), 7.22-7.28 (4H, m), 7.12 (2H, d, J=10.0 Hz), 7.03 (2H, d, J=10 Hz), 5.40 (2H, s).

1C. Preparation of 4,5-bis(4-chlorophenyl)pyridazin-3(2H)-one

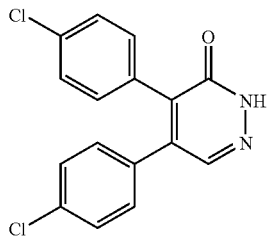

The crude 2-benzyl-4,5-bis(4-chlorophenyl)pyridazin-3(2H)-one from the above reaction was dissolved in toluene (350 mL). Aluminum chloride (AlCl$_3$, 46.3 g, 348.0 mmol) was then added to the toluene solution, producing an exotherm. The reaction was then placed in an oil bath preheated at 75° C. for 3 h. After this time, the reaction mixture was poured into ice-water (1000 mL), and the resulting mixture was extracted with EtOAc (3×500 mL). The combined organic layers were washed with water (500 mL), then filtered through a silica gel pad (~50 g) to remove residual alumina salts. The organic solvents were evaporated under reduced pressure to nearly dryness. Diethyl ether (Et$_2$O, 500 mL) was added with stirring. After stirring for 15 min at RT, hexane (1000 mL) was added subsequently. The resultant beige colored solid was collected by filtration and subsequently washed with a hexane-ether mixture (8:2). The title compound, 4,5-bis(4-chlorophenyl)pyridazin-3(2H)-one, (33.0 g, 92%) was obtained as a solid. MS: M+H=317. $^1$H NMR (CDCl$_3$, 500 MHz): δ 11.94 (1H, br), 7.89 (1H, s), 7.23-7.32 (4H, m), 7.18 (2H, d, J=10.0 Hz), 7.07 (2H, d, J=10 Hz).

1D. Preparation of 3-Chloro-4,5-bis(4-chlorophenyl)pyridazine

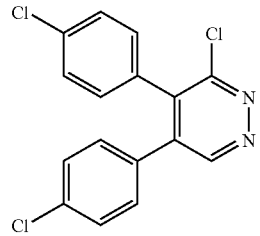

4,5-Bis(4-chlorophenyl)pyridazin-3(2H)-one (16.5 g, 52.2 mmol) was suspended in toluene (50 mL). To the resultant solution was added pyridine (8.3 mL, 104.4 mmol), followed by the addition of POCl$_3$ (14.3 mL, 156.6 mmol). The reaction mixture was placed in an oil bath preheated at 110° C. After 4 h, the reaction mixture was cooled to RT, then poured over 500 g ice to quench the excess POCl$_3$. The dark mixture was extracted with EtOAc (2×300 mL). The combined organic layers were washed with water (500 mL), and filtered through a silica gel pad (~50 g). The filtrate was concentrated under reduced pressure to give the title compound, 3-chloro-4,5-bis(4-chlorophenyl)pyridazine as a pale colored solid (16.0 g, 92%). MS: M+H=335. $^1$H NMR (CDCl$_3$, 500 MHz): δ 9.24 (1H, s), 7.35 (2H, d, J=10 Hz), 7.26 (2H, d, J=10.0 Hz), 7.08-7.16 (4H, m).

1E. Preparation of 1-(4,5-Bis(4-chlorophenyl)pyridazin-3-yl)hydrazine

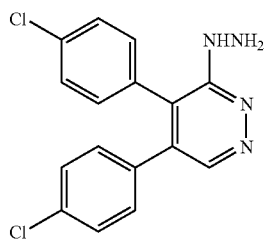

3-Chloro-4,5-bis(4-chlorophenyl)pyridazine (10.0 g, 30.0 mmol) was dissolved in pyridine (30 mL) and hydrazine mono-hydrate was added (4.5 g, 90.0 mmol). The reaction mixture was refluxed for 3 h and was then added to water (100 mL). The pale colored solid was collected by filtration and rinsed thoroughly with water. The product was dried in a vacuum oven to give the title compound, 1-(4,5-bis(4-chlorophenyl)pyridazin-3-yl)hydrazine (9.5 g, 96%). MS: M+H=331. $^1$H NMR (DMSO-$d_6$, 500 MHz): δ 8.59 (1H, s), 8.56 (1H, br), 7.40 (2H, d, J=10 Hz), 7.35 (2H, d, J=10.0 Hz), 7.14-7.16 (4H, m).

1F. Preparation of 7,8-bis(4-chlorophenyl)-[1,2,4]triazolo[4,3-b]pyridazin-3(2H)-one

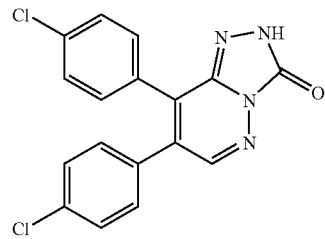

To a THF (20 mL) solution of carbonyldiimidazole (CDI), (1.7 g, 10.5 mmol) was added 1-(4,5-bis(4-chlorophenyl)pyridazin-3-yl)hydrazine (0.7 g, 2.1 mmol). The resultant brown solution was stirred at RT for 15 min. After this time, the reaction solution was poured into water (50 mL). The resultant pale colored solid was collected by filtration. Water was used to rinse the solid thoroughly to afford 7,8-bis(4-chlorophenyl)-[1,2,4]triazolo[4,3-b]pyridazin-3(2H)-one (0.75 g, 100%). MS (M+H)=357; $^1$H NMR (DMSO-$d_6$, 500 MHz): δ 12.86 (1H, s), 8.37 (1H, s), 7.42-7.48 (4H, m), 7.35 (2H, d, J=10.0 Hz), 7.27 (2H, d, J=10.0 Hz).

Example 2

Preparation of 2-(4-Chlorobenzyl)-7,8-bis(4-chlorophenyl)-[1,2,4]triazolo[4,3-b]pyridazin-3(2H)-one

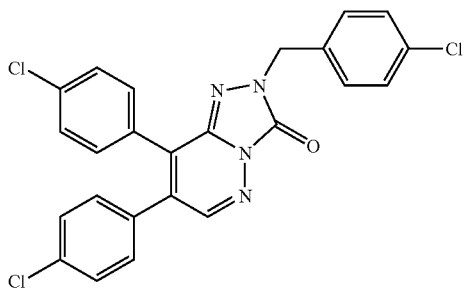

To a solution of 7,8-bis(4-chlorophenyl)-[1,2,4]triazolo[4,3-b]pyridazin-3(2H)-one (0.4 g, 1.1 mmol), prepared as described in Example 1 in DMF (5 mL) was added $K_2CO_3$ (0.46 g, 3.3 mmol) and 4-chlorobenzyl bromide (0.28 g, 1.3 mmol). The reaction mixture was heated at 60° C. for 20 min. After this time, water (50 mL) was added to the reaction mixture and the resultant solid was collected by filtration. The final product (0.32 g, 60%) was obtained by purification using reverse phase preparative HPLC. MS (M+H)=481; $^1$H NMR (CDCl$_3$): δ 8.18 (1H, s), 7.25-7.40 (10H, m), 7.08 (2H, d, J=10.0 Hz), 5.18 (2H, s).

Example 3

Preparation of 7,8-Bis(4-chlorophenyl)-2-((5-(trifluoromethyl)pyridin-2-yl)methyl)-[1,2,4]triazolo[4,3-b]pyridazin-3(2H)-one

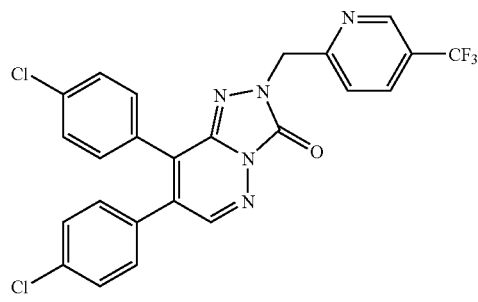

To a solution of 7,8-bis(4-chlorophenyl)-[1,2,4]triazolo[4,3-b]pyridazin-3(2H)-one (100 mg, 0.28 mmol), prepared as described in Example 1, Ph$_3$P (220 mg, 0.84 mmol) and (5-trifluoromethyl-pyridin-2-yl)methanol (50 mg, 0.28 mmol) in THF (2.0 mL) was added 40 wt % diethyl azodicarboxylate (DEAD) solution in toluene (0.33 mL, 0.84 mmol) at RT under argon. The reaction was stirred at RT for 30 min. Water (5.0 mL) was then added and the resulting mixture was extracted with EtOAc (3×5 mL). The combined organic layers were washed with water (2×5 mL) followed by saturated aqueous NaCl (2×5 mL). The combined organic layers were concentrated under reduced pressure to obtain the crude product. This crude product was purified using reverse phase preparative HPLC to give the title compound 7,8-bis(4-chlorophenyl)-2-((5-(trifluoromethyl)pyridin-2-yl)methyl)-[1,2,4]triazolo[4,3-b]pyridazin-3(2H)-one (69.2 mg, 48%) as a yellow solid. MS (M+H)=516; $^1$H NMR (CDCl$_3$): δ 8.83 (1H, s), 8.20 (1H, s), 7.93 (1H, d, J=8.2 Hz), 7.40 (1H, d, J=10.0 Hz), 7.26-7.34 (6H, m), 7.11 (2H, d, J=10.0 Hz), 5.47 (2H, s).

Example 4

Preparation of 7,8-Bis(4-chlorophenyl)-2-((1-(pyrimidin-2-yl)piperidin-4-yl)methyl)-[1,2,4]triazolo[4,3-b]pyridazin-3(2H)-one

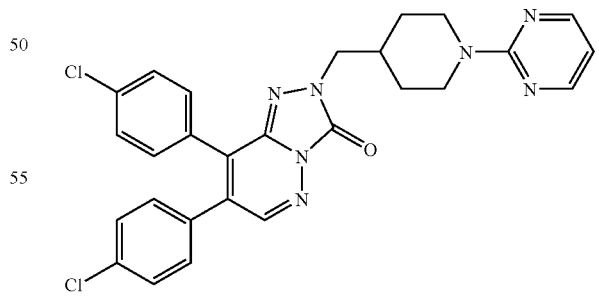

The title compound was prepared using 7,8-bis(4-chlorophenyl)-[1,2,4]triazolo[4,3-b]pyridazin-3(2H)-one, (50 mg, 0.14 mmol), prepared as described in Example 1, Ph$_3$P (110 mg, 0.42 mmol) and (1-(pyrimidin-2-yl)piperdin-4-yl-)methanol (28 mg, 0.14 mmol) in THF (1.0 mL) and by following the procedure described in Example 2. The title compound, 7,8-bis(4-chlorophenyl)-2-((1-(pyrimidin-2-yl)

piperidin-4-yl)methyl)-[1,2,4]triazolo[4,3-b]pyridazin-3 (2H)-one, (31 mg, 42%) was obtained as yellow powder. MS M+H=532; ¹H NMR (CDCl₃) δ 8.28 (2H, d, J=5.0 Hz), 8.16 (1H, s), 7.28-7.36 (6H, m), 7.11 (2H, d, J=10.0 Hz), 6.44 (1H, t, J=5.0 Hz), 4.75 (2H, d, J=15.0 Hz), 3.96 (2H, d, J=10.0 Hz), 2.85 (2H, m), 2.20-2.30 (1H, m), 1.74 (2H, d, J=10.0 Hz), 1.30-1.40 (2H, m).

Example 5

Preparation of (R)-7,8-bis(4-chlorophenyl)-2-((5-oxopyrrolidin-2-yl)methyl)-[1,2,4]triazolo[4,3-b]pyridazin-3(2H)-one

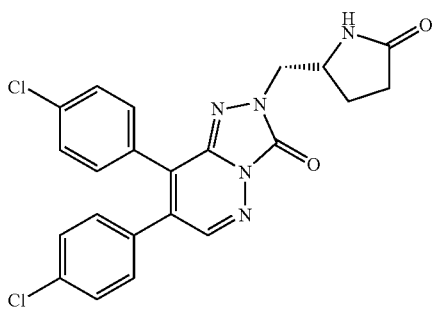

The title compound was prepared using 7,8-bis(4-chlorophenyl)-[1,2,4]triazolo[4,3-b]pyridazin-3(2H)-one, (50 mg, 0.14 mmol), prepared as described in Example 1, Ph₃P (110 mg, 0.42 mmol) and (R)-5-(hydroxymethyl)pyrrolidin-2-one (17 mg, 0.14 mmol) in THF (1.0 mL) and by following the procedure described in Example 2. The title compound, (R)-7,8-bis(4-chlorophenyl)-2-((5-oxopyrrolidin-2-yl)methyl)-[1,2,4]triazolo[4,3-b]pyridazin-3(2H)-one, (38.5 mg, 85%) was obtained as yellow powder. MS M+H=454; ¹H NMR (CDCl₃) δ 8.15 (1H, s), 7.24-7.36 (6H, m), 7.09 (2H, d, J=10.0 Hz), 6.59 (1H, s), 4.17-4.20 (1H, m), 4.03-4.10 (2H, m), 2.25-2.35 (3H, m), 1.92-2.02 (1H, m).

Example 6

Preparation of (R)-2-((1-Benzylpyrrolidin-2-yl)methyl)-7,8-bis(4-chlorophenyl)-[1,2,4]triazolo[4,3-b]pyridazin-3(2H)-one

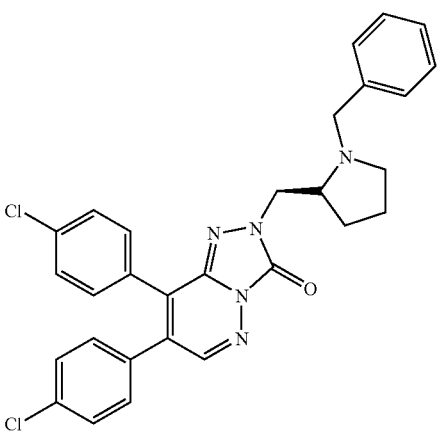

The title compound was prepared using 7,8-bis(4-chlorophenyl)-[1,2,4]triazolo[4,3-b]pyridazin-3(2H)-one, (50 mg, 0.14 mmol), prepared as described in Example 1, Ph₃P (110 mg, 0.42 mmol) and (S)-1-benzyl-2-pyrrolidinemethanol (27 mg, 0.14 mmol) in THF (1.0 mL) and by following the procedure described in Example 2. The title compound, (R)-2-((1-benzylpyrrolidin-2-yl)methyl)-7,8-bis(4-chlorophenyl)-[1,2,4]triazolo[4,3-b]pyridazin-3(2H)-one, (8 mg, 11%) was obtained as yellow powder. MS M+H=530; ¹H NMR (CDCl₃) δ 8.14 (1H, s), 7.22-7.38 (11H, m), 7.10 (2H, d, J=10.0 Hz), 4.61-4.63 (1H, m), 3.50-3.56 (2H, q, J=13.2 Hz), 3.01 (1H, d, J=10.0 Hz), 2.85 (1H, d, J=10.0 Hz), 2.37-2.42 (1H, t, J=10.7 Hz), 1.99-2.02 (2H, m), 1.82-1.95 (1H, m), 1.70-1.80 (2H, m).

Example 7

Preparation of 7,8-Bis(4-chlorophenyl)-2-((6-morpholinopyridin-3-yl)methyl)-[1,2,4]triazolo[4,3-b]pyridazin-3(2H)-one

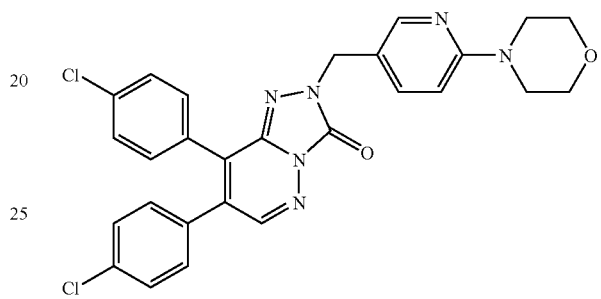

The title compound was prepared using 7,8-bis(4-chlorophenyl)-[1,2,4]triazolo[4,3-b]pyridazin-3(2H)-one, (50 mg, 0.14 mmol), prepared as described in Example 1, Ph₃P (110 mg, 0.42 mmol) and (6-morpholinopyridin-3-yl)methanol (29 mg, 0.14 mmol) in THF (1.0 mL) and by following the procedure described in Example 2. The title compound, 7,8-bis(4-chlorophenyl)-2-((6-morpholinopyridin-3-yl)methyl)-[1,2,4]triazolo[4,3-b]pyridazin-3(2H)-one, (20.5 mg, 11%) was obtained as yellow powder. MS M+H=533; ¹H NMR (CDCl₃) 8.26 δ (1H, d, J=5.0 Hz), 8.15 (1H, s), 7.65 (1H, d, J=5.0 Hz), 7.25-7.36 (6H, m), 7.09 (2H, d, J=10.0 Hz), 6.60 (1H, d, J=10.0 Hz), 5.10 (2H, s), 3.80 (4H, t, J=5.0 Hz), 3.50 (4H, t, J=5.0 Hz).

Example 8

Preparation of 7,8-bis(4-chlorophenyl)-2-(pyridine-N-oxide-4-ylmethyl)-[1,2,4]triazolo[4,3-b]pyridazin-3(2H)-one

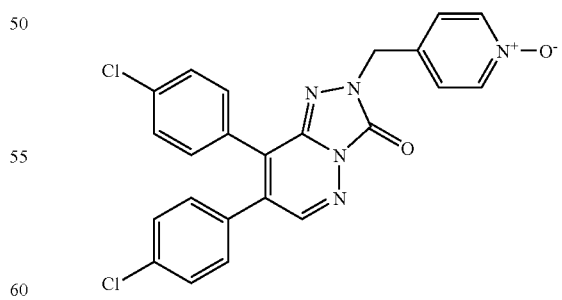

The title compound was prepared using 7,8-bis(4-chlorophenyl)-[1,2,4]triazolo[4,3-b]pyridazin-3(2H)-one, (40 mg, 0.11 mmol), prepared as described in Example 1, Ph₃P (32 mg, 0.12 mmol) and 4-pyridyl carbinol-N-oxide (15 mg, 0.12 mmol) in THF (1.0 mL) and by following the procedure described in Example 2. The title compound, 7,8-bis(4- chlorophenyl)-2-(pyridine-N-oxide-4-ylmethyl)-[1,2,4]triazolo[4,3-b]pyridazin-3(2H)-one (14 mg, 27%) was obtained as yellow solid. MS M+H=464; ¹H NMR (CDCl₃) δ 8.20 (1H, s), 8.15 (2H, d, J=5.0 Hz), 7.28-7.36 (6H, m), 7.25 (2H, d, J=5.0 Hz), 7.10 (2H, d, J=5.0 Hz), 5.16 (2H, s).

Example 9

Preparation of 7,8-Bis(4-chlorophenyl)-2-(2-morpholinoethyl)-[1,2,4]triazolo[4,3-b]pyridazin-3(2H)-one

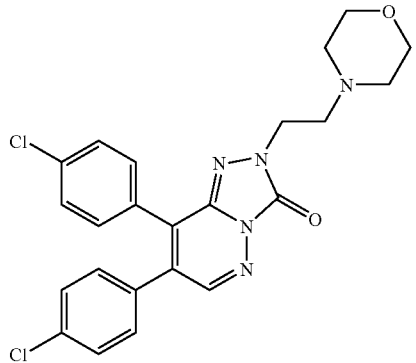

To 7,8-bis(4-chlorophenyl)-[1,2,4]triazolo[4,3-b]pyridazin-3(2H)-one, (40 mg, 0.11 mmol), prepared as described in Example 1, in DMF (1 mL) was added Cs₂CO₃ (110 mg, 0.33 mmol) and 4-(2-chloroethyl)morpholine hydrochloride (31 mg, 0.166 mmol). The reaction mixture was stirred at 70° C. for 30 min under argon. After this time, the reaction mixture was diluted with water (5 mL). The resulting solution was extracted with EtOAc (3×5 mL). The combined organic layers were washed with water (2×5 mL) and saturated aqueous sodium chloride (2×5 mL). The organic layer was concentrated. The resultant crude material was purified by preparative HPLC to give the title compound, 7,8-bis(4-chlorophenyl)-2-(2-morpholinoethyl)-[1,2,4]triazolo[4,3-b]pyridazin-3(2H)-one (35 mg, 67%) as yellow solid. MS M+H=470; ¹H NMR (CDCl₃) δ 8.17 (1H, s), 7.28-7.34 (6H, m), 7.10 (2H, d, J=10.0 Hz), 4.44 (4H, t, J=5.0 Hz), 3.96-4.01 (4H), 3.50 (4H, t, J=5.0 Hz).

Example 10

Preparation of 7,8-bis(4-chlorophenyl)-2-cyclohexyl-[1,2,4]triazolo[4,3-b]pyridazin-3(2H)-one

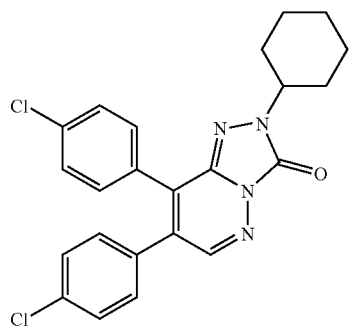

The title compound was prepared using 7,8-bis(4-chlorophenyl)-[1,2,4]triazolo[4,3-b]pyridazin-3(2H)-one, (40 mg, 0.11 mmol), prepared as described in Example 1, Cs₂CO₃ (44 mg, 0.135 mmol), bromoclohexane (100 mg, 0.61 mmol) in DMF (1 mL) and by following the procedure described in Example 9. The title compound, 7,8-bis(4-chlorophenyl)-2-cyclohexyl-[1,2,4]triazolo[4,3-b]pyridazin-3(2H)-one (26 mg, 54%) was obtained as yellow lyophilate. MS M+H=439; ¹H NMR (CDCl₃) δ 8.17 (1H, s), 7.30-7.38 (6H, m), 7.11 (2H, d, J=5.0 Hz), 4.38-4.41 (1H, m), 1.75-2.0 (6H, m), 1.65-1.75 (1H, m), 1.35-1.50 (2H, m), 1.1-1.30 (1H, m).

Example 11

Preparation of 2,7,8-tris(4-chlorophenyl)-[1,2,4]triazolo[4,3-b]pyridazin-3(2H)-one

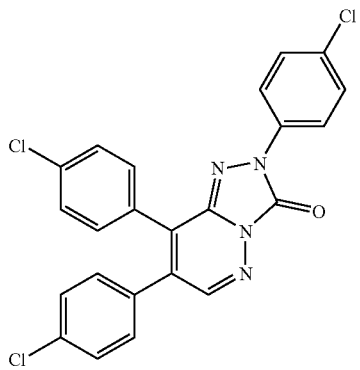

To a solution of 7,8-bis(4-chlorophenyl)-[1,2,4]triazolo[4,3-b]pyridazin-3(2H)-one, (50 mg, 0.14 mmol), prepared as described in Example 1 and 4-chlorophenyboronic acid (44 mg, 0.28 mmol) in pyridine (1.5 mL) was added copper (II) acetate (51 mg, 0.28 mmol) followed by triethylamine (0.04 mL, 0.28 mmol) and 3 Å molecular sieves (100 mg) under argon. The reaction mixture was stirred at reflux for 6 h. After this time, the reaction mixture was cooled to RT and diluted with water (5 mL). The resultant mixture was extracted with EtOAc (3×5 mL). The combined organic layers were washed with water (2×5 mL) and saturated aqueous NaCl (2×5 mL). The organic layer was dried over MgSO₄, filtered and concentrated to obtain a crude product. The crude product was purified by preparative HPLC to give 2,7,8-tris(4-chlorophenyl)-[1,2,4]triazolo[4,3-b]pyridazin-3(2H)-one (5 mg, 8%) as yellow lyophilate. HPLC: 4.35 min; M+H=467; ¹H NMR (CDCl₃) δ 8.22 (1H, s), 8.10 (2H, d, J=10.0 Hz), 7.43 (2H, d, J=10.0 Hz), 7.35-7.38 (6H, m), 7.15 (2H, d, J=10.0 Hz).

Example 12

Preparation of 7,8-Bis(4-chlorophenyl)-2-(3-phenylpropyl)-[1,2,4]triazolo[4,3-b]pyridazin-3(2H)-one

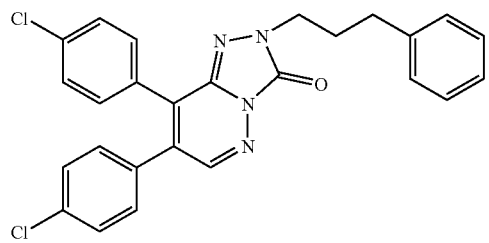

To a tetrahydrofuran solution (2 ml) of 7,8-bis(4-chlorophenyl)-[1,2,4]triazolo[4,3-b]pyridazin-3(2H)-one, (40 mg, 0.11 mmol), prepared as described in Example 1,3- phenylpropan-1-ol (0.018 ml, 0.13 mmol), and triphenylphosphine (86 mg, 0.32 mmol) was added diethyl azodicarboxylate (0.15 ml, 0.38 mmol). After 1 h, the solution was concentrated. The crude material was purified by preparative HPLC to give the title compound, 7,8-bis(4-chlorophenyl)-2-(3-phenylpropyl)-[1,2,4]triazolo[4,3-b]pyridazin-3(2H)-one (17.9 mg, 34%) as a yellow solid. MS M+H=475; $^1$H NMR (CDCl$_3$) 8.18 (1H, s), 7.3-7.1 (13H, m), 4.13 (2H), 2.70 (2H), 2.21 (2H).

Example 13

Preparation of 2-(4-Fluorophenethyl)-7,8-bis(4-chlorophenyl)-[1,2,4]triazolo[4,3-b]pyridazin-3(2H)-one

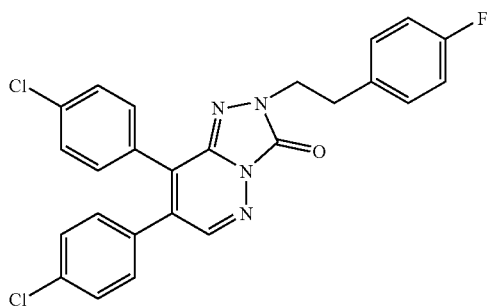

A solution of 7,8-bis(4-chlorophenyl)-[1,2,4]triazolo[4,3-b]pyridazin-3(2H)-one, (40 mg, 0.11 mmol), prepared as described in Example 1,2-(4-fluorophenyl)ethyl bromide (22 mg), and K$_2$CO$_3$ (35 mg, 0.25 mmol) in DMF (1 ml), was heated at 70° C. for 6 hours. After this time, the reaction mixture was cool to RT and diluted with ethyl acetate. The resultant mixture was washed with water. The organic layer was dried over Na$_2$SO$_4$, filtered and concentrated. The crude product was purified using reverse phase preparative HPLC to give the title compound, 2-(4-fluorophenethyl)-7,8-bis(4-chlorophenyl)-[1,2,4]triazolo[4,3-b]pyridazin-3(2H)-one (21.2 mg, 40%) as a yellow foam. MS M+H=479; $^1$H NMR (CDCl$_3$) δ 8.18 (1H), 7.35 (4H), 7.26 (4H), 7.12 (2H), 6.95 (2H), 4.29 (2H), 3.13 (2H).

Example 14

Preparation of 7,8-Bis(4-chlorophenyl)-2-(2-hydroxycyclohexyl)-[1,2,4]triazolo[4,3-b]pyridazin-3(2H)-one

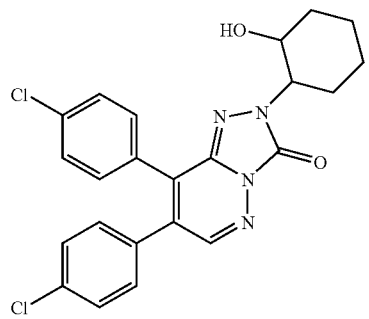

A solution of 7,8-bis(4-chlorophenyl)-[1,2,4]triazolo[4,3-b]pyridazin-3(2H)-one, (40 mg, 0.11 mmol), prepared as described in Example 1, cyclohexene oxide (12 mg, 0.12 mmol) and K$_2$CO$_3$ (35 mg, 0.25 mmol) in DMF (1 ml), was heated at 100° C. for 3 hours. After this time the solution was cool to RT and diluted with ethyl acetate. The resultant solution was washed with water. The organic layer was dried over Na$_2$SO$_4$, filtered and concentrated. The crude product was purified by preparative HPLC to give the title compound, 7,8-bis(4-chlorophenyl)-2-(2-hydroxycyclohexyl)-[1,2,4]triazolo[4,3-b]pyridazin-3(2H)-(24.1 mg, 48%) as yellow solid. MS M+H=455; $^1$H NMR (CDCl$_3$) δ 8.17 (1H), 7.33 (6H), 7.08 (2H), 4.26 (1H), 3.98 (1H), 2.17 (1H), 1.99 (1H), 1.82 (3H), 1.50-1.30 (3H).

Example 15

Preparation of 2-((1-Benzylpiperidin-4-yl)methyl)-7,8-bis(4-chlorophenyl)-[1,2,4]triazolo[4,3-b]pyridazin-3(2H)-one

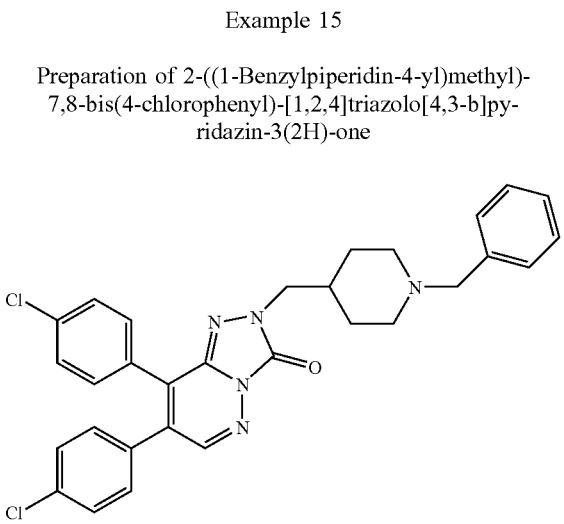

To a THF solution (2 ml) of 7,8-bis(4-chlorophenyl)-[1,2,4]triazolo[4,3-b]pyridazin-3(2H)-one, (40 mg, 0.11 mmol), prepared as described in Example 1, (1-benzyl-4-piperidyl)methanol (27 mg 0.13 mmol), and triphenylphospine (86 mg, 0.32 mmol) was added diethyl azodicarboxylate (0.15 ml, 0.38 mmol). After 1 hour, the reaction mixture was concentrated. The crude material was purified by preparative HPLC to give the title compound, 2-((1-benzylpiperidin-4-yl)methyl)-7,8-bis(4-chlorophenyl)-[1,2,4]triazolo[4,3-b]pyridazin-3(2H)-one (6.1 mg, 10%) as a yellow solid. MS M+H=544; $^1$HNMR (CDCl$_3$) δ 8.19 (1H), 7.42 (2H), 7.32-7.20 (9H), 7.11 (2H), 4.19 (1H), 4.02 (2H), 3.66 (2H), 2.63 (2H), 2.12 (2H), 1.91 (4H).

Example 16

Preparation of 2-(7,8-Bis(4-chlorophenyl)-3-oxo-[1,2,4]triazolo[4,3-b]pyridazin-2(3H)-yl)-N,4-dimethylpentanamide

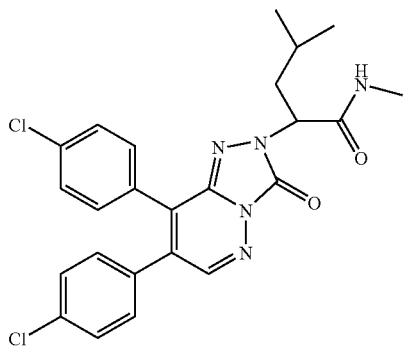

16A Preparation of 2-bromo-N,4-dimethylpentanamide

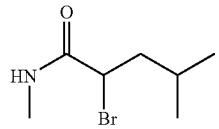

To the solution of DL-alpha-bromoisocaproic acid in THF (4 ml) was added N-methylmorphine (0.18 ml, 1.63 mmol), followed by dropwise addition of isobutylchloroformate (0.15 ml, 1.16 mmol). A white solid precipitate was formed. After stirring at RT for 1.5 h, the white solid was filtered. Methylamine (1 ml, 2N in THF) was added to the filtrate. The reaction mixture was concentrated after 0.5 hour. The resultant crude material was diluted with ethyl acetate and washed with water. The organic layer was dried over $Na_2SO_4$ and concentrated to give the title compound, 2-bromo-N,4-dimethylpentanamide, (0.18 g, 78%) as an oil.

16B. Preparation of 2-(7,8-Bis(4-chlorophenyl)-3-oxo-[1,2,4]triazolo[4,3-b]pyridazin-2(3H)-yl)-N,4-dimethylpentanamide

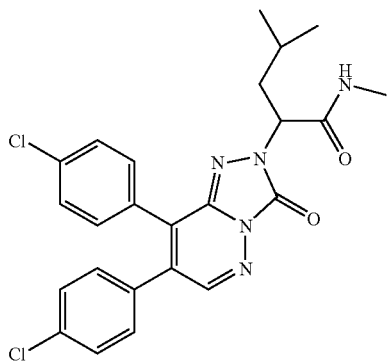

A solution of 7,8-bis(4-chlorophenyl)-[1,2,4]triazolo[4,3-b]pyridazin-3(2H)-one, (40 mg, 0.11 mmol), prepared as described in Example 1,2-bromo-N,4-dimethylpentanamide (25 mg) and $K_2CO_3$ (31 mg, 0.22 mmol) in DMF (2 ml), was heated at 85° C. for 1.5 hours. After this time, the reaction mixture was cooled to RT and diluted with ethyl acetate. The resultant solution was washed with water. The organic layer was dried over $Na_2SO_4$, filtered and concentrated. The crude product was purified using reverse phase preparative HPLC to give the title compound, 2-(7,8-bis(4-chlorophenyl)-3-oxo-[1,2,4]triazolo[4,3-b]pyridazin-2(3H)-yl)-N,4-dimethylpentanamide (28 mg, 40%) as a yellow solid. MS M+H=484; $^1$H NMR ($CDCl_3$) δ 8.23 (1H), 7.36-7.30 (6H), 7.12 (2H), 6.90 (1H), 5.13 (1H), 2.81 (3H), 2.22 (1H), 1.98 (1H), 1.42 (1H), 0.93 (6H).

Example 17

Preparation of 2-(4-(Trifluoromethyl)benzyl)-7,8-bis(4-chlorophenyl)-[1,2,4]triazolo[4,3-b]pyridazin-3(2H)-one

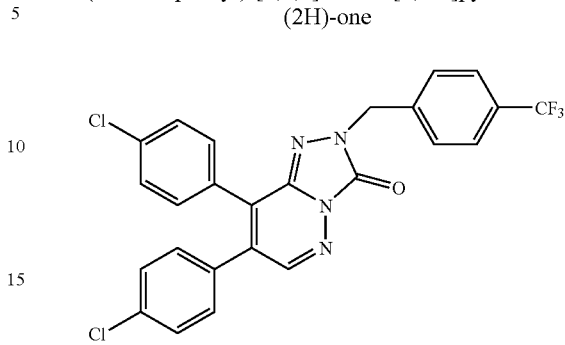

A solution of 7,8-bis(4-chlorophenyl)-[1,2,4]triazolo[4,3-b]pyridazin-3(2H)-one, (300 mg, 0.84 mmol), prepared as described in Example 1, 4-(trifluoromethyl)benzyl bromide (200 mg, 0.84 mmol) and $K_2CO_3$ (290 mg, 2.1 mmol) in DMF (10 ml), was heated at 90° C. for 2 hours. After this time, the reaction mixture was cooled to RT and diluted with ethyl acetate. The resultant solution was then washed with water. The organic layer was dried over $Na_2SO_4$, filtered and concentrated. The crude material was purified by preparative HPLC to give the title compound, 2-(4-(trifluoromethyl)benzyl)-7,8-bis(4-chlorophenyl)-[1,2,4]triazolo[4,3-b]pyridazin-3(2H)-one (120 mg, 28%) as a yellow solid. MS M+H=515; $^1$H NMR ($CDCl_3$) δ 8.19 (1H), 7.60 (2H), 7.50 (2H), 7.34 (4H), 7.28 (2H), 7.10 (2H), 5.27 (2H).

Example 18

Preparation of 2-(2-(4-Chlorophenoxy)ethyl)-7,8-bis(4-chlorophenyl)-[1,2,4]triazolo[4,3-b]pyridazin-3(2H)-one

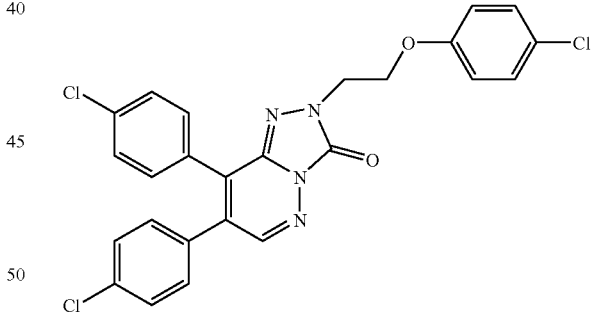

The solution of 7,8-bis(4-chlorophenyl)-[1,2,4]triazolo[4,3-b]pyridazin-3(2H)-one, (30 mg, 0.084 mmol), prepared as described in Example 1,1-(2-bromoethoxy)-4-chlorobenzene (22 mg, 0.094 mmol) and $K_2CO_3$ (18 mg, 0.013 mmol) in DMF (1 ml) was heated at 70° C. for 4 hours. After this time, the solution was cool to RT and diluted with ethyl acetate. The resultant solution was then washed with water. The organic layer was dried over $Na_2SO_4$, filtered and concentrated. The crude material was purified by preparative HPLC to give the title compound, 2-(2-(4-chlorophenoxy)ethyl)-7,8-bis(4-chlorophenyl)-[1,2,4]triazolo[4,3-b]pyridazin-3(2H)-one, (25.5 mg, 59%) was obtained as a yellow solid. MS M+H=511; $^1$H NMR ($CDCl_3$) δ 8.19 (1H), 7.34 (4H), 7.28 (2H), 7.18 (2H), 7.28 (2H), 6.80 (2H), 4.44 (2H), 4.36 (2H).

Example 19

Preparation of 7,8-Bis(4-chlorophenyl)-2-(2-(phenylamino)ethyl)-[1,2,4]triazolo[4,3-b]pyridazin-3(2H)-one

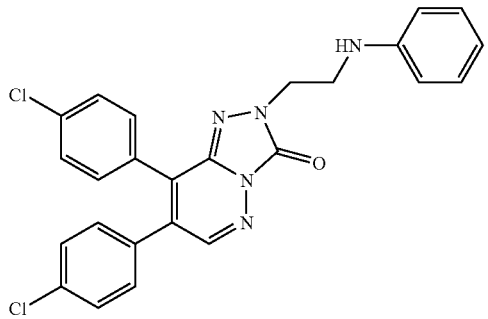

To a THF solution (2 ml) of 7,8-bis(4-chlorophenyl)-[1,2,4]triazolo[4,3-b]pyridazin-3(2H)-one, (50 mg, 0.14 mmol), prepared as described in Example 1, 2-(phenylamino)ethanol (19 mg, 0.13 mmol), triphenylphosphine (55 mg, 0.21 mmol) was added diethyl azodicarboxylate (0.09 ml, 42% wt in toluene, 0.21 mmol). After 1 h, the reaction mixture was concentrated. The crude material was purified by preparative HPLC to give the title compound, 7,8-bis(4-chlorophenyl)-2-(2-(phenylamino)ethyl)-[1,2,4]triazolo[4,3-b]pyridazin-3(2H)-one (14.4 mg, 23%) as a yellow solid. MS M+H=476; $^1$H NMR (CDCl$_3$) δ 8.20 (1H), 7.41-7.20 (11H), 7.10 (2H), 4.51 (2H), 3.91 (2H).

Example 20

Preparation of 2-(7,8-Bis(4-chlorophenyl)-3-oxo-[1,2,4]triazolo[4,3-b]pyridazin-2(3H)-yl)-N-(4-(trifluoromethyl)phenyl)acetamide

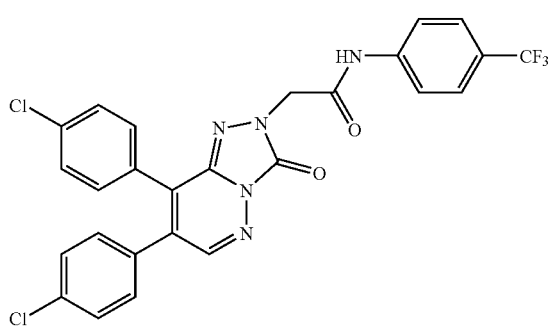

A solution of 7,8-bis(4-chlorophenyl)-[1,2,4]triazolo[4,3-b]pyridazin-3(2H)-one, (30 mg, 0.084 mmol), prepared as described in Example 1, 2-chloro-N-(4-(trifluoromethyl)phenyl)acetamide (22 mg, 0.092 mmol), K$_2$CO$_3$ (35 mg, 0.25 mmol) in DMF (1 ml), was heated at 80° C. for 1 hour. After this time, the solution was cooled to RT and diluted with ethyl acetate. The resultant solution was then washed with water. The organic layer was dried over Na$_2$SO$_4$, filtered and concentrated. The crude material was purified by preparative HPLC to give the title compound, 2-(7,8-bis(4-chlorophenyl)-3-oxo-[1,2,4]triazolo[4,3-b]pyridazin-2(3H)-yl)-N-(4-(trifluoromethyl)phenyl)acetamide (38 mg, 81%) as a yellow solid. MS M+H=558; $^1$H NMR (CDCl$_3$) δ 8.26 (1H), 7.60 (2H), 7.38-7.20 (8H), 7.11 (2H), 5.07 (2H).

Example 21

Preparation of 2-(2-Aminoethyl)-7,8-bis(4-chlorophenyl)-[1,2,4]triazolo[4,3-b]pyridazin-3(2H)-one

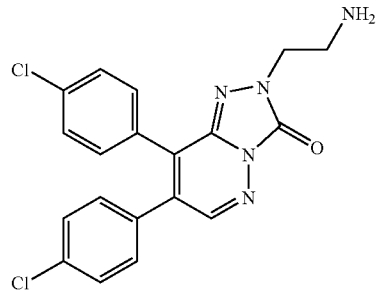

21A. Preparation of 2-(2-(7,8-Bis(4-chlorophenyl)-3-oxo-[1,2,4]triazolo[4,3-b]pyridazin-2(3H)-yl)ethyl)isoindoline-1,3-dione

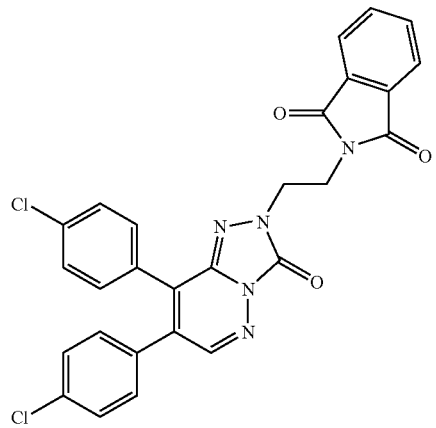

A solution of 7,8-bis(4-chlorophenyl)-[1,2,4]triazolo[4,3-b]pyridazin-3(2H)-one, (290 mg, 0.81 mmol), prepared as described in Example 1, N-(2-bromoethyl)phthalimide (215 mg, 0.84 mmol) and K$_2$CO$_3$ (337 mg, 2.44 mmol) in DMF (3 ml), was heated at 80° C. for 2.5 hours. After this time, the reaction mixture was cooled to RT and diluted with ethyl acetate. The resultant solution was then washed with water. The organic layer was dried over Na$_2$SO$_4$, filtered and concentrated. The crude material was purified using silica gel column chromatography using an automated system eluting with a 1:1 mixture of ethyl acetate:hexane to give the title compound, 2-(2-(7,8-bis(4-chlorophenyl)-3-oxo-[1,2,4]triazolo[4,3-b]pyridazin-2(3H)-yl)ethyl)isoindoline-1,3-dione as a yellow solid (290 mg, 68%). MS M+H=530.

21B. Preparation of 2-(2-Aminoethyl)-7,8-bis(4-chlorophenyl)-[1,2,4]triazolo[4,3-b]pyridazin-3(2H)-one

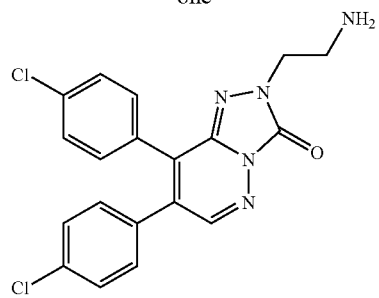

2-(2-(7,8-Bis(4-chlorophenyl)-3-oxo-[1,2,4]triazolo[4,3-b]pyridazin-2(3H)-yl)ethyl)isoindoline-1,3-dione (180 mg, 0.34 mmol) was reacted with hyrazine hydrate (0.9 ml, 18.5 mmol) in ethanol (10 ml) and stirred overnight. After this time, the reaction mixture was diluted with ethyl acetate and washed with saturated aqueous NaCl. The organic layer was dried over $Na_2SO_4$, filtered and concentrated. The crude material was purified by preparative HPLC to give the title compound, 2-(2-aminoethyl)-7,8-bis(4-chlorophenyl)-[1,2,4]triazolo[4,3-b]pyridazin-3(2H)-one (22 mg, 13%) as a yellow foam. MS M+H=400; $^1$H NMR (CDCl$_3$) δ 8.12 (broad, 2H), 7.38-7.15 (6H), 7.05 (2H), 4.45 (2H), 3.59 (2H).

Example 22

Preparation of (R)-7,8-Bis(4-chlorophenyl)-2-(2-(3-chlorophenyl)-2-hydroxyethyl)-[1,2,4]triazolo[4,3-b]pyridazin-3(2H)-one

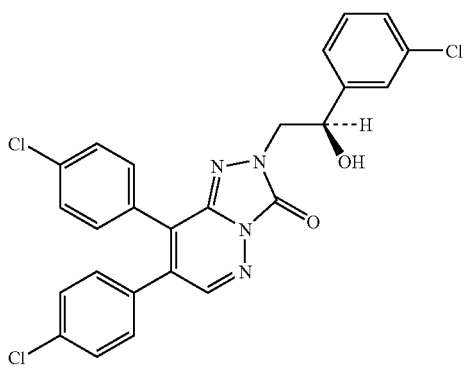

To a stirred solution of 7,8-bis(4-chlorophenyl)-[1,2,4]triazolo[4,3-b]pyridazin-3(2H)-one, (20 mg, 0.06 mmol) prepared as described in Example 1, in 0.25 mL of DMF was added R-(+)-3-chlorostyrene oxide (0.007 mL, 0.06 mmol) and 15 mg of $K_2CO_3$. The resulting red solution was heated to 60° C. for 19 h and, upon cooling to RT, the mixture was diluted with 5 mL of ethyl acetate and 5 mL of 1N HCl. The layers were separated, and the organic layer was washed with 5 mL of saturated aqueous NaCl. The organic layer was dried over $MgSO_4$, filtered and evaporated to give a yellow oil. The material was purified using reverse-phase HPLC to give the title compound, (R)-7,8-bis(4-chlorophenyl)-2-(2-(3-chlorophenyl)-2-hydroxyethyl)-[1,2,4]triazolo[4,3-b]pyridazin-3(2H)-one, (15 mg, 52% yield) as a yellow solid. HRMS Anal. Calc'd for $C_{25}H_{17}Cl_3N_4O_2$, 510.04, [M+H]+ =511.0509 observed. $^1$H NMR (400 MHz, CDCl$_3$) δ 8.01 (s, 1H), 7.16 (s, 1H), 7.15-7.05 (m, 9H), 6.92 (d, 2H, J=8.6 Hz), 5.05-4.95 (m, 1H), 4.13-4.08 (m, 2H), 1.55 (br s, 1H).

Example 23

Preparation of 7,8-Bis(4-chlorophenyl)-2-(2-hydroxy-3-phenylpropyl)-[1,2,4]triazolo[4,3-b]pyridazin-3(2H)-one

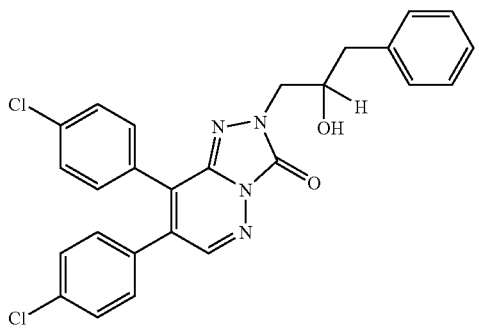

To a stirred solution of 7,8-bis(4-chlorophenyl)-[1,2,4]triazolo[4,3-b]pyridazin-3(2H)-one, (500 mg, 1.4 mmol), prepared as described in Example 1, in 7 mL of DMF was added 2,3-epoxypropylbenzene (0.18 mL, 1.4 mmol) and 0.39 g of $K_2CO_3$. The resulting red solution was heated to 85° C. for 27 h and, upon cooling to room temp, the mixture was diluted with 200 mL of ethyl acetate and 200 mL of 1N HCL. The layers were extracted, and the organic layer was washed with 200 mL of saturated aqueous NaCl. The organic layer was dried over $MgSO_4$, filtered and evaporated to a yellow oil. The material was purified by silica gel column chromatography using a gradient of 0-100% ethyl acetate/hexanes to give 484 mg of racemic 7,8-bis(4-chlorophenyl)-2-(2-hydroxy-3-phenylpropyl)-[1,2,4]triazolo[4,3-b]pyridazin-3(2H)-one as a yellow solid containing 15% starting material 7,8-bis(4-chlorophenyl)-[1,2,4]triazolo[4,3-b]pyridazin-3(2H)-one. Separation of enantiomers was performed on 200 mg of material using Chiracel OD 5 cm×50 cm 20 micron column, flow rate 50 mL/min isocratic 65% heptane/17.5% ethanol/17.5% methanol, monochrome detection at 220 nm. Fraction A was collected at 49 min post injection to give 47 mg of 7,8-bis(4-chlorophenyl)-[1,2,4]triazolo[4,3-b]pyridazin-3(2H)-one enantiomer A as a yellow solid; Fraction B was collected at 55 min post injection to give 45 mg of 7,8-bis(4-chlorophenyl)-[1,2,4]triazolo[4,3-b]pyridazin-3(2H)-one enantiomer B as a yellow solid.

enantiomer A of 7,8-bis(4-chlorophenyl)-[1,2,4]triazolo[4,3-b]pyridazin-3(2H)-one: HRMS Anal. Calc'd for $C_{26}H_{20}Cl_2N_4O_2$, 490.0963, [M+H] 491.1057 observed; $^1$H NMR (400 MHz, CDCl$_3$) δ 8.18 (s, 1H), 7.33-7.09 (m, 13H), 5.05-4.95 (m, 1H), 4.33-4.30 (m, 1H), 4.20 (dd, 1H, J=3.1, 14.5 Hz), 4.06 (dd, 1H, J=7.9, 14.1 Hz) 2.88 (m, 2H).

enantiomer B of 7,8-bis(4-chlorophenyl)-[1,2,4]triazolo[4,3-b]pyridazin-3(2H)-one: HRMS Anal. Calc'd for $C_{26}H_{20}Cl_2N_4O_2$, 490.0963, [M+H] 491.1042 observed; $^1$H NMR (400 MHz, CDCl$_3$) δ 8.18 (s, 1H), 7.33-7.09 (m, 13H), 5.05-4.95 (m, 1H), 4.33-4.30 (m, 1H), 4.20 (dd, 1H, J=3.1, 14.5 Hz), 4.06 (dd, 1H, J=7.9, 14.1 Hz) 2.88 (m, 2H).

Example 24

Preparation of 7,8-Bis(4-chlorophenyl)-2-(1-phenyl-1H-tetrazol-5-yl)-[1,2,4]triazolo[4,3-b]pyridazin-3(2H)-one

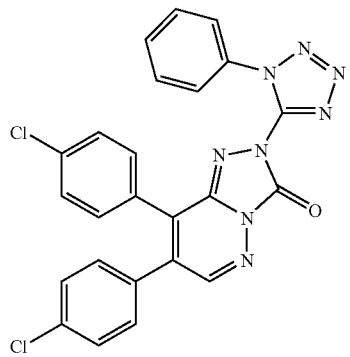

To a stirred solution of 7,8-bis(4-chlorophenyl)-[1,2,4]triazolo[4,3-b]pyridazin-3(2H)-one, (50 mg, 0.14 mmol), prepared as described in Example 1, in 0.7 mL of DMF was added N-phenyl-5-chlorotetrazole (25 mg, 0.14 mmol) and 19 mg of $K_2CO_3$. The resulting red solution was heated at 80° C. for 4 days and, upon cooling to room temp, the mixture was diluted with 50 mL of ethyl acetate and 50 mL of 1N HCl. The layers were extracted, and the organic layer was washed with 50 mL of saturated aqueous NaCl. The organic layer was dried over $MgSO_4$, filtered and evaporated to an orange solid. The material was purified via silica gel column chromatography followed by reverse phase HPLC to give the title compound, 7,8-bis(4-chlorophenyl)-2-(1-phenyl-1H-tetrazol-5-yl)-[1,2,4]triazolo[4,3-b]pyridazin-3(2H)-one, (7 mg, 10%) yield as a yellow solid. LCMS Anal. Calc'd for $C_{24}H_{14}Cl_2N_8O$, 500.07, [M+H] 501 observed; $^1H$ NMR (400 MHz, $CD_3CN$) δ 8.30 (s, 1H), 7.69-7.55 (m, 5H), 7.39 (dt, 2H, J=2.1, 6.6 Hz), 7.28 (dt, 2H, J=1.9, 8.6 Hz), 7.23 (dt, 2H, J=2.2, 8.6 Hz), 7.06 (dt, 2H, J=2.1, 8.7 Hz).

Example 25

Preparation of 2-(2-Hydroxybenzyl)-7,8-bis(4-chlorophenyl)-[1,2,4]triazolo[4,3-b]pyridazin-3(2H)-one

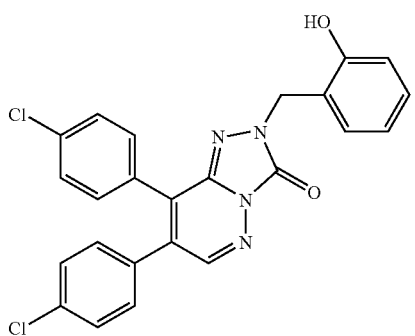

25A. Preparation of 2-((7,8-Bis(4-chlorophenyl)-3-oxo-[1,2,4]triazolo[4,3-b]pyridazin-2(3H)-yl)methyl)phenyl Acetate

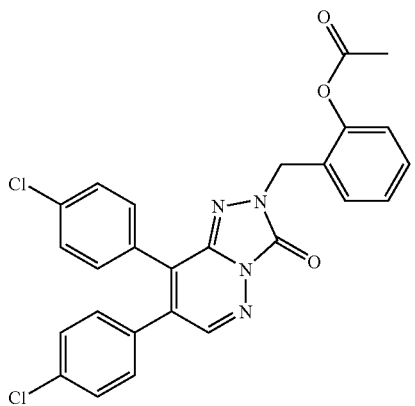

To a solution of the 7,8-bis(4-chlorophenyl)-[1,2,4]triazolo[4,3-b]pyridazin-3(2H)-one, (800 mg, 2.24 mmol), prepared as described in Example 1, in 30 mL of DMF was added 2-(chloromethyl)phenyl acetate (497 mg, 2.69 mmol), followed by $K_2CO_3$ (619 mg, 4.48 mmol). The reaction was heated at 60° C. for overnight. After this time, the reaction was allowed to cool to RT and then was diluted with 250 mL of EtOAc. The resultant solution was washed with saturated aqueous NaCl (100 mL×3). The organic layer was dried over $MgSO_4$, filtered, evaporated under reduced pressure to provide the title compound, 2-((7,8-bis(4-chlorophenyl)-3-oxo-[1,2,4]triazolo[4,3-b]pyridazin-2(3H)-yl)methyl)phenyl acetate, (1.13 gm) as a yellow solid.

25B. Preparation of 2-(2-Hydroxybenzyl)-7,8-bis(4-chlorophenyl)-[1,2,4]triazolo[4,3-b]pyridazin-3(2H)-one

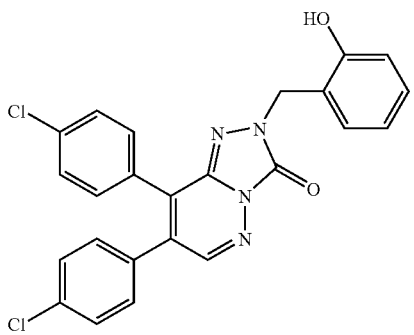

2-((7,8-Bis(4-chlorophenyl)-3-oxo-[1,2,4]triazolo[4,3-b]pyridazin-2(3H)-yl)methyl)phenyl acetate, prepared as described in 25A, (1.13 g), was dissolved in 25 mL of $CH_3OH$. A solution of $NaOCH_3$ (121 mg, 2.24 mmol) in a small amount of $CH_3OH$ (2 mL) was added to the reaction, and then, the reaction was stirred overnight. After this time, 0.3 mL of acetic acid was added to the reaction. The reaction was stirred for an additional 10 min, and then the resultant solution was concentrated under reduced pressure. The crude residue was purified using silica gel column chromatography using an automated system, eluting with a gradient of 0% to 60% EtOAc/hexanes for 30 min followed by 60% EtOAc/hexanes for an additional 15 min. The title compound, 2-(2-hydroxybenzyl)-7,8-bis(4-chlorophenyl)-[1,2,4]triazolo[4,3-b]pyridazin-3(2H)-one (818 mg, 79% yield) was obtained as yellow solid. MS [M+H]$^+$=463; $^1H$ NMR ($CDCl_3$, 400 MHz) δ 8.54 (s, 1H), 8.14 (s, 1H), 7.32-7.17 (m, 8H), 7.04-7.00 (m, 2H), 6.94 (dd, 1H), 6.81 (td, 1H), 5.13 (s, 2H).

Example 26

Preparation of 7,8-Bis(4-chlorophenyl)-2-(2-hydroxy-2-methylpropyl)-[1,2,4]triazolo[4,3-b]pyridazin-3(2H)-one

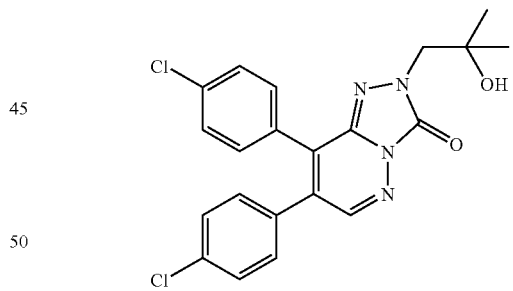

To a solution of 7,8-bis(4-chlorophenyl)-[1,2,4]triazolo[4,3-b]pyridazin-3(2H)-one, (20 mg, 0.056 mmol), prepared as described in Example 1, in 0.6 mL of DMF was added isobutylene oxide (4.0 mg, 0.056 mmol), followed by $K_2CO_3$ (15.5 mg, 0.112 mmol). The mixture was heated to 85° C. After stirring overnight, the reaction was allowed to cool to RT The reaction mixture was filtered (to remove excess of $K_2CO_3$). The collected solution was concentrated under reduced pressure. The crude product was purified by reverse phase HPLC to give the title compound, 7,8-bis(4-chlorophenyl)-2-(2-hydroxy-2-methylpropyl)-[1,2,4]triazolo[4,3-b]pyridazin-3(2H)-one, (18.4 mg, 77% yield) as a yellow oil. MS [M+H]$^+$: found 429; $^1H$ NMR ($CDCl_3$, 400 MHz) δ 8.28 (s, 1H), 7.39-7.27 (m, 6H), 7.16-7.12 (m, 2H), 4.16 (s, 2H), 4.00 (s, 1H), 1.34 (s, 6H).

Example 27

Preparation of (R)-7,8-Bis(4-chlorophenyl)-2-(2-hydroxyhexyl)-[1,2,4]triazolo[4,3-b]pyridazin-3(2H)-one

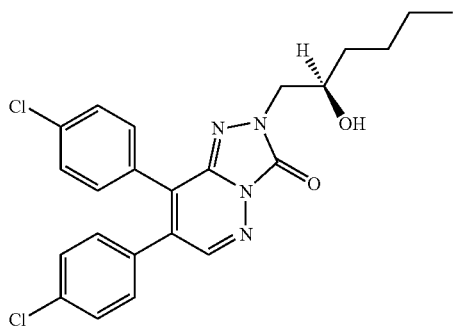

To a solution of 7,8-bis(4-chlorophenyl)-[1,2,4]triazolo[4,3-b]pyridazin-3(2H)-one, (20 mg, 0.056 mmol), prepared as described in Example 1, in 0.6 mL of DMF was added (R)-(+)-1,2-epoxyhexane (5.6 mg, 0.056 mmol), followed by $K_2CO_3$ (15.5 mg, 0.112 mmol). The mixture was heated at 85° C. After stirring overnight, the reaction was allowed to cool to RT The reaction mixture was filtered to remove excess of $K_2CO_3$. The collected solution was concentrated under reduced pressure. The crude product was purified using silica gel column chromatography using an automated system, eluting with a gradient of (0% to 60% EtOAc/hexanes for 30 min followed by 60% EtOAc/hexanes to 100% EtOAc for 10 min. The title compound, (R)-7,8-Bis(4-chlorophenyl)-2-(2-hydroxyhexyl)-[1,2,4]triazolo[4,3-b]pyridazin-3(2H)-one (8.3 mg, 32% yield) was obtained as a yellow oil. MS [M+H]$^+$: found 457; $^1$H NMR (CDCl$_3$, 400 MHz) δ 8.12 (s, 1H), 7.28-7.19 (m, 6H), 7.06-7.02 (m, 2H), 4.13-4.08 (m, 1H), 4.00-3.90 (m, 2H), 1.49-1.24 (m, 6H), 0.83 (t, 3H).

Example 28

Preparation of 3,4-Bis(4-chlorophenyl)-6-(2-hydroxy-3-isobutoxypropyl)imidazo[1,5-b]pyridazin-7(6H)-one

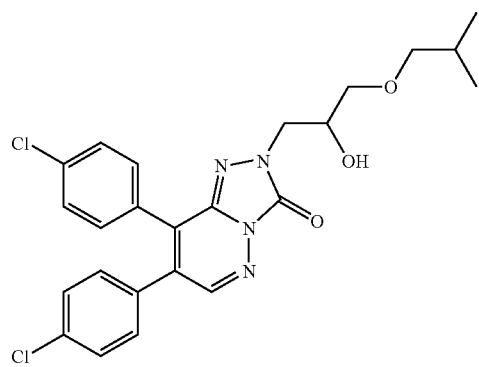

To a solution of 7,8-bis(4-chlorophenyl)-[1,2,4]triazolo[4,3-b]pyridazin-3(2H)-one, (20 mg, 0.056 mmol), prepared as described in Example 1, in 0.6 mL of DMF was added glycidyl isobutyl ether (7.3 mg, 0.056 mmol), followed by $K_2CO_3$ (15.5 mg, 0.112 mmol). The mixture was heated at 85° C. After stirring overnight, the reaction was allowed to cool to RT The reaction mixture was filtered to remove excess of $K_2CO_3$. The collected solution was concentrated under reduced pressure. The crude product was purified using reverse phase HPLC to give the title compound, 3,4-bis(4-chlorophenyl)-6-(2-hydroxy-3-isobutoxypropyl)imidazo[1,5-b]pyridazin-7(6H)-one (17.8 mg, 65% yield) as a yellow solid. in 65% yield. MS [M+H]$^+$: found 487; $^1$H NMR (CDCl$_3$, 400 MHz) δ 8.08 (s, 1H), 7.23-7.15 (m, 6H), 7.00-6.96 (m, 2H), 4.20-4.00 (m, 3H), 3.41 (d, 2H), 3.11 (d, 2H), 1.80-1.65 (m, 1H), 0.76 (d, 6H).

Example 29

Preparation of 7,8-bis(4-chlorophenyl)-2-(3-ethoxy-2-hydroxypropyl)-[1,2,4]triazolo[4,3-b]pyridazin-3(2H)-one

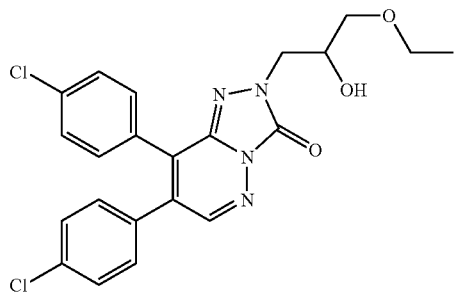

To a solution of 7,8-bis(4-chlorophenyl)-[1,2,4]triazolo[4,3-b]pyridazin-3(2H)-one, (300 mg, 0.84 mmol), prepared as described in Example 1, in 8 mL of DMF was added ethyl glycidyl ether (86 mg, 0.84 mmol), followed by $K_2CO_3$ (232 mg, 1.68 mmol). The mixture was heated at 85° C. After stirring overnight, the reaction was allowed to cool to RT The reaction mixture was diluted with EtOAc (200 mL). The resultant solution was washed with saturated aqueous NaCl (3×40 mL). The organic layer was dried over MgSO$_4$, filtered, and concentrated under reduced pressure. The crude product was purified using silica gel column chromatography using an automated system, eluting with a gradient of 0% to 60% EtOAc/hexanes for 30 min followed by 100% EtOAc for 40 min. The title compound, 7,8-bis(4-chlorophenyl)-2-(3-ethoxy-2-hydroxypropyl)-[1,2,4]triazolo[4,3-b]pyridazin-3(2H)-one, (0.3 gm, 78% yield) as a yellow solid. MS [M+H]$^+$: found 459; $^1$H NMR (CDCl$_3$, 400 MHz) δ 8.20 (s, 1H), 7.34-7.25 (m, 6H), 7.09 (d, 2H), 4.29-4.24 (m, 2H), 4.18-4.13 (m, 1H), 3.57-3.49 (m, 4H), 1.17 (t, 3H).

Example 30

Preparation of 7,8-bis(4-chlorophenyl)-2-(3-ethoxy-2-oxopropyl)-[1,2,4]triazolo[4,3-b]pyridazin-3(2H)-one

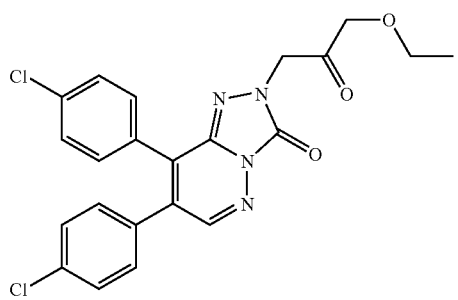

The Dess-Martin reagent (56 mg, 0.131 mmol) was added to a solution of 7,8-bis(4-chlorophenyl)-2-(3-ethoxy-2-hydroxypropyl)-[1,2,4]triazolo[4,3-b]pyridazin-3(2H)-one, prepared as described in Example 29, (50 mg, 0.109 mmol) in 1 mL of CH$_2$Cl$_2$. The reaction was stirred for 2 h., filtered, and concentrated under reduced pressure. The crude material was purified by reverse phase HPLC to give the title compound, 7,8-bis(4-chlorophenyl)-2-(3-ethoxy-2-oxopropyl)-[1,2,4]triazolo[4,3-b]pyridazin-3(2H)-one, (47 mg, 95% yield) as a yellow solid. MS [M+H]$^+$: found 457.

Example 31

Preparation of 7,8-Bis(4-chlorophenyl)-2-(3-ethoxy-2-hydroxy-2-methylpropyl)-[1,2,4]triazolo[4,3-b]pyridazin-3(2H)-one

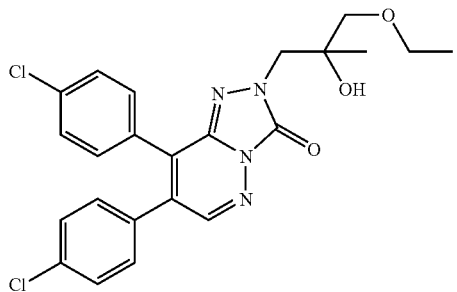

MeMgBr (0.03 mL, 0.08 mmol, 3.0 M in Et$_2$O) was added to a solution of 7,8-bis(4-chlorophenyl)-2-(3-ethoxy-2-oxopropyl)-[1,2,4]triazolo[4,3-b]pyridazin-3(2H)-one, prepared as described in Example 30, (23 mg, 0.05 mmol) at −78° C. The reaction was stirred for 30 min. at −78° C. After this time, saturated aqueous NH$_4$Cl (2 mL) was added to the reaction and the resultant solution was warmed to RT. The layers were separated and the aqueous layer was extracted with EtOAC (3×10 mL). The combined organic layers were dried (MgSO$_4$), filtered, and concentrated. The crude product was purified by reverse phase HPLC to give the title compound, 7,8-bis(4-chlorophenyl)-2-(3-ethoxy-2-hydroxy-2-methylpropyl)-[1,2,4]triazolo[4,3-b]pyridazin-3(2H)-one (4 mg, 16% yield) as a yellow oil. MS [M+H]$^+$: found 473; $^1$H NMR (CDCl$_3$, 400 MHz) δ 8.13 (s, 1H), 7.29-7.18 (m, 6H), 7.06-7.02 (m, 2H), 4.25 (d, 1H), 3.98 (d, 1H), 3.43 (q, 2H), 3.35 (d, 1H), 3.25 (d, 1H), 1.18 (s, 3H), 1.07 (t, 3H).

Example 32

Preparation of 7,8-Bis(4-chlorophenyl)-2-(3-hydroxy-3-methylbutan-2-yl)-[1,2,4]triazolo[4,3-b]pyridazin-3(2H)-one

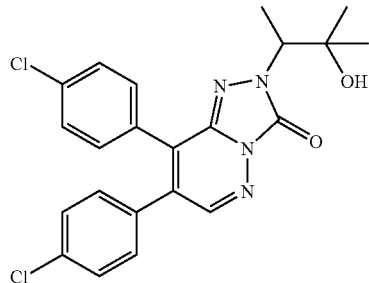

To a solution of 7,8-bis(4-chlorophenyl)-[1,2,4]triazolo[4,3-b]pyridazin-3(2H)-one, (300 mg, 0.84 mmol), prepared as described in Example 1, in 0.6 mL of DMF was added 2,3-epoxy-2-methylbutane (4.8 mg, 0.056 mmol), followed by K$_2$CO$_3$ (15.5 mg, 0.112 mmol). The mixture was heated at 85° C. for 16 h. After this time, an additional 10 mg of K$_2$CO$_3$ and 2,3-epoxy-2-methylbutane (4.8 mg, 0.056 mmol) were added. The reaction was allowed to continue stirring at 85° C. for an additional 48 h. The reaction was cooled to RT and filtered. The collected solution was concentrated under reduced pressure. The residue was purified by reverse phase HPLC to give the title compound, 7,8-bis(4-chlorophenyl)-2-(3-hydroxy-3-methylbutan-2-yl)-[1,2,4]triazolo[4,3-b]pyridazin-3(2H)-one, (5 mg, 20% yield) as a yellow oil. MS [M+H]$^+$: found 443; $^1$H NMR (CDCl$_3$, 400 MHz) δ 8.25 (s, 1H), 7.39-7.27 (m, 6H), 7.14 (dd, 2H), 4.55 (q, 1H), 1.52 (d, 3H), 1.34 (s, 1H), 1.23 (s, 1H).

Example 33

Preparation of 4-((7,8-bis-(4-chlorophenyl)-3-oxo-[1,2,4]triazolo[4,3-b]pyridazin-2(3H)-yl)methyl)benzonitrile

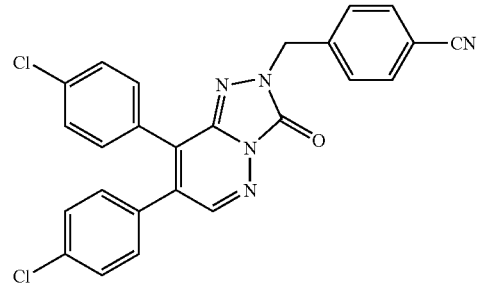

A solution of 7,8-bis(4-chlorophenyl)-[1,2,4]triazolo[4,3-b]pyridazin-3(2H)-one, (192 mg, 0.54 mmol), prepared as described in Example 1, K$_2$CO$_3$ (90 mg), and α-bromo-p-toluonitrile (127 mg, 0.645 mmol) in DMF (2 mL) was heated at 75° C. for 1 h. After this time, the solution was concentrated under redcued pressure. The resulting crude product was purified by reverse phase HPLC to provided the title compound, 4-((7,8-bis-(4-chlorophenyl)-3-oxo-[1,2,4]triazolo[4,3-b]pyridazin-2(3H)-yl)methyl)benzonitrile (80 mg) as a yellow solid. MS M+H=472; $^1$H NMR (CDCl$_3$): δ 8.17 (s, 1H), 7.63 (d, J=8.4 Hz, 2H), 7.49 (d, J=8.3 Hz, 2H), 7.33 (m, 2H), 7.25 (m, 2H), 7.24 (m, 2H), 7.09 (m, 2H), 5.25 (2H).

Examples 34 to 243

The following Examples were prepared according to the procedures given for the preparation of Examples 1-33:

| Example Number | Structure | HPLC Retention Time (min) | Mass Specs Observed (M + H) |
|---|---|---|---|
| 34 | 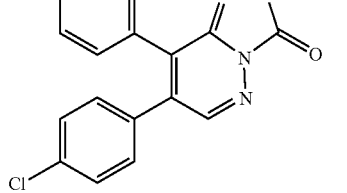 | 3.53 | 396 |
| 35 | 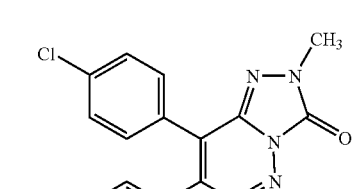 | 3.64 | 371 |
| 36 | 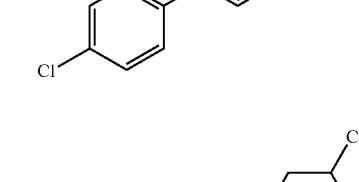 | 4.06 | 413 |
| 37 | 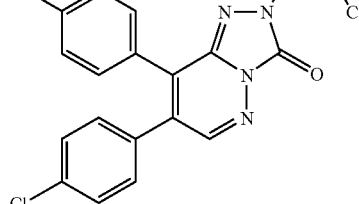 | 4.05 | 465 |
| 38 | 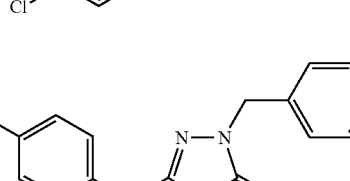 | 4.33 | 453 |

-continued
| Example Number | Structure | HPLC Retention Time (min) | Mass Specs Observed (M + H) |
|---|---|---|---|
| 39 | 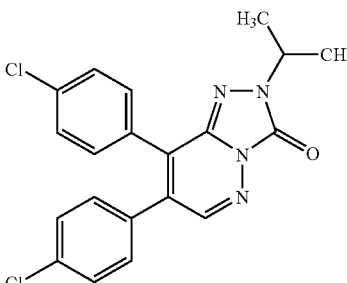 | 3.98 | 399 |
| 40 | 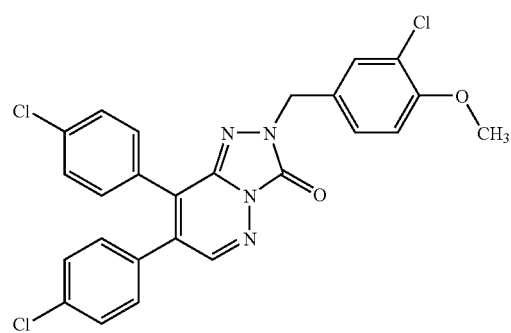 | 4.15 | 511 |
| 41 | 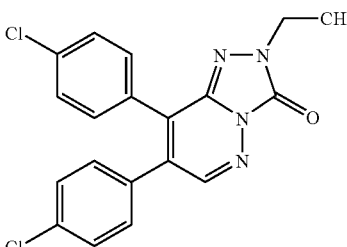 | 3.82 | 385 |
| 42 | 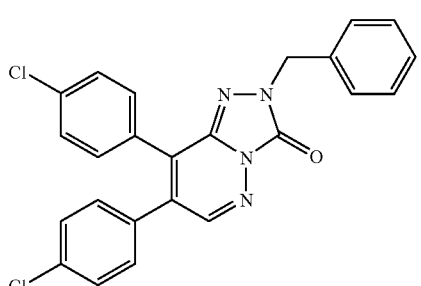 | 4.06 | 447 |
| 43 | 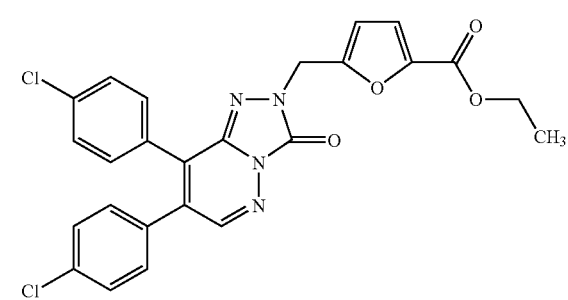 | 3.92 | 509 |

-continued

| Example Number | Structure | HPLC Retention Time (min) | Mass Specs Observed (M + H) |
|---|---|---|---|
| 44 | 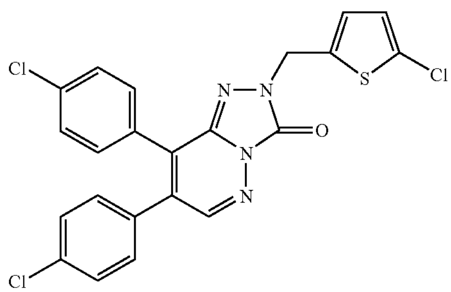 | 4.22 | 487 |
| 45 | 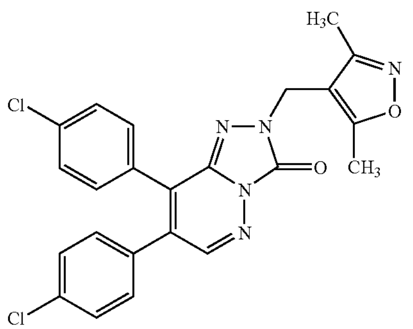 | 3.83 | 466 |
| 46 | 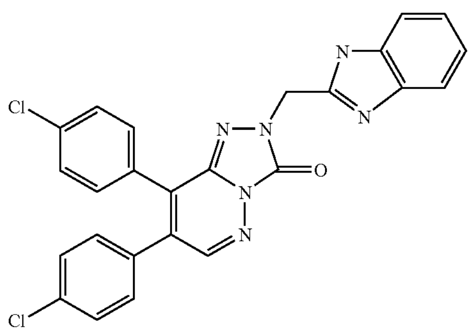 | 3.35 | 487 |
| 47 | 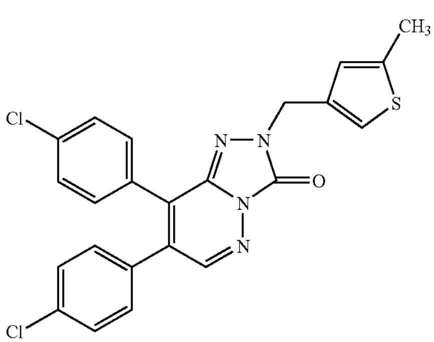 | 3.78 | 468 |

-continued

| Example Number | Structure | HPLC Retention Time (min) | Mass Specs Observed (M + H) |
| --- | --- | --- | --- |
| 48 | 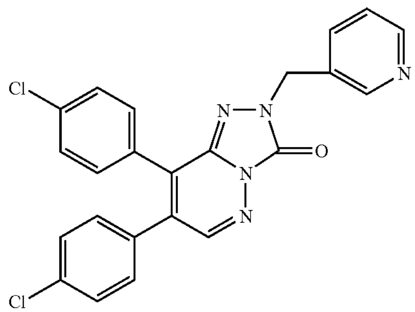 | 3.14 | 448 |
| 49 | 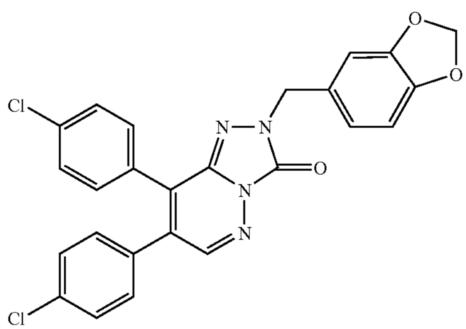 | 4.03 | 491 |
| 50 | 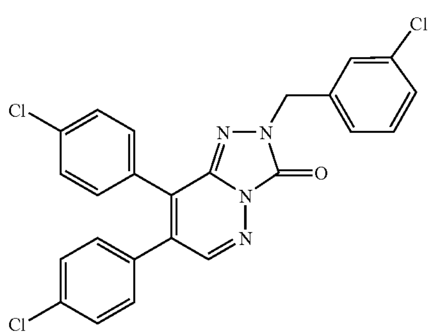 | 4.18 | 481 |
| 51 | 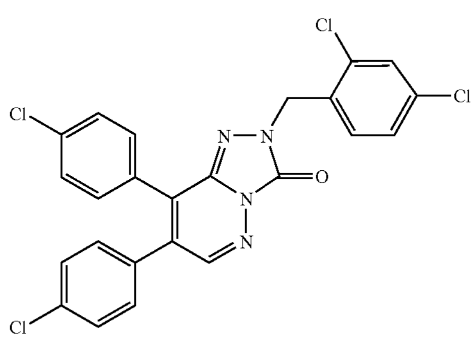 | 4.34 | 515 |

-continued

| Example Number | Structure | HPLC Retention Time (min) | Mass Specs Observed (M + H) |
|---|---|---|---|
| 52 | 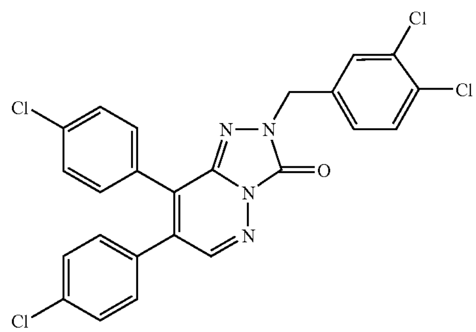 | 4.3 | 517 |
| 53 | 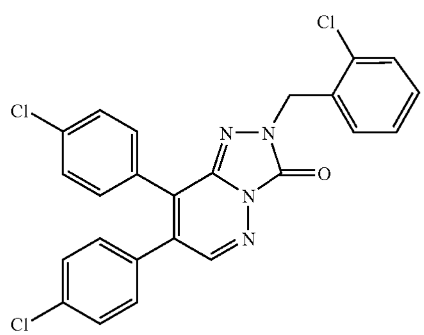 | 4.14 | 481 |
| 54 | 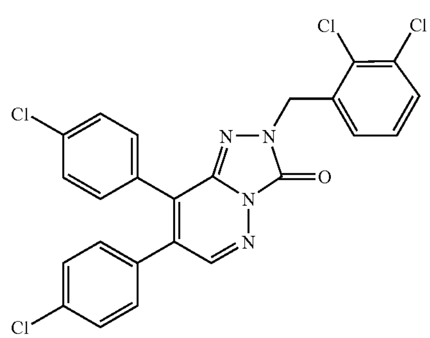 | 4.27 | 517 |
| 55 | 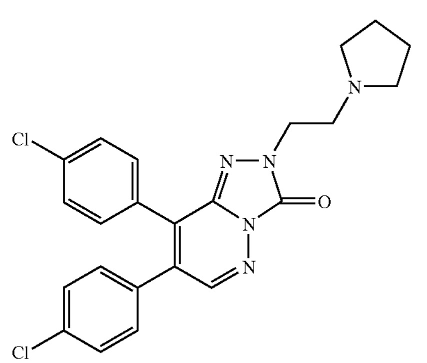 | 2.78 | 454 |

-continued

| Example Number | Structure | HPLC Retention Time (min) | Mass Specs Observed (M + H) |
|---|---|---|---|
| 56 | 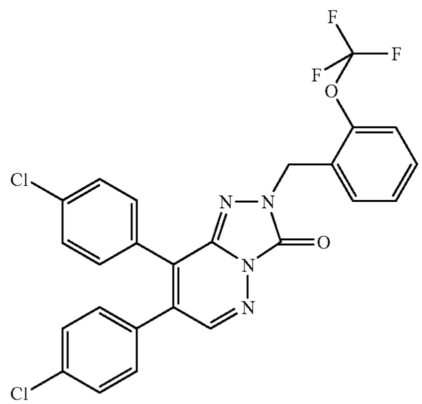 | 4.02 | 531 |
| 57 | 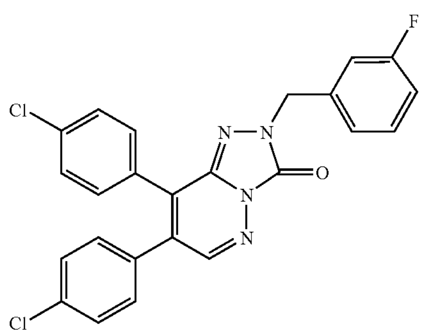 | 4.02 | 465 |
| 58 | 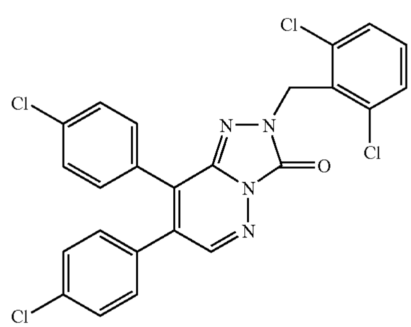 | 4.2 | 517 |
| 59 | 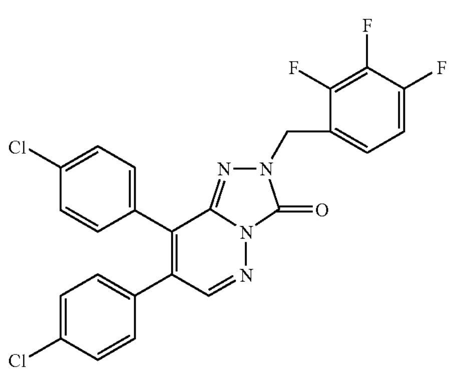 | 4.11 | 501 |

-continued
| Example Number | Structure | HPLC Retention Time (min) | Mass Specs Observed (M + H) |
|---|---|---|---|
| 60 | 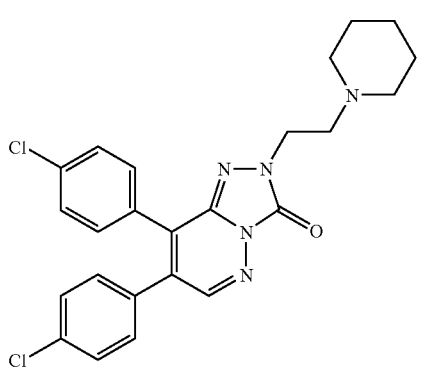 | 2.84 | 468 |
| 61 | 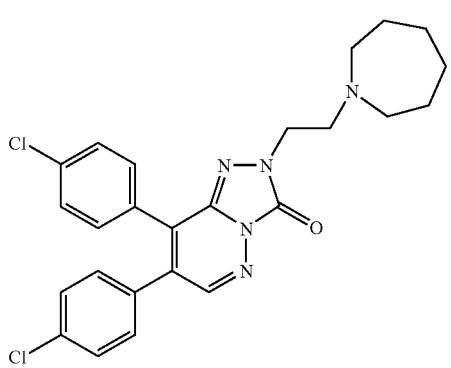 | 2.93 | 482 |
| 62 | 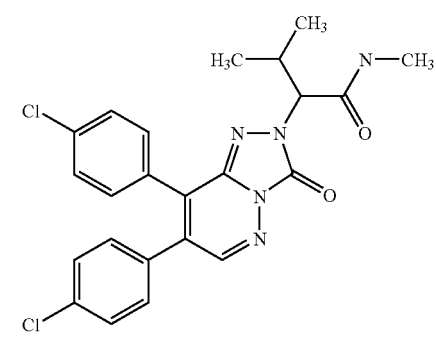 | 3.8 | 470 |
| 63 | 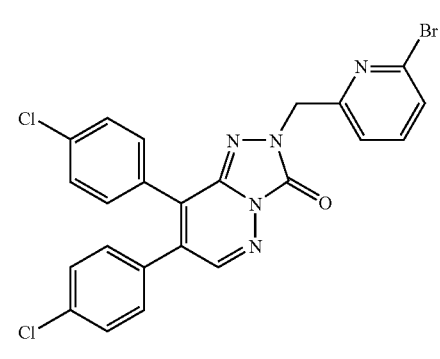 | 3.93 | 528 |

-continued

| Example Number | Structure | HPLC Retention Time (min) | Mass Specs Observed (M + H) |
|---|---|---|---|
| 64 | 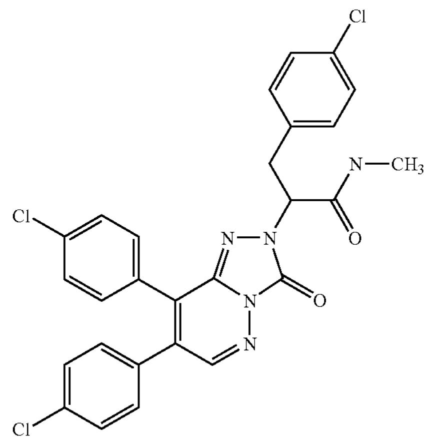 | 4.11 | 552 |
| 65 | (Chiral) | 4.09 | 554 |
| 66 | 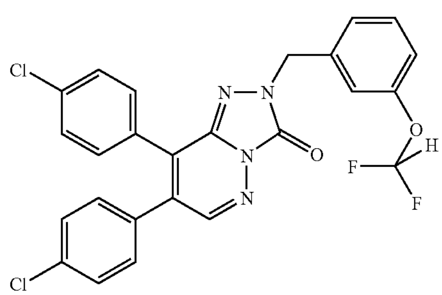 | 4.06 | 513 |
| 67 | 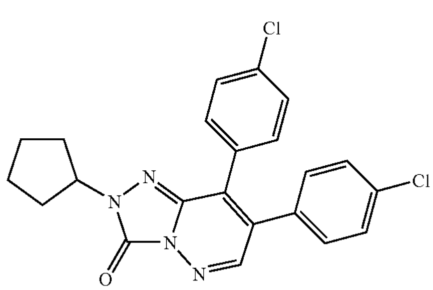 | 1.83[f] | 425 |

-continued

| Example Number | Structure | HPLC Retention Time (min) | Mass Specs Observed (M + H) |
|---|---|---|---|
| 68 | 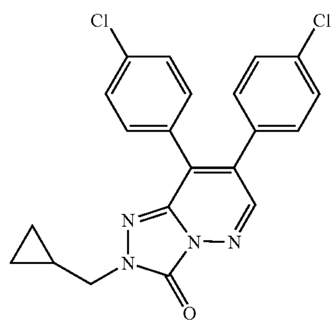 | 1.65[f] | 411 |
| 69 | 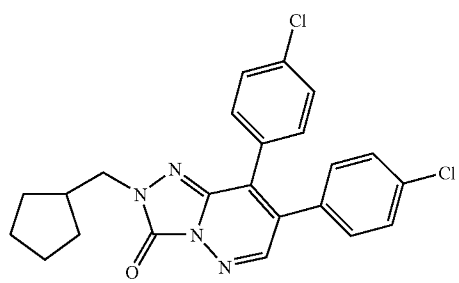 | 1.93[f] | 439 |
| 70 | 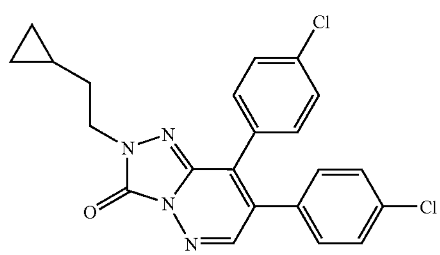 | 1.7[f] | 425 |
| 71 | 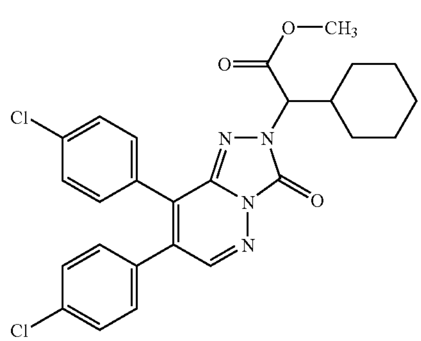 | 4.29 | 511 |

-continued
| Example Number | Structure | HPLC Retention Time (min) | Mass Specs Observed (M + H) |
|---|---|---|---|
| 72 | 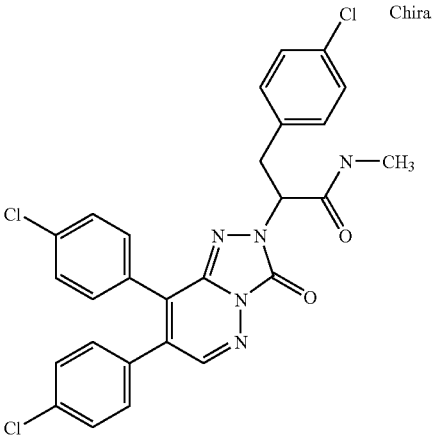 Chiral | 4.08 | 554 |
| 73 | 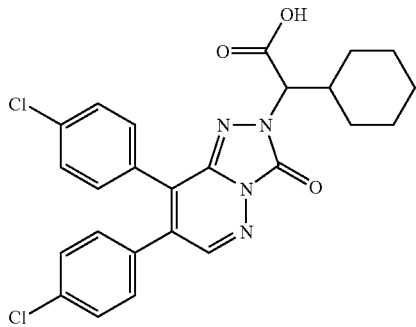 | 4.2 | 497 |
| 74 | 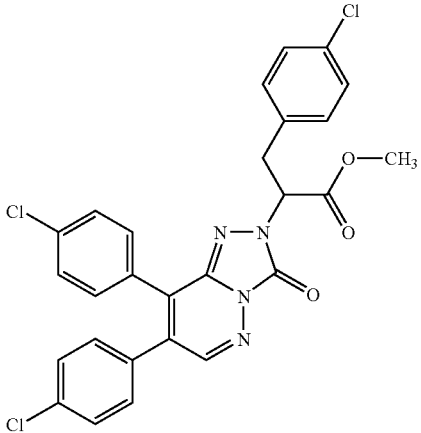 | 4.17 | 553 |

-continued

| Example Number | Structure | HPLC Retention Time (min) | Mass Specs Observed (M + H) |
|---|---|---|---|
| 75 | 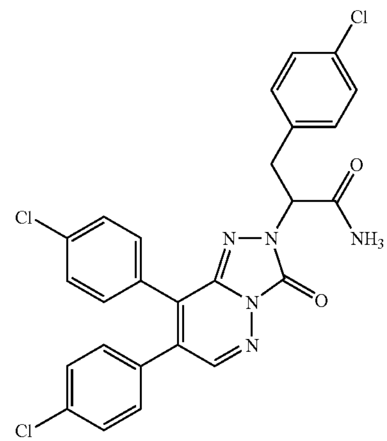 | 4.01 | 538 |
| 76 | 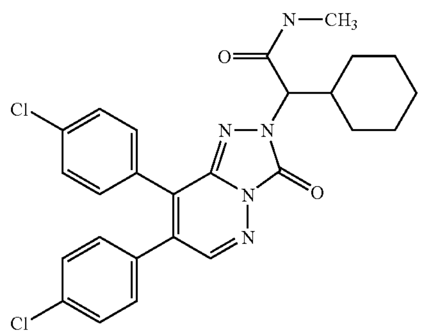 | 4.09 | 510 |
| 77 | 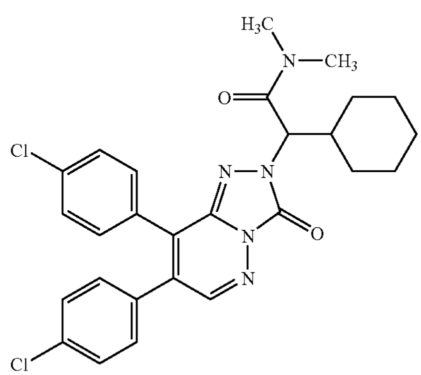 | 4.11 | 524 |
| 78 | 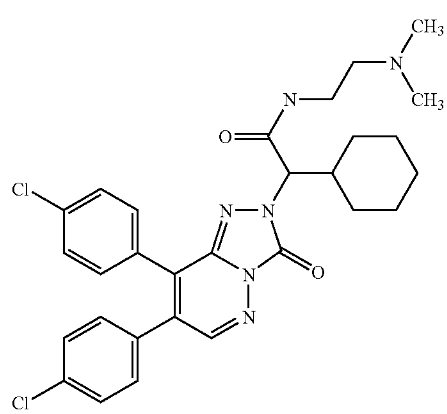 | 3.4 | 567 |

-continued

| Example Number | Structure | HPLC Retention Time (min) | Mass Specs Observed (M + H) |
|---|---|---|---|
| 79 | 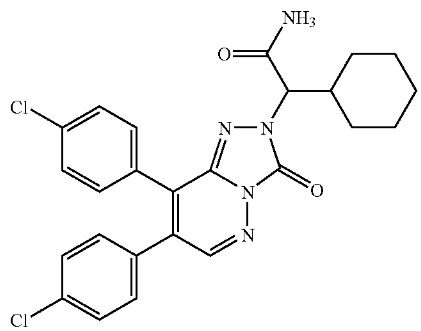 | 4.04 | 496 |
| 80 | 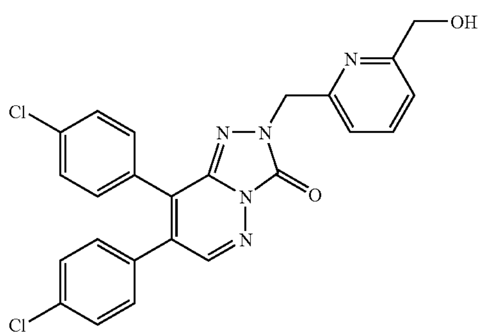 | 3.56[e] | 478 |
| 81 | 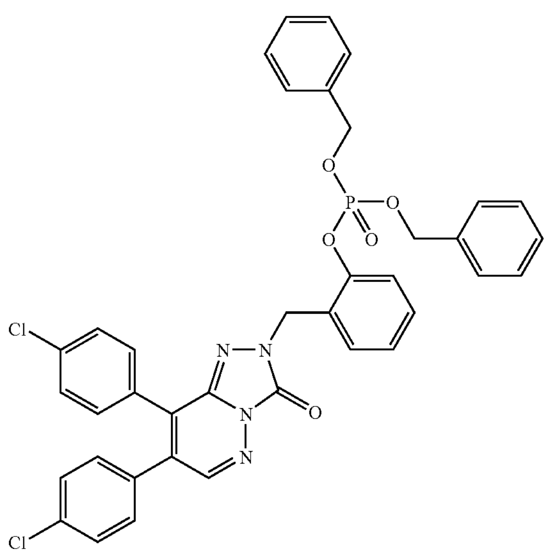 | 4.29 | 723 |

-continued

| Example Number | Structure | HPLC Retention Time (min) | Mass Specs Observed (M + H) |
|---|---|---|---|
| 82 | 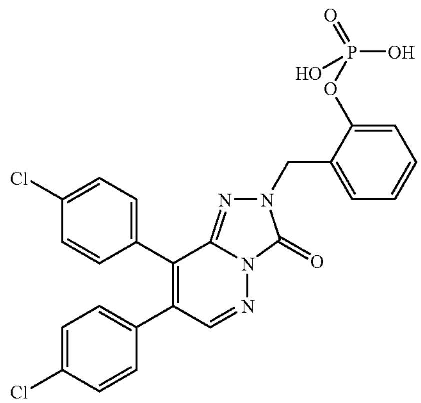 | 4.21 | 543 |
| 83 | 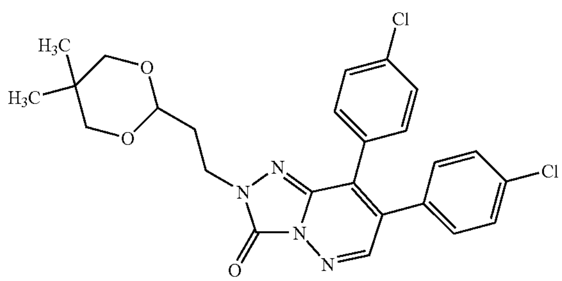 | 1.74g | 499 |
| 84 | 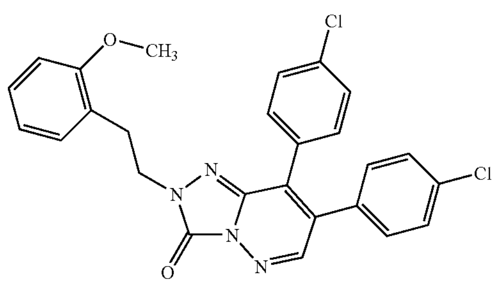 | 1.82g | 491 |
| 85 | 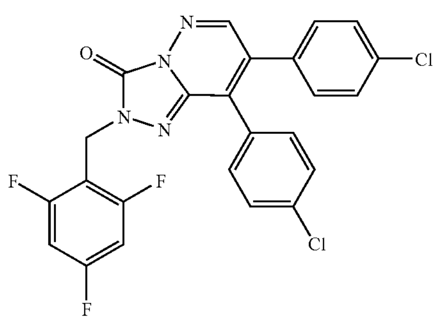 | 1.77g | 501 |
| 86 | 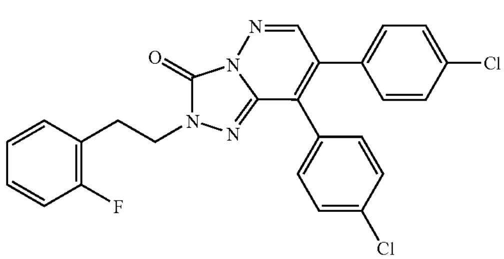 | 1.8g | 479 |

-continued
| Example Number | Structure | HPLC Retention Time (min) | Mass Specs Observed (M + H) |
|---|---|---|---|
| 87 | 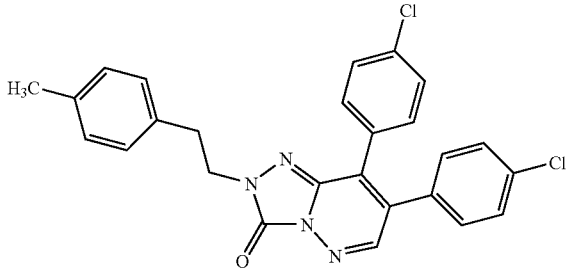 | 1.86[g] | 475 |
| 88 | 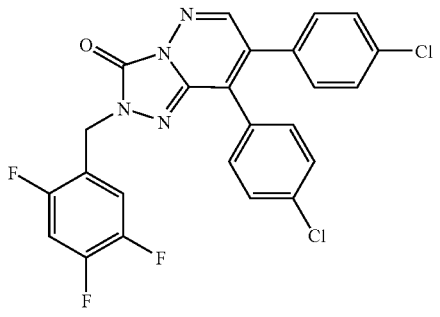 | 1.79[g] | 501 |
| 89 | 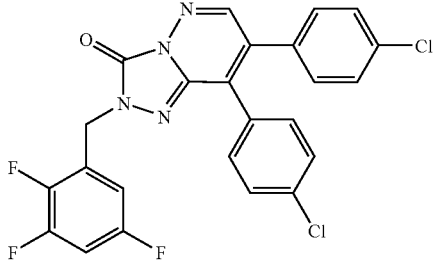 | 1.8[g] | 501 |
| 90 | 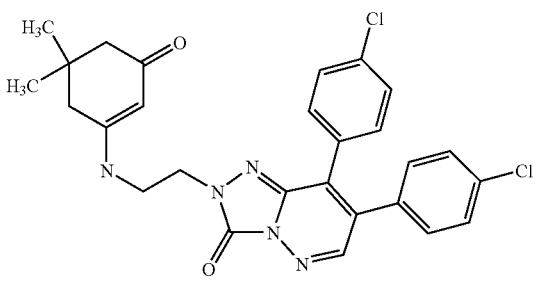 | 1.33[g] | 522 |
| 91 | 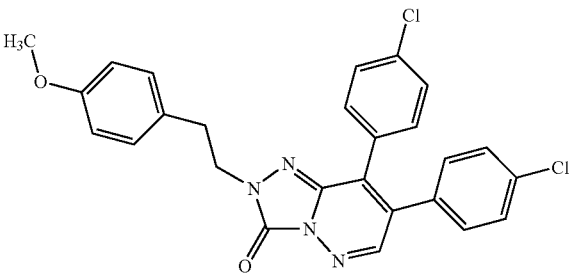 | 1.79[g] | 491 |

-continued

| Example Number | Structure | HPLC Retention Time (min) | Mass Specs Observed (M + H) |
|---|---|---|---|
| 92 | 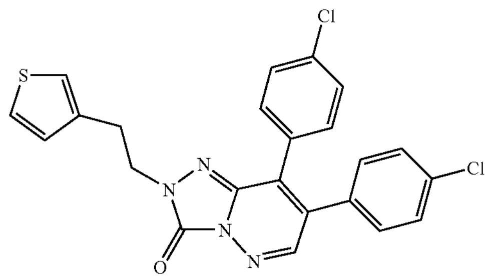 | 1.77[g] | 467 |
| 93 | 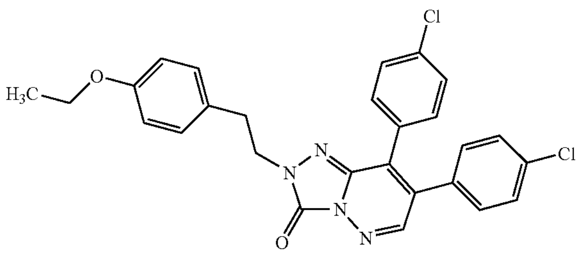 | 1.86[g] | 505 |
| 94 | 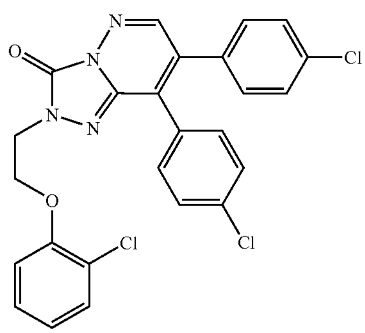 | 1.84[g] | 511 |
| 95 | 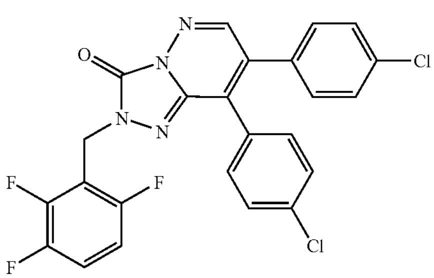 | 1.75[g] | 501 |
| 96 | 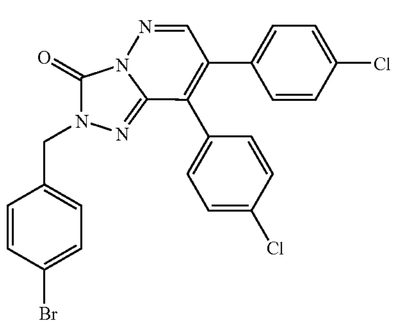 | 1.88[g] | 527[M + 2] |

-continued

| Example Number | Structure | HPLC Retention Time (min) | Mass Specs Observed (M + H) |
|---|---|---|---|
| 97 | 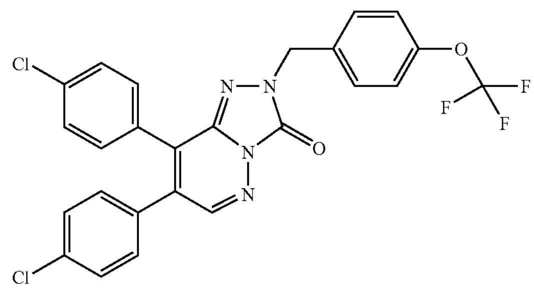 | 4.19 | 531 |
| 98 | 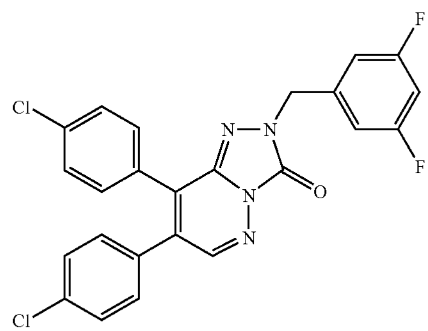 | 4.08 | 483 |
| 99 | 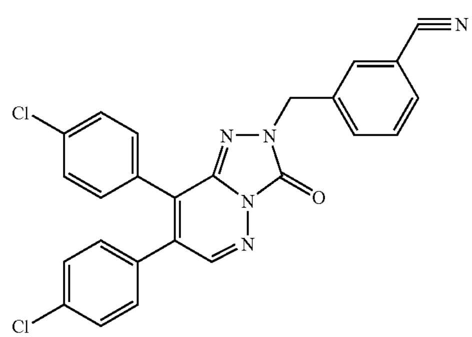 | 3.84 | 472 |
| 100 | 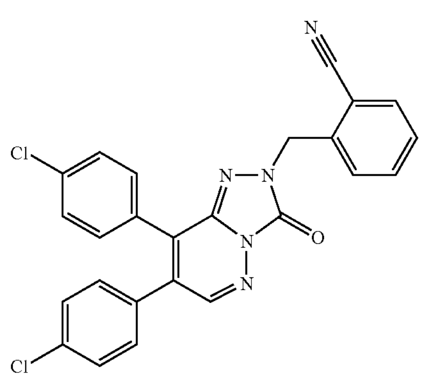 | 3.83 | 472 |

| Example Number | Structure | HPLC Retention Time (min) | Mass Specs Observed (M + H) |
|---|---|---|---|
| 101 | 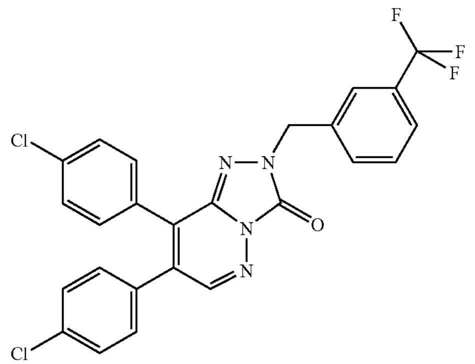 | 4.19 | 515 |
| 102 | 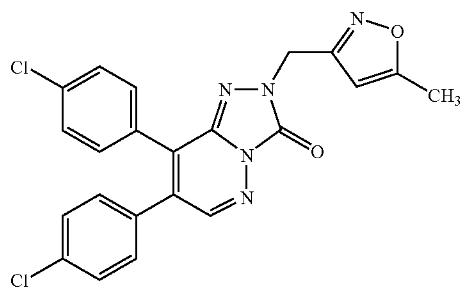 | 3.69 | 452 |
| 103 | 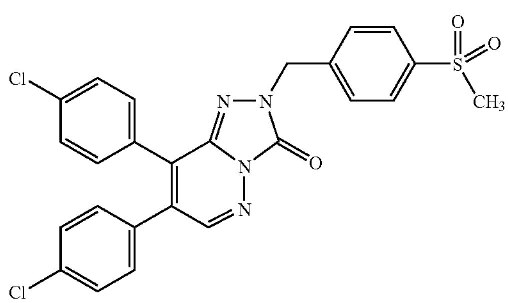 | 3.61 | 525 |
| 104 | 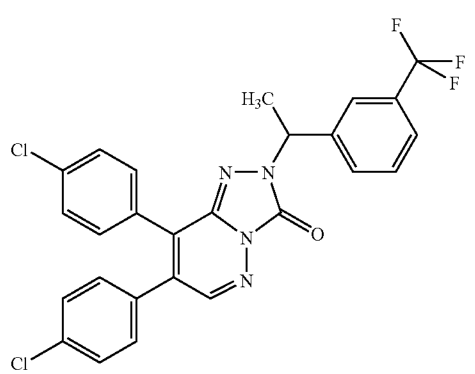 | 4.32 | 529 |

-continued

| Example Number | Structure | HPLC Retention Time (min) | Mass Specs Observed (M + H) |
|---|---|---|---|
| 105 | 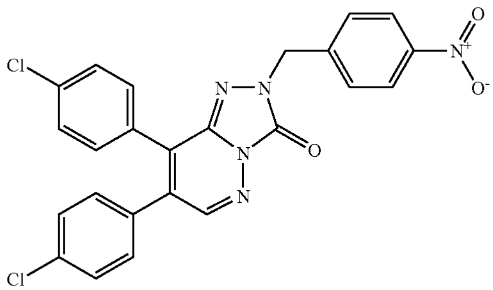 | 4 | 492 |
| 106 | 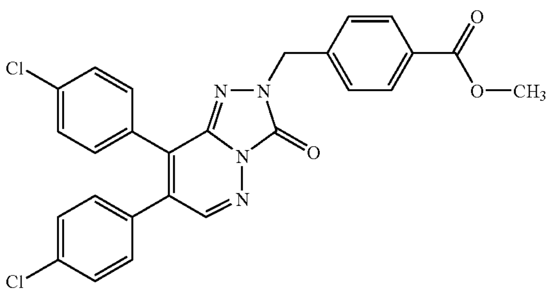 | 4.01[d] | 505 |
| 107 | 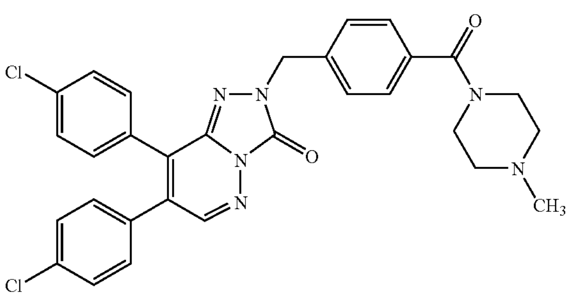 | 3.19[d] | 573 |
| 108 | 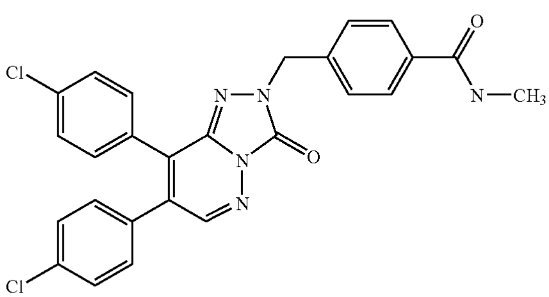 | 3.66[e] | 504 |
| 109 | 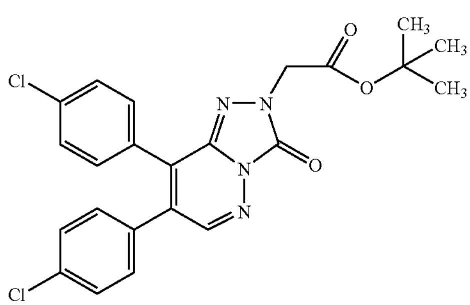 | 3.93 | 471 |

-continued

| Example Number | Structure | HPLC Retention Time (min) | Mass Specs Observed (M + H) |
|---|---|---|---|
| 110 | 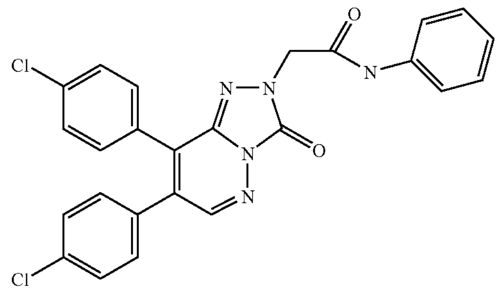 | 3.78 | 490 |
| 111 | 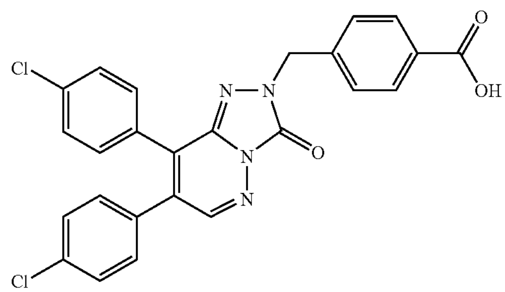 | 3.8 | 491 |
| 112 | 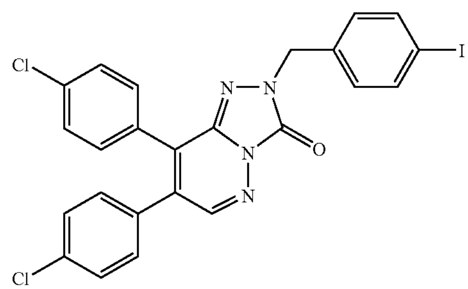 | 4.33[e] | 573 |
| 113 | 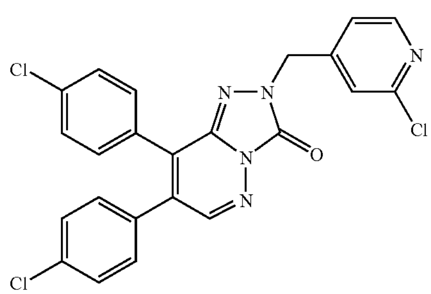 | 3.86[e] | 484[M + 2] |
| 114 | 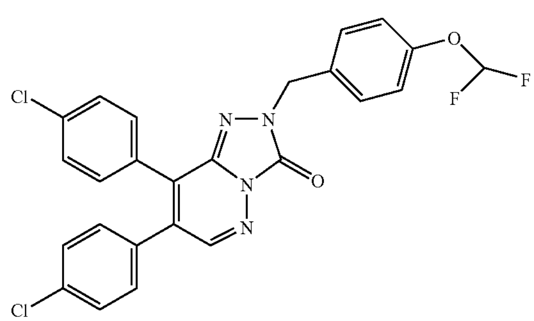 | 4 | 513 |

-continued

| Example Number | Structure | HPLC Retention Time (min) | Mass Specs Observed (M + H) |
|---|---|---|---|
| 115 | 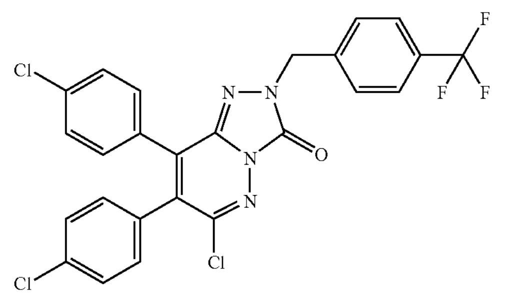 | 4.22 | 549 |
| 116 | 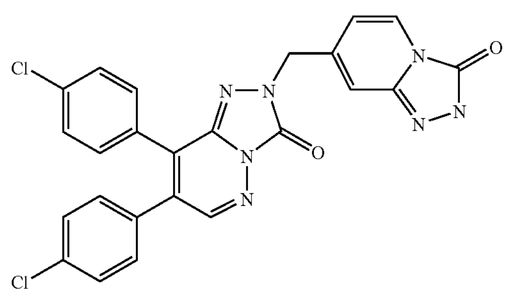 | 3.45[d] | 504 |
| 117 | 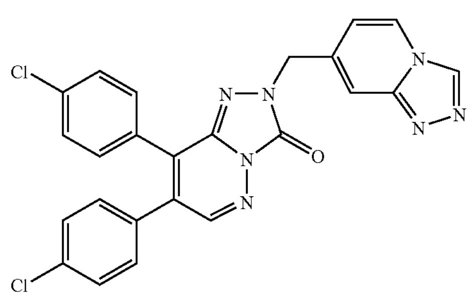 | 3.23[d] | 488 |
| 118 | 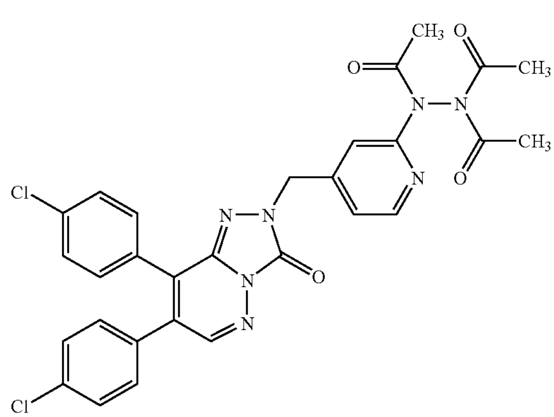 | 3.69[d] | 604 |

-continued

| Example Number | Structure | HPLC Retention Time (min) | Mass Specs Observed (M + H) |
|---|---|---|---|
| 119 | 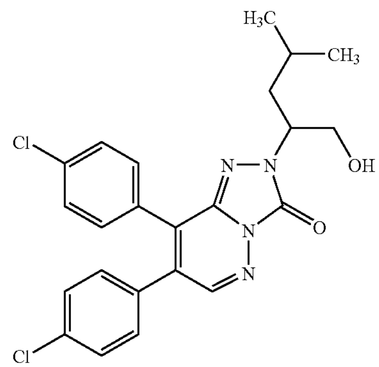 | 4.07 | 457 |
| 120 | 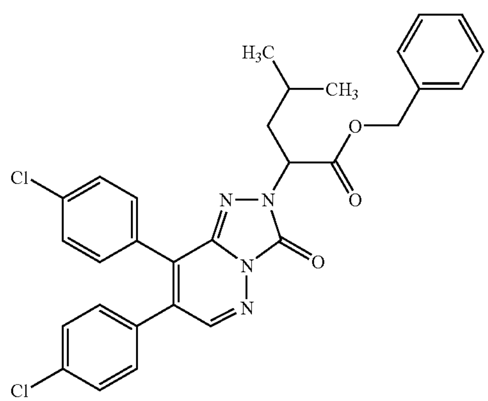 | 4.36 | 561 |
| 121 | 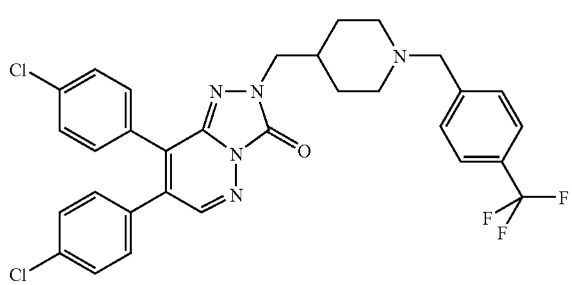 | 3.16 | 612 |
| 122 | 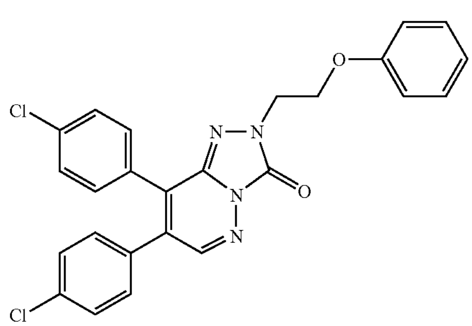 | 4.04 | 477 |

-continued
| Example Number | Structure | HPLC Retention Time (min) | Mass Specs Observed (M + H) |
|---|---|---|---|
| 123 | 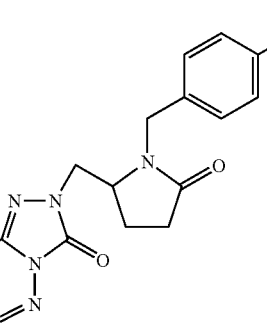 Chiral | 4 | 612 |
| 124 | 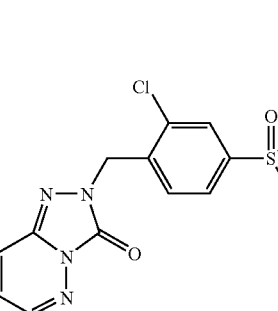 | 3.8 | 559 |
| 125 | 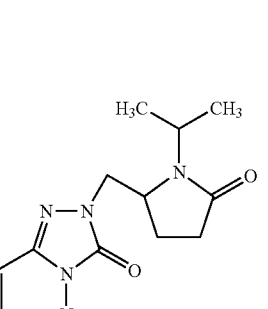 Chiral | 3.85 | 490 |
| 126 | 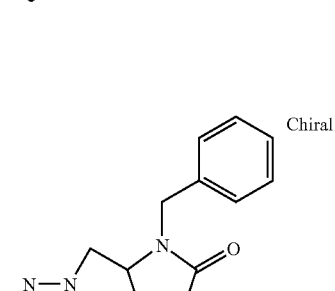 Chiral | 3.91 | 544 |

-continued

| Example Number | Structure | HPLC Retention Time (min) | Mass Specs Observed (M + H) |
|---|---|---|---|
| 127 | 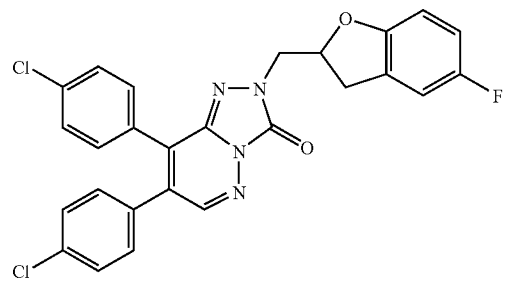 | 4.08 | 507 |
| 128 | Chiral | 3.85 | 510 |
| 129 | 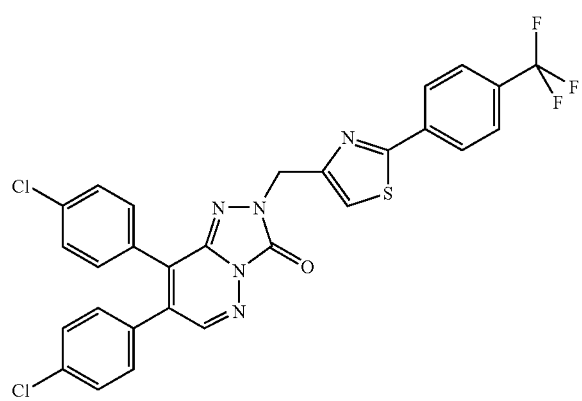 | 4.36 | 598 |
| 130 | 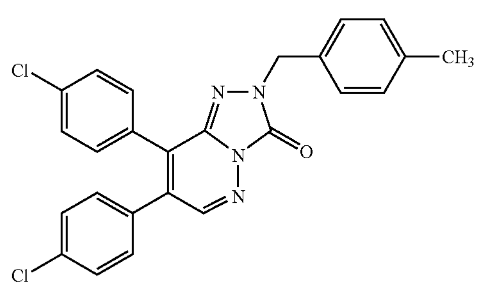 | 4.18[d] | 461 |

-continued

| Example Number | Structure | HPLC Retention Time (min) | Mass Specs Observed (M + H) |
|---|---|---|---|
| 131 | 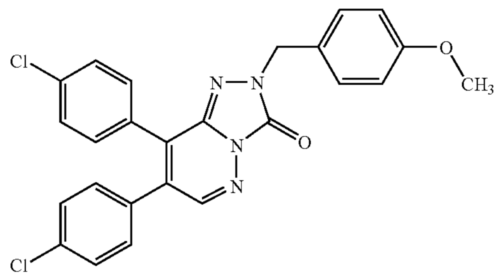 | 4.1 | 477 |
| 132 | 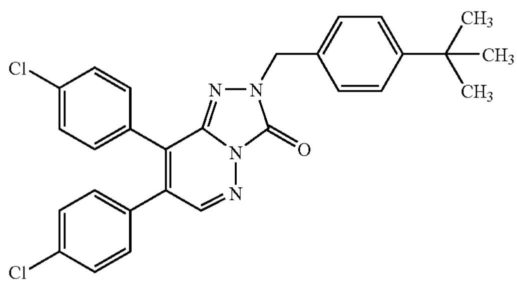 | 4.46[d] | 503 |
| 133 | 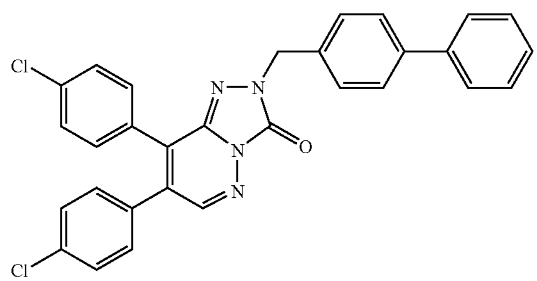 | 4.37[d] | 523 |
| 134 | 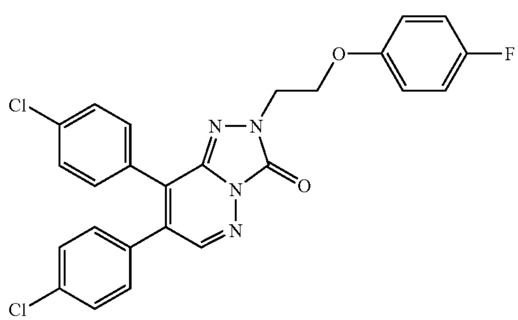 | 4.12 | 495 |
| 135 | 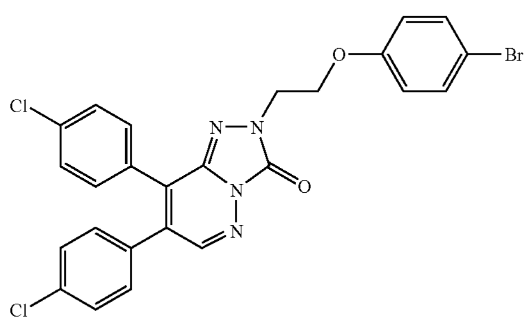 | 4.27 | 556 |

-continued

| Example Number | Structure | HPLC Retention Time (min) | Mass Specs Observed (M + H) |
| --- | --- | --- | --- |
| 136 | 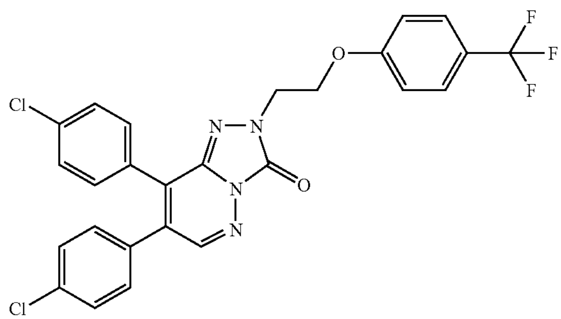 | 4.23 | 545 |
| 137 | 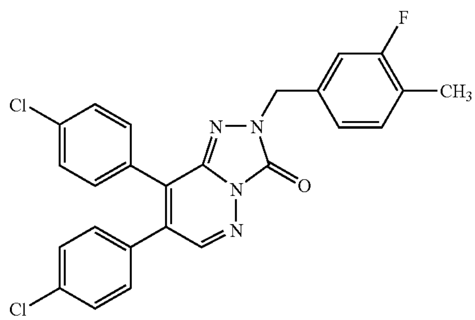 | 4.16[d] | 479 |
| 138 | 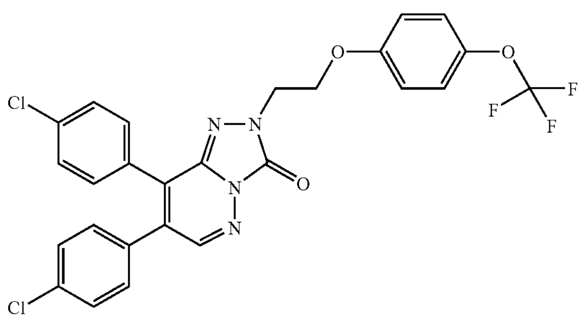 | 4.23 | 561 |
| 139 | 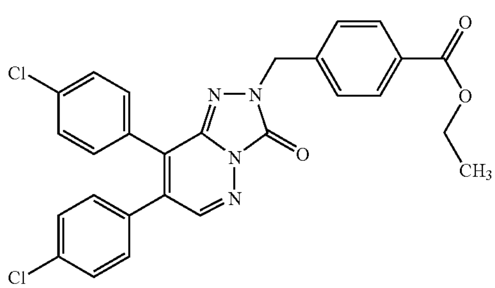 | 4.14 | 519 |
| 140 | 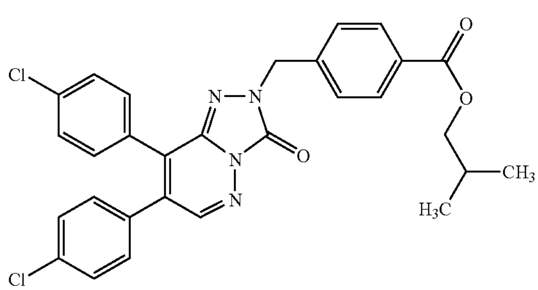 | 4.34 | 547 |

-continued

| Example Number | Structure | HPLC Retention Time (min) | Mass Specs Observed (M + H) |
|---|---|---|---|
| 141 | 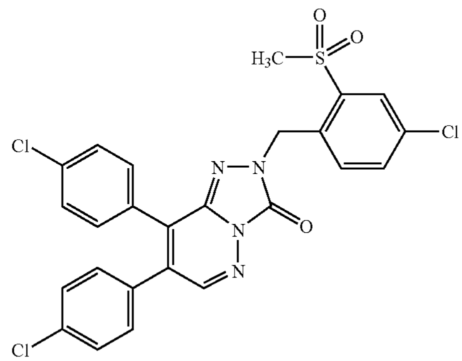 | 4.01 | 559 |
| 142 | 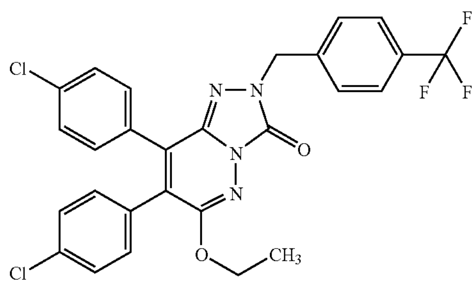 | 4.36 | 559 |
| 143 | 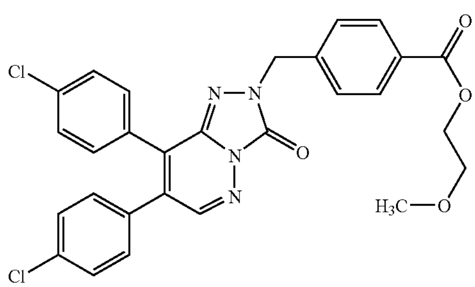 | 3.94 | 549 |
| 144 | 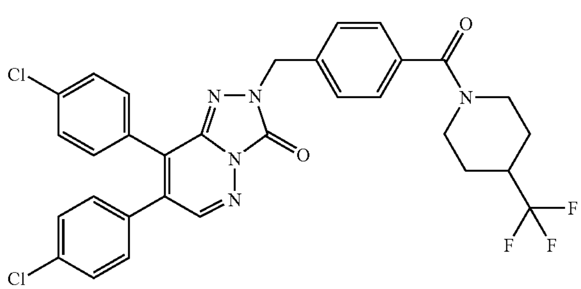 | 4 | 626 |
| 145 | 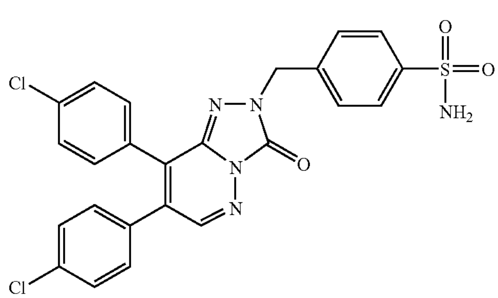 | 3.5 | 526 |

-continued

| Example Number | Structure | HPLC Retention Time (min) | Mass Specs Observed (M + H) |
|---|---|---|---|
| 146 | 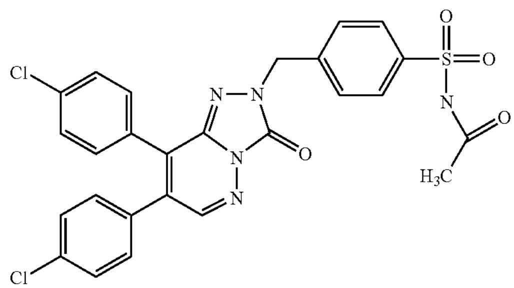 | 3.61 | 568 |
| 147 | 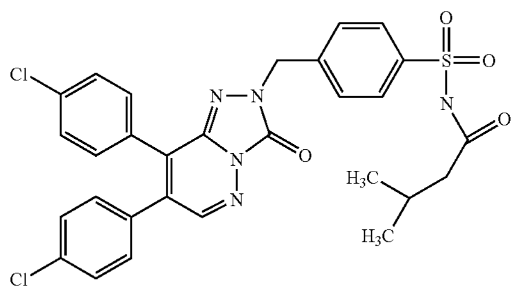 | 3.86 | 610 |
| 148 | 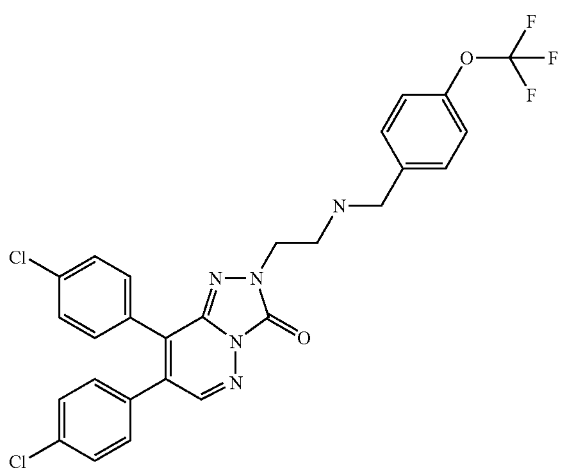 | 3.42 | 574 |
| 149 | 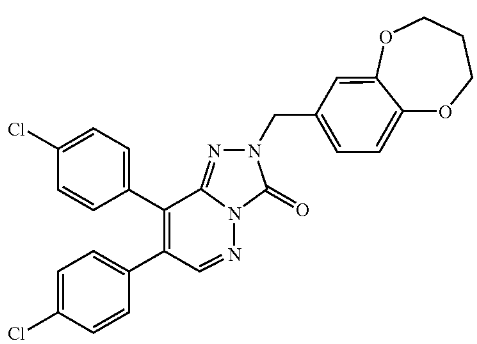 | 4[d] | 519 |

-continued

| Example Number | Structure | HPLC Retention Time (min) | Mass Specs Observed (M + H) |
|---|---|---|---|
| 150 | 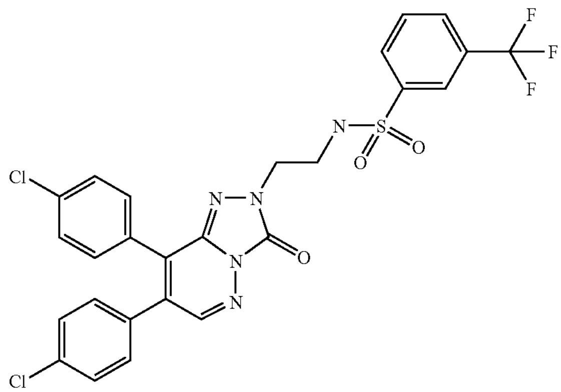 | 3.98 | 608 |
| 151 | 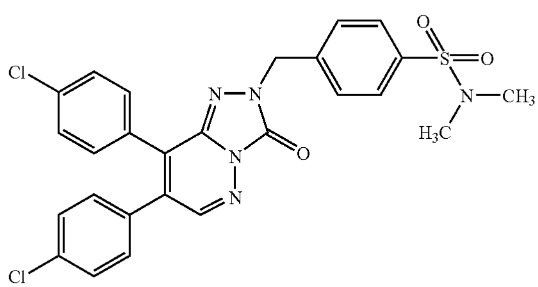 | 3.76 | 554 |
| 152 | 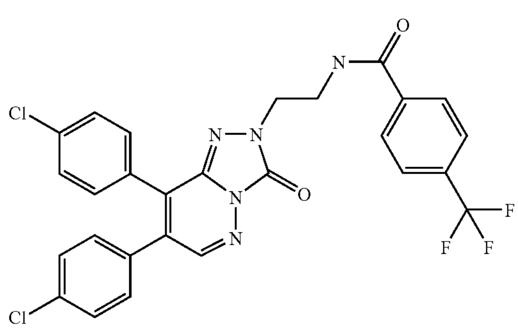 | 4.01 | 572 |
| 153 | 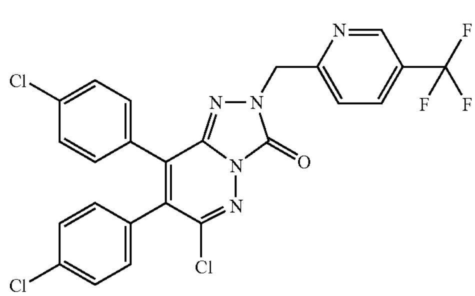 | 4.06 | 550 |

-continued

| Example Number | Structure | HPLC Retention Time (min) | Mass Specs Observed (M + H) |
|---|---|---|---|
| 154 | 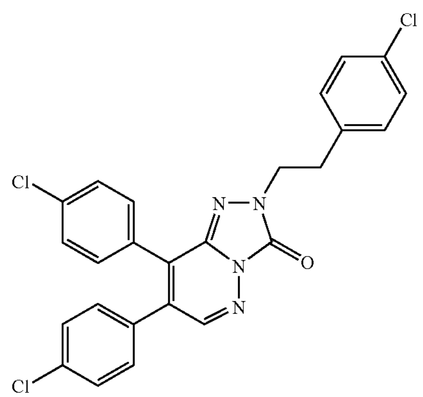 | 4.21 | 495 |
| 155 | 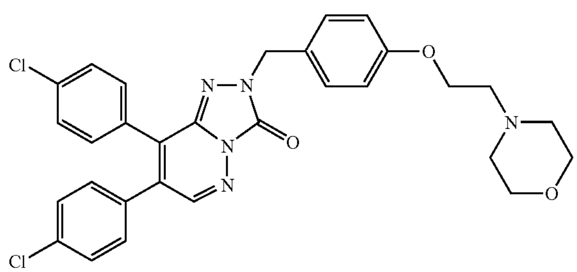 | 3.14 | 576 |
| 156 | 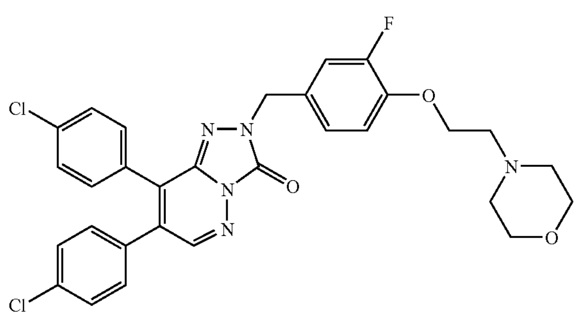 | 3.16 | 594 |
| 157 | 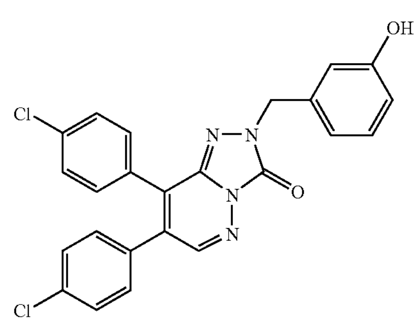 | 3.84 | 463 |

-continued

| Example Number | Structure | HPLC Retention Time (min) | Mass Specs Observed (M + H) |
|---|---|---|---|
| 158 | 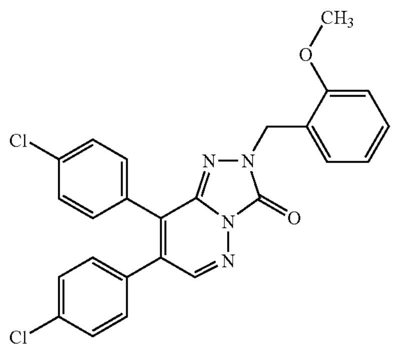 | 4.1 | 477 |
| 159 | 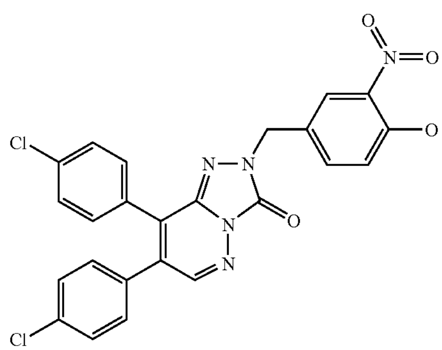 | 4.1 | 526 |
| 160 | 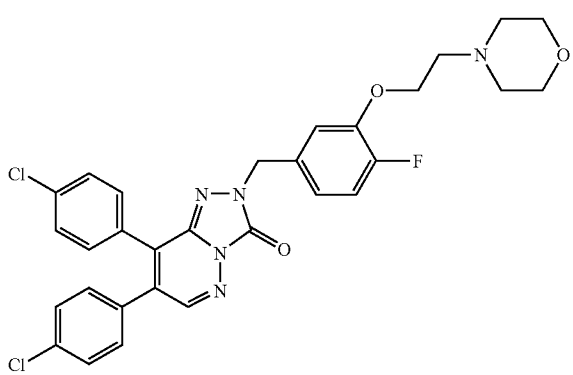 | 3.24 | 594 |
| 161 | 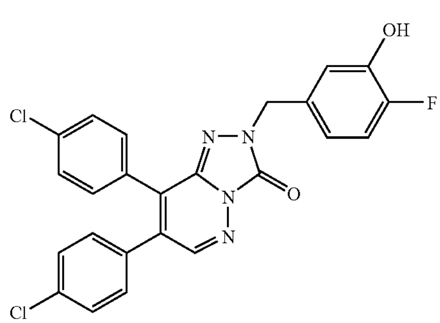 | 3.81 | 479 |

| Example Number | Structure | HPLC Retention Time (min) | Mass Specs Observed (M + H) |
|---|---|---|---|
| 162 | 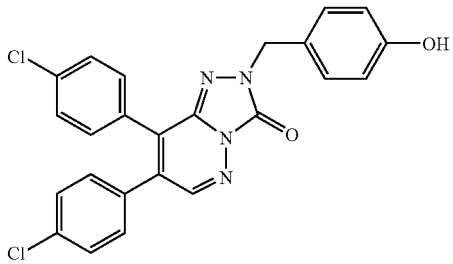 | 3.78 | 463 |
| 163 | 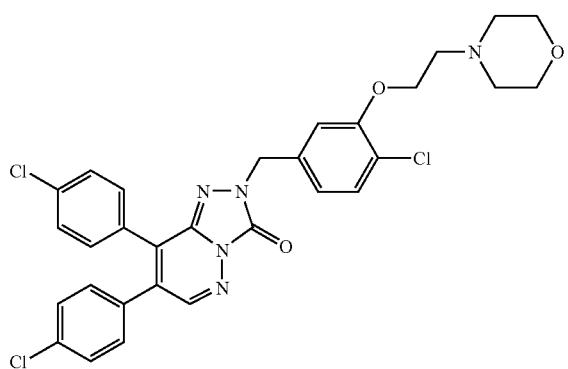 | 3.36 | 610 |
| 164 | 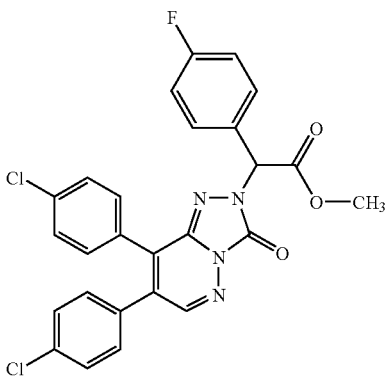 | 4.04 | 523 |
| 165 | 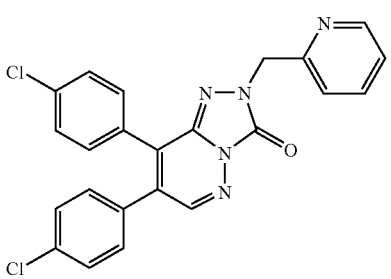 | 3.71[e] | 448 |

-continued

| Example Number | Structure | HPLC Retention Time (min) | Mass Specs Observed (M + H) |
|---|---|---|---|
| 166 | 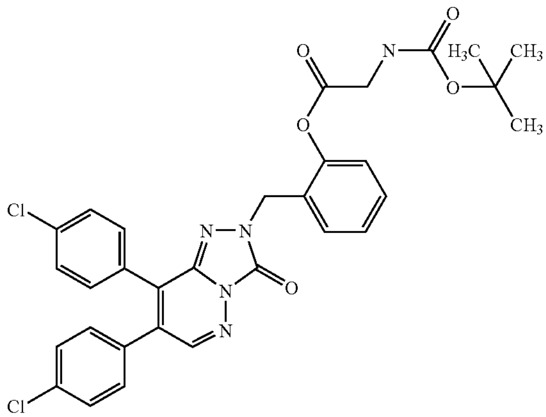 | 4.08 | 620 |
| 167 | 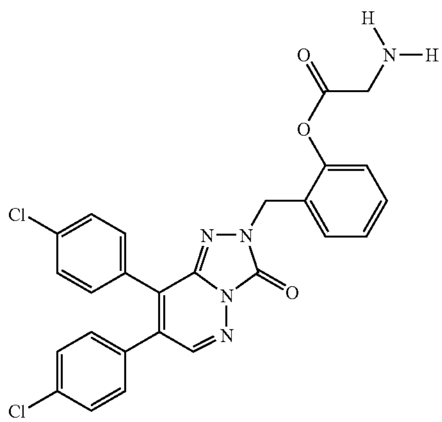 | 3.13 | 520 |
| 168 | 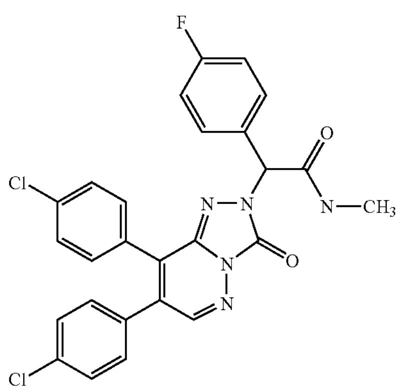 | 3.91 | 522 |
| 169 | 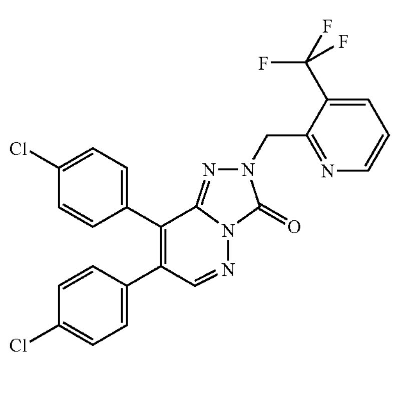 | 4 | 516 |

-continued
| Example Number | Structure | HPLC Retention Time (min) | Mass Specs Observed (M + H) |
|---|---|---|---|
| 170 | 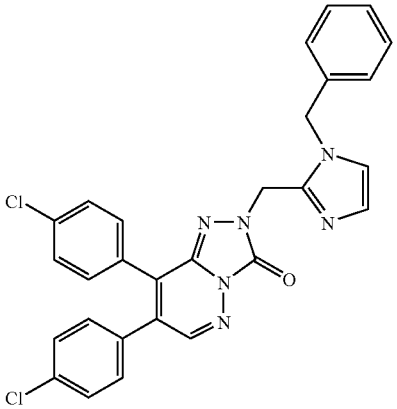 | 2.93 | 527 |
| 171 | 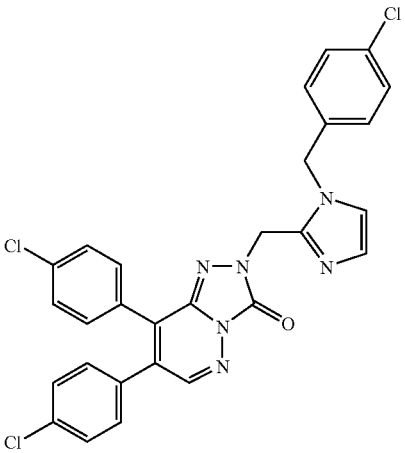 | 3.2 | 561 |
| 172 | 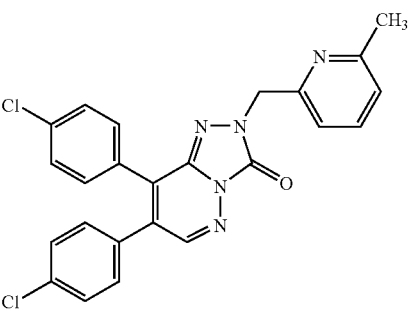 | 3.38 | 462 |
| 173 | 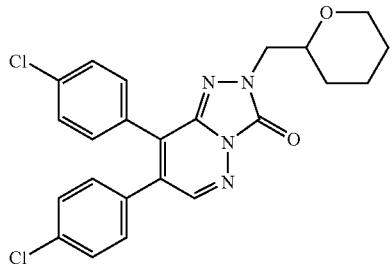 | 3.94 | 455 |

-continued

| Example Number | Structure | HPLC Retention Time (min) | Mass Specs Observed (M + H) |
|---|---|---|---|
| 174 | 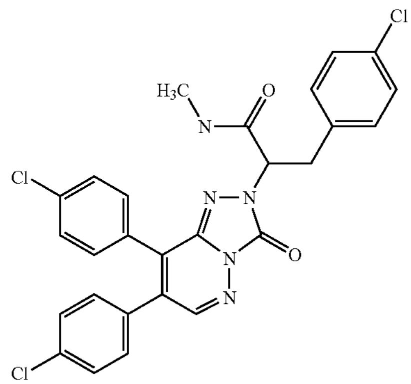 | 4.11 | 552 |
| 175 | 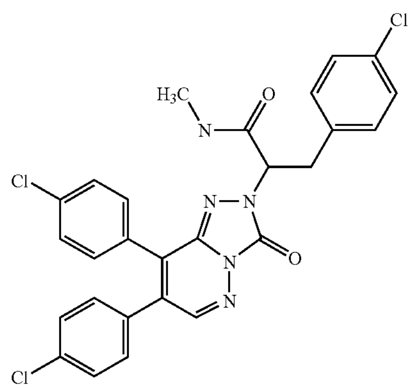 | 4.01 | 552 |
| 176 | 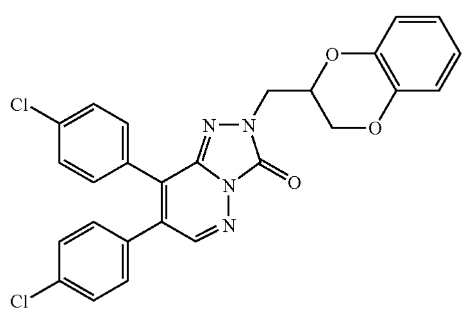 | 4.15 | 505 |
| 177 | 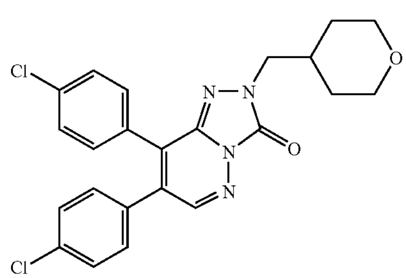 | 3.82 | 455 |

-continued

| Example Number | Structure | HPLC Retention Time (min) | Mass Specs Observed (M + H) |
|---|---|---|---|
| 178 | 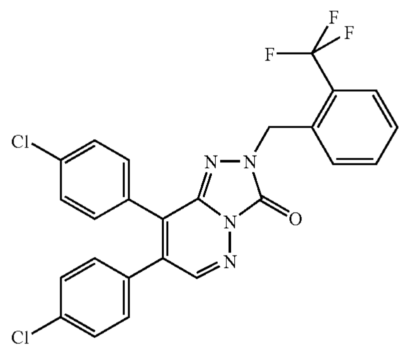 | 4.21 | 515 |
| 179 | 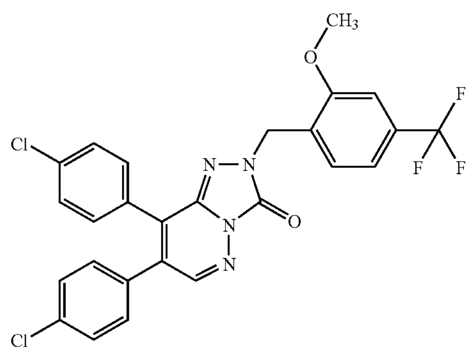 | 4.25 | 545 |
| 180 | 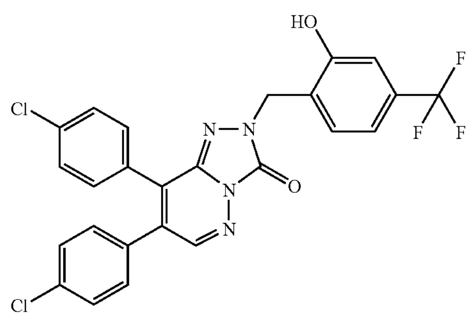 | 4.14 | 531 |
| 181 | 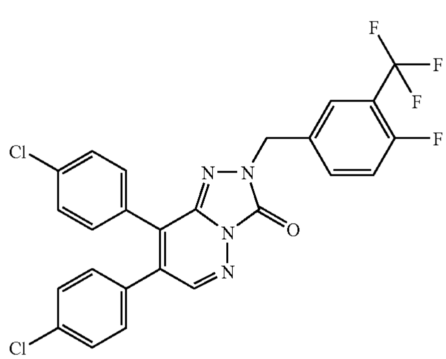 | 4.21 | 533 |

| Example Number | Structure | HPLC Retention Time (min) | Mass Specs Observed (M + H) |
| --- | --- | --- | --- |
| 182 | 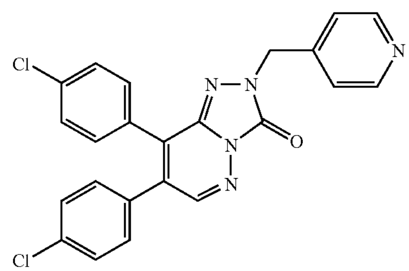 | 2.87 | 448 |
| 183 | 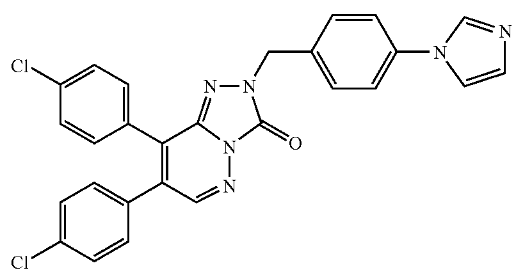 | 3.03 | 513 |
| 184 | 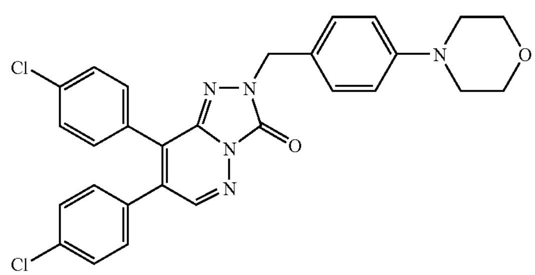 | 4 | 532 |
| 185 | 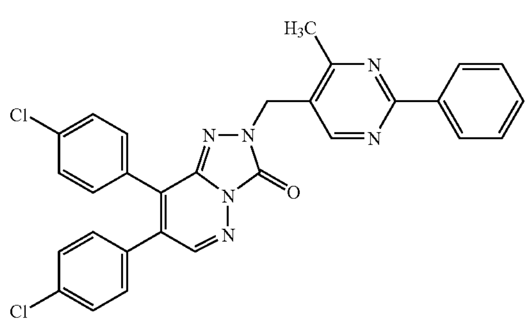 | 4.28 | 539 |
| 186 | 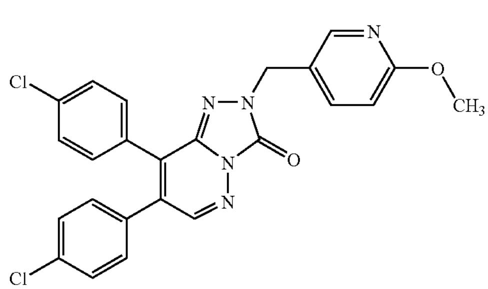 | 3.9 | 478 |

-continued

| Example Number | Structure | HPLC Retention Time (min) | Mass Specs Observed (M + H) |
|---|---|---|---|
| 187 | 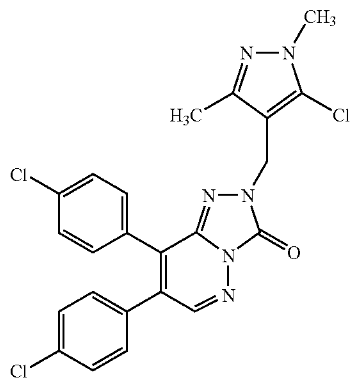 | 3.9 | 500 |
| 188 | 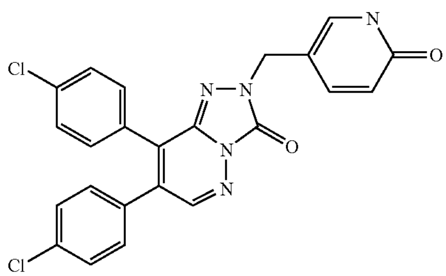 | 3.4 | 464 |
| 189 | 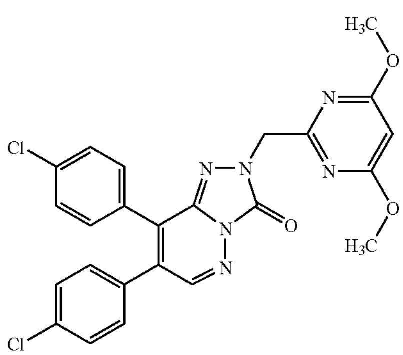 | 4 | 509 |
| 190 | 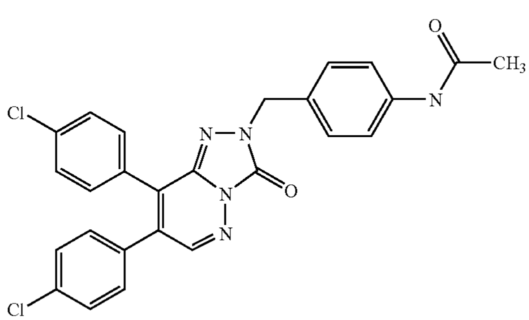 | 3.7 | 504 |

-continued

| Example Number | Structure | HPLC Retention Time (min) | Mass Specs Observed (M + H) |
|---|---|---|---|
| 191 | 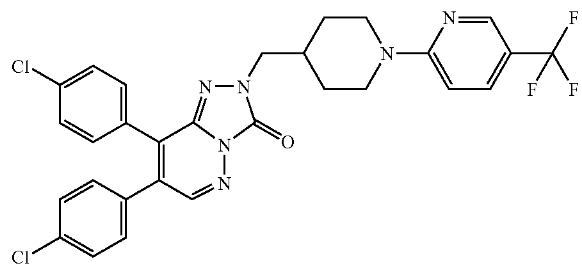 | 4.27 | 599 |
| 192 | 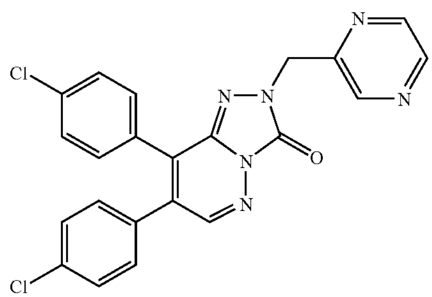 | 3.5 | 449 |
| 193 | 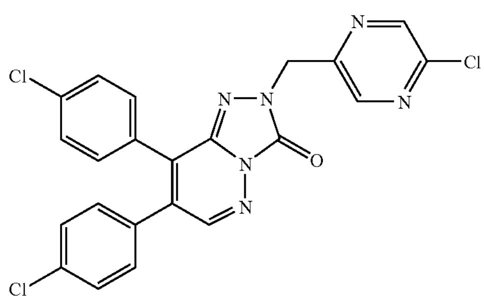 | 3.8 | 484 |
| 194 | 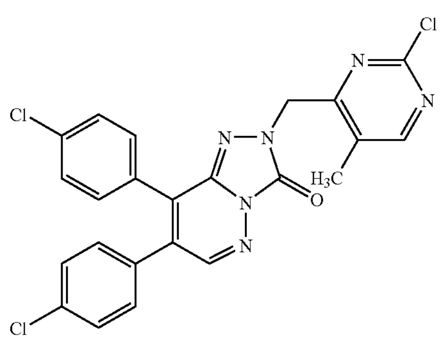 | 3.8 | 498 |
| 195 | 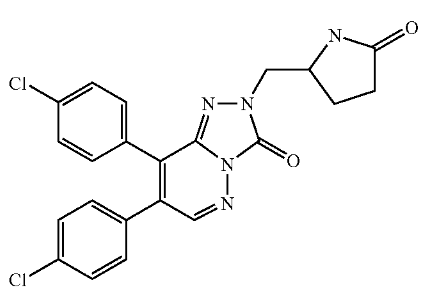 | 3.43 | 454 |

-continued

| Example Number | Structure | HPLC Retention Time (min) | Mass Specs Observed (M + H) |
|---|---|---|---|
| 196 | 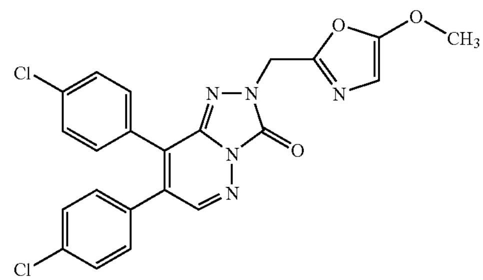 | 3.6 | 468 |
| 197 | 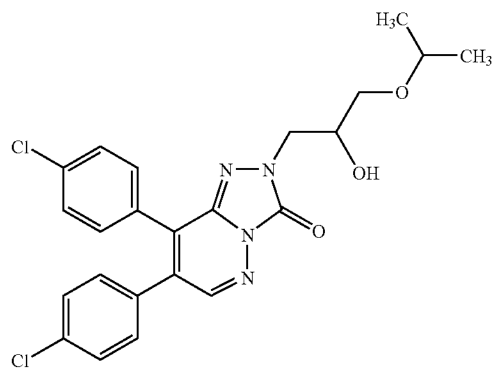 | 3.88 | 473 |
| 198 | 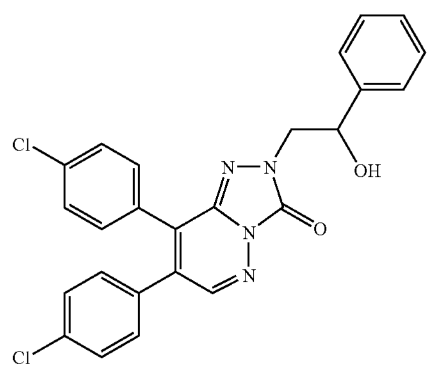 | 7.86[b] | 477 |
| 199 | 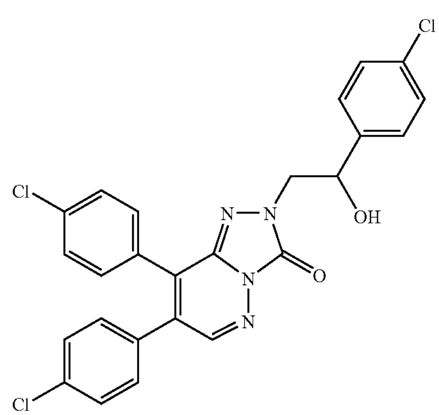 | 4.08 | 511 |

-continued
| Example Number | Structure | HPLC Retention Time (min) | Mass Specs Observed (M + H) |
|---|---|---|---|
| 200 | 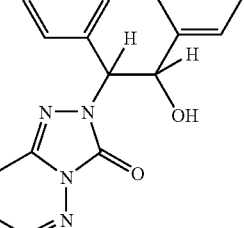 | 4.03 | 553 |
| 201 | 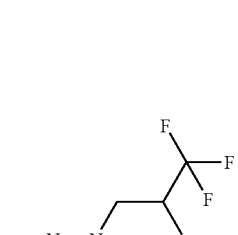 | 3.79 | 469 |
| 202 | 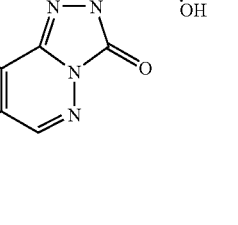 | 3.93 | 581 |
| 203 | 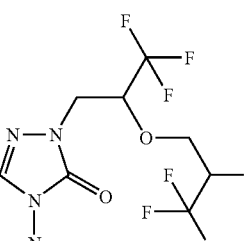 | 4.05 | 693 |

-continued

| Example Number | Structure | HPLC Retention Time (min) | Mass Specs Observed (M + H) |
|---|---|---|---|
| 204 | 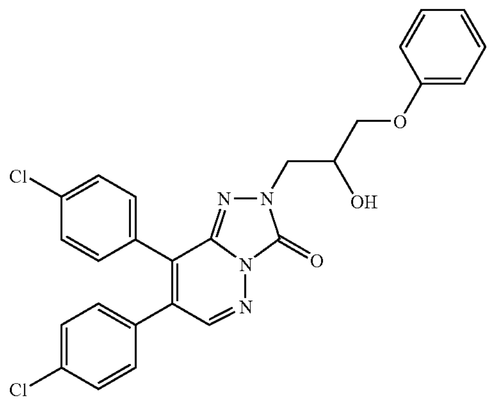 | 3.99 | 507 |
| 205 | 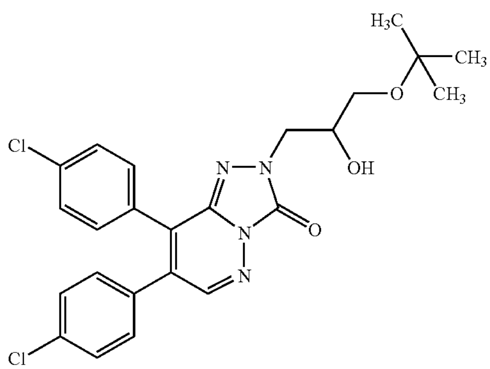 | 3.99 | 487 |
| 206 | 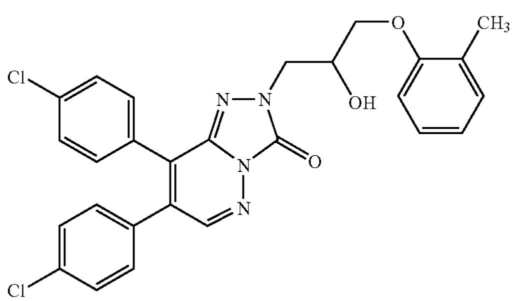 | 4.15 | 521 |
| 207 | 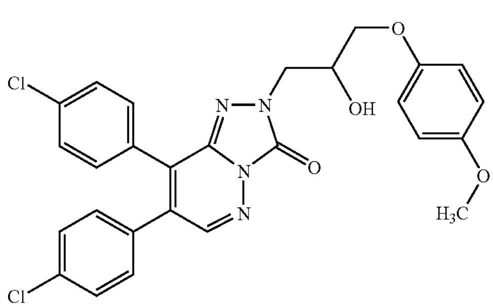 | 3.94 | 537 |

-continued
| Example Number | Structure | HPLC Retention Time (min) | Mass Specs Observed (M + H) |
|---|---|---|---|
| 208 | 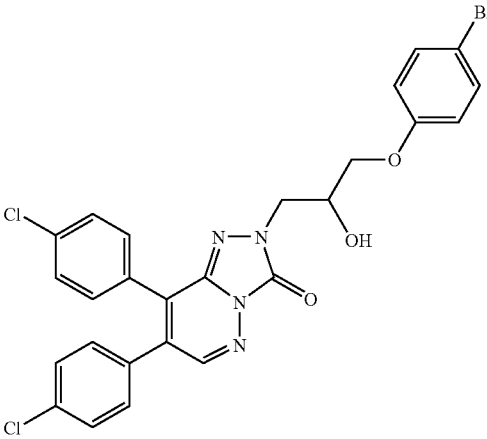 | 4.16 | 587[M + 2] |
| 209 | 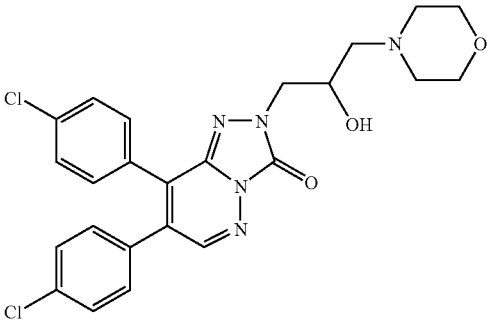 | 2.67 | 500 |
| 210 | 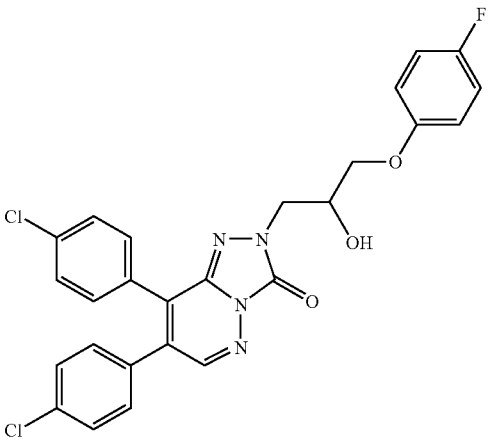 | 4 | 525 |

-continued
| Example Number | Structure | HPLC Retention Time (min) | Mass Specs Observed (M + H) |
|---|---|---|---|
| 211 | 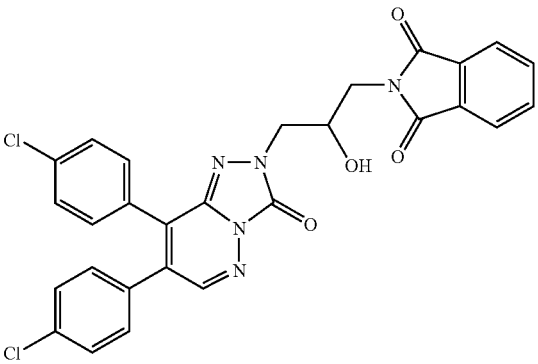 | 3.79 | 560 |
| 212 | 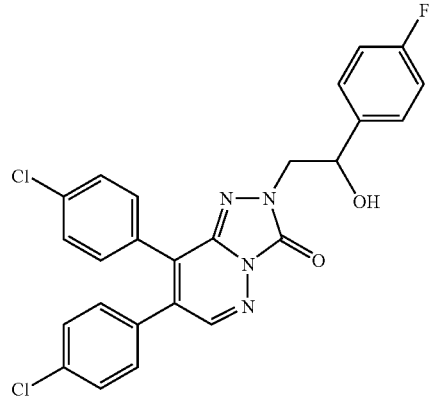 | 3.91 | 495 |
| 213 | 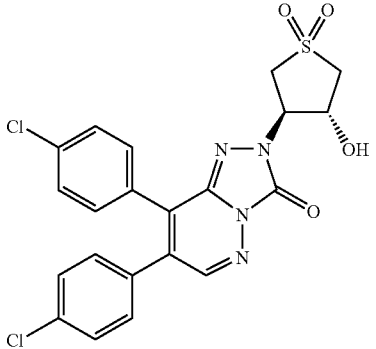 | 3.41 | 491 |

-continued

| Example Number | Structure | HPLC Retention Time (min) | Mass Specs Observed (M + H) |
|---|---|---|---|
| 214 | 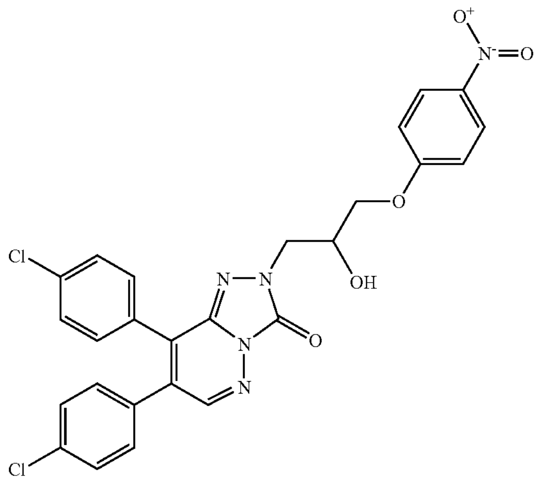 | 3.89 | 552 |
| 215 | 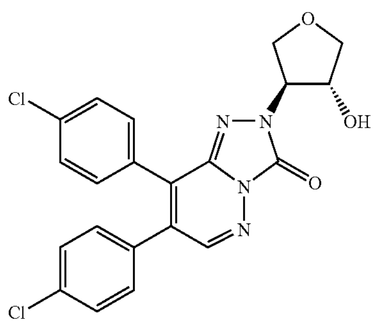 | 3.54 | 443 |
| 216 | 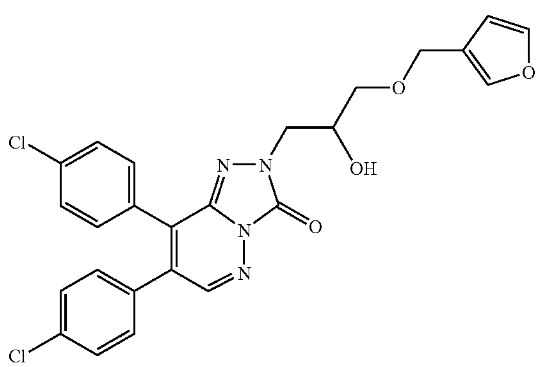 | 3.81 | 511 |
| 217 | 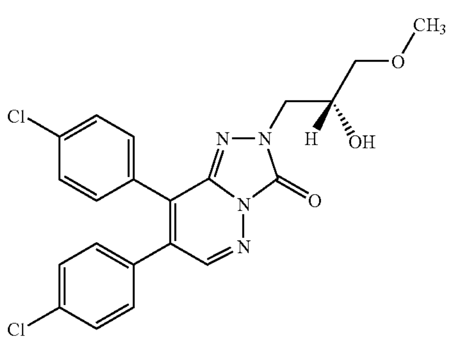 | 3.62 | 445 |

-continued
| Example Number | Structure | HPLC Retention Time (min) | Mass Specs Observed (M + H) |
|---|---|---|---|
| 218 | 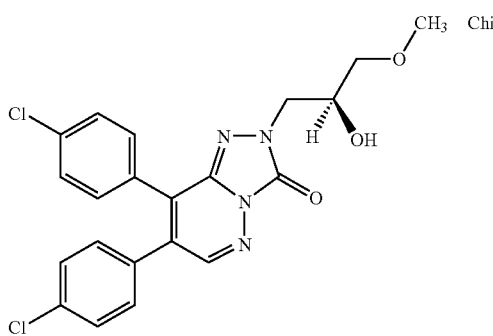 Chiral | 3.62 | 445 |
| 219 | 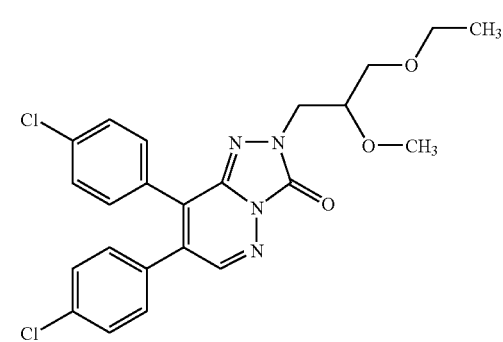 | 3.88 | 473 |
| 220 | 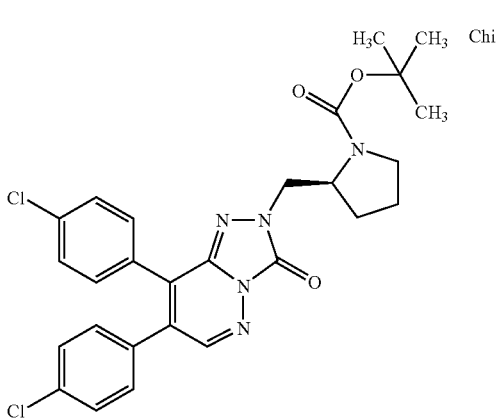 Chiral | 4.06[d] | 540 |

-continued
| Example Number | Structure | HPLC Retention Time (min) | Mass Specs Observed (M + H) |
|---|---|---|---|
| 221 | 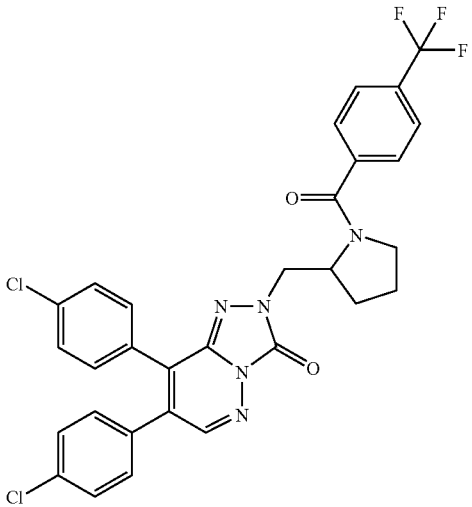 | 4.01[d] | 612 |
| 222 | 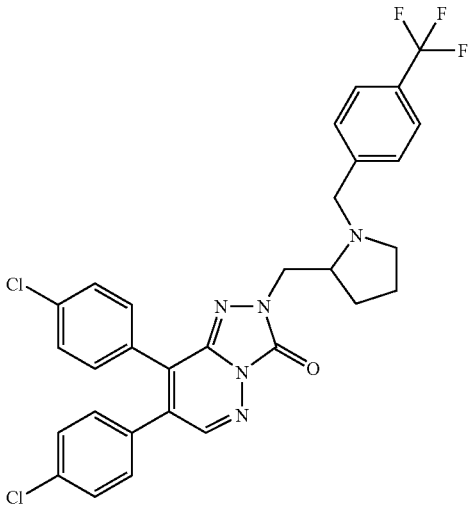 | 3.43[d] | 598 |
| 223 | 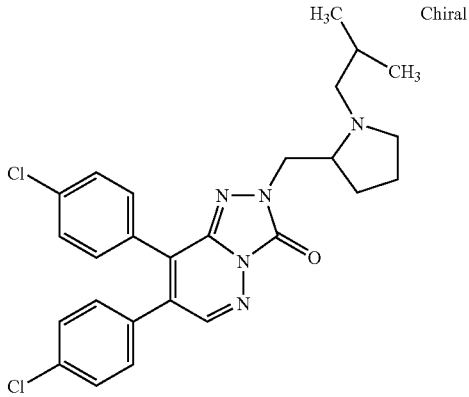 | 3.12[d] | 496 |

| Example Number | Structure | HPLC Retention Time (min) | Mass Specs Observed (M + H) |
|---|---|---|---|
| 224 | 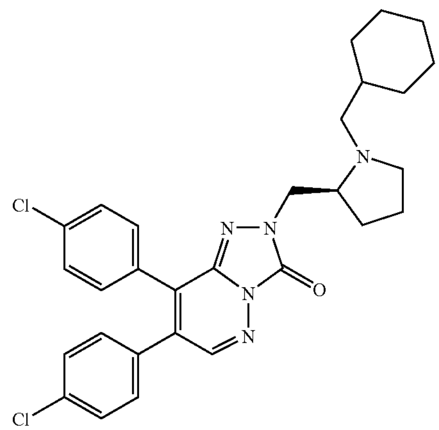 | 3.43[d] | 536 |
| 225 | 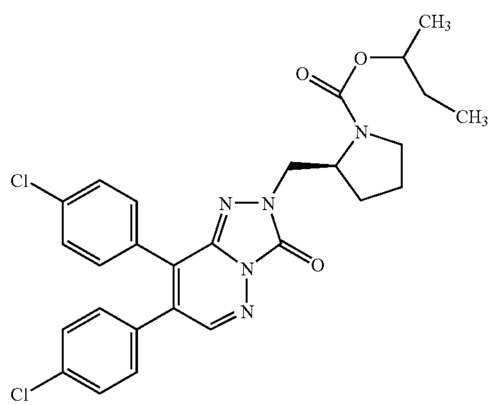 | 4.11[d] | 540 |
| 226 | Chiral | 3.14 | 546 |
| 227 | Chiral | 3.47[d] | 518 |

-continued

| Example Number | Structure | HPLC Retention Time (min) | Mass Specs Observed (M + H) |
|---|---|---|---|
| 228 | 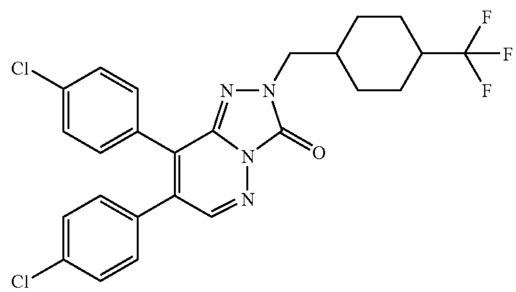 | 4.27[d] | 521 |
| 229 | 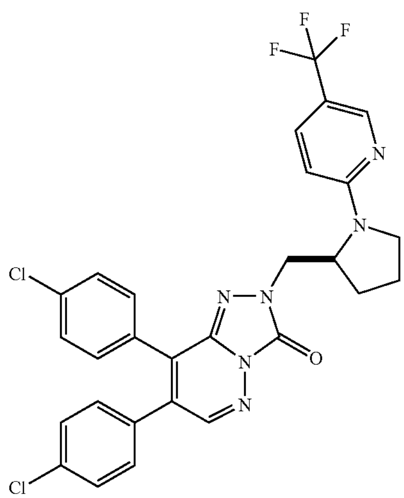 | 4.29[e] | 585 |
| 230 | Chiral | 3.24[d] | 530 |
| 231 | 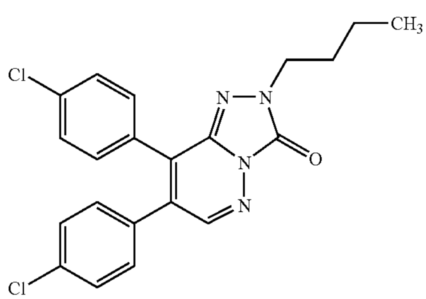 | 4.07[d] | 413 |

-continued

| Example Number | Structure | HPLC Retention Time (min) | Mass Specs Observed (M + H) |
|---|---|---|---|
| 232 | 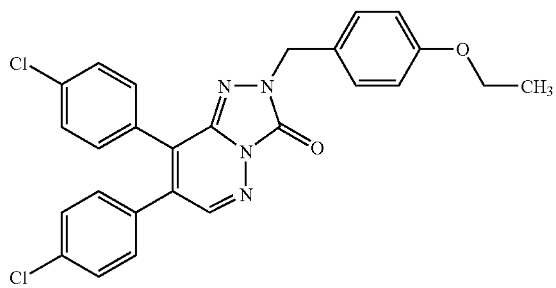 | 4.12[d] | 491 |
| 233 | 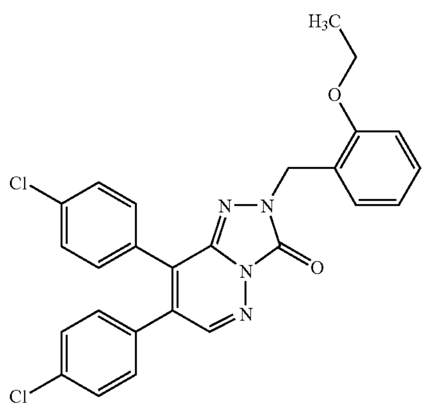 | 4.16[d] | 491 |
| 234 | 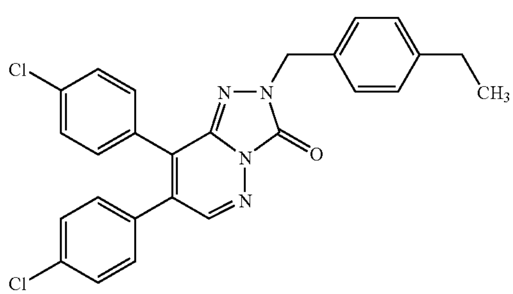 | 4.26[d] | 475 |
| 235 | 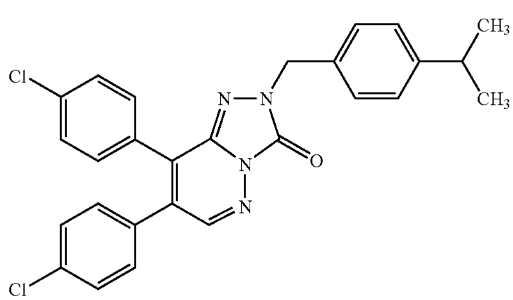 | 4.34[d] | 489 |

-continued
| Example Number | Structure | HPLC Retention Time (min) | Mass Specs Observed (M + H) |
|---|---|---|---|
| 236 | 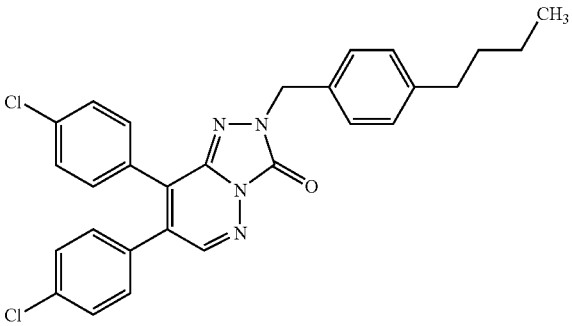 | 4.65[e] | 503 |
| 237 | 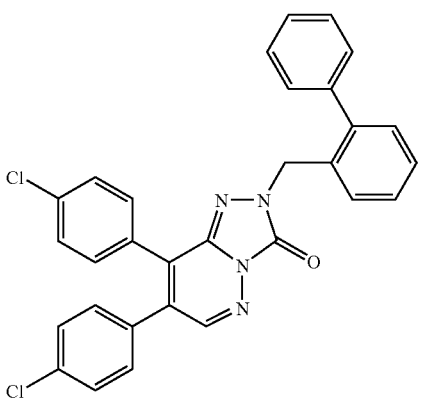 | 4.45[e] | 523 |
| 238 | 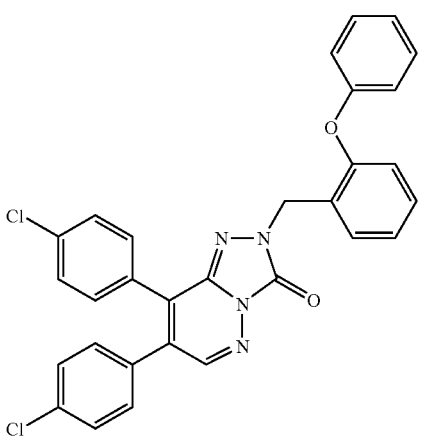 | 4.25[d] | 539 |
| 239 | 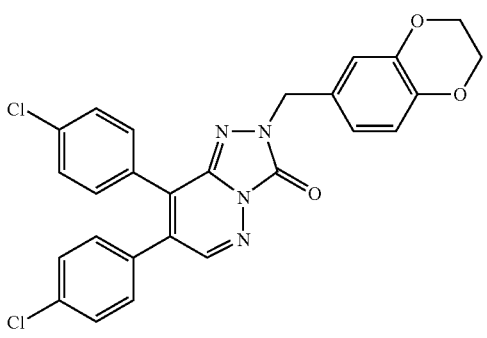 | 4.07[e] | 505 |

-continued

| Example Number | Structure | HPLC Retention Time (min) | Mass Specs Observed (M + H) |
|---|---|---|---|
| 240 | 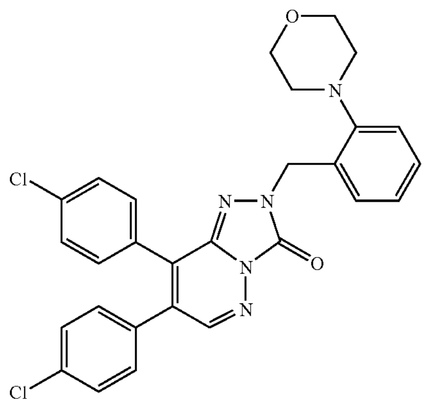 | 4.06[d] | 532 |
| 241 | 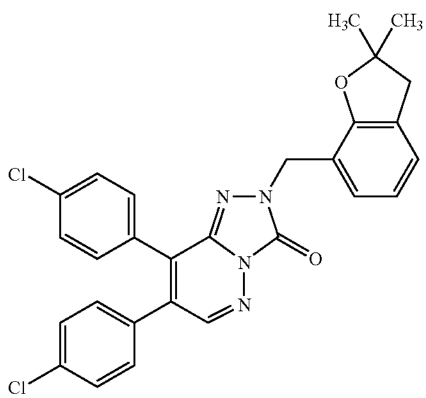 | 4.18[d] | 517 |
| 242 | 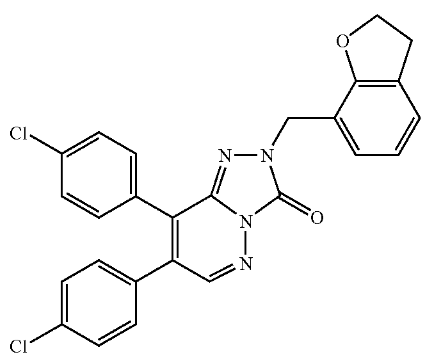 | 3.99[d] | 489 |
| 243 | 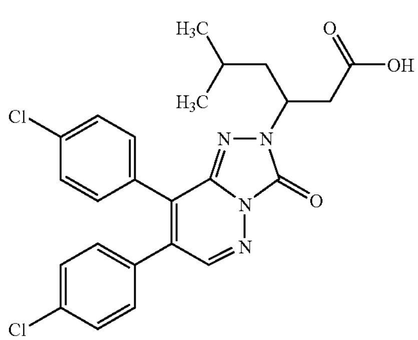 | 4.1 | 485 |

Example 244

Preparation of 7-(4-Chlorophenyl)-8-(pyridin-4-yl)-[1,2,4]triazolo[4,3-b]pyridazin-3(2H)-one

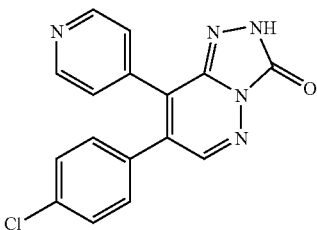

244A. Preparation of 2-benzyl-4,5-dichloropyridazin-3(2H)-one

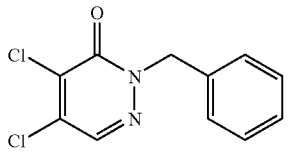

To a solution of dichloropyridazinone (50.0 g, 303.0 mmol) in DMF (200 mL) was added K₂CO₃ (50.3 g, 364.0 mmol) at RT under vigorous stirring. Benzylbromide (40.0 mL, 336.0 mmol) was added in rapid drops via a syringe. The resulting suspension was stirred at 50° C. for 1 h until all the pyridazinone was consumed as judged by HPLC. The reaction mixture was then poured into water (400 mL). The resultant suspension was stirred for 15 min at RT, and then filtered. The collected solid was rinsed thoroughly with water until no color was apparent in the filtrate. The solid was dried in a vacuum oven at 50° C. overnight to give the title compound, 2-benzyl-4,5-dichloropyridazin-3(2H)-one, (73.1 g, 95%) as pale yellow solid. HPLC: 3.17 min; MS, M+H=255.

244B. Preparation of 2-Benzyl-5-chloro-4-methoxypyridazin-3(2H)-one

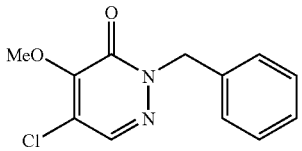

To a stirred solution of 2-benzyl-4,5-dichloropyridazin-3(2H)-one (73.1 g, 286.6 mmol) in 1,4-dioxane (700 mL) was added 25 wt. % solution of NaOMe in MeOH (72.0 mL, 315 mmol) at RT under argon over 15 min. The resultant dark reaction mixture was stirred at RT for 1.5 h. The solvent was evaporated and to the resultant residue was added water (500 mL). The aqueous mixture was extracted with methylene chloride (4×120 mL). The combined organic layers were washed with water (2×300 mL) and then by saturated aqueous NaCl (2×150 mL). The organic layer was dried over MgSO₄, filtered and concentrated to obtain the crude product. This crude product was purified by silica gel column chromatography eluting with 30% EtOAc/hexanes to give the title compound, 2-benzyl-5-chloro-4-methoxypyridazin-3(2H)-one (56.0 g, 78%) as pale yellow oil. HPLC: 3.19 min; MS, M+H=251. ¹H NMR (DMSO-d₆, 500 MHz): δ 8.05 (1H, s), 7.26-7.34 (5H, m), 5.24 (2H, s), 4.15 (3H, s).

244C. Preparation of 2-Benzyl-5-(4-chlorophenyl)-4-methoxypyridazin-3(2H)-one

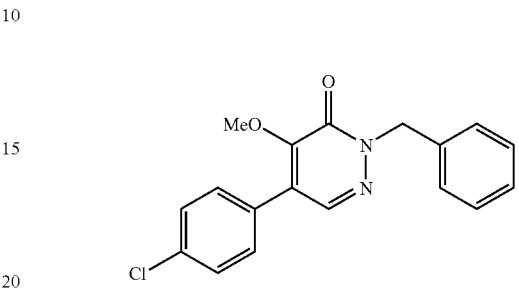

To a stirred solution of 2-benzyl-5-chloro-4-methoxypyridazin-3(2H)-one (20.0 g, 79.8 mmol) in toluene (500 mL) was added Pd(PPh₃)₄ (5.5 g, 4.76 mmol) under an atmosphere of argon. 4-Chlorophenylboronic acid (18.7 g, 119.6 mmol) was added subsequently. Under vigorous stirring, Na₂CO₃ (33.8 g, 318.9 mmol) pre-dissolved in water (90 mL) was added to the suspension. A stream of argon was bubbled through this suspension for 10 min. After this time, the flask was placed in an oil bath preheated at 120° C. The reaction was refluxed for 3 h. After this time, the reaction was cooled to RT The reaction mixture was then poured into water (200 mL). The layers were separated and the aqueous mixture was extracted with EtOAc (100 mL×3). The combined organic layers were washed with water (2×200 mL) followed by saturated aqueous NaCl (2×100 mL). The organic layer was then concentrated under reduced pressure to obtain crude product. This crude product was purified by silica gel column chromatography eluting with 8% EtOAc/hexanes to give the title compound, 2-benzyl-5-(4-chlorophenyl)-4-methoxypyridazin-3(2H)-one, (21.5 g, 82%) as a white solid. HPLC: 3.79 min; M+H=327. ¹H NMR (CDCl₃, 500 MHz): δ 7.76 (1H, s), 7.48 (2H, d, J=10.0 Hz), 7.40-7.45 (4H, m), 7.28-7.36 (3H, m), 5.35 (2H, s), 4.10 (3H, s).

244D. Preparation of 2-Benzyl-4-chloro-5-(4-chlorophenyl)pyridazin-3(2H)-one

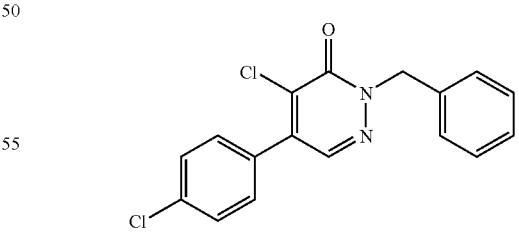

A mixture of 2-benzyl-5-(4-chlorophenyl)-4-methoxypyridazin-3(2H)-one (13.8 g, 42.23 mmol) and POCl₃ (20.0 mL) was stirred at 75° C. for 4 h. The reaction mixture was cooled to RT and concentrated under reduced pressure. The residue was cooled in an ice bath and water (200 mL) was added. The undissolved material was filtered and washed with water (3×150 mL). To the solid thus obtained was added MeOH (100 mL). The resultant mixture was sonicated for 10 mins, and then was filtered. The collected solid was washed with MeOH (2×50 mL). The solid was then dried in an vacuum oven at 50° C. to give the title compound, 2-benzyl-4-chloro-5-(4-chlorophenyl)pyridazin-3(2H)-one, (9.2 g, 66%) as a light brown solid. HPLC: 3.75 min; M+H=331. ¹H NMR (CDCl₃, 500 MHz): δ 7.73 (1H, s), 7.50 (2H, d, J=10.0 Hz), 7.47 (2H, d, J=10.0 Hz), 7.42 (2H, d, J=10.0 Hz), 7.30-7.38 (3H, m), 5.39 (2H, s).

244E. Preparation of 2-Benzyl-5-(4-chlorophenyl)-4-(pyridin-4-yl)pyridazin-3(2H)-one

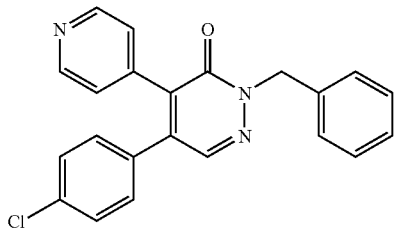

To a stirred solution of 2-benzyl-5-(4-chlorophenyl)-4-(pyridin-4-yl)pyridazin-3(2H)-one (7.0 g, 21.14 mmol) in toluene (140 mL) in a round bottomed flask was added Pd(PPh₃)₄ (1.5 g, 1.3 mmol) under a stream of argon. 4-(4,4,5,5-Tetramethyl-1,3,2-dixoborolan-2-yl)pyridine (5.63 g, 27.5 mmol) was added subsequently. Under vigorous stirring, Na₂CO₃ (9.2 g, 86.8 mmol) pre-dissolved in water (25 mL) was added to the suspension. A stream of argon was bubbled through reaction mixture for 10 min. The flask was then placed in an oil bath preheated at 120° C. The reaction was stirred at reflux for 48 h. After this time, the reaction mixture was cooled to RT and then poured into water (100 mL). The layers were separated. The aqueous layer was extracted with EtOAc (3×75 mL). The combined organic layers were washed with water (2×100 mL) followed by saturated aqueous NaCl (2×50 mL). The organic layer was concentrated under reduced pressure to obtain the crude product. This crude product was purified by silica gel column chromatography eluting with 40% EtOAc/hexanes to give the title compound, 2-benzyl-5-(4-chlorophenyl)-4-(pyridin-4-yl)pyridazin-3(2H)-one, (7.0 g, 89%) as a white solid. HPLC: 2.89 min; M+H=374. ¹H NMR (CDCl₃, 500 MHz): δ 8.50 (2H, d, J=5.0 Hz), 7.86 (1H, s), 7.52 (2H, d, J=10.0 Hz), 7.28-7.36 (3H, m), 7.24 (2H, d, J=10.0 Hz), 7.09 (2H, d, J=5.0 Hz), 7.00 (2H, J=10.0 Hz), 5.38 (2H, s).

244F. Preparation of 5-(4-Chlorophenyl)-4-(pyridin-4-yl)pyridazin-3(2H)-one

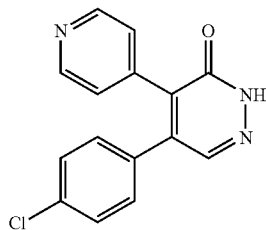

To a solution of 2-benzyl-5-(4-chlorophenyl)-4-(pyridin-4-yl)pyridazin-3(2H)-one (7.0 g, 18.73 mmol) in toluene (50 mL) in a round bottomed flask was added AlCl₃ (7.5 g, 56.25 mmol) under a stream of argon. The flask was placed in an oil bath preheated at 80° C. After 2 hours, the reaction mixture was cooled to RT and then poured into crushed ice (200 g). The precipitate formed was collected by filtration, washed with water (2×50 mL) followed by ether (50 mL) and dried in a vacuum oven at 40° C. to give the title compound, 5-(4-chlorophenyl)-4-(pyridin-4-yl)pyridazin-3(2H)-one (5.1 g, 96%) as a white solid. HPLC: 1.37 min; MS, M+H=284.

244G. Preparation of 3-Chloro-5-(4-chlorophenyl)-4-(pyridin-4-yl)pyridazine

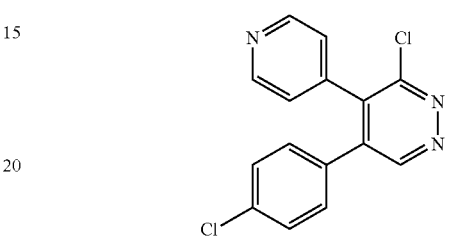

A mixture of 5-(4-chlorophenyl)-4-(pyridin-4-yl)pyridazin-3(2H)-one (5.1 g, 18.0 mmol) and POCl₃ (20 mL) was stirred at 80° C. for 2 h. The reaction mixture was cooled to RT and the POCl₃ was removed by rotary evaporator to obtain a gum. This gum was cooled in an ice bath and water (50 mL) was added. The pH of this mixture was adjusted to 6 with aqueous NaHCO₃. The resulting mixture was extracted with EtOAc (2×75 mL). The combined organic layers were washed with water (2×50 mL) followed by saturated aqueous NaCl (2×25 mL). The organic layer was dried over MgSO₄ and filtered through a silica gel pad (~20 g). Upon evaporation of the solvents under reduced pressure, the title compound, 3-chloro-5-(4-chlorophenyl)-4-(pyridin-4-yl)pyridazine, (5.1 g, 94%) was obtained as a white solid. HPLC: 2.01 min; MS, M+H=302. ¹H NMR (CDCl₃, 500 MHz): δ 9.08 (1H, s), 8.56 (2H, d, J=5.0 Hz), 7.21 (2H, d, J=10.0 Hz), 7.09 (2H, d, J=5.0 Hz), 7.01 (2H, J=10.0 Hz).

244H. Preparation of 1-(5-(4-Chlorophenyl)-4-(pyridin-4-yl)pyridazin-3-yl)hydrazine

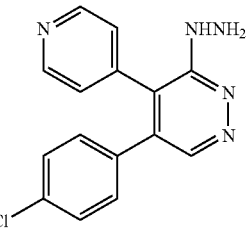

3-Chloro-5-(4-chlorophenyl)-4-(pyridin-4-yl)pyridazine (5.1 g, 16.9 mmol) was dissolved in pyridine (20 mL) and hydrazine mono-hydrate (17.0 mL, 350.5 mmol) was added. The reaction mixture was stirred at reflux for 40 min. After this time, the reaction mixture was cooled to RT and then concentrated to half of the original volume under reduced pressure. The resultant mixture was diluted with water (100 mL). The yellow colored solid was collected by filtration and rinsed thoroughly with water. The solid was dried in a vacuum oven at 40° C. to give the title compound, 1-(5-(4- chlorophenyl)-4-(pyridin-4-yl)pyridazin-3-yl)hydrazine, (4.4 g, 88%) as a yellow powder. HPLC: 1.01 min; MS, M+H=298.

2441. Preparation of 7-(4-Chlorophenyl)-8-(pyridin-4-yl)-[1,2,4]triazolo[4,3-b]pyridazin-3(2H)-one

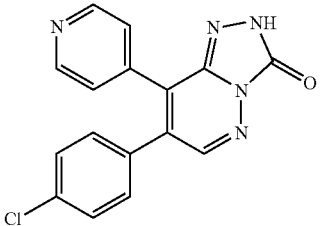

To a THF (100 mL) solution of carbonyldiimidazole (CDI) (7.25 g, 44.71 mmol) was added 1-(5-(4-chlorophenyl)-4-(pyridin-4-yl)pyridazin-3-yl)hydrazine (3.8 g, 12.76 mmol) portionwise at RT under an atmosphere of argon. The reaction mixture was heated to reflux for 30 min. After this time, the reaction mixture was cooled to RT, and subsequently concentrated under reduced pressure to obtain a gum to which water (100 mL) was added. The resulting solid was collected by filtration, washed with water (2×50 mL) followed by 1:1 (v/v) of hexanes/ether (2×50 mL) to give the title compound, 7-(4-chlorophenyl)-8-(pyridin-4-yl)-[1,2,4]triazolo[4,3-b]pyridazin-3(2H)-one (3.75 g, 91%) as yellow solid. HPLC: 1.67 min; MS, M+H=324; $^1$H NMR (DMSO-$d_6$) δ 12.90 (1H, s), 8.59 (2H, d, J=10.0 Hz), 8.41 (1H, s), 7.44 (2H, d, J=10.0 Hz), 7.32 (2H, d, J=5.0 Hz), 7.28 (2H, d, J=5.0 Hz).

Example 245

Preparation of 7-(4-Chlorophenyl)-2-((6-chloropyridin-3-yl)methyl)-8-(pyridin-4-yl)-[1,2,4]triazolo[4,3-b]pyridazin-3(2H)-one

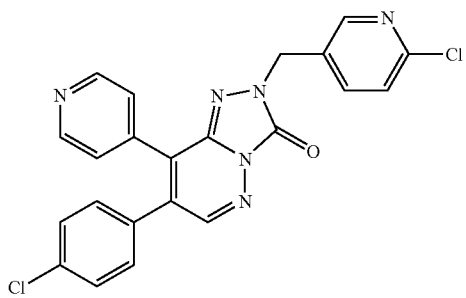

To a solution of 7-(4-chlorophenyl)-8-(pyridin-4-yl)-[1,2,4]triazolo[4,3-b]pyridazin-3(2H)-one (150 mg, 0.46 mmol), prepared as described in Example 244, in DMF (3 mL) was added $K_2CO_3$ (80 mg, 0.58 mmol) and 2-chloro-5-(chloromethyl)pyridine (90 mg, 0.556 mmol). The reaction mixture was stirred at 70° C. for 15 min. After this time, the solution was cooled to RT and diluted with water (20 mL). The resulting solid was collected by filtration and the crude product was purified by reverse phase HPLC to give the title compound, 7-(4-chlorophenyl)-2-((6-chloropyridin-3-yl)methyl)-8-(pyridin-4-yl)-[1,2,4]triazolo[4,3-b]pyridazin-3 (2H)-one, (110 mg, 52%), as a yellow solid. HPLC: 2.61 min; MS, M+H=449; $^1$H NMR (CDCl$_3$) δ 8.62 (2H, d, J=5.0 Hz), 8.43 (1H, d, J=5.0 Hz), 8.19 (1H, s), 7.33 (1H, d, J=5.0 Hz), 7.29-7.31 (3H, m), 7.20 (2H, d, J=5.0 Hz), 7.08 (2H, d, J=10.0 Hz), 5.17 (2H, s).

Example 246

Preparation of 7-(4-Chlorophenyl)-2-((6-(dimethylamino)pyridin-3-yl)methyl)-8-(pyridin-4-yl)-[1,2,4]triazolo[4,3-b]pyridazin-3(2H)-one

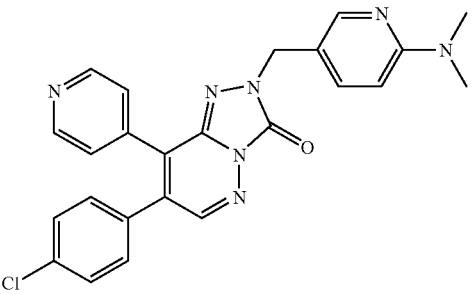

A mixture of 7-(4-chlorophenyl)-2-((6-(chloro)pyridin-3-yl)methyl)-8-(pyridin-4-yl)-[1,2,4]triazolo[4,3-b]pyridazin-3(2H)-one (30 mg, 0.0667 mmol), prepared as described in Example 245, and N,N-dimethyl amine in water (1.0 mL) was heated to reflux. After 8 h, the solution was cooled to RT. The reaction mixture was concentrated under reduced pressure. The reside was purified by reverse phase HPLC to give the title compound, 7-(4-chlorophenyl)-2-((6-(dimethylamino)pyridin-3-yl)methyl)-8-(pyridin-4-yl)-[1,2,4]triazolo[4,3-b]pyridazin-3(2H)-one, (17.5 mg, 57%) as a yellow solid. HPLC: 1.41 min; M+H=458; $^1$H NMR (CDCl$_3$) δ 8.63 (2H, d, J=5.0 hz), 8.23 (1H, d, J=5.0 Hz), 8.17 (1H, s), 7.58 (1H, d, J=10.0 Hz), 7.33 (2H, d, J=10.0 Hz), 7.23 (2H, d, J=5.0 Hz), 7.09 (2H, d, J=10.0 Hz), 6.47 (1H, d, J=10.0 Hz), 5.08 (2H, s), 3.07 (6H, s).

Example 247

Preparation of 7-(4-Chlorophenyl)-8-(pyridin-4-yl)-2-((6-(trifluoromethyl)pyridin-3-yl)methyl)-[1,2,4]triazolo[4,3-b]pyridazin-3(2H)-one

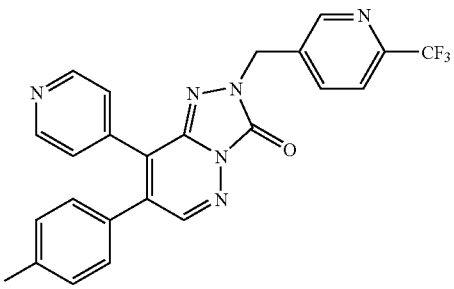

A solution of 7-(4-chlorophenyl)-8-(pyridin-4-yl)-[1,2,4]triazolo[4,3-b]pyridazin-3(2H)-one (1.1 g, 3.4 mmol), prepared as described in Example 244, $K_2CO_3$ (940 mg, 6.8 mmol), and 5-chloromethyl-2-trifluoromethylpyridine (800 mg, 4.1 mmol) in DMF (8.3 mL) was heated at 65° C. for 40 min. After this time, the solution was cooled to RT The reaction mixture was partitioned between water and EtOAc. The organic layer separated, washed with water and saturated aqueous NaCl. The organic layer was dried over magnesium sulfate, filtered and concentrated under reduced pressure. The crude product was purified by silica gel column chromatography eluting with hexanes/EtOAc to give the title compound, 7-(4-chlorophenyl)-8-(pyridin-4-yl)-2-((6-(trifluoromethyl)pyridin-3-yl)methyl)-[1,2,4]triazolo[4,3-b]pyridazin-3(2H)-one, (1.25 g, 76%) as a yellow solid. HPLC: 2.84 min; MS, M+H=483; $^1$H NMR (CDCl$_3$) δ 8.80 (d, J=1.4 Hz, 1H), 8.65 (Abq, J=1.6, 4.4 Hz, 2H), 8.23 (s, 1H), 7.96 (m, 1H), 7.68 (d, J=8.3 Hz, 1H), 7.34 (m, 2H), 7.23 (m, 2H), 7.10 (m, 2H), 5.31 (2H).

Example 248

Preparation of 7-(4-chlorophenyl)-8-(pyridin-4-yl)-2-((5-(trifluoromethyl)pyridin-2-yl)methyl)-[1,2,4]triazolo[4,3-b]pyridazin-3(2H)-one

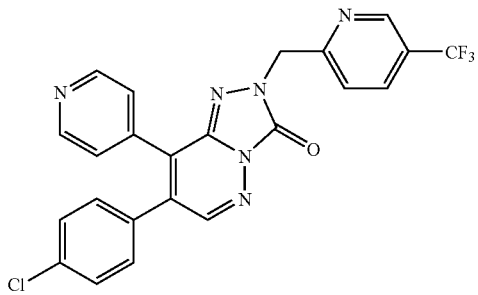

A solution of 7-(4-chlorophenyl)-8-(pyridin-4-yl)-[1,2,4]triazolo[4,3-b]pyridazin-3(2H)-one (32.4 mg, 0.1 mmol), prepared as described in Example 244, K$_2$CO$_3$ (56 mg, 0.4 mmol), and 2-chloromethyl-5-trifluoromethylpyridine hydrochloride (37 mg, 0.4 mmol) in DMF (0.4 mL) was heated at 65° C. for 2 h. Using a similar procedure as described in Example 247, the crude product was obtained. The crude product was purified by reverse phase HPLC to give the title compound, 7-(4-chlorophenyl)-8-(pyridin-4-yl)-2-((5-(trifluoromethyl)pyridin-2-yl)methyl)-[1,2,4]triazolo[4,3-b]pyridazin-3(2H)-one, (27 mg) as a yellow solid. HPLC RT: 2.78 min; M+H=483; $^1$H NMR (CDCl$_3$): δ 8.82 (s, 1H), 8.62 (m, 2H), 8.24 (s, 1H), 7.91 (m, 1H), 7.38-7.10 (m, 7H), 5.45 (2H).

Example 249

Preparation of 4-((7-(4-Chlorophenyl)-3-oxo-8-(pyridin-4-yl)-[1,2,4]triazolo[4,3-b]pyridazin-2(3H)-yl)methyl)benzonitrile

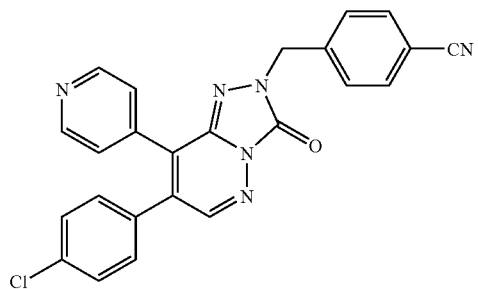

A solution of 7-(4-chlorophenyl)-8-(pyridin-4-yl)-[1,2,4]triazolo[4,3-b]pyridazin-3(2H)-one (96 mg, 0.3 mmol), prepared as described in Example 244, K$_2$CO$_3$ (82 mg, 0.59 mmol), and α-bromo-p-toluonitrile (70 mg, 0.356 mmol) in DMF (1 mL) was heated at 65° C. for 2.5 h. Using a similar procedure as described in Example 247, the crude product was obtained. The crude product was purified by reverse phase HPLC to give the title compound, 4-((7-(4-Chlorophenyl)-3-oxo-8-(pyridin-4-yl)-[1,2,4]triazolo[4,3-b]pyridazin-2(3H)-yl)methyl)benzonitrile (27 mg) as a yellow solid. HPLC RT: 2.45 min; M+H=439; $^1$H NMR (CDCl$_3$): δ 8.63 (d, J=6.04 Hz, 2H), 8.21 (s, 1H), 7.63 (d, J=8.2 Hz, 2H), 7.49 (d, J=8.2 Hz, 2H), 7.33 (m, 2H), 7.21 (m, 2H), 7.08 (m, 2H), 5.25 (2H).

Example 250

Preparation of 2-(4-(Isoxazol-5-yl)benzyl)-7-(4-chlorophenyl)-8-(pyridin-4-yl)-[1,2,4]triazolo[4,3-b]pyridazin-3(2H)-one

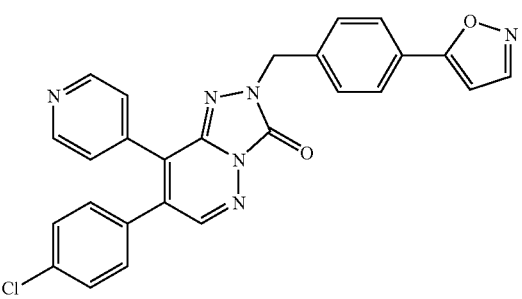

250A. Preparation of 5-(4-(bromomethyl)phenyl)isoxazole

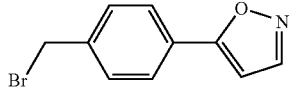

To a solution of 5-(4-methylphenyl)isoxazole (4.0 g, 25.13 mmol) in carbon tetrachloride (125 mL), N-bromosuccinimide (4.47 g, 25.13 mmol) and benzoyl peroxide (0.12 g, 0.50 mmol) were added. The resulting mixture refluxed for 1 h. After this time, the raction mixture was then cooled to room temperature and filtered. The filtrate was concentrated and the residue was purified by silica gel chromatography eluting with hexanes/EtOAc to give the title compound, 5-(4-(bromomethyl)phenyl)isoxazole, 4.2 g as an off-white solid. $^1$H NMR (CDCl$_3$): δ 8.30 (d, J=2.2 Hz, 1H), 7.78 (d, J=8.3 Hz, 2H), 7.50 (d, J=8.3 Hz, 2H), 6.54 (d, J=1.7 Hz, 1H), 4.51 (s, 2H).

250b. Preparation of 2-(4-(Isoxazol-5-yl)benzyl)-7-(4-chlorophenyl)-8-(pyridin-4-yl)-[1,2,4]triazolo[4,3-b]pyridazin-3(2H)-one

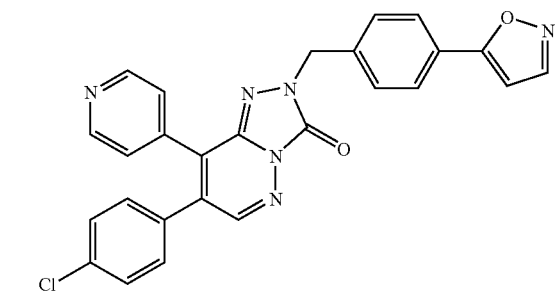

A solution of 7-(4-chlorophenyl)-8-(pyridin-4-yl)-[1,2,4]triazolo[4,3-b]pyridazin-3(2H)-one (3.0 g, 9.27 mmol), prepared as described in Example 244, K₂CO₃ (2.56 g, 18.53 mmol) and 5-(4-(bromomethyl)phenyl)isoxazole (2.65 g, 11.12 mmol), in DMF (23 mL), were added. The resulting mixture was heated to 60° C. After 2 h, the reaction mixture was cooled to RT and partitioned between water and EtOAc. The organic layer was separated and the aqueous layer was extracted with EtOAc (2×200 mL). The combined organic extracts were dried over magnesium sulfate, filtered and concentrated. The residue was purified by silica gel column chromatography using hexanes/EtOAc 1:10 to give the title compound, 2-(4-(isoxazol-5-yl)benzyl)-7-(4-chlorophenyl)-8-(pyridin-4-yl)-[1,2,4]triazolo[4,3-b]pyridazin-3(2H)-one, as a light yellow solid. HPLC RT: 2.64 min; MS, M+H=481; ¹H NMR (CDCl₃): δ 8.62-8.64 (m, 2H), 8.29 (d, J=1.8 Hz, 1H), 8.20 (s, 1H), 7.77 (d, J=8.4 Hz, 2H), 7.51 (d, J=8.4 Hz, 2H), 7.33 (d, J=8.4 Hz, 2H), 7.22 (m, 2H), 7.09 (d, J=8.4 Hz, 2H), 6.51 (d, J=1.6 Hz, 1H), 5.25 (s, 2H).

Example 251

Preparation of 2-(4-(Isoxazol-3-yl)benzyl)-7-(4-chlorophenyl)-8-(pyridin-4-yl)-[1,2,4]triazolo[4,3-b]pyridazin-3(2H)-one

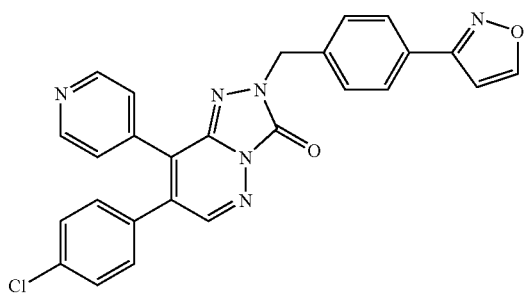

251A. Preparation of 3-(4-(Bromomethyl)phenyl)isoxazole

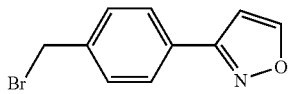

To a solution of 3-(4-methylphenyl)isoxazole (prepared using literature methods) (1.95 g, 12.25 mmol) in carbon tetrachloride (60 mL), N-bromosuccinimide (2.18 g, 12.25 mmol) and benzoyl peroxide (0.059 g, 0.245 mmol) were added and the mixture refluxed for 1 h. The reaction mixture was then cooled to room temperature and filtered. The filtrate was concentrated and the residue was purified by silica gel column chromatography eluting with hexanes/EtOAc to give the title compound, 3-(4-(bromomethyl)phenyl)isoxazole, (0.6 g) as a white solid. ¹H NMR (CDCl₃): δ 8.48 (d, J=1.6 Hz, 1H), 7.83 (d, J=8.2 Hz, 2H), 7.50 (d, J=8.2 Hz, 2H), 6.67 (d, J=1.6 Hz, 1H), 4.53 (s, 2H).

251B. Preparation of 2-(4-(Isoxazol-3-yl)benzyl)-7-(4-chlorophenyl)-8-(pyridin-4-yl)-[1,2,4]triazolo[4,3-b]pyridazin-3(2H)-one

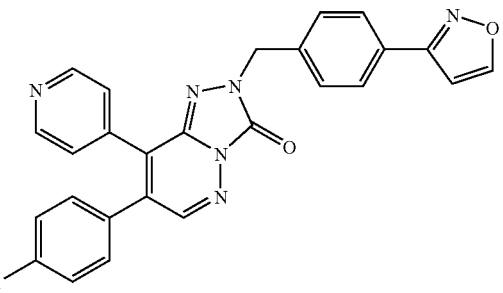

To a solution of 7-(4-chlorophenyl)-8-(pyridin-4-yl)-[1,2,4]triazolo[4,3-b]pyridazin-3(2H)-one (0.27 g, 0.834 mmol), prepared as described in Example 244, in DMF (4 mL), potassium carbonate (0.23 g, 1.67 mmol) and 3-(4-(bromomethyl)phenyl)isoxazole (0.248 g, 1.04 mmol) were added. The resulting mixture was heated to 65° C. After 2 h, the reaction mixture was then cooled to RT and diluted with EtOAc (200 mL). The resultant solution was then washed with water and saturated aqueous NaCl. The organic layer was dried over magnesium sulfate, filtered and concentrated under reduced pressure. The residue was purified by column chromatography eluting with hexanes/EtOAc to give the title compound, 2-(4-(isoxazol-3-yl)benzyl)-7-(4-chlorophenyl)-8-(pyridin-4-yl)-[1,2,4]triazolo[4,3-b]pyridazin-3(2H)-one, as a light yellow solid. HPLC RT: 2.60 min; ¹H NMR (CDCl₃): δ 8.64 (d, J=1.1 Hz, 1H), 8.63 (d, J=1.7 Hz, 1H), 8.45 (d, J=1.7 Hz, 1H), 8.20 (s, 1H), 7.80 (d, J=8.2 Hz, 2H), 7.50 (d, J=8.2 Hz, 2H), 7.34 (m, 2H), 7.23 (m, 2H), 7.10 (m, 2H), 6.65 (d, J=2.2 Hz, 1H), 5.26 (s, 2H).

Examples 252 to 272

The following Examples were prepared according to methods and procedures above:

| Example Number | Structure | HPLC Retention Time (min) | Mass Specs Observed (M + H) |
| --- | --- | --- | --- |
| 252 | 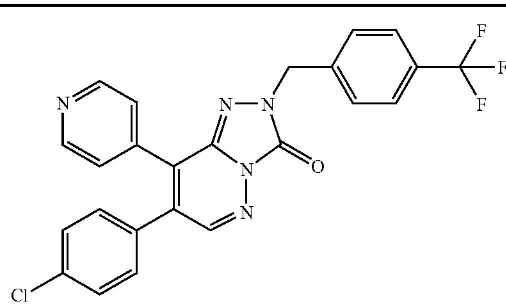 | 3.28 | 482 |

-continued

| Example Number | Structure | HPLC Retention Time (min) | Mass Specs Observed (M + H) |
|---|---|---|---|
| 253 | 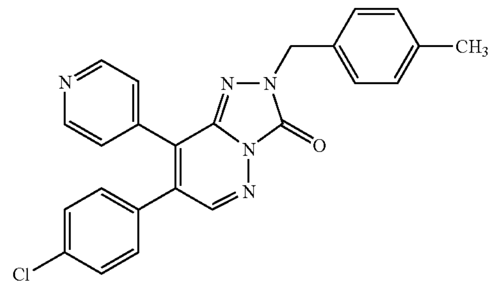 | 2.94 | 423 |
| 254 | 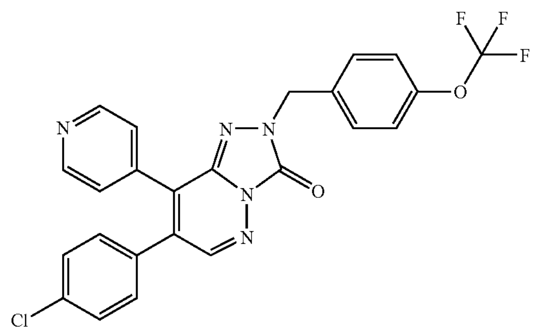 | 3.34 | 498 |
| 255 | 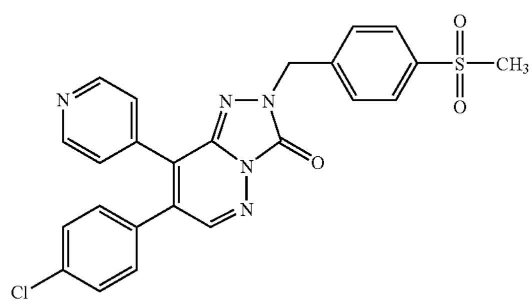 | 2.12 | 492 |
| 256 | 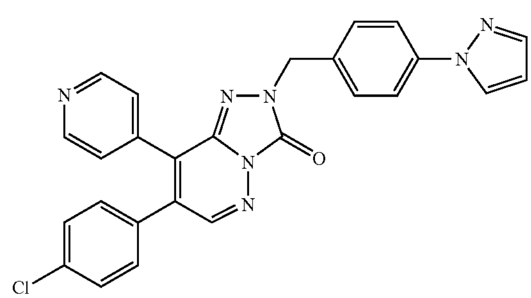 | 2.64 | 480 |
| 257 | 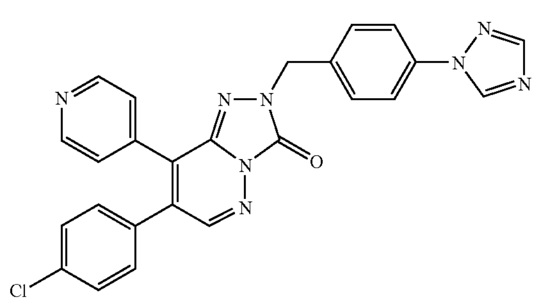 | 2.37 | 481 |

-continued

| Example Number | Structure | HPLC Retention Time (min) | Mass Specs Observed (M + H) |
|---|---|---|---|
| 258 | 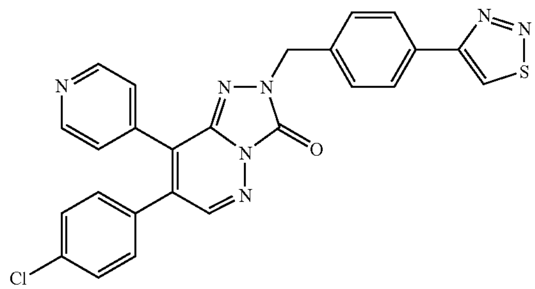 | 2.68 | 498 |
| 259 | 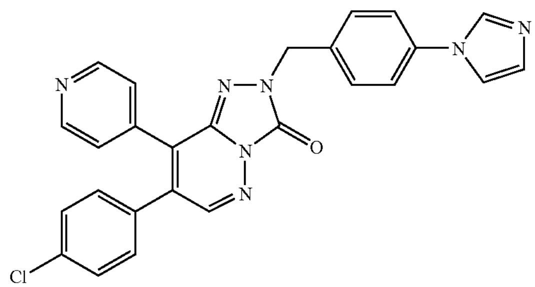 | 1.64 | 480 |
| 260 | 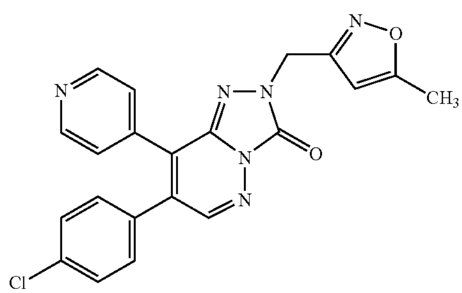 | 2.23 | 419 |
| 261 | 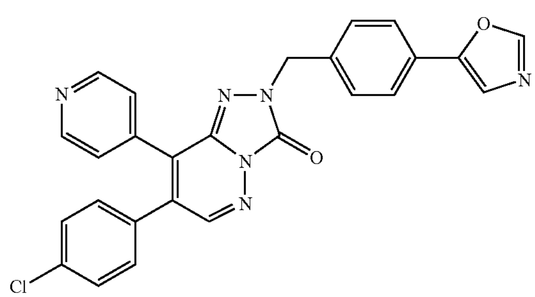 | 2.63 | 481 |
| 262 | 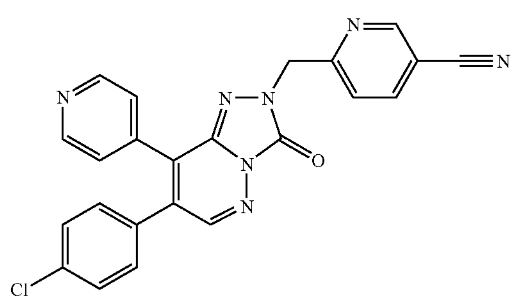 | 1.99 | 440 |

-continued

| Example Number | Structure | HPLC Retention Time (min) | Mass Specs Observed (M + H) |
|---|---|---|---|
| 263 | 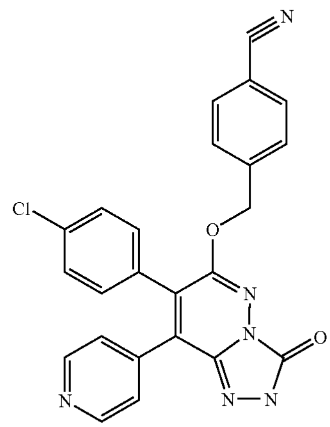 | 2.89 | 454 |
| 264 | 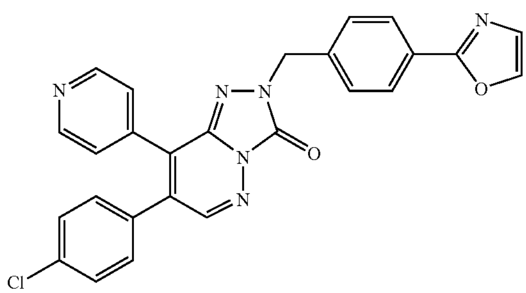 | 2.68 | 481 |
| 265 | 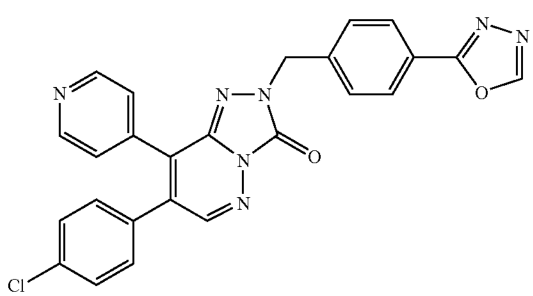 | 2.29 | 482 |
| 266 | 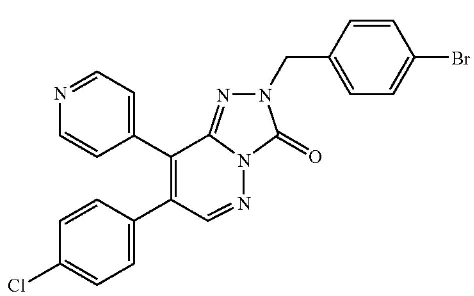 | 3.32 | 492 |

-continued

| Example Number | Structure | HPLC Retention Time (min) | Mass Specs Observed (M + H) |
|---|---|---|---|
| 267 | 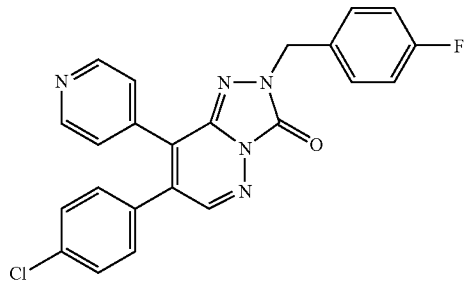 | 2.96 | 432 |
| 268 | 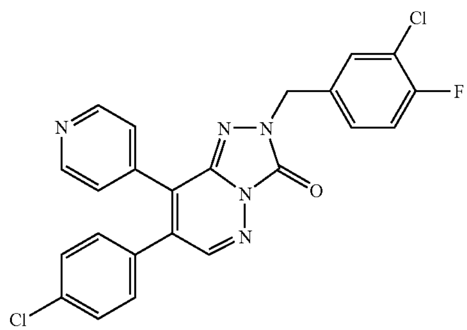 | 3.31 | 466 |
| 269 | 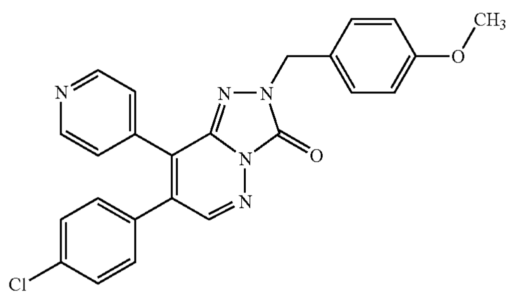 | 2.72 | 444 |
| 270 | 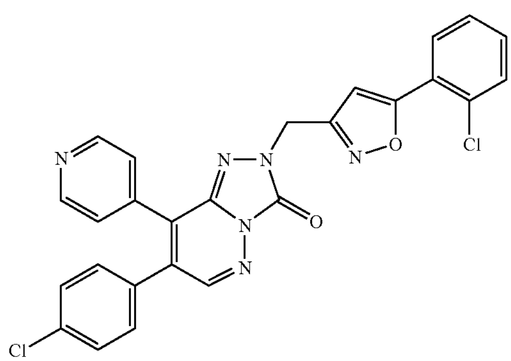 | 3.33 | 515 |
| 271 | 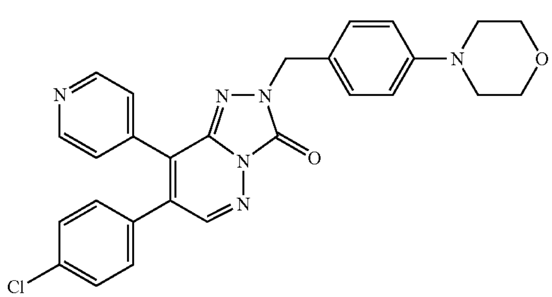 | 2.58 | 499 |

| Example Number | Structure | HPLC Retention Time (min) | Mass Specs Observed (M + H) |
| --- | --- | --- | --- |
| 272 | 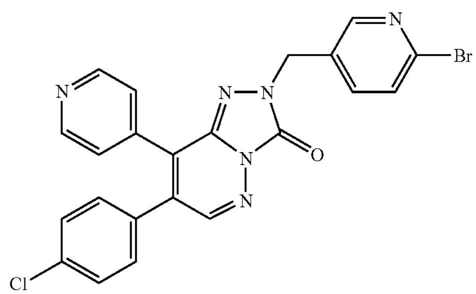 | 2.73 | 493 |

Example 273

Preparation of 2-(4-(Trifluoromethyl)benzyl)-7-chloro-8-(4-chlorophenyl)-[1,2,4]triazolo[4,3-b]pyridazin-3(2H)-one 273A. Preparation of 2-Benzyl-5-chloro-4-(4-chlorophenyl)pyridazin-3(2H)-one

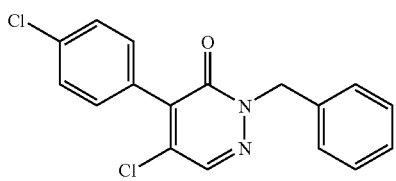

To a mixture of 2-benzyl-4,5-dichloropyridazin-3(2H)-one (30.6 g, 120 mmol), prepared as described in Example 244A, 4-chlorophenyl boronic acid (20.6 g, 132 mmol) and tetrakis(triphenylphosphine)palladium (5 g, 4.3 mmol) in toluene (300 mL) under an atmosphere of argon, and was added an aqueous Na₂CO₃ solution (2M, 66 mL, 132 mmol). The reaction mixture was stirred at 100° C. under argon for 16 h. The reaction was then allowed to cool to RT and was subsequently poured into water (200 mL). The resulting mixture was extracted with EtOAc (3×150 mL). The combined organic layers were washed with saturated aqueous NaCl. The organic layer was dried over Na₂SO₄, filtered and concentrated under reduced pressure. The obtained thick syrup was dissolved in MeOH (100 mL) and the resulting solution kept at 0° C. until white solid precipitated. The solid was collected by filtration, washed with hexanes, and then triturated with EtOAc-hexanes to give the title compound, 2-benzyl-5-chloro-4-(4-chlorophenyl)pyridazin-3(2H)-one (12 g, 30%) as a white powder. LC/MS (method A, general procedure): RT=3.81 min, (M+H)⁺=331.

273B. Preparation of 5-Chloro-4-(4-chlorophenyl)pyridazin-3(2H)-one

To a solution of 2-benzyl-5-chloro-4-(4-chlorophenyl)pyridazin-3(2H)-one (10.2 gm, 30.8 mmol) in toluene (154 mL) was added aluminum chloride (10.3 g, 77 mmol). The mixture was stirred at 50° C. for 1 h. After this time, the solution was cooled to RT, and the reaction mixture was poured into water (200 mL). The reaction mixture was extracted with EtOAc (3×100 mL). The combined organic layers were washed with saturated NaCl. The organic layer was dried (Na₂SO₄), filtered and concentrated. The resulting residue was triturated with EtOAc-hexane to give the title compound, 5-chloro-4-(4-chlorophenyl)pyridazin-3(2H)-one as an off-white solid (6.8 g, 92%). LC/MS (method A): RT=2.91 min, (M+H)⁺=241;

273C. Preparation of 3,5-Dichloro-4-(4-chlorophenyl)pyridazine

A suspension of 5-chloro-4-(4-chlorophenyl)pyridazin-3(2H)-one, (6.8 g, 28.2 mmol) in POCl₃ (14 mL) was heated at 100° C. for 1 h. After this time, the reaction mixture was cooled to RT The reaction mixture was then concentrated under reduced pressure. The residue was partitioned between EtOAc and water. The aqueous layer was extracted with EtOAc (2×100 mL). The combined organic layers were washed with saturated aqueous NaHCO₃ and saturated aqueous NaCl. The organic layer was dried (Na₂SO₄), filtered and concentrated to give the title compound, 3,5-dichloro-4-(4-chlorophenyl)pyridazine as an off-white solid (6.9 g, 96%). LC/MS (method A): RT=3.20 min, (M+H)⁺=259.

273D. Preparation of 1-(5-Chloro-4-(4-chlorophenyl)pyridazin-3-yl)hydrazine

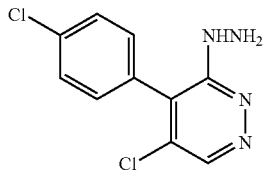

To a solution of 3,5-dichloro-4-(4-chlorophenyl)pyridazine (2.56 g, 10 mmol) in dioxane (36 mL) at RT was added hydrazine (3.2 mL, 100 mL). After addition, the reaction was heated to 70° C. for 2 h. After cooling to RT, the reaction was concentrated under reduced pressure. To the obtained residue was added 2-propanol (80 mL) and the resulting white solid was removed by filtration. The collected liquid was concentrated under reduced pressure to give the title compound 1-(5-chloro-4-(4-chlorophenyl)pyridazin-3-yl)hydrazine as an off-white solid (560 mg, 22%) which contained 15% of by-product (1-(3-chloro-4-(4-chlorophenyl)pyridazin-5-yl)hydrazine). The mixture was used directly in the next step, 273E. LC/MS (method A): RT=1.89 min, (M+H)⁺=255.

273E. Preparation of 7-Chloro-8-(4-chlorophenyl)-[1,2,4]triazolo[4,3-b]pyridazin-3(2H)-one

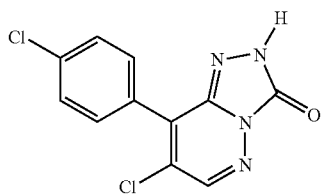

To a solution of 1,1'-carbonyldiimidazole (1.78 g, 11 mmol) in THF (10 mL) at RT was added a suspension of 1-(5-chloro-4-(4-chlorophenyl)pyridazin-3-yl)hydrazine (560 mg, 2.19 mmol) in THF (10 mL). After addition, the reaction became a clear solution and was stirred at RT for 1 h. The reaction mixture was then poured into water and extracted with EtOAc (3×50 mL). The combined organic layers were washed with saturated NaCl. The organic layer was dried (Na₂SO₄), filtered and concentrated. To the obtained residue was added EtOAc (20 mL), and the resulting yellow precipitate was collected by filtration and washed with hexane to give the title compound, 7-chloro-8-(4-chlorophenyl)-[1,2,4]triazolo[4,3-b]pyridazin-3(2H)-one as a yellow solid (300 mg, 61%). LC/MS (method A): RT=2.86 min, (M+H)⁺=281.

Example 274

Preparation of 2-(4-Trifluoromethyl)benzyl)-7-chloro-8-(4-chlorophenyl)-[1,2,4]triazolo[4,3-b]pyridazin-3(2H)-one

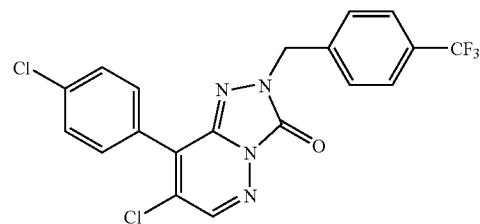

To a solution of 7-chloro-8-(4-chlorophenyl)-[1,2,4]triazolo[4,3-b]pyridazin-3(2H)-one (86.4 mg, 0.31 mmol), prepared as described in Example 273, in DMF (1 mL) at RT was added 4-trifluoromethylbenzyl bromide (112 mg, 0.47 mmol), followed by K₂CO₃ (86 mg, 0.62 mmol). The reaction mixture was heated to 50° C. for 1 h. After this time, the reaction mixture was cooled to RT The reaction mixture was poured into water (30 mL), and the resultant mixture was extracted with EtOAc (3×20 mL). The combined organic layers were washed with saturated NaCl. The organic layer was dried (Na₂SO₄), filtered and concentrated. The resulting residue was purified by silica gel (12 g) column chromatography eluting with a gradient of EtOAc (0-60%) in hexane to give the title compound, 2-(4-trifluoromethyl)benzyl)-7-chloro-8-(4-chlorophenyl)-[1,2,4]triazolo[4,3-b]pyridazin-3(2H)-one as a yellow solid (100 mg, 74%). HPLC: 99% at 7.76 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min. UV detection at 220 nm). MS (ES): m/z 439 [M+H]⁺; ¹H NMR (DMSO-d₆, 400 MHz): δ 5.25 (s, 2H), 7.49 (d, J=8 Hz, 2H), 7.65 (S, 4H), 7.70 (d, J=8 Hz, 2H), 8.53 (s, 1H).

Example 275

Preparation of 2-(4-(Trifluoromethyl)benzyl)-8-(4-chlorophenyl)-7-phenoxy-[1,2,4]triazolo[4,3-b]pyridazin-3(2H)-one

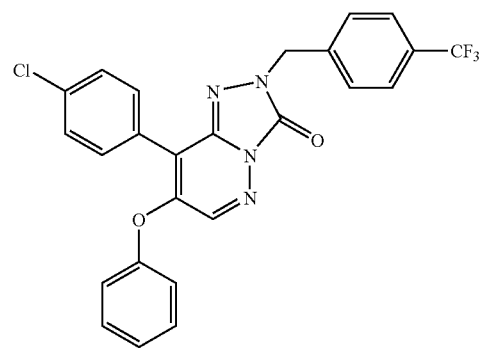

To a solution of 2-(4-(trifluoromethyl)benzyl)-8-(4-chlorophenyl)-7-chloro-[1,2,4]triazolo[4,3-b]pyridazin-3(2H)-one (17 mg, 0.039 mmol), prepared as described in Example 274 in DMF (0.5 mL) was added phenol (7.2 mg, 0.077 mmol), followed by K₂CO₃ (11 mg, 0.077 mmol). The reaction mixture was stirred at RT for 16 h, and then diluted with 1M aqueous NaOH (3 mL). A yellow precipitate was formed. The solid was collected by filtration and washed thoroughly with H₂O. The crude product was purified by reverse phase HPLC to give the title compound, 2-(4-trifluoromethyl)benzyl)-8-(4-chlorophenyl)-7-phenoxy-[1,2,4]triazolo[4,3-b]pyridazin-3(2H)-one (12 mg, 62%) as a yellow solid. HPLC: 99% at 8.31 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min. UV detection at 220 nm). MS (ES): m/z 497 [M+H]⁺; ¹H NMR (CDCl₃, 400 MHz): δ 5.25 (s, 2H), 6.99 (d, J=8 Hz, 2H), 7.21 (t, J=8 Hz, 1H), 7.37-7.44 (m, 4H), 7.54 (d, J=8 Hz, 2H), 7.61 (d, J=8 Hz, 2H), 7.79-7.82 (m, 2H), 7.90 (s, 1H).

Example 276

Preparation of 2-(4-Trifluoromethyl)benzyl)-8-(4-chlorophenyl)-7-(4-fluorophenyl)-[1,2,4]triazolo[4,3-b]pyridazin-3(2H)-one

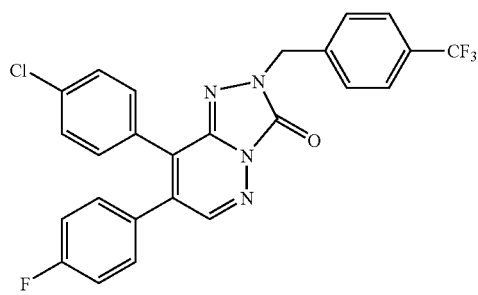

To a mixture of 2-(4-(trifluoromethyl)benzyl)-8-(4-chlorophenyl)-7-chloro-[1,2,4]triazolo[4,3-b]pyridazin-3(2H)-one (30 mg, 0.068 mmol), prepared as described in Example 274, 4-fluorophenylbronic acid (47.6 mg, 0.34 mmol), in toluene (1 mL), was added tetrakis(triphenylphosphine)palladium (12 mg, 0.01 mmol) followed by a solution of Na₂CO₃ in H₂O (2M, 0.19 mL, 0.38 mmol). The reaction mixture was stirred at 100° C. for 16 h, and then diluted with water. The resulting mixture was extracted with EtOAc (3×5 mL). The combined organic layers were washed with saturated NaCl. The organic layer was dried (Na₂SO₄), filtered and concentrated. The resulting residue was purified by silica gel (12 g) chromatography eluting with a gradient of EtOAc (0-60%) in hexane to give the title compound, 2-(4-trifluoromethyl)benzyl)-8-(4-chlorophenyl)-7-(4-fluorophenyl)-[1,2,4]triazolo[4,3-b]pyridazin-3(2H)-one (27 mg, 79%) as a yellow solid. HPLC: 99% at 8.13 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min. UV detection at 220 nm). MS (ES): m/z 499 [M+H]⁺; ¹H NMR (CDCl₃, 400 MHz): δ 5.26 (s, 2H), 7.03-7.08 (m, 2H), 7.12-7.18 (m, 2H), 7.25-7.28 (m, 2H), 7.30-7.34 (m, 2H), 7.52 (d, J=8 Hz, 2H), 7.60 (d, J=8 Hz, 2H), 8.19 (s, 1H).

Example 277

Preparation of 7-Chloro-8-(4-chlorophenyl)-2-(6-(trifluoromethyl)pyridin-3-yl)methyl-[1,2,4]triazolo[4,3-b]pyridazin-3(2H)-one

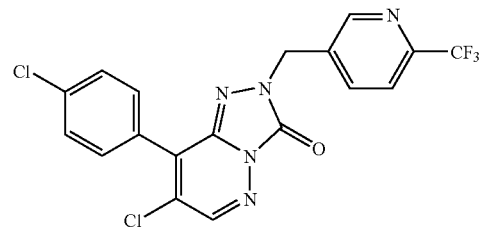

Using the procedure described in Example 274, 7-chloro-8-(4-chlorophenyl)-[1,2,4]triazolo[4,3-b]pyridazin-3(2H)-one prepared as described in Example 273 was reacted with 5-(bromomethyl)-2-(trifluoromethyl)pyridine to give the title compound, 7-chloro-8-(4-chlorophenyl)-2-(6-(trifluoromethyl)pyridin-3-yl)methyl-[1,2,4]triazolo[4,3-b]pyridazin-3 (2H)-one.

Example 278

Preparation of 8-(4-Chlorophenyl)-7-(4-(oxazol-2-yl)phenyl)-2-((6-(trifluoromethyl)pyridin-3-yl)methyl)-[1,2,4]triazolo[4,3-b]pyridazin-3(2H)-one

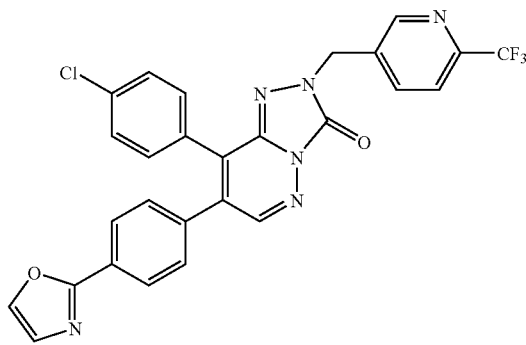

278A. Preparation of 2-(4-Bromophenyl)oxazole

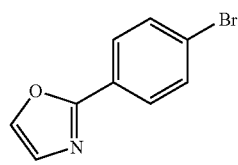

2-(4-Bromophenyl)oxazole was prepared from 4-bromobenzoyl chloride and aminoacetaldehyde dimethyl acetal following literature procedures.

278B. Preparation of 2-(4-(4,4,5,5-Tetramethyl-1,3,2-dioxaborolan-2-yl)phenyl)oxazole

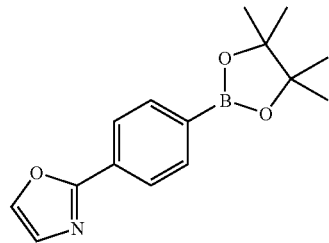

2-(4-Bromophenyl)oxazole was reacted with bis(pinacolato)diboron following literature procedures to give the title compound, 2-(4-(4,4,5,5-tetramethyl-1,3,2-dioxaborolan-2-yl)phenyl)oxazole.

278C. Preparation of 8-(4-Chlorophenyl)-7-(4-(oxazol-2-yl)phenyl)-2-((6-(trifluoromethyl)pyridin-3-yl)methyl)-[1,2,4]triazolo[4,3-b]pyridazin-3(2H)-one

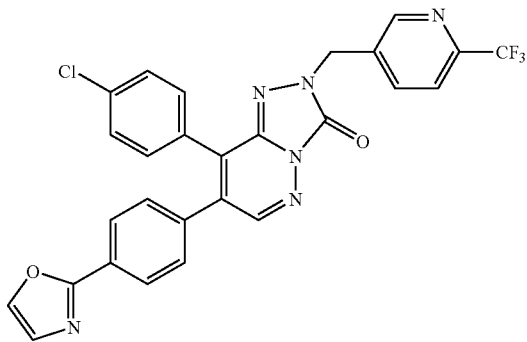

7-Chloro-8-(4-chlorophenyl)-2-(6-(trifluoromethyl)pyridin-3-yl)methyl-[1,2,4]triazolo[4,3-b]pyridazin-3(2H)-one, prepared as described in Example 277 and 2-(4-(4,4,5,5-tetramethyl-1,3,2-dioxaborolan-2-yl)phenyl)oxazole were reacted using procedures analogous to those described in Example 276 to give the title compound, 8-(4-chlorophenyl)-7-(4-(oxazol-2-yl)phenyl)-2-((6-(trifluoromethyl)pyridin-3-yl)methyl)-[1,2,4]triazolo[4,3-b]pyridazin-3(2H)-one. HPLC: 99% at 8.42 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$); Flow rate at 2.5 mL/min. UV detection at 220 nm). MS (ES): m/z 549 $[M+H]^+$; $^1H$ NMR (CDCl$_3$, 400 MHz): δ 5.32 (s, 2H), 7.23-7.32 (m, 2H), 7.40-7.59 (m, 4H), 7.62-7.78 (m, 4H), 7.90-8.05 (m, 2H), 8.24-8.27 (m, 1H), 8.81 (s, 1H).

Example 279

Preparation of 7-(4-Fluorophenyl)-8-(pyridin-4-yl)-[1,2,4]triazolo[4,3-b]pyridazin-3(2H)-one

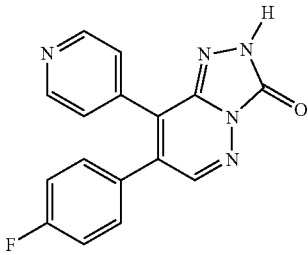

279A. Preparation of 2-Benzyl-5-chloro-4-(4-pyridin-4-yl)pyridazin-3(2H)-one

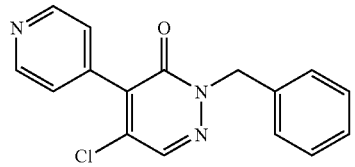

To a mixture of 2-benzyl-4,5-dichloropyridazin-3(2H)-one (10.8 g, 42 mmol), prepared as described in Example 244A, 4-(4,4,5,5,-tetramethyl-1,3,2-dioxoborolan-2-yl)pyridine (7.9 g, 38.5 mmol) in toluene (80 mL) under a stream of argon, was added tetrakis(triphenylphosphine)palladium (4.4 g, 3.8 mmol), followed by an aqueous $Na_2CO_3$ solution (2M, 21 mL, 42 mmol). The reaction mixture was heated to 100° C. under argon for 16 h. After cooling to RT, the reaction mixture was poured into water (200 mL) and extracted with EtOAc (3×150 mL). The combined organic layers were washed with saturated aqueous NaCl. The organic layer was dried ($Na_2SO_4$), filtered and concentrated under reduced pressure. The resulting residue was purified by silica gel (330 g) column chromatography eluting with a gradient of EtOAc (30-100%) in hexanes to give the title compound, 2-benzyl-5-chloro-4-(4-pyridin-4-yl)pyridazin-3(2H)-one (3.1 g, 27%) as a yellow solid. LC/MS (method A): RT=1.95 min, $(M+H)^+$=298.

279B. Preparation of 2-Benzyl-5-(4-fluorophenyl)-4-(pyridin-4-yl)pyridazin-3(2H)-one

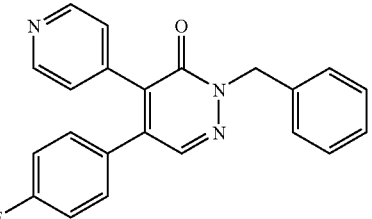

The title compound was prepared from 2-benzyl-5-chloro-4-(4-pyridin-4-yl)pyridazin-3(2H)-one and 4-fluorophenyl boronic acid using procedures analogous to those described in Example 276. The crude product was purified by silica gel column chromatography to give the title compound, 2-benzyl-5-(4-fluorophenyl)-4-(pyridin-4-yl)pyridazin-3(2H)-one. LC/MS (method A): RT=2.52 min, $(M+H)^+$=358.

279C. Preparation of 5-(4-Fluorophenyl)-4-(pyridin-4-yl)pyridazin-3(2H)-one

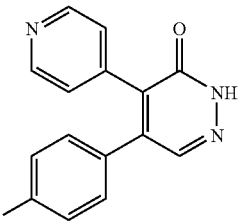

To a solution of 2-benzyl-5-(4-fluorophenyl)-4-(pyridin-4-yl)pyridazin-3(2H)-one (1.04 g, 2.91 mmol) in toluene (15 mL) was added aluminum chloride (970 mg, 7.28 mmol). The reaction was stirred at 90° C. for 30 min. After cooling to RT, the reaction mixture was poured into water (50 mL). The resulting mixture was extracted with EtOAc (3×50 mL). The combined organic layers were washed with saturated aqueous $NaHCO_3$, saturated aqueous NaCl. The organic layer was dried (Na$_2$SO$_4$), filtered and concentrated. The resulting residue was triturated with EtOAc-hexane to give the title compound, 5-(4-fluorophenyl)-4-(pyridin-4-yl)pyridazin-3(2H)-one as an off-white solid (560 mg, 70%). LC/MS (method A): RT=1.25 min, (M+H)$^+$=268.

279D. Preparation of 3-Chloro-5-(4-fluorophenyl)4-(pyridin-4-yl)pyridazine

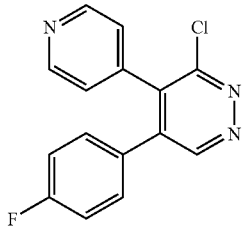

5-(4-Fluorophenyl)-4-(pyridin-4-yl)pyridazin-3(2H)-one was reacted with POCl$_3$ using procedures analogous to those described in Example 273C to give the title compound, 3-chloro-5-(4-fluorophenyl)4-(pyridin-4-yl)pyridazine. LC/MS (method A): RT=1.43 min, (M+H)$^+$=286.

279E. Preparation of 1-(5-(4-fluorophenyl)4-(pyridin-4-yl)pyridazin-3-yl)hydrazine

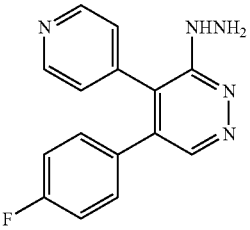

To a solution of 3-chloro-5-(4-fluorophenyl)4-(pyridin-4-yl)pyridazine (586 mg, 2.05 mmol) in pyridine (3 mL) at RT was added hydrazine monohydrate (0.6 mL). After addition, the reaction was heated to 100° C. for 3 h. After this time, the reaction mixture was cooled to RT. The reaction mixture was concentrated under reduced pressure and the residue was diluted with water. The resulting mixture was then extracted with EtOAc (3×50 mL). The combined organic layers were washed with saturted Nacl. The organic layer was dried (Na$_2$SO$_4$), filtered and concentrated. The resulting residue was triturated with EtOAc-hexane to give the title compound, 1-(5-(4-fluorophenyl)4-(pyridin-4-yl)pyridazin-3-yl)hydrazine (450 mg, 78%) as an off-white solid. LC/MS (method A): RT=1.10 min, (M+H)$^+$=282.

279F. Preparation of 7-(4-Fluorophenyl)-8-(pyridine-4-yl)-[1,2,4]triazolo[4,3-b]pyridazin-3(2H)-one

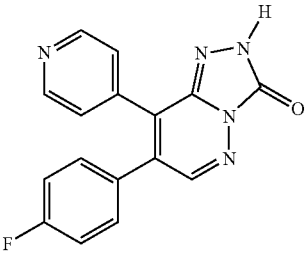

To a solution of 1,1'-carbonyldiimidazole (1.27 g, 7.86 mmol) in THF (20 mL) was added a suspension of 1-(5-(4-fluorophenyl)4-(pyridin-4-yl)pyridazin-3-yl)hydrazine (442 mg, 1.57 mmol) in THF (5 mL). After addition, the reaction mixture was heated to 66° C. After 20 min., the reaction mixture was cooled to RT and the reaction mixture was then concentrated under reduced pressure. The residue was diluted with water. The resultant mixture was extracted with EtOAc (3×100 mL). The combined organic layers were washed with saturated NaCl. The organic layer was dried (Na$_2$SO$_4$), filtered and concentrated. The resulting residue was triturated with EtOAc-hexane to give the title compound, 7-(4-fluorophenyl)-8-(pyridine-4-yl)-[1,2,4]triazolo[4,3-b]pyridazin-3(2H)-one (440 mg, 91%) as a yellow solid. LC/MS (method A): RT=1.27 min, (M+H)$^+$=308.

Example 280

Preparation of 2-(4-(Isoxazol-5-yl)benzyl)-7-(4-fluorophenyl)-8-(pyridin-4-yl)-[1,2,4]triazolo[4,3-b]pyridazin-3(2H)-one

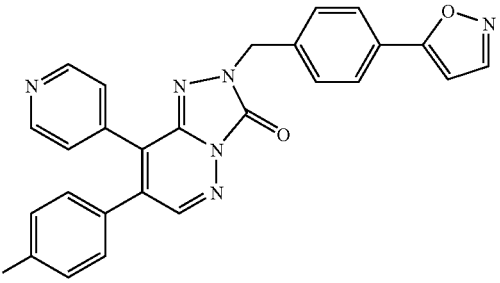

The title compound was prepared by reacting 7-(4-fluorophenyl)-8-(pyridine-4-yl)-[1,2,4]-triazolo[4,3-b]pyridazin-3(2H)-one, prepared as described in Example 279F, 5-(4-(bromomethyl)phenyl)isoxazole, prepared as described in Example 250A by procedures analogous to those described in Example 2 as a yellow solid (68%). HPLC: 99% at 5.46 min (retention time) (Conditions: Zorbax SB C18 (4.6×75 mm); Eluted with 0% to 100% B, 8 min gradient. (A=90% H$_2$O—10% MeOH—0.1% H$_3$PO$_4$ and B=10% H$_2$O—90% MeOH—0.1% H$_3$PO$_4$); Flow rate at 2.5 mL/min. UV detection at 220 nm). MS (ES): m/z 465 [M+H]$^+$; $^1$H NMR (CDCl$_3$, 400 MHz): δ 5.25 (s, 2H), 6.51 (d, J=0.96 Hz, 1H), 7.01-7.09 (m, 2H), 7.11-7.18 (m, 2H), 7.23 (dd, J$_1$=4.40 Hz, J$_2$=1.76 Hz, 2H), 7.51 (d, J=8.3 Hz, 2H), 7.77 (d, J=8.3 Hz, 2H), 8.21 (s, 1H), 8.28 (d, J=1.76 Hz, 1H), 8.61-8.64 (m, 2H).

Example 281

Preparation of 2-(4-Isoxazol-3-yl)benzyl)-7-(4-fluorophenyl)-8-(pyridin-4-yl)-[1,2,4]triazolo[4,3-b]pyridazin-3(2H)-one

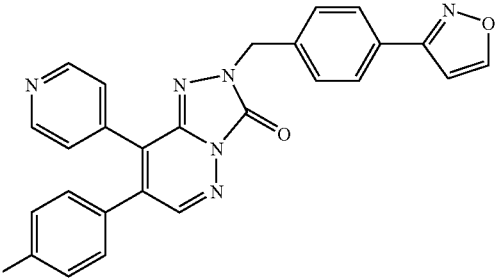

The title compound was prepared by reacting 7-(4-fluorophenyl)-8-(pyridine-4-yl)-[1,2,4]-triazolo[4,3-b]pyridazin-3(2H)-one, prepared as described in Example 279F, 3-(4-(bromomethyl)phenyl)isoxazole, prepared as described in Example 251A by procedures analogous to those described in Example 2 to give 2-(4-isoxazol-3-yl)benzyl)-7-(4-fluorophenyl)-8-(pyridin-4-yl)-[1,2,4]triazolo[4,3-b]pyridazin-3(2H)-one as a yellow solid (59%). HPLC: 99% at 5.33 min (retention time) (Conditions: Zorbax SB C18 (4.6×75 mm); Eluted with 0% to 100% B, 8 min gradient. (A=90% H$_2$O—10% MeOH—0.1% H$_3$PO$_4$ and B=10%

H$_2$O—90% MeOH—0.1% H$_3$PO$_4$); Flow rate at 2.5 mL/min. UV detection at 220 nm). MS (ES): m/z 465 [M+H]$^+$; $^1$H NMR (CDCl$_3$, 400 MHz): δ 5.26 (s, 2H), 6.65 (S, 1H), 7.07 (t, J=8.36 Hz, 2H), 7.10-7.18 (m, 2H), 7.23 (d, J=5.30 Hz, 2H), 7 51 (d, J=8.36 Hz, 2H), 7.80 (d, J=7.88 Hz, 2H), 8.21 (s, 1H), 8.45 (s, 1H), 8.62 (d, J=5.30 Hz, 2H).

Example 282

Preparation of 7-(4-Methoxyphenyl)-8-(pyridine-4-yl)-[1,2,4]triazolo[4,3-b]pyridazin-3(2H)-one

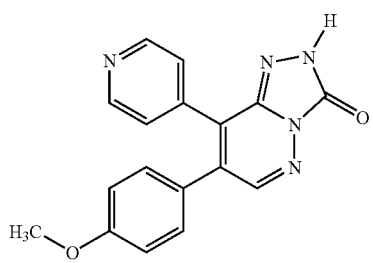

282A. Preparation of 5-Chloro-4-(pyridin-4-yl)pyridazin-3 (2H)-one

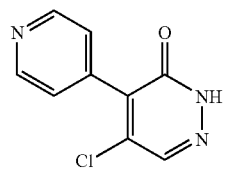

To a suspension of 2-benzyl-5-chloro-4-(4-pyridin-4-yl)pyridazin-3(2H)-one (3.9 g, 13.1 mmol) prepared as described in 279A, in toluene (65 mL) was added aluminum chloride (4.37 g, 32.7 mmol). The mixture was stirred at 90° C. for 1 h. After this time, the reaction mixture was cooled to RT. The reaction mixture was partitioned between EtOAc and saturated aqueous NaHCO$_3$ (adjusted pH to 7). The formed precipitate was collected by filtration and washed with EtOAc to give 1.8 g of the title compound. The aqueous layer was extracted with EtOAc (2×) and the combined organic layers were washed with saturated aqueous NaCl. The organic layer was dried (Na$_2$SO$_4$), filtered and concentrated. The obtained residue was triturated with EtOAc-hexane to give additional 0.7 g. Together 2.5 g (92%) of the title compound, 5-chloro-4-(pyridin-4-yl)pyridazin-3(2H)-one was obtained as an off-white solid. LC/MS (method A): RT=0.48 min, (M+H)$^+$=208.

282B. Preparation of 3,5-Dichloro-4-(pyridin-4-yl)pyridazine

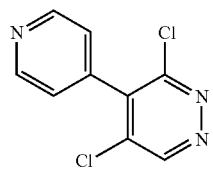

A suspension of compound 5-chloro-4-(pyridin-4-yl)pyridazin-3(2H)-one (2.5 g, 12 mmol) in POCl$_3$ (20 mL) was heated at 120° C. for 3 h. After this time, the reaction mixture was cooled to RT. The reaction mixture was concentrated under reduced pressure. The obtained residue was treated with ice-cold saturated aqueous NaHCO$_3$. The formed precipitate was collected by filtration and washed with water to give the title compound, 3,5-dichloro-4-(pyridin-4-yl)pyridazine as an off-white solid (1.8 g, 67%). LC/MS (method A): RT=0.70 min, (M+H)$^+$=226.

282C. Preparation of 3-Chloro-5-(4-methoxyphenyl)-4-pyridin-4-yl)pyridazine

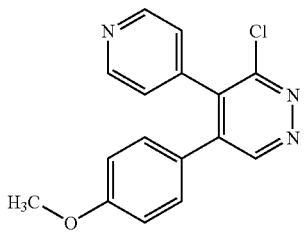

The title compound was prepared by reacting 3,5-dichloro-4-(pyridin-4-yl)pyridazine with 4-methoxyphenyl boronic acid by procedures analogous to those described in Example 279D to give 3-chloro-5-(4-methoxyphenyl)-4-pyridin-4-yl)pyridazine. LC/MS (method A): RT=1.58 min, (M+H)$^+$=298.

282D. Preparation of 1-(5-(4-Methoxyphenyl)-4-(pyridin-4-yl)pyridazin-3-yl)hydrazine

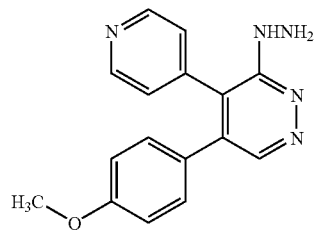

The title compound was prepared by reacting 3-chloro-5-(4-methoxyphenyl)-4-pyridin-4-yl)pyridazine with hydrazine monohydrate by procedures analogous to those described in Example 244H to give 1-(5-(4-methoxyphenyl)-4-(pyridin-4-yl)pyridazin-3-yl)hydrazine. LC/MS (method A): RT=1.18 min, (M+H)$^+$=294.

282E. Preparation of 7-(4-Methoxyphenyl)-8-(pyridine-4-yl)-[1,2,4]triazolo[4,3-b]pyridazin-3(2H)-one

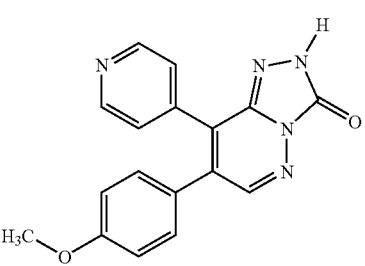

The title compound was prepared by reacting 1-(5-(4-methoxyphenyl)-4-(pyridin-4-yl)pyridazin-3-yl)hydrazine with carbonyldiimidazole (CDI) by procedures analogous to those described in Example 279F to give 7-(4-methoxyphenyl)-8-(pyridine-4-yl)-[1,2,4]triazolo[4,3-b]pyridazin-3 (2H)-one. LC/MS (method A): RT=1.37 min, (M+H)$^+$=320.

Example 283

Preparation of 2-(4-Isoxazol-5-yl)benzyl)-7-(4-methoxyphenyl)-8-(pyridin-4-yl)-[1,2,4]triazolo[4,3-b]pyridazin-3(2H)-one

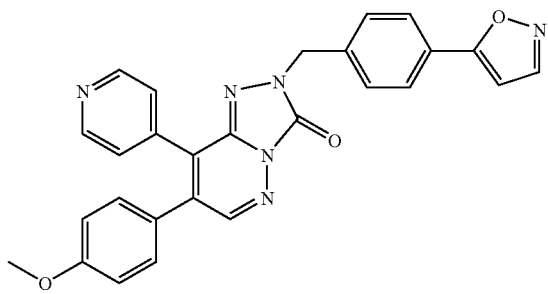

The title compound was prepared by reacting 7-(4-methoxyphenyl)-8-(pyridine-4-yl)-[1,2,4]triazolo[4,3-b]pyridazin-3(2H)-one, prepared as described in Example 282, 5-(4-(bromomethyl)phenyl)isoxazole, prepared as described in Example 250A by procedures analogous to those described Example 2 to give as a yellow solid. HPLC: 99% at 5.53 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$); Flow rate at 2.5 mL/min. UV detection at 220 nm). MS (ES): m/z 477 [M+H]$^+$; $^1$H NMR (CDCl$_3$, 400 MHz): δ 3.81 (s, 3H), 5.25 (s, 2H), 6.51 (s, 1H), 6.84 (d, J=8.8 Hz, 2H), 7.07 (d, J=8.8 Hz, 2H), 7.10=7.30 (m, 2H), 7.51 (d, J=8.3 Hz, 2H), 7.77 (d, J=8.3 Hz, 2H), 8.22-8.30 (m, 2H), 8.60-8.70 (m, 2H).

Examples 284 to 353

The following Examples were prepared according to methods and procedures above.

| Example Number | Structure | HPLC Retention Time (min) | Mass Specs Observed (M + H) |
|---|---|---|---|
| 284 | 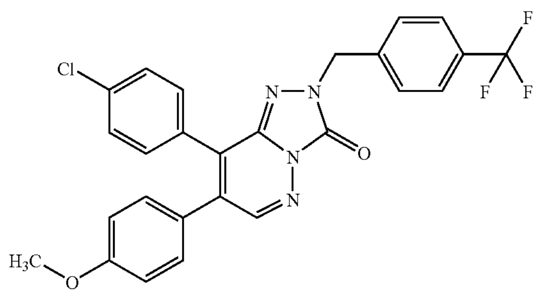 | 8.22[b] | 511 |
| 285 | 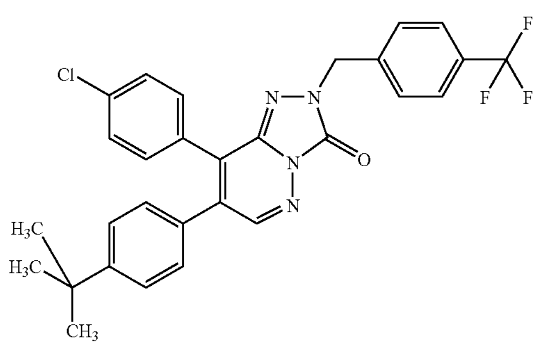 | 9.01[b] | 537 |
| 286 | 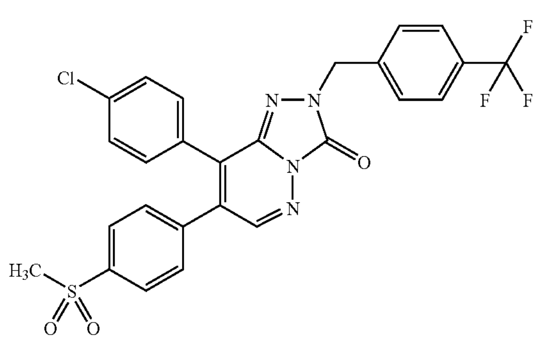 | 7.26[b] | 559 |

-continued
| Example Number | Structure | HPLC Retention Time (min) | Mass Specs Observed (M + H) |
|---|---|---|---|
| 287 | 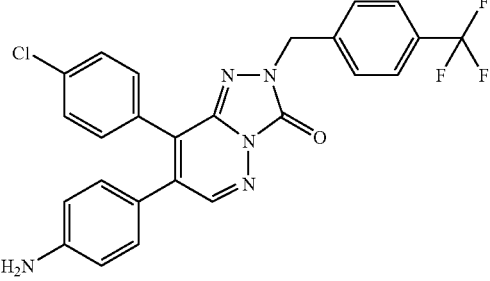 | 7.2[b] | 496 |
| 288 | 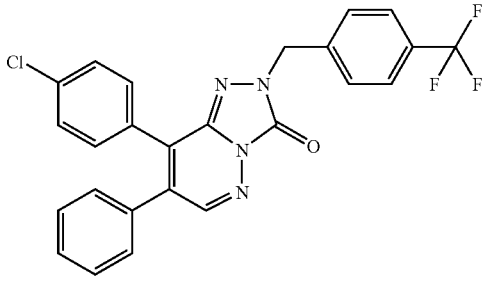 | 8.15[b] | 481 |
| 289 | 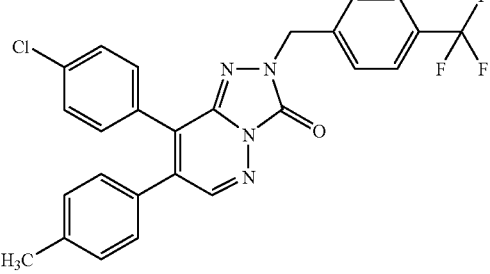 | 8.46[b] | 495 |
| 290 | 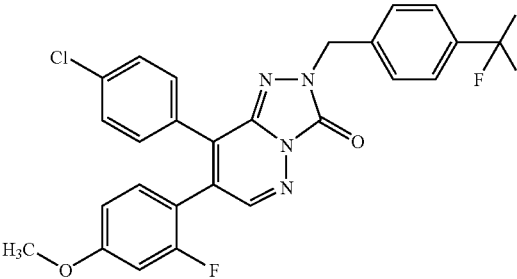 | 8.23[b] | 529 |
| 291 | 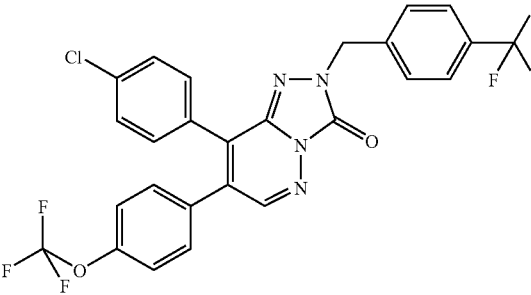 | 8.41[b] | 565 |

| Example Number | Structure | HPLC Retention Time (min) | Mass Specs Observed (M + H) |
| --- | --- | --- | --- |
| 292 | 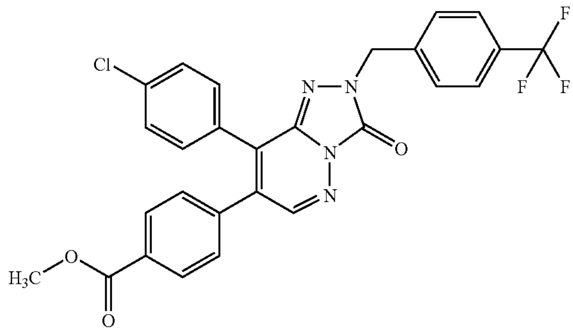 | 8.1[b] | 539 |
| 293 | 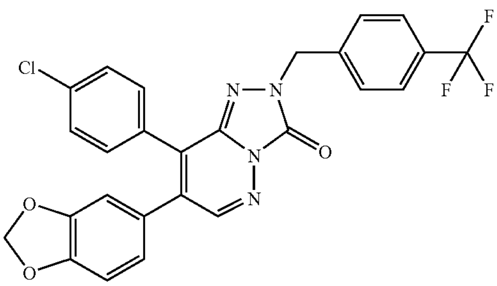 | 8.07[b] | 525 |
| 294 | 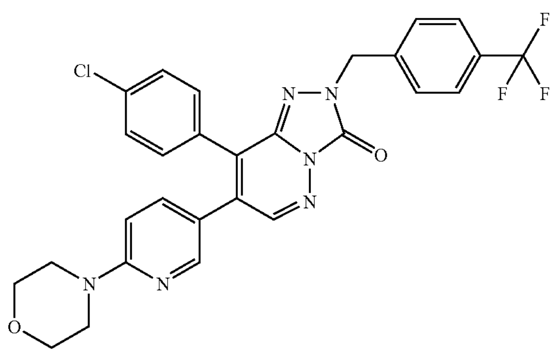 | 7.53[b] | 567 |
| 295 | 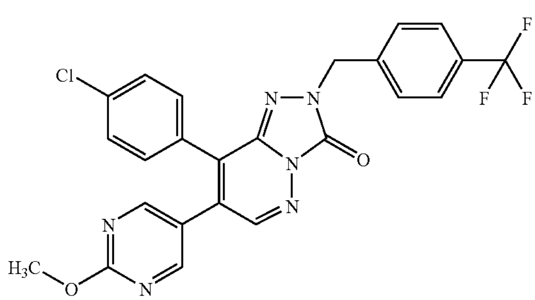 | 7.36[b] | 513 |

-continued

| Example Number | Structure | HPLC Retention Time (min) | Mass Specs Observed (M + H) |
|---|---|---|---|
| 296 | 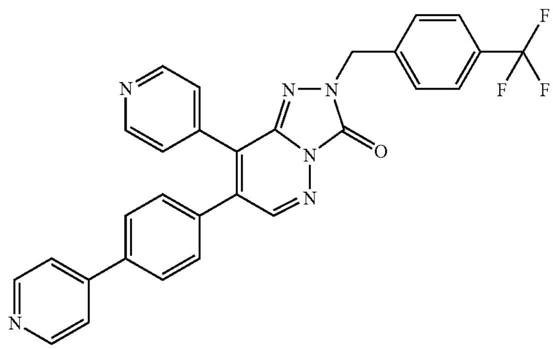 | 3.42[e] | 525 |
| 297 | 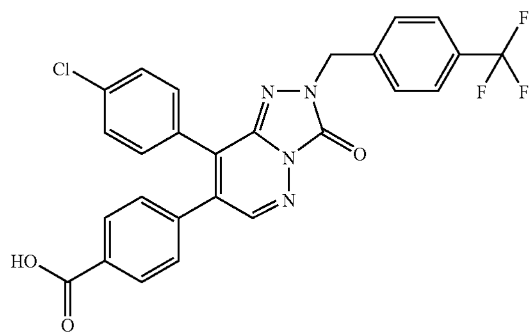 | 7.66[b] | 525 |
| 298 | 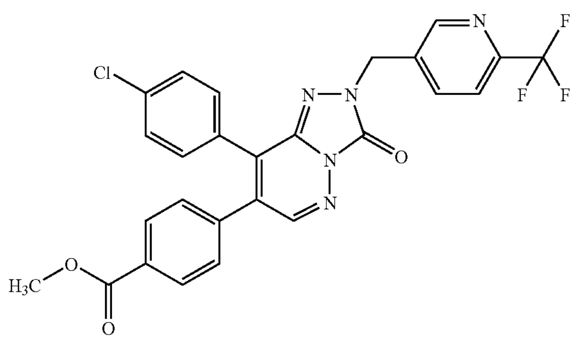 | 7.44[b] | 540 |
| 299 | 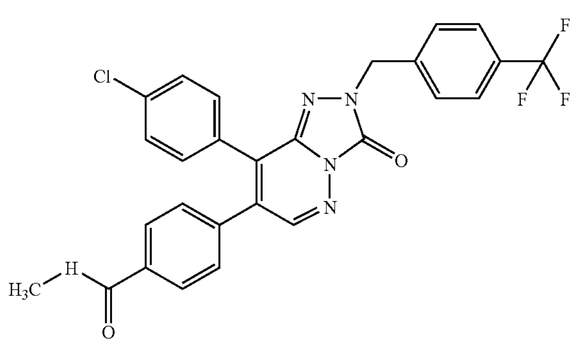 | 7.39[b] | 538 |

-continued
| Example Number | Structure | HPLC Retention Time (min) | Mass Specs Observed (M + H) |
|---|---|---|---|
| 300 | 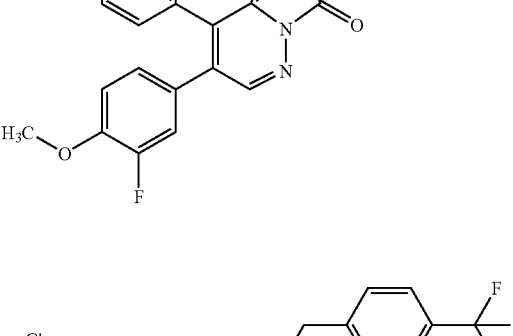 | 8.05[b] | 529 |
| 301 | 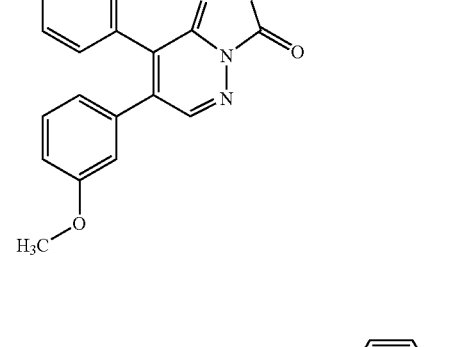 | 8.18[b] | 511 |
| 302 | 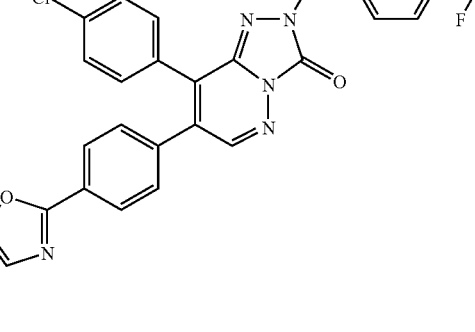 | 8.03[b] | 548 |
| 303 | 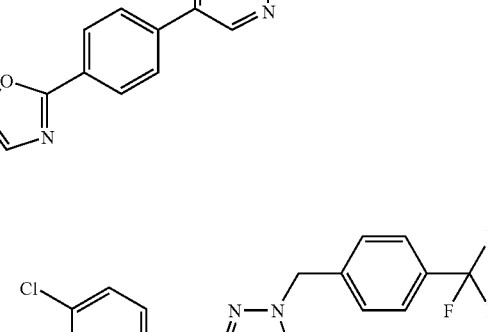 | 7.68[b] | 506 |

-continued

| Example Number | Structure | HPLC Retention Time (min) | Mass Specs Observed (M + H) |
|---|---|---|---|
| 304 | 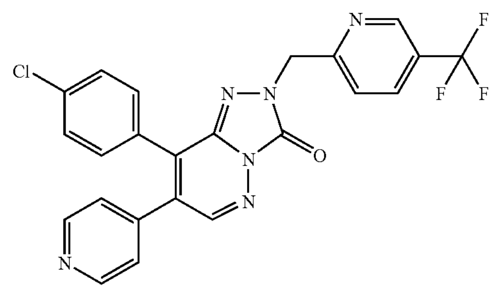 | 6[b] | 483 |
| 305 | 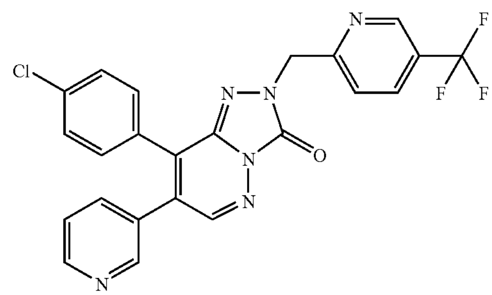 | 6.34[b] | 483 |
| 306 | 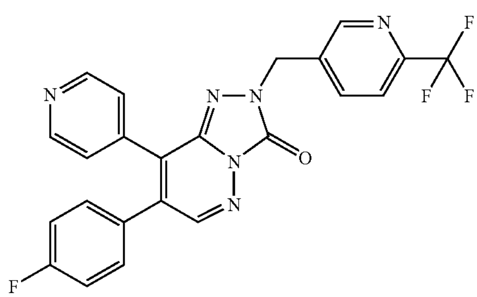 | 5.27[b] | 467 |
| 307 | 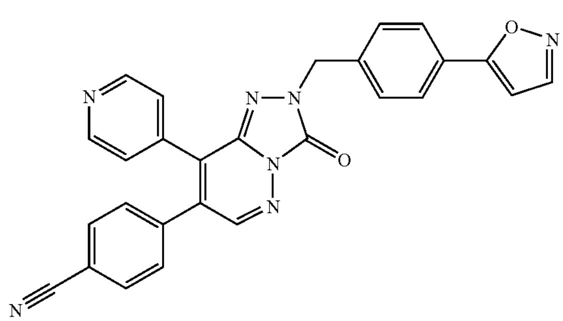 | 5.02[b] | 472 |
| 308 | 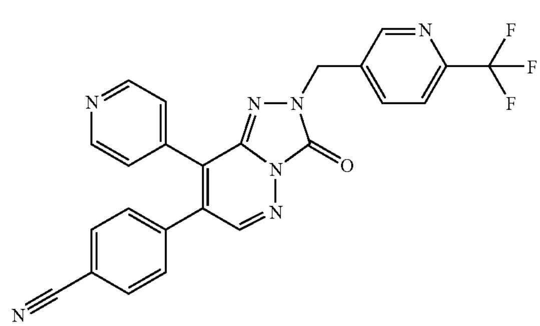 | 4.79[b] | 474 |

-continued

| Example Number | Structure | HPLC Retention Time (min) | Mass Specs Observed (M + H) |
|---|---|---|---|
| 309 | 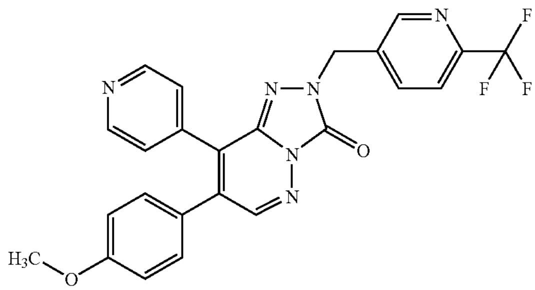 | 5.35[b] | 479 |
| 310 | 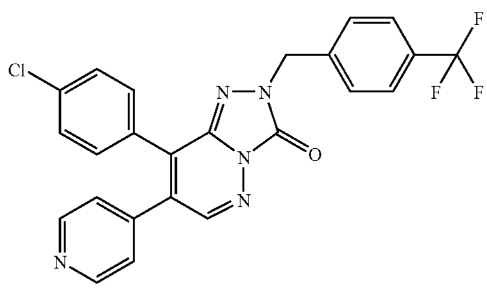 | 6.93[b] | 482 |
| 311 | 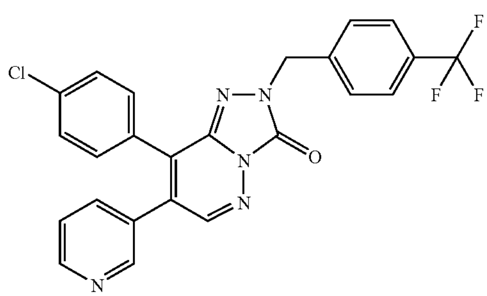 | 7.11[b] | 482 |
| 312 | 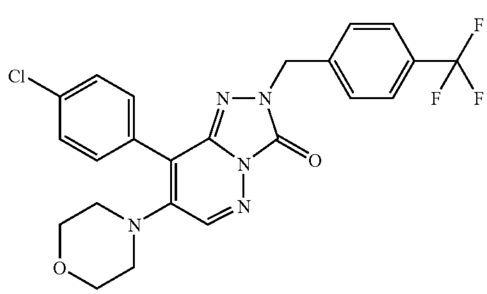 | 7.6[b] | 490 |
| 313 | 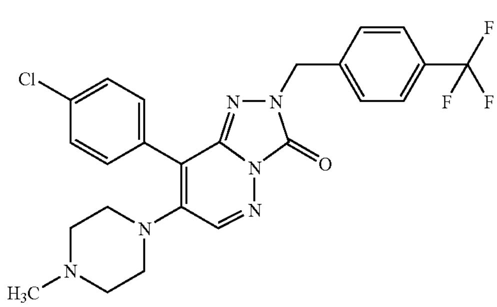 | 5.87[b] | 503 |

-continued

| Example Number | Structure | HPLC Retention Time (min) | Mass Specs Observed (M + H) |
|---|---|---|---|
| 314 | 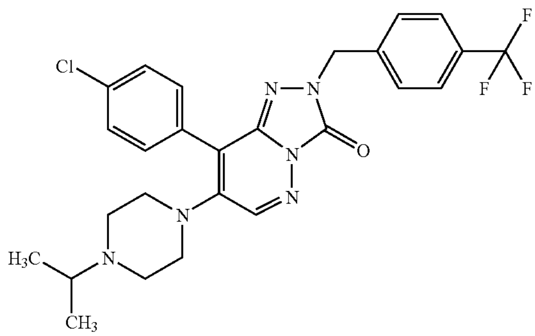 | 5.99[b] | 531 |
| 315 | 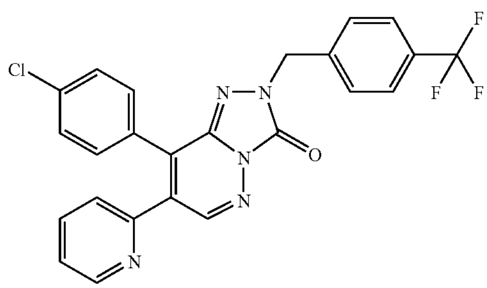 | 7.47[b] | 482 |
| 316 | 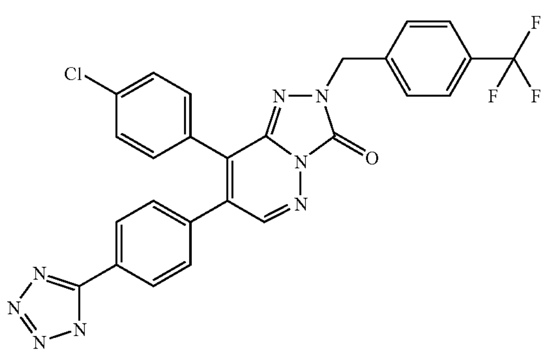 | 7.53[b] | 549 |
| 317 | 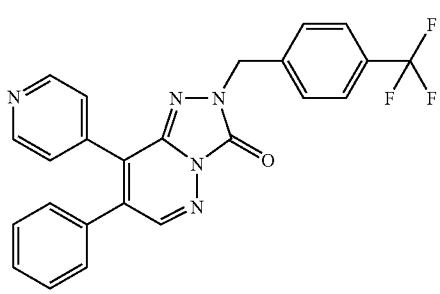 | 3.43[e] | 448 |

-continued
| Example Number | Structure | HPLC Retention Time (min) | Mass Specs Observed (M + H) |
|---|---|---|---|
| 318 | 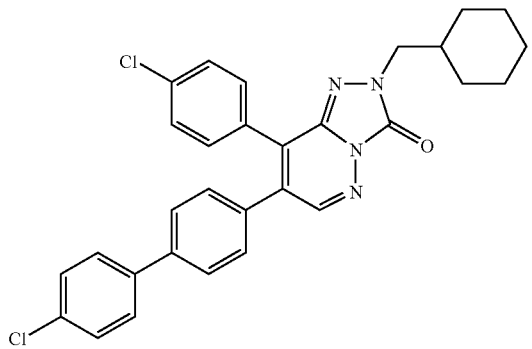 | 4.69 | 529 |
| 319 | 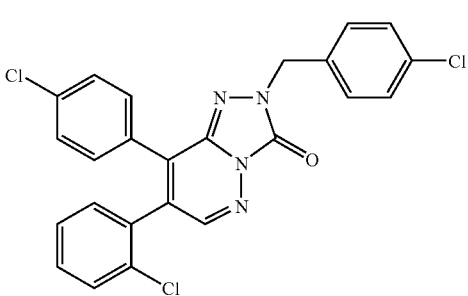 | 4.15 | 481 |
| 320 | 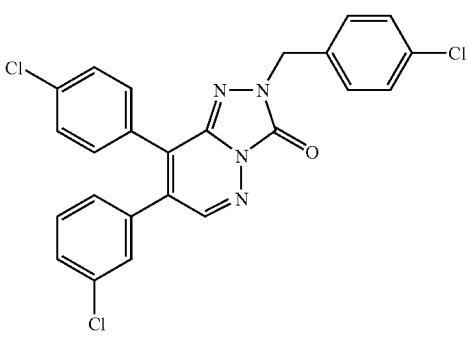 | 4.13 | 481 |
| 321 | 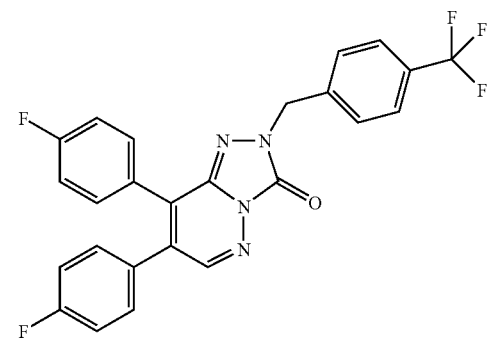 | 3.85 | 482 |

-continued

| Example Number | Structure | HPLC Retention Time (min) | Mass Specs Observed (M + H) |
|---|---|---|---|
| 322 | 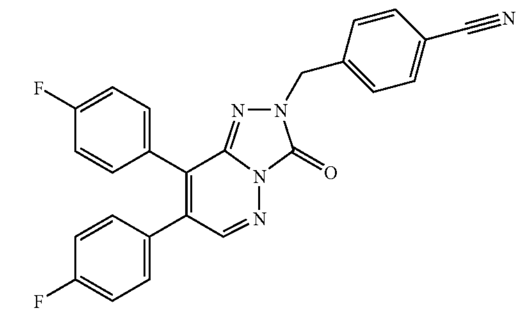 | 3.4 | 440 |
| 323 | 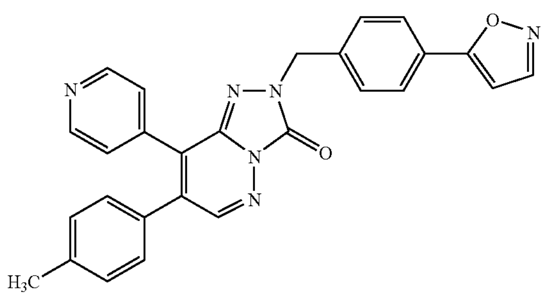 | 2.62 | 461 |
| 324 | 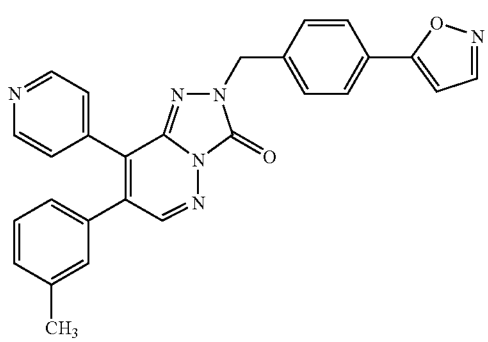 | 2.53[d] | 461 |
| 325 | 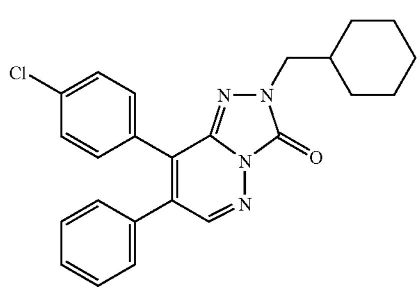 | 4.25 | 419 |

-continued

| Example Number | Structure | HPLC Retention Time (min) | Mass Specs Observed (M + H) |
|---|---|---|---|
| 326 | 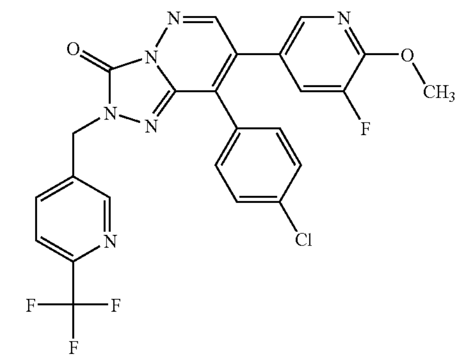 | 3.29<sup>c</sup> | 533 |
| 327 | 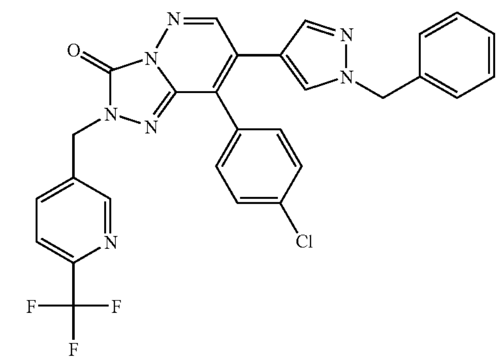 | 3.27<sup>c</sup> | 562 |
| 328 | 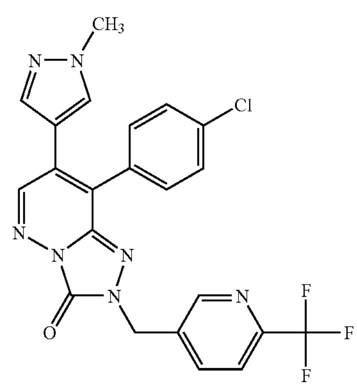 | 2.77<sup>c</sup> | 486 |
| 329 | 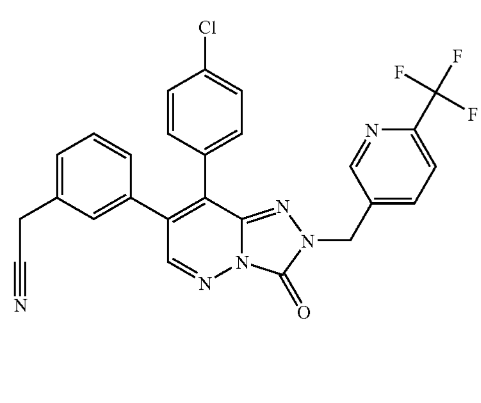 | 3.13<sup>c</sup> | 521 |

-continued
| Example Number | Structure | HPLC Retention Time (min) | Mass Specs Observed (M + H) |
|---|---|---|---|
| 330 | 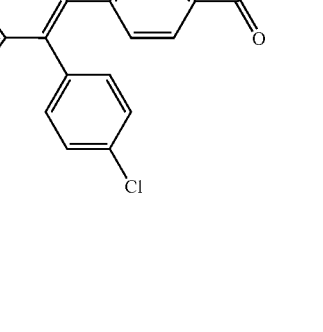 | 2.82[c] | 553 |
| 331 | 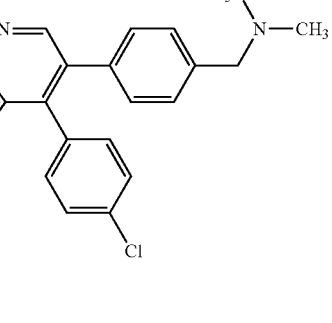 | 3.23[c] | 539 |
| 332 | 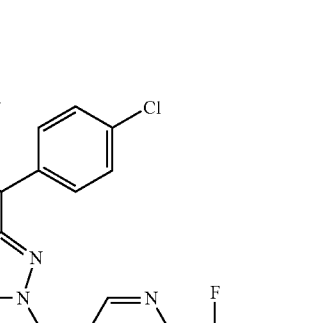 | 3.34[c] | 488 |
| 333 | 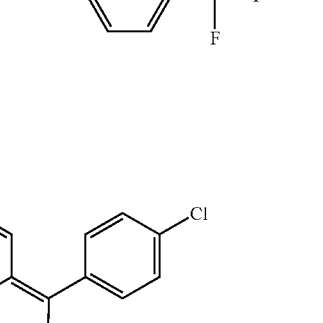 | 3.96[c] | 488 |

US 7,378,418 B2

-continued

| Example Number | Structure | HPLC Retention Time (min) | Mass Specs Observed (M + H) |
|---|---|---|---|
| 334 | 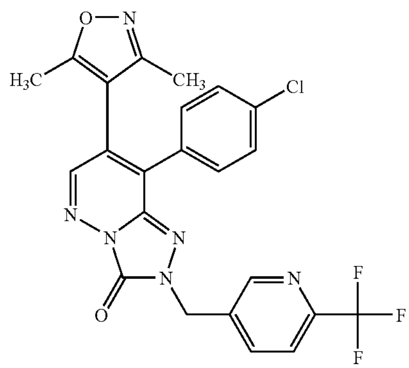 | 3.08ᶜ | 501 |
| 335 | 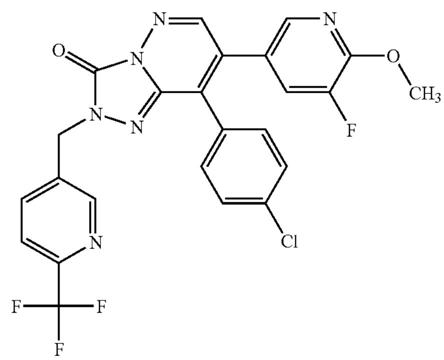 | 3.29ᶜ | 533 |
| 336 | 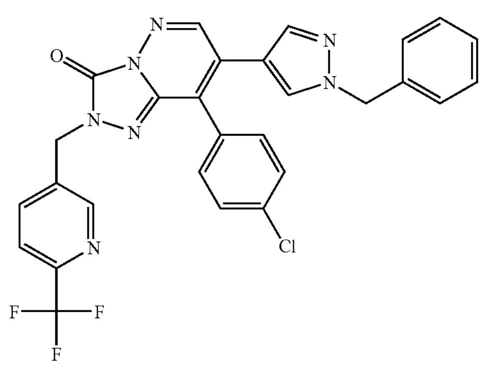 | 3.27ᶜ | 562 |
| 337 | 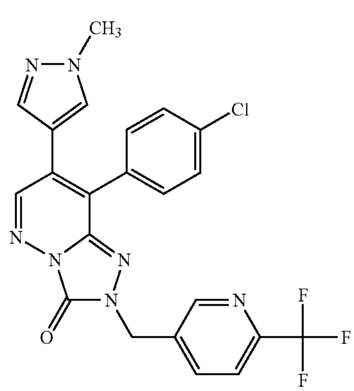 | 2.77ᶜ | 486 |

-continued
| Example Number | Structure | HPLC Retention Time (min) | Mass Specs Observed (M + H) |
|---|---|---|---|
| 338 | 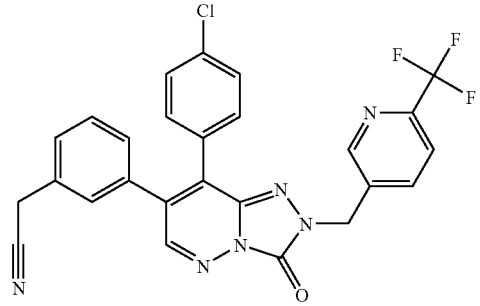 | 3.13$^c$ | 521 |
| 339 | 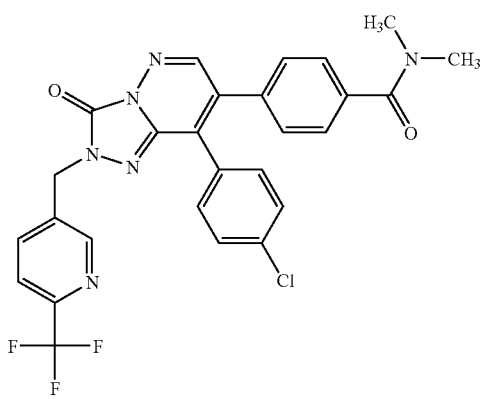 | 2.82$^c$ | 553 |
| 340 | 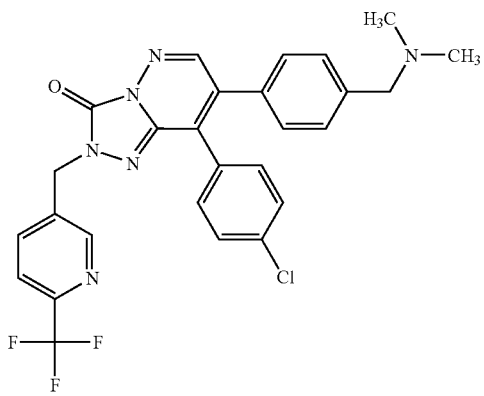 | 3.23$^c$ | 539 |
| 341 | 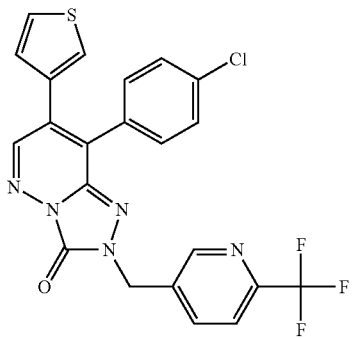 | 3.34$^c$ | 488 |

-continued
| Example Number | Structure | HPLC Retention Time (min) | Mass Specs Observed (M + H) |
|---|---|---|---|
| 342 | 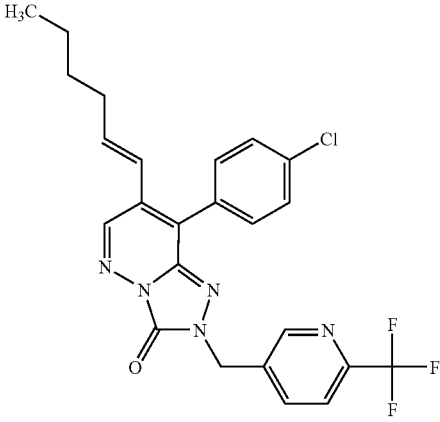 | 3.96ᵉ | 488 |
| 343 | 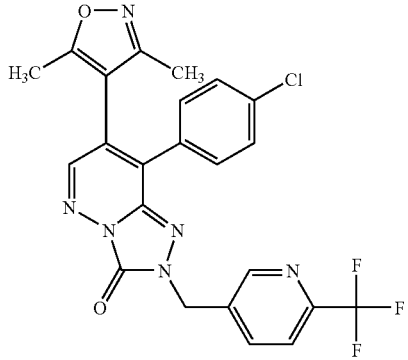 | 3.08ᵉ | 501 |
| 344 | 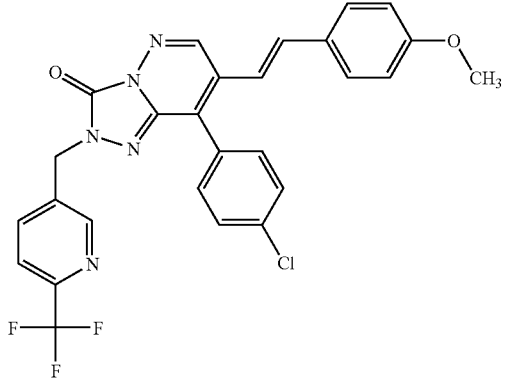 | 3.65ᵉ | 538 |

| Example Number | Structure | HPLC Retention Time (min) | Mass Specs Observed (M + H) |
| --- | --- | --- | --- |
| 345 | 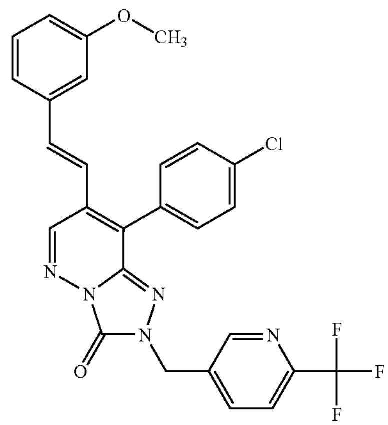 | 3.65ᶜ | 538 |
| 346 | 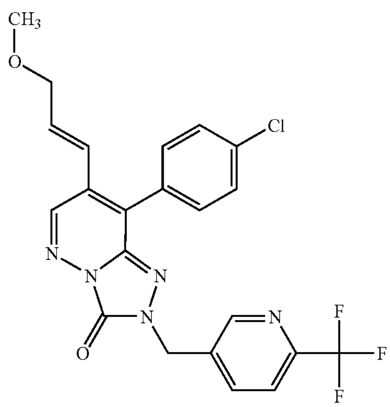 | 3.11ᶜ | 476 |
| 347 | 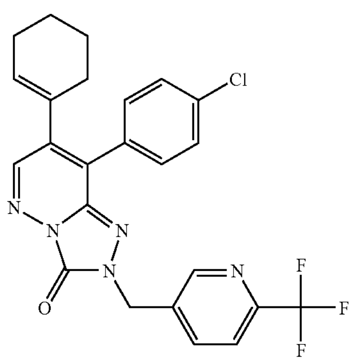 | 3.74ᶜ | 486 |
| 348 | 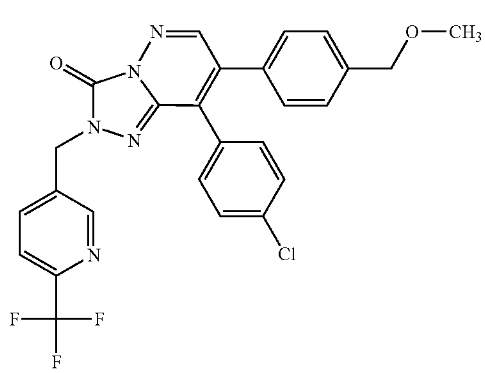 | 3.36ᶜ | 526 |

-continued

| Example Number | Structure | HPLC Retention Time (min) | Mass Specs Observed (M + H) |
|---|---|---|---|
| 349 | 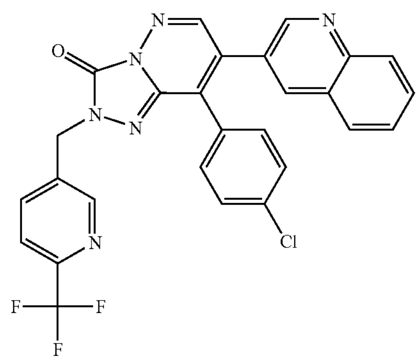 | 3.15[c] | 533 |
| 350 | 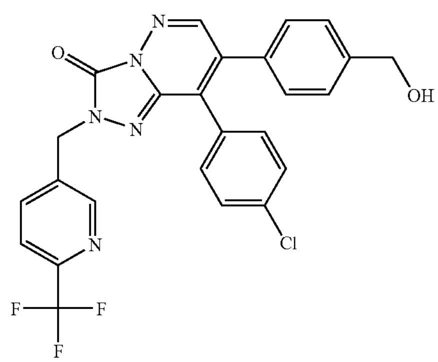 | 2.82[c] | 512 |
| 351 | 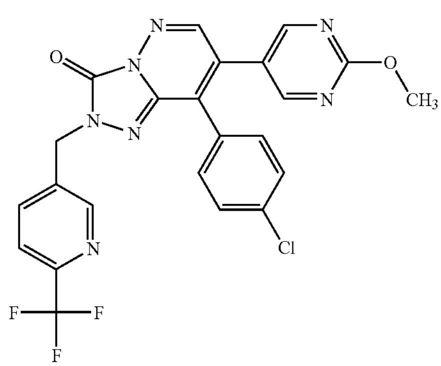 | 2.87[c] | 514 |
| 352 | 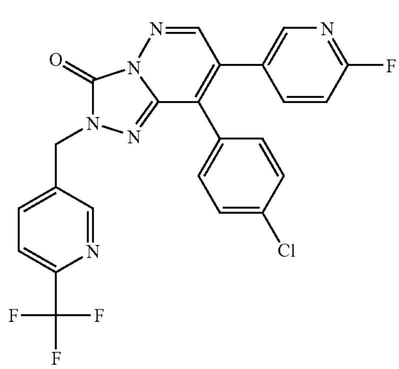 | 3.08[c] | 501 |

| Example Number | Structure | HPLC Retention Time (min) | Mass Specs Observed (M + H) |
| --- | --- | --- | --- |
| 353 | 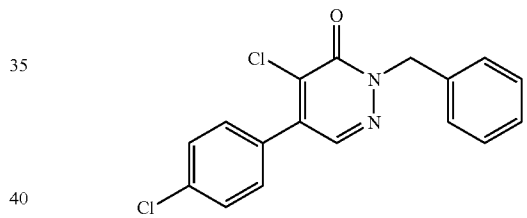 | 3.2ᶜ | 513 |

Example 354

Preparation of 8-Chloro-7-(4-chloro-phenyl)-2H-[1,2,4]triazolo[4,3-b]pyridazin-3-one

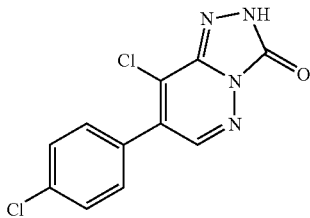

354A. Preparation of 2-Benzyl-4-chloro-5-methoxypyridazin-3(2H)-one

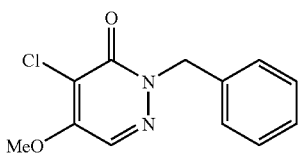

To a solution of 2-benzyl-4,5-dichloro-2H-pyridazine-3-one (22.31 g, 87.47 mmol), prepared as described in Example 244A, in dry MeOH (175 mL) at 0° C., was added dropwise a solution of sodium methoxide in methanol (25% weight in MeOH, 25 mL). The mixture was slowly warmed up to room temperature and stirred for 18 h. The reaction mixture was diluted with methylene chloride (200 mL) and filtered. The filtrate was concentrated to afford the title compound, 2-benzyl-4-chloro-5-methoxypyridazin-3(2H)-one (22.2 g) which was >95% pure as judged by HPLC and was used in the next reaction, Example 354B, without further purification.

354B. Preparation of 2-Benzyl-4-chloro-5-hydroxypyridazin-3(2H)-one

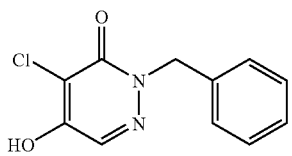

To a suspension of 2-benzyl-4-chloro-5-methoxypyridazin-3(2H)-one (22.2 g, 87.47 mmol) in water (150.0 mL), potassium hydroxide (5.89 g) was added and the mixture was heated to reflux. After 3 h, the mixture was then cooled to room temperature and 6N aqueous hydrochloric acid was added and the pH of the solution was adjusted to 3.0. The precipitate was filtered, washed with water and dried under reduced pressure to give the title compound, 2-benzyl-4-chloro-5-hydroxypyridazin-3(2H)-one (20.45 g) as a white solid. HPLC: 2.40 min.

354C. Preparation of 2-Benzyl-4-Chloro-5-(4-chlorophenyl)-2H-pyridazin-3-one To a solution of 2-benzyl-4-chloro-5-hydroxypyridazin-3(2H)-one (7.84 g, 33.1 mmol) in methylene chloride (110.0 mL) at −10° C., was added triethylamine (4.02 g, 39.75 mmol) followed by trifluromethanesulfonic anhydride (10 g, 35.45 mmol). The mixture was stirred for 30 min and then poured into an ice-cold solution of 0.5N aqueous hydrochloric acid (200 mL). The mixture was then extracted with methylene chloride (3×200 mL). The combined organic layers were washed with water and saturated aqueous NaCl. The organic layer was dried (MgSO₄), filtered and concentrated under reduced pressure to give the corresponding triflate (12.91 g) as a pink oil. This material was dissolved in a 1:1 mixture of THF (55 mL) and MeOH (55 mL) and the solution was degassed with argon. 4-Chlorophenylboronic acid (2.37 g, 15.18 mmol), dichloro-bis(chlorodi-tert-butylphosphine)palladium (0.89 g, 1.65 mmol) and potassium carbonate (13.67 g) were added and the reaction mixture was stirred at room temperature for 1.5 h. The reaction mixture was then diluted with water (200 mL). The resulting solution was extracted with CH₂Cl₂ (2×200 mL). The combined organic layers were washed with water and saturated aqueous NaCl. The organic layer was dried (MgSO₄), filtered and concentrated under reduced pressure. The residue was then purified by column chromatography on silica gel using hexanes/EtOAc (2:1) to give the title compound, 2-benzyl-4-chloro-5-(4-chloro-phenyl)-2H-pyridazin-3-one 3.9 g as a white solid. HPLC: 3.72 min.

354D. Preparation of 4-Chloro-5-(4-chlorophenyl)-2H-pyridazin-3-one

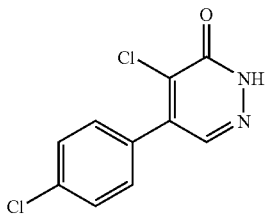

2-Benzyl-4-Chloro-5-(4-chloro-phenyl)-2H-pyridazin-3-one (3.19 g, 9.65 mmol) was dissolved in toluene (50 mL). Aluminum chloride (AlCl₃, 3.22 g, 24.1 mmol) was then added and the reaction mixture was heated at 50° C. After 20 min, the reaction mixture was cooled to RT and then poured into ice-water (200 mL). The resultant solution was extracted with EtOAc (3×200 mL). The combined organic layers were washed with water (500 mL). The organic layer was dried (MgSO₄), filtered and concentrated under reduced pressure. The residue was purified by column chromatography on silica gel using EtOAc to give the title compound, 4-chloro-5-(4-chlorophenyl)-2H-pyridazin-3-one (2.33 g) as a white solid. HPLC: 2.74 min.

354E. Preparation of 3,4-Dichloro-5-(4-chlorophenyl)-pyridazine

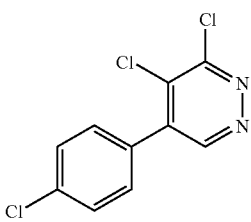

4-Chloro-5-(4-chlororphenyl-2H-pyridazine-3-one (2.33 g, 9.65 mmol) was suspended in POCl₃ (11 mL). The reaction mixture was placed in an oil bath preheated at 110° C. for 1 h. After cooling to RT, the mixture was poured over 200 g ice to quench the excess POCl₃ and the resultant solution was extracted with EtOAc. The combined organic layers were washed with water. The organic layer was dried (MgSO₄), filtered and concentrated under reduced pressure to give the title compound, 3,4-dichloro-5-(4-chlorophenyl)-pyridazine (2.6 g) as a light yellow solid. HPLC: 3.26 min.

354F. Preparation of 1-[4-Chloro-5-(4-chlorophenyl)-pyridazin-3-yl]-hydrazine

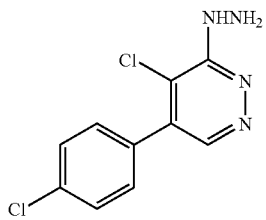

3,4-Dichloro-5-(4-chlorophenyl)-pyridazine (6.0 g, 23.1 mmol) was suspended in isobutanol (150 mL) at 0° C. and hydrazine monohydrate (11.1 g) was added dropwise over 10 min. The reaction mixture was slowly warmed up to RT and stirred for 24 h. The mixture was cooled in an ice/water bath for 15 min and filtered. The white solid thus obtained was washed with cold isopropanol and dried to give the title compound, 1-[4-chloro-5-(4-chloro-phenyl)-pyridazin-3-yl]-hydrazine, (5.0 g) as a white solid. HPLC: 1.65 min.

354G. Preparation of 8-Chloro-7-(4-chlorophenyl)-2H-[1,2,4]triazolo[4,3-b]pyridazin-3-one

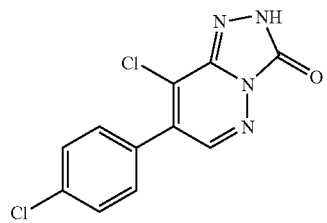

To a solution of triphosgene (30.4 g, 102.4 mmol) in THF (300 mL), 1-[4-chloro-5-(4-chloro-phenyl)-pyridazin-3-yl]-hydrazine (6.52 g, 25.61 mmol) was added in portions over 15 min at room temperature. The mixture was stirred at room temperature for 4 h. After this time, the solution was poured into ice/water (500 mL), and the resulting light yellow solid was collected by filtration. The solid was rinsed with aqueous 0.5N HCl and water. It was then dried under vacuum to give the title compound, 2.81 g of 8-chloro-7-(4-chlorophenyl)-2H-[1,2,4]triazolo[4,3-b]pyridazin-3-one as a light yellow solid. HPLC: 2.78 min; MS, M+H=281.

Example 355

Preparation of 2-(4-(Isoxazol-5-yl)benzyl)-8-chloro-7-(4-chlorophenyl)-[1,2,4]triazolo[4,3-b]pyridazin-3(2H)-one

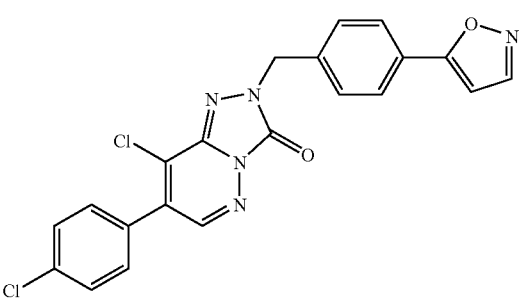

To a solution of 8-chloro-7-(4-chlorophenyl)-[1,2,4]triazolo[4,3-b]pyridazin-3(2H)-one (300 mg, 1.07 mmol), prepared as described in Example 354, in DMF (5 mL) was added K₂CO₃ (180 mg, 1.3 mmol) followed by 5-(4-(bromomethyl)phenyl)isoxazole (305 mg, 1.28 mmol), prepared as described in Example 250A. The reaction mixture was stirred at 70° C. for 2 h. The reaction mixture was cooled to RT, diluted with water (25 mL) and a precipitate formed. The solid was collected by filtration. The solid was washed with water (2×25 mL) followed by hexanes (20 mL). The solid was dried in a vacuum oven at 40° C. The title compound 2-(4-(isoxazol-5-yl)benzyl)-8-chloro-7-(4-chlorophenyl)-[1,2,4]triazolo[4,3-b]pyridazin-3(2H)-one (450 mg, 96%) was obtained as a yellow solid. HPLC: 3.50 min; M+H=438.

Example 357

Preparation of 2-(4-(Isoxazol-5-yl)benzyl)-7-(4-chlorophenyl)-8-(pyridin-3-yl)-[1,2,4]triazolo[4,3-b]pyridazin-3(2H)-one

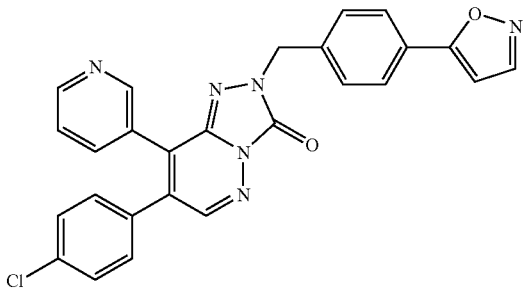

To a stirred solution of 2-(4-(isoxazol-5-yl)benzyl)-8-chloro-7-(4-chlorophenyl)-[1,2,4]triazolo[4,3-b]pyridazin-3(2H)-one (100 mg, 0.23 mmol), prepared as described in Example 355, in toluene (2 mL) in a round bottomed flask was added Pd(PPh$_3$)$_4$ (16 mg, 0.014 mmol) under a stream of argon. 3-(4,4,5,5-tetramethyl-1,3,2-dixoborolan-2-yl)pyridine (61 mg, 0.3 mmol) was added subsequently. Under vigorous stirring, Na$_2$CO$_3$ (97 mg, 0.91 mmol) pre-dissolved in water (0.25 mL) was added to the suspension. argon was bubbled through this suspension for 10 min before the flask was placed in an oil bath preheated at 120° C. The reaction was stirred at reflux for 6 days. The reaction was then allowed to cool to RT and poured into water (10 mL). The resulting mixture was extracted with EtOAc (3×10 mL). The combined organic layers were washed with water (2×10 mL) followed by saturated aqueous NaCl (2×5 mL). The organic layer was concentrated under reduced pressure. Obtained product was purified by reverse phase HPLC to give the title compound, 2-(4-(isoxazol-5-yl)benzyl)-7-(4-chlorophenyl)-8-(pyridin-3-yl)-[1,2,4]triazolo[4,3-b]pyridazin-3(2H)-one (8.5 mg, 8%) as a pale yellow solid. HPLC: 2.98 min; M+H=481; $^1$H NMR (CDCl$_3$), ppm: 8.61 (1H, d, J=6.05 Hz), 8.55 (1H, d, J=5.0 Hz), 8.28 (1H, d, J=2.0 Hz)), 8.19 (1H, s), 7.76 (2H, d, J=10.0 Hz), 7.69 (1H, d, J=5.0 Hz), 7.51 (2H, d, J=10.0 Hz), 7.31-7.33 (3H, m), 7.09 (2H, d, J=5.0 Hz), 6.51 (1H, s), 5.25 (2H, s).

Example 357

Preparation of 2-(4-(Isoxazol-5-yl)benzyl)-7-(4-chlorophenyl)-8-phenyl-[1,2,4]triazolo[4,3-b]pyridazin-3(2H)-one

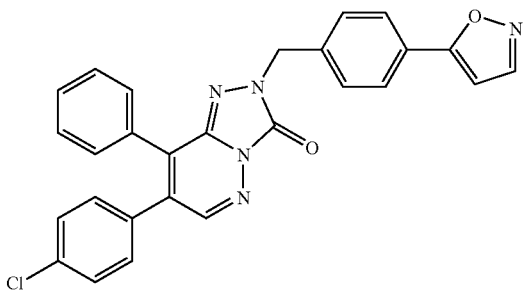

To a stirred solution of 2-(4-(isoxazol-5-yl)benzyl)-8-chloro-7-(4-chlorophenyl)-[1,2,4]triazolo[4,3-b]pyridazin-3(2H)-one (100 mg, 0.23 mmol), prepared as described in Example 355 in toluene (2 mL) in a round bottomed flask was added Pd(PPh$_3$)$_4$ (16 mg, 0.014 mmol) under bubbling argon. Phenyl boronic acid (36 mg, 0.3 mmol) was added subsequently. Under vigorous stirring, Na$_2$CO$_3$ (97 mg, 0.91 mmol) pre-dissolved in water (0.25 mL) was added to the suspension. Argon was bubbled through this suspension for 10 min before the flask was placed in an oil bath preheated at 120° C. The reaction was stirred at reflux for 6 days. The reaction was then allowed to cool to RT. After this time, the reaction mixture was poured into water (10 mL). The resultant solution was extracted with EtOAc (3×10 mL). The combined organic layers were washed with water (2×10 mL) followed by saturated aqueous NaCl (2×5 mL). The organic layer was dried (MgSO$_4$), filtered and concentrated to obtain crude product. This crude product was purified by reverse phase HPLC to give the title compound, 2-(4-(isoxazol-5-yl)benzyl)-7-(4-chlorophenyl)-8-phenyl-[1,2,4]triazolo[4,3-b]pyridazin-3(2H)-one, (15.5 mg, 14%) as pale yellow solid. HPLC: 3.68 min; MS, M+H=480; $^1$H NMR (CDCl$_3$), ppm: 8.31 (1H, d, J=2.0 Hz), 8.22 (1H, s), 7.77 (2H, d, J=10.0 Hz), 7.51 (2H, d, J=10.0 Hz), 7.26-7.42 (7H, m), 7.09 (2H, d, J=10.0 Hz), 6.54 (1H, d, J=5.0 Hz), 5.29 (2H, s).

Example 358

Preparation of 8-Chloro-7-(4-chlorophenyl)-2-(pyrazin-2-ylmethyl)-2H-[1,2,4]triazolo[4,3-b]pyridazin-3-one

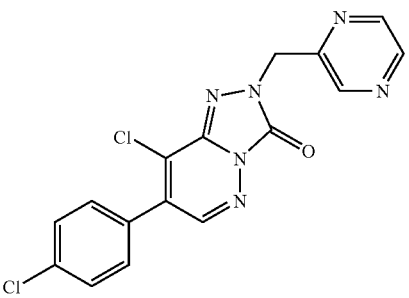

To a solution of 8-chloro-7-(4-chlorophenyl)-2H-[1,2,4]triazolo[4,3-b]pyridazin-3-one (0.62 g, 2.21 mmol), prepared as described in Example 354, in DMF (10 mL) at RT was added K$_2$CO$_3$ (0.61 g, 4.4 mmol) and 2-(chloromethyl)pyrazine (0.83 g). The reaction mixture was heated at 50° C. for 2 h. After this time, the mixture was diluted with EtOAc (150 mL). The resultant solution was washed with water and saturated aqueous NaCl. The organic layer was dried (MgSO$_4$), filtered and concentrated under reduced pressure. The residue was purified by column chromatography on silica gel eluting with hexanes:EtOAc 1:2 to afford 0.61 g of the title compound, 8-chloro-7-(4-chlorophenyl)-2-(pyrazin-2-ylmethyl)-2H-[1,2,4]triazolo[4,3-b]pyridazin-3-one as a yellow solid. HPLC RT: 2.86 min; MS, M+H=373; $^1$H NMR (CDCl$_3$): δ 8.64 (d, 1H), 8.54 (m, 2H), 8.11 (s, 1H), 7.54-7.49 (m, 4H), 5.48 (s, 2H).

Example 359

Preparation of 2-(4-(Trifluoromethyl)benzyl-8-chloro-7-(4-chlorophenyl)-2H-[1,2,4]triazolo[4,3-b]pyridazin-3-one

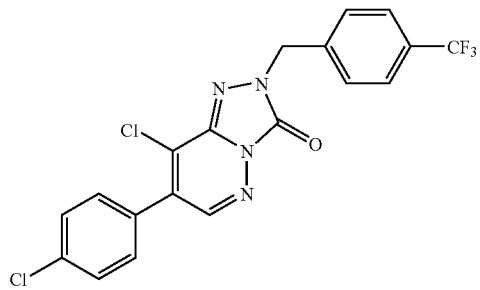

To a solution of 8-chloro-7-(4-chlorophenyl)-2H-[1,2,4]triazolo[4,3-b]pyridazin-3-one (0.54 g, 1.91 mmol), prepared as described in Example 354, in DMF (5 mL) at RT was added $K_2CO_3$ (0.40 g, 2.87 mmol) and 2-(trifluoromethyl)benzyl bromide (0.595 g, 2.49 mmol). The reaction mixture was heated at 55° C. for 4 h. After this time, the mixture was diluted with EtOAc (150 mL). The resultant solution was washed with water and saturated aqueous NaCl. The organic layer was dried ($MgSO_4$), filtered and concentrated under reduced pressure. The residue was purified by chromatography on silica gel using hexanes:EtOAc (2:1) to afford 0.74 g of the title compound, 2-(4-(trifluoromethyl)benzyl-8-chloro-7-(4-chloro-phenyl)-2H-[1,2,4]triazolo[4,3-b]pyridazin-3-one as a yellow solid. HPLC RT: 3.84 min; MS, M+H=439. $^1$H NMR (CDCl$_3$): δ 8.08 (s, 1H), 7.44-7.61 (m, 8H), 5.30 (s, 2H).

Example 360

Preparation of 2-(4-(Trifluoromethyl)benzyl-7-(4-chloro-phenyl)-8-phenoxy-2H-[1,2,4]triazolo[4,3-b]pyridazin-3-one

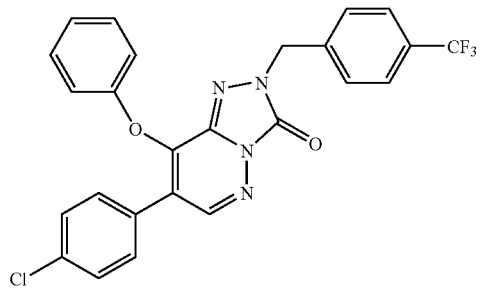

To a solution of 2-(4-(trifluoromethyl)benzyl-8-chloro-7-(4-chlorophenyl)-2H-[1,2,4]triazolo[4,3-b]pyridazin-3-one (16.5 mg, 0.376 mmol) prepared as described in Example 359, in 0.3 mL of DMF at RT, potassium carbonate (19.4 mg, 0.14 mmol) was added followed by phenol (13.2 mg, 0.14 mmol). The mixture was stirred for 4 h. After this time, the reaction mixture was diluted with 5 mL of 1N aqueous sodium hydroxide. The precipitate was collected by filtration and washed with 1N aqueous NaOH, and water. The solid was dried to the title compound, 2-(4-(trifluoromethyl)benzyl-7-(4-chlorophenyl)-8-phenoxy-2H-[1,2,4]triazolo[4,3-b]pyridazin-3-one (15.8 mg) as light yellow solid. HPLC RT: 4.02 min; MS, M+H=497; $^1$H NMR (CDCl$_3$): δ 8.21 (s, 1H), 7.52-6.97 (m, 13H), 5.12 (s, 2H).

Example 361

Alterative Preparation of 2-(4-(Trifluoromethyl)benzyl)-8-chloro-7-(4-chlorophenyl)-[1,2,4]triazolo[4,3-b]pyridazin-3(2H)-one

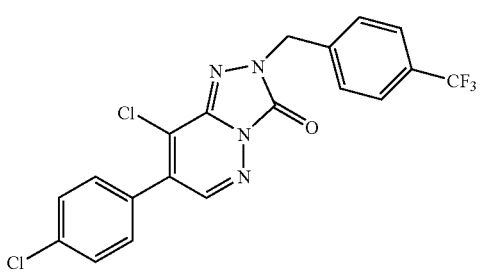

361A. Preparation of 2-Benzyl-4,5-dichloropyridazin-3(2H)-one

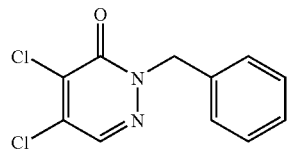

To a stirring suspension of 4,5-dichloro-3-hydroxypyridazine (33 g, 200 mmol) in DMF (260 mL) at room temperature under argon was added $K_2CO_3$ (55 g, 400 mmol), followed by benzyl bromide (41 g, 505.8 mmol). After 16 h the reaction mixture was poured into a flask containing water (500 mL) with stirring. After 15 min stirring, the precipitated product was collected by filtration and washed thoroughly with water. The solid was dried in a vacuum oven at 50° C. for 16 h to obtain the title compound, 2-benzyl-4,5-dichloropyridazin-3(2H)-one, (49.2 g, 96%) as an off-white solid. MS [M+H]$^+$ 255; HPLC retention time=3.02 min.

361B. Preparation of 2-benzyl-5-chloro-4-methoxypyridazin-3(2H)-one

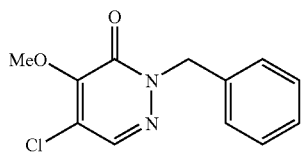

To a stirring solution of 2-benzyl-4,5-dichloropyridazin-3(2H)-one (22.9 g, 89.8 mmol) in 1,4-dioxane (300 mL) at RT under argon was added NaOMe (22.4 mL, 25% solution in MeOH, 97.9 mmol) over 10 min by syringe. After 2 h, TLC indicated the reaction was completed. The reaction mixture was concentrated under reduced pressure. A saturated solution of NaCl (200 mL) was added and the resulting solution was extracted with $CH_2Cl_2$ (2×100 mL). The combined organic layers were dried ($Na_2SO_4$), concentrated under vacuum and purified by silica gel column chromatography eluting with $CH_2Cl_2$ to give the title compound, 2-benzyl-5-chloro-4-methoxypyridazin-3(2H)-one (20.3 g, 90%) as a colorless oil. TLC (CH$_2$Cl$_2$, R$_f$=0.4); MS [M+H]$^+$ 251; HPLC retention time=2.74 min.

361C. Preparation of 2-Benzyl-5-(4-chlorophenyl)-4-methoxypyridazin-3(2H)-one

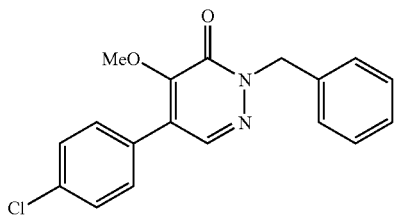

To a solution of 2-benzyl-5-chloro-4-methoxypyridazin-3(2H)-one (20 g, 80 mmol) and 4-chlorophenylboronic acid (15.6 g, 100 mmol) in toluene/EtOH (2:1, 600 mL) at RT under argon was added (Ph$_3$P)$_4$Pd (1.85 g, 1.8 mmol) and 2 M aqueous Na$_2$CO$_3$ solution (160 mL, 320 mmol). The resulting suspension was heated at 90° C. for 16 h with stirring. HPLC/MS indicated about 4% of the 2-benzyl-5-chloro-4-methoxypyridazin-3(2H)-one still remained. After cooling the reaction mixture to RT, the solution was extracted with CH$_2$Cl$_2$ (2×150 mL). The combined organic layers were dried (Na$_2$SO$_4$), filtered and concentrated under vacuum. The crude product was purified by silica gel column chromatography (ISCO) eluting with hexanes/EtOAc to obtain pure title compound, 2-Benzyl-5-(4-chlorophenyl)-4-methoxypyridazin-3(2H)-one, (21.7 g, 83%) as a white solid. MS [M+H]$^+$ 327; HPLC retention time=3.85 min.

361D. Preparation of 3,4-dichloro-5-(4-chlorophenyl)pyridazine

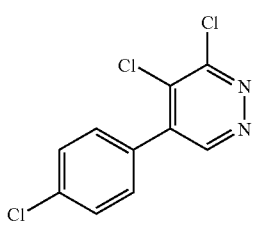

A stirring solution of 2-benzyl-5-(4-chlorophenyl)-4-methoxypyridazin-3(2H)-one (16.3 g, 50 mmol) in POCl$_3$ (100 mL) was heated in the sealed flask at 80° C. for 16 h. The reaction mixture was cooled to room temperature and additional POCl$_3$ (50 mL) was added. The reaction mixture was then heated at 120° C. for 1 d and then cooled to room temperature. Most of the solvent was removed under vacuum. Ice (300 g) was carefully added to the residue while stirring, and the resulting mixture was extracted with CH$_2$Cl$_2$ (250 mL×2). The combined organic phases were dried (Na$_2$SO$_4$) and concentrated under vacuum. The crude product was purified by silica gel column chromatography (ISCO) eluting with hexanes/EtOAc/CH$_2$Cl$_2$. Desired product (9.6 g) was obtained as a brown solid with a purity of 95%. This was washed with methanol (20 mL×2) and dried to obtain the pure title compound, 3,4-dichloro-5-(4-chlorophenyl)pyridazine (5.3 g, 41%) as an off-white solid. MS [M+H]$^+$=259; HPLC retention time=3.40 min; $^1$HNMR (400 MHz, CDCl$_3$) δ 9.00 (s, 1H), 7.47-7.55 (m, 4H); $^{13}$CNMR (100 MHz, CDCl$_3$) δ 156.4, 150.6, 139.4, 136.7, 135.1, 130.6, 130.3, 129.3.

361E. Preparation of 1-(4-chloro-5-(4-chlorophenyl)pyridazin-3-yl)hydrazine

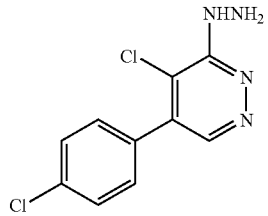

To a stirring suspension of 3,4-dichloro-5-(4-chlorophenyl)pyridazine (2.58 g, 10 mmol) in 2-BuOH (150 mL) at RT was added anhydrous hydrazine (4.80 g, 150 mmol). The reaction mixture was heated at 60° C. under argon. HPLC/MS analysis indicated that the reaction was complete after 5 h. The reaction mixture was cooled to 0° C., and the product was collected by filtration. The solid was then washed with ice-cold 2-propanol (10 mL×2). After drying the solid under vacuum at room temperature for 16 h, the title compound, 1-(4-chloro-5-(4-chlorophenyl)pyridazin-3-yl)hydrazine was obtained in a 1.6:1 ratio with undesired 1-(3-chloro-5-(4-chlorophenyl)pyridazin-4-yl)hydrazine (2.16 g gross). 1-(4-chloro-5-(4-chlorophenyl)pyridazin-3-yl)hydrazine MS [M+H]$^+$ 255; HPLC retention time=1.63 min. 1-(3-chloro-5-(4-chlorophenyl)pyridazin-4-yl)hydrazine MS [M+H]$^+$ 255; HPLC retention time=1.09 min.

361F. Preparation of 8-Chloro-7-(4-chlorophenyl)-[1,2,4]triazolo[4,3-b]pyridazin-3(2H)-one

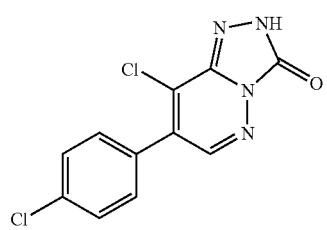

A stirring solution of triphosgene (17.5 g, 59.0 mmol) in THF (150 mL) was cooled to 0° C. under argon and a mixture of 1-(4-chloro-5-(4-chlorophenyl)pyridazin-3-yl)hydrazine and 1-(3-chloro-5-(4-chlorophenyl)pyridazin-4-yl)hydrazine, as prepared in Example 361E, (3.0 g gross) was added over 3 min. The reaction mixture was then allowed to warm to RT gradually and then was stirred for 16 h. The solvent was removed under vacuum to reduce the reaction mixture to half its original volume, and the resulting suspension was cooled in an ice bath. Ice water (300 mL) was added, followed by stirring for 30 min. The product was collected by filtration and washed with 0.5 N aqueous HCl (20 mL×2), then H$_2$O (20 mL×2). After drying under vacuum at room temperature for 16 h, the title compound, 8-chloro-7-(4-chlorophenyl)-[1,2,4]triazolo[4,3-b]pyridazin-3(2H)-one, (2.1 g) was obtained as a yellow solid. MS [M+H]$^+$ 281; HPLC retention time=2.71 min.

361G. Preparation of 2-(4-(trifluoromethyl)benzyl)-8-chloro-7-(4-chlorophenyl)-[1,2,4]triazolo[4,3-b]pyridazin-3(2H)-one

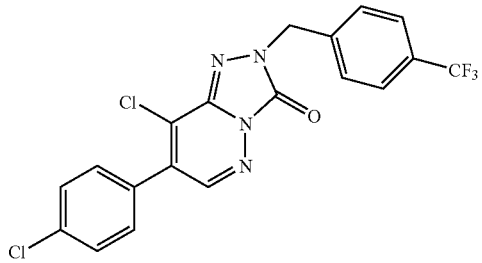

To a stirring suspension of 8-chloro-7-(4-chlorophenyl)-[1,2,4]triazolo[4,3-b]pyridazin-3(2H)-one (1.12 g, 4.0 mmol) and 4-(trifluoromethyl)benzyl bromide (1.24 g, 5.2 mmol) in DMF (15 mL) at RT under argon was added $K_2CO_3$ (0.83 g, 5.2 mmol). The resulting mixture was heated at 55° C. for 2 h. After 2 h, HPLC/MS analysis indicated the reaction was complete. The reaction mixture was cooled to RT and EtOAc (100 mL) was added. The resulting mixture was washed with saturated NaCl (50 mL×2). The organic layer was dried ($Na_2SO_4$), filtered and concentrated under vacuum with co-evaporation of toluene (10 mL×2) to obtain a dark yellow solid. This crude product was washed with MeOH (10 mL×2), then dried under vacuum at room temperature for 3 h to obtain the title compound, 2-(4-(trifluoromethyl)benzyl)-8-chloro-7-(4-chlorophenyl)-[1,2,4]triazolo[4,3-b]pyridazin-3(2H)-one (1.3 g, 74%) as a yellow solid. MS $[M+H]^+$ 439; HPLC retention time=3.92 min; $^1$HNMR (400 MHz, $CDCl_3$) δ 9.00 (s, 1H), 7.45-7.61 (m, 8H), 5.32 (s, 2H).

Example 362

Preparation of 8-Chloro-7-p-tolyl-2-((6-(trifluoromethyl)pyridin-3-yl)methyl)-[1,2,4]triazolo[4,3-b]pyridazin-3(2H)-one

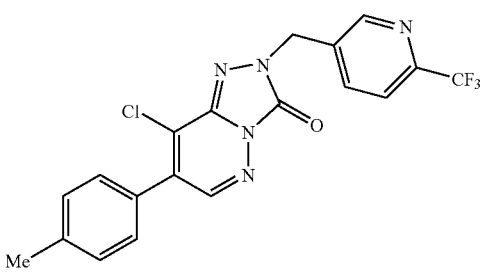

362A. Preparation of 2-Benzyl-4-methoxy-5-p-tolylpyridazin-3(2H)-one

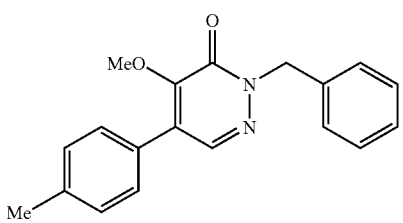

To a solution of 2-benzyl-5-chloro-4-methoxypyridazin-3(2H)-one (20 g, 80 mmol), prepared as described in Example 361B, and 4-methylphenylboronic acid (13 g, 96 mmol) in toluene (300 mL) at RT under argon was added $(Ph_3P)_4Pd$ (1.85 g, 1.8 mmol) and 2 M aqueous $Na_2CO_3$ solution (160 mL, 320 mmol). The resulting suspension was heated at 100° C. for 5 h with stirring. HPLC/MS indicated complete reaction. After cooling the reaction mixture to room temperature, it was extracted with $CH_2Cl_2$ (200 mL×2), then dried ($Na_2SO_4$), filtered and concentrated under vacuum. The crude product was purified by silica gel column chromatography (ISCO) eluting with hexanes/EtOAc to give the title compound, 2-benzyl-4-methoxy-5-p-tolylpyridazin-3(2H)-one, (21.9 g, 89%) as a white foam. MS $[M+H]^+$ 307; HPLC retention time=3.78 min.

362B. Preparation of 3,4-Dichloro-5-p-tolylpyridazine

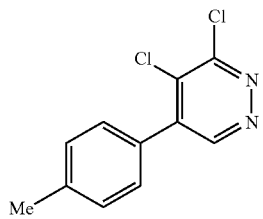

A stirring solution of 2-benzyl-4-methoxy-5-p-tolylpyridazin-3(2H)-one (15.3 g, 50 mmol) in $POCl_3$ (100 mL) was heated in the sealed flask at 120° C. for 24 h. The reaction mixture was cooled to RT and additional $POCl_3$ (50 mL) was added. The reaction mixture was heated again at 120° C. for 1 d and then cooled to room temperature. Most of the solvent was removed under vacuum. Ice (200 g) was carefully added to the residue while stirring, and the resulting mixture was extracted with $CH_2Cl_2$ (250 mL×2). The combined organic phases were dried ($Na_2SO_4$) and concentrated under vacuum. The crude product was purified by silica gel column chromatography (ISCO) eluting with hexanes/EtOAc/$CH_2Cl_2$. Impure desired product (10 g) was obtained as a brown solid. Washing with methanol (15 mL×2), then drying the solid, provided pure title compound, 3,4-dichloro-5-p-tolylpyridazine, (5.1 g, 43%) as an off-white solid. MS $[M+H]^+$ 239; HPLC retention time=3.34 mm.

362C. Preparation of 1-(4-Chloro-5-p-tolylpyridazin-3-yl)hydrazine

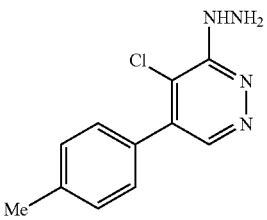

To a stirring suspension of 3,4-dichloro-5-p-tolylpyridazine (4.5 g, 18.9 mmol) in 2-BuOH (200 mL) at room temperature was added anhydrous hydrazine (9.1 g, 284 mmol). The reaction mixture was heated at 60° C. under argon. HPLC/MS analysis indicated complete reaction after 15 h. The reaction mixture was cooled to 0° C., and the product was collected by filtration and further washed with ice-cold 2-propanol (20 mL×2). After drying under vacuum at room temperature for 16 h, the title compound, 1-(4-chloro-5-p-tolylpyridazin-3-yl)hydrazine, was obtained in a 2.6:1 ratio with undesired 1-(3-chloro-5-p-tolylpyridazin-4-yl)hydrazine (3.6 g gross). 1-(4-chloro-5-p-tolylpyridazin-3-yl)hydrazine MS $[M+H]^+$ 235; HPLC retention time=1.84 min. 1-(3-chloro-5-p-tolylpyridazin-4-yl)hydrazine MS $[M+H]^+$ 235; HPLC retention time=1.35 min.

362D. Preparation of 8-Chloro-7-p-tolyl-[1,2,4]triazolo[4,3-b]pyridazin-3(2H)-one

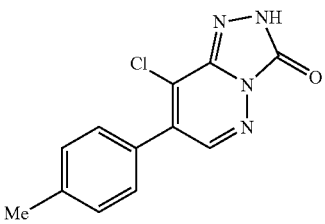

A stirring solution of triphosgene (19.0 g, 64.0 mmol) in THF (200 mL) was cooled to 0° C. under argon and the mixture of 1-(4-chloro-5-p-tolylpyridazin-3-yl)hydrazine and 1-(3-chloro-5-p-tolylpyridazin-4-yl)hydrazine (3.0 g gross), prepared as described in Example 362C, was added over 3 min. The reaction mixture was allowed to warm to RT gradually and then stirred for 16 h. Solvent was removed under vacuum to reduce the reaction mixture to half its original volume, and the resulting suspension was cooled to an ice bath. Ice water (300 mL) was added, followed by stirring for 1 h. The product was collected by filtration and washed with 0.1 M aqueous HCl (50 mL×2), then H$_2$O (50 mL×2). After drying under vacuum at 50° C. for 2 d, the title compound, 8-chloro-7-p-tolyl-[1,2,4]triazolo[4,3-b]pyridazin-3(2H)-one, (2.2 g) was obtained as a yellow solid. MS [M+H]$^+$ 261; HPLC retention time=2.75 min; $^1$HNMR (400 MHz, THF-d$_8$) δ 11.69 (s, 1H), 8.10 (s, 1H), 7.49-7.51 (m, 2H), 7.34-7.35 (m, 2H).

362E. Preparation of 8-Chloro-7-p-tolyl-2-((6-(trifluoromethyl)pyridin-3-yl)methyl)-[1,2,4]triazolo[4,3-b]pyridazin-3(2H)-one

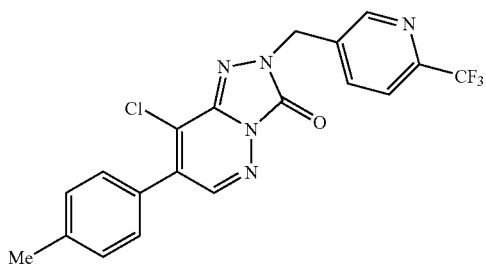

To a stirring suspension of 8-chloro-7-p-tolyl-[1,2,4]triazolo[4,3-b]pyridazin-3(2H)-one (2.2 g, 8.4 mmol) and 5-(chloromethyl)-2-(trifluoromethyl)pyridine (2.1 g, 11 mmol) in DMF (15 mL) at room temperature under argon was added K$_2$CO$_3$ (1.74 g, 12.6 mmol). The resulting mixture was heated at 55° C. for 2 h. HPLC/MS analysis indicated complete reaction. The reaction mixture was concentrated under vacuum with co-evaporation of toluene (10 mL×2) to obtain a dark yellow solid. The crude product was purified by silica gel column chromatography (ISCO) eluting with hexanes/EtOAc/CH$_2$Cl$_2$. Desired product (2.1 g) was obtained as a brown solid. Washing with MeOH (10 mL×2) and drying provided pure title compound, 8-chloro-7-p-tolyl-2-((6-(trifluoromethyl)pyridin-3-yl)methyl)-[1,2,4]triazolo[4,3-b]pyridazin-3(2H)-one, (1.76 g, 56%) as a light yellow solid. MS [M+H]$^+$ 420; HPLC retention time=3.53 min; $^1$HNMR (400 MHz, CDCl$_3$) δ 8.89 (s, 1H), 8.13 (s, 1H), 8.00 (d, 1H), 7.70 (d, 1H), 7.30-7.50 (m, 4H), 5.36 (s, 2H), 2.45 (s, 3H).

Example 363

Preparation of 2-(4-(Isoxazol-5-yl)benzyl)-7-(4-chlorophenyl)-8-(1H-imidazol-1-yl)-[1,2,4]triazolo[4,3-b]pyridazin-3(2H)-one

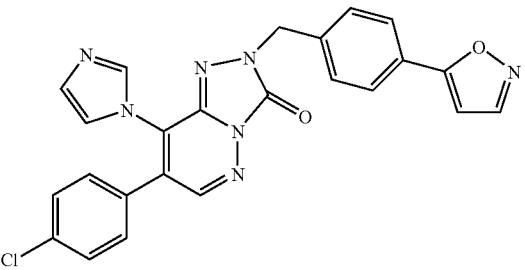

363A. Preparation of 2-(4-(Isoxazol-5-yl)benzyl)-8-chloro-7-(4-chlorophenyl)-[1,2,4]triazolo[4,3-b]pyridazin-3(2H)-one

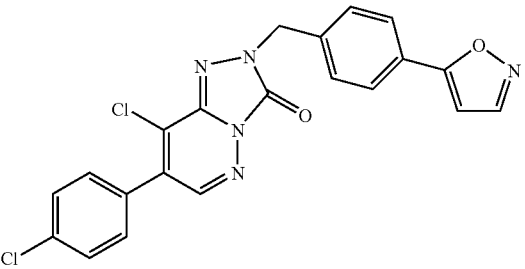

To a stirring suspension of 8-chloro-7-(4-chlorophenyl)-[1,2,4]triazolo[4,3-b]pyridazin-3(2H)-one prepared as described in example 354G, and 5-(4-(bromomethyl)phenyl)isoxazole (122 mg, 0.51 mmol), prepared as described as in Example 250A in DMF (5 mL) at RT under argon was added K$_2$CO$_3$ (119 mg, 0.86 mmol). The resulting mixture was heated at 50° C. for 3 h. HPLC/MS analysis indicated complete reaction. The reaction mixture was concentrated under vacuum with co-evaporation of toluene (10 mL×2) to obtain a dark yellow solid. The crude product was purified by silica gel column chromatography (ISCO) eluting with hexanes/EtOAc to obtain pure title compound, 2-(4-(isoxazol-5-yl)benzyl)-8-chloro-7-(4-chlorophenyl)-[1,2,4]triazolo[4,3-b]pyridazin-3(2H)-one, (149 mg, 79%) as a yellow solid. MS [M+H]$^+$ 438; HPLC retention time=3.55 min.

363B. Preparation of 2-(4-(Isoxazol-5-yl)benzyl)-7-(4-chlorophenyl)-8-(1H-imidazol-1-yl)-[1,2,4]triazolo[4,3-b]pyridazin-3(2H)-one

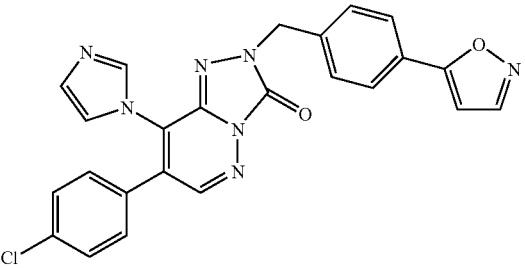

A solution of 2-(4-(isoxazol-5-yl)benzyl)-8-chloro-7-(4-chlorophenyl)-[1,2,4]triazolo[4,3-b]pyridazin-3(2H)-one (149 mg, 0.34 mmol) and imidazole (69.5 mg, 1.02 mmol) in dry 1-methyl-2-pyrrolidinone (3 mL) was heated at 100°

C. for 18 h. HPLC/MS analysis indicated 90% complete reaction. The reaction mixture was concentrated under vacuum with co-evaporation of toluene (5 mL×2) to obtain a dark yellow solid. The crude product was purified by silica gel column chromatography (ISCO) eluting with $CH_2Cl_2$/EtOAc to obtain pure title compound (87 mg, 55%) as a yellow solid. MS [M+H]$^+$ 470; HPLC retention time=2.59 min; $^1$HNMR (400 MHz, CDCl$_3$) δ 8.29 (d, 1H, J=0.5 Hz), 8.18 (s, 1H), 7.80-7.85 (m, 2H), 7.78 (s, 1H), 7.49 (d, 2H, J=7.0 Hz), 7.43 (d, 2H, J=7.0 Hz), 7.13-7.15 (m, 3H), 6.94 (m, 1H), 6.53 (d, 1H, J=0.5 Hz), 5.27 (s, 2H).

Example 364

Preparation of 2-(4-(Isoxazol-3-yl)benzyl)-7-(4-chlorophenyl)-8-(1H-imidazol-1-yl)-[1,2,4]triazolo[4,3-b]pyridazin-3(2H)-one

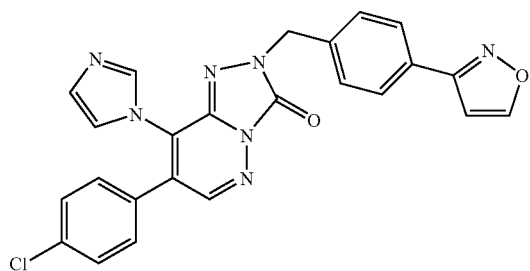

364A. Preparation of 7-(4-Chlorophenyl)-8-(1H-imidazol-1-yl)-[1,2,4]triazolo[4,3-b]pyridazin-3(2H)-one

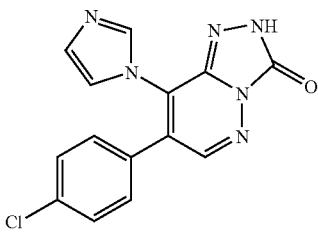

A stirring solution of 8-chloro-7-(4-chlorophenyl)-[1,2,4]triazolo[4,3-b]pyridazin-3(2H)-one (56 mg, 0.20 mmol), prepared as described in example 361F, and imidazole (100 mg, 1.5 mmol) in dry 1-methyl-2-pyrrolidinone (1 mL) was heated to 100° C. for 5 h. HPLC/MS analysis indicated complete reaction. The reaction mixture was reduced to half its original volume with a stream of argon while still heated to 100° C. After cooling to room temperature, 0.7 M aqueous TFA solution (3 mL) was added to lower pH to 1. A precipitate formed. The supernatant, and subsequent extracts of the precipitate obtained by repeated dissolving in NMP and dilution with water, were purified by reversed phase preparative HPLC (C-18, MeOH/H2O gradient, 0.1% TFA). This provided the desired product as the TFA salt, which was free based by passing it, in 1:1 MeOH/$CH_2Cl_2$ solution, through Polymer Laboratories PL-PIP piperidine resin (100 mg, 3.21 mmol/g). Evaporation under vacuum then give title compound, 7-(4-chlorophenyl)-8-(1H-imidazol-1-yl)-[1,2,4]triazolo[4,3-b]pyridazin-3(2H)-one (15 mg, 24%) as a yellow solid. MS [M+H]$^+$ 313; HPLC retention time=1.37 min (C-18, MeOH/H$_2$O (containing 0.1% TFA) gradient).

364B. Preparation of 2-(4-(Isoxazol-3-yl)benzyl)-7-(4-chlorophenyl)-8-(1H-imidazol-1-yl)-[1,2,4]triazolo[4,3-b]pyridazin-3(2H)-one

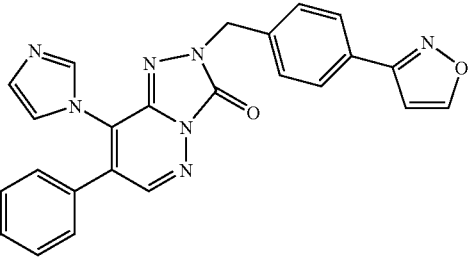

A stirring mixture of 7-(4-chlorophenyl)-8-(1H-imidazol-1-yl)-[1,2,4]triazolo[4,3-b]pyridazin-3(2H)-one (15 mg, 0.048 mmol), 3-(4-(bromomethyl)phenyl)isoxazole (14 mg, 0.59 mmol), and K$_2$CO$_3$ (40 mg, 1.0 mmol) in DMF (0.5 mL) under argon was heated to 55° C. for 30 min. HPLC/MS analysis indicated complete reaction. After cooling to RT, the reaction mixture was diluted with MeOH (3 mL) and filtered through cotton. The filtrate was diluted with water (3 mL), which caused some precipitation, and acidified to pH 1 with TFA. The supernatant, and subsequent extracts of the precipitate obtained by repeated stirring in MeOH and dilution with water, were purified by reversed phase preparative HPLC (C-18, MeOH/H$_2$O gradient, 0.1% TFA). This provided the desired product as the TFA salt, which was free based by passing it, in 1:1 MeOH/CH$_2$Cl$_2$ solution, through Polymer Laboratories PL-PIP piperidine resin (100 mg, 3.21 mmol/g). Evaporation then provided pure title compound (5.6 mg, 25%) as a yellow solid. MS [M+H]$^+$ 470, [M−H]$^-$ 468; HPLC retention time=2.96 min (C-18, MeOH/H$_2$O (10 mM NH$_4$OAc) gradient); $^1$HNMR (500 MHz, CD$_3$OD) δ 8.70 (d, 1H, J=1.6 Hz), 8.43 (s, 1H), 7.85 (d, 2H, J=8.2 Hz), 7.85 (s, 1H), 7.53 (d, 2H, J=8.2 Hz), 7.46 (d, 2H, J=8.8 Hz), 7.29 (d, 2H, J=8.8 Hz), 7.15 (t, 1H, J=1.6 Hz), 7.07 (s, 1H), 6.90 (d, 1H, J=1.6 Hz), 5.30 (s, 2H).

Example 365

Preparation of 2-(4-(Trifluoromethyl)benzyl)-8-amino-7-(4-chlorophenyl)-[1,2,4]triazolo[4,3-b]pyridazin-3(2H)-one

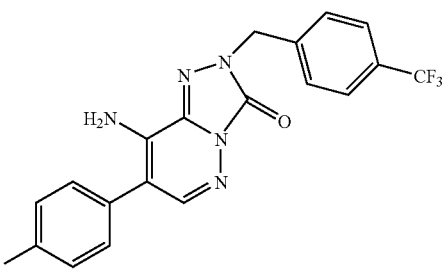

A solution of 2-(4-(trifluoromethyl)benzyl)-8-chloro-7-(4-chlorophenyl)-[1,2,4]triazolo[4,3-b]pyridazin-3(2H)-one (43.8 mg, 0.10 mmol), prepared as described in example 361 step G, and KOCN (81 mg, 1.0 mmol) in dry 1-methyl-2-pyrrolidinone (2 mL) was heated at 120° C. for 2 h under argon. HPLC/MS analysis indicated complete reaction. The reaction mixture was concentrated under vacuum with co-evaporation of toluene (5 mL×2) to obtain a yellow solid. The crude product was purified by reversed phase preparative HPLC (C-18, MeOH/H$_2$O gradient, 0.1% TFA) to give the title compound 2-(4-(trifluoromethyl)benzyl)-8-amino-7-(4-chlorophenyl)-[1,2,4]triazolo[4,3-b]pyridazin-3(2H)- one, (34 mg, 81%) as a yellow solid. MS [M+H]⁺ 420; HPLC retention time=3.70 min.

Example 366

Preparation of 2-(4-(Trifluoromethyl)benzyl)-7-(4-chlorophenyl)-3-oxo-2,3-dihydro-[1,2,4]triazolo[4,3-b]pyridazine-8-carbonitrile

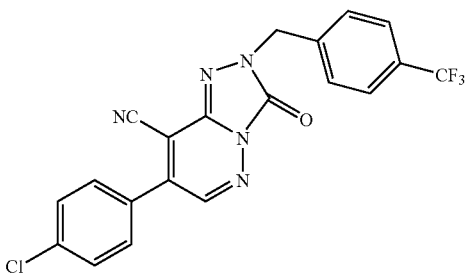

A suspension of 2-(4-(trifluoromethyl)benzyl)-8-chloro-7-(4-chlorophenyl)-[1,2,4]triazolo[4,3-b]pyridazin-3(2H)-one, (43.8 mg, 0.10 mmol), prepared as described in example 361G, and KCN (33 mg, 0.5 mmol) in dry 1-methyl-2-pyrrolidinone (1 mL) was heated at 120° C. for 2 h under argon. HPLC/MS analysis indicated complete reaction. The reaction mixture was concentrated under vacuum with co-evaporation of toluene (5 mL×2) to obtain a yellow solid. The crude product was purified by reversed phase preparative HPLC (C-18, MeOH/H₂O gradient, 0.1% TFA) to obtain title compound (31 mg, 72%), 2-(4-(trifluoromethyl)benzyl)-7-(4-chlorophenyl)-3-oxo-2,3-dihydro-[1,2,4]triazolo[4,3-b]pyridazine-8-carbonitrile as a yellow solid. MS [M+H]⁺ 430; HPLC retention time=3.76 min.

Example 367

Preparation of 8-(6-Fluoropyridin-3-yl)-7-p-tolyl-2-((6-(trifluoromethyl)pyridin-3-yl)methyl)-[1,2,4]triazolo[4,3-b]pyridazin-3(2H)-one

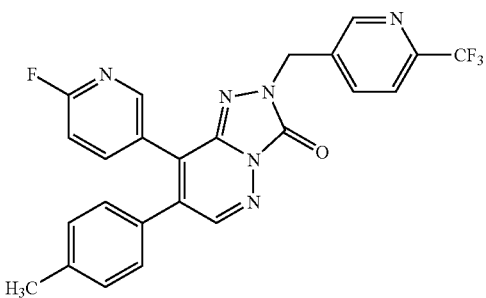

To a microwave reaction vessel containing a stir bar, was added Pd(Ph₃P)₄ catalyst (30 mg, 25 μmol), followed by anhydrous dioxane (0.5 mL). To this was added 8-chloro-7-p-tolyl-2-((6-(trifluoromethyl)pyridin-3-yl)methyl)-[1,2,4]triazolo[4,3-b]pyridazin-3(2H)-one (20 mg, 47 μmol), prepared as described in Example 362, 2-fluoropyridine-5-boronic acid (28.2 mg, 200 μmol), anhydrous dioxane (0.5 mL) and 2M K₃PO₄ aqueous solution (0.25 mL). The reaction vessel was flushed with nitrogen, capped and heated at 120° C. for 10 minutes in a microwave reactor. Reaction mixture was filtered through a Whatman 0.45 μm syringe filter and the crude product was purified using preparative HPLC (Xterra MS-C18, 30×50 mm); Eluted with 30% to 100% B, 8 min gradient, (A=water+0.1% TFA and B=acetonitrile+0.1% TFA); Flow rate at 30 mL/min. UV detection at 220 nm) to give the title compound, 8-(6-fluoropyridin-3-yl)-7-p-tolyl-2-((6-(trifluoromethyl)pyridin-3-yl)methyl)-[1,2,4]triazolo[4,3-b]pyridazin-3(2H)-one as a TFA salt. This compound was taken in 2 mL methanol in a filtration column attached with a stopcock and polystyrene based carbonate resin, PL-CO3 MP-resin, (100 mg, loading 2.4 mmol/g) was added. Contents were shaken for 2 h and methanol solution was filtered and evaporated under reduced pressure to give the title compound, 8-(6-fluoropyridin-3-yl)-7-p-tolyl-2-((6-(trifluoromethyl)pyridin-3-yl)methyl)-[1,2,4]triazolo[4,3-b]pyridazin-3(2H)-one in a freebase form (7.6 mg, 32% yield), as a yellow crystalline solid. MS (M+H)=481; ¹H NMR CDCl₃: δ 8.8 (1H, s), 8.21 (1H, s), 8.23 (1H, s), 7.95 (1H, d, J=8.2 Hz), 7.79 (1H, m), 7.66-7.68 (1H, m), 7.03-7.18 (4H, m), 6.94 (1H, m), 5.3 (2H, s). Analytical HPLC purity: 99% at 2.27 min (retention time), (Xterra MS-C18, 4.6×50 mm); Eluted with 30% to 100% B, 4.5 min gradient, (A=water+0.1% TFA and B=acetonitrile+0.1% TFA); Flow rate at 2.5 mL/min. UV detection at 220 nm.

Example 368

Preparation of 8-(5-Fluoro-6-methoxypyridin-3-yl)-7-p-tolyl-2-((6-(trifluoromethyl)pyridin-3-yl)methyl)-[1,2,4]triazolo[4,3-b]pyridazin-3(2H)-one

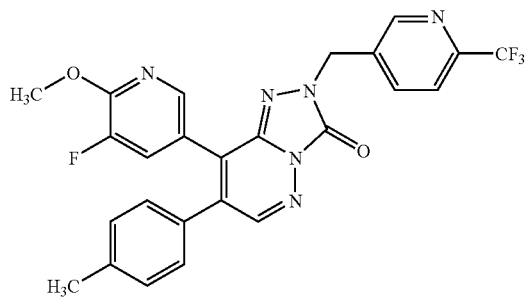

To a microwave reaction vessel containing a stir bar, was added Pd(Ph₃P)₄ catalyst (30 mg, 25 μmol), followed by anhydrous dioxane (0.5 mL). To this was added 8-chloro-7-p-tolyl-2-((6-(trifluoromethyl)pyridin-3-yl)methyl)-[1,2,4]triazolo[4,3-b]pyridazin-3(2H)-one (20 mg, 47 μmol), prepared as described in Example 362, 3-fluoro-2-methoxy-pyridine-5-boronic acid (34.2 mg, 200 μmol), anhydrous dioxane (0.5 mL) and 2M K₃PO₄ aqueous solution (0.25 mL). The reaction vessel was flushed with nitrogen, capped and heated at 120° C. for 10 minutes in a microwave reactor. Reaction mixture was filtered through a 0.45 μm syringe filter and the crude product was purified using preparative HPLC (Xterra MS-C18, 30×50 mm); Eluted with 30% to 100% B, 8 min gradient, (A=water+0.1% TFA and B=acetonitrile+0.1% TFA); Flow rate at 30 mL/min. UV detection at 220 nm) to give the title compound, 8-(5-fluoro-6-methoxypyridin-3-yl)-7-p-tolyl-2-((6-(trifluoromethyl)pyridin-3-yl)methyl)-[1,2,4]triazolo[4,3-b]pyridazin-3(2H)-one as a TFA salt. This compound was taken in 2 mL methanol in a filtration column attached with a stopcock and polystyrene based carbonate resin, PL-CO3 MP-resin, (100 mg, loading 2.4 mmol/g) was added. Contents were shaken for 2 h and methanol solution was filtered and evaporated under reduced pressure to give the title compound, 8-(5-fluoro-6-methoxypyridin-3-yl)-7-p-tolyl-2-((6-(trifluoromethyl)pyridin-3-yl)methyl)-[1,2,4]triazolo[4,3-b]pyridazin-3(2H)-one in a freebase form (9.6 mg, 38% yield), as a yellow crystalline solid. MS (M+H)=511; ¹H NMR (CD₃OD): δ 8.67 (1H, s), 8.25 (1H, s), 7.97 (1H, d, J=8.2 Hz), 7.82 (1H, s), 7.7 (1H, m), 7.38-7.40 (1H, m), 7.09-7.14 (4H, m), 5.3 (2H, s), 3.8 (3H, s). Analytical HPLC purity:

99% at 2.44 min (retention time), (Xterra MS-C18, 4.6×50 mm); Eluted with 30% to 100% B, 4.5 min gradient, (A=water+0.1% TFA and B=acetonitrile+0.1% TFA); Flow rate at 2.5 mL/min. UV detection at 220 nm.

Example 369

Preparation of 8-(2-Methoxypyrimidin-5-yl)-7-p-tolyl-2-((6-(trifluoromethyl)pyridin-3-yl)methyl)-[1,2,4]triazolo[4,3-b]pyridazin-3(2H)-one

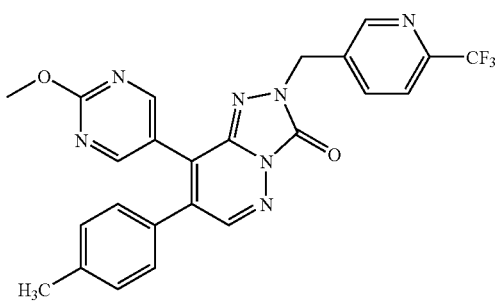

To a microwave reaction vessel containing a stir bar, was added Pd(Ph₃P)₄ catalyst (30 mg, 25 μmol), followed by anhydrous dioxane (0.5 mL). To this was added 8-chloro-7-p-tolyl-2-((6-(trifluoromethyl)pyridin-3-yl)methyl)-[1,2,4]triazolo[4,3-b]pyridazin-3(2H)-one (20 mg, 47 μmol), prepared as described in Example 362, 2-methoxypyrimidine-5-boronic acid (28.2 mg, 200 μmol), anhydrous dioxane (0.5 mL) and 2M K₃PO₄ aqueous solution (0.25 mL). The reaction vessel was flushed with nitrogen, capped and heated at 120° C. for 10 minutes in a microwave reactor. Reaction mixture was filtered through a Whatman 0.45 μm syringe filter and the crude product was purified using preparative HPLC (Xterra MS-C18, 30×50 mm); Eluted with 30% to 100% B, 8 min gradient, (A=water+0.1% TFA and B=acetonitrile+0.1% TFA); Flow rate at 30 mL/min. UV detection at 220 nm) to give the title compound 8-(2-methoxypyrimidin-5-yl)-7-p-tolyl-2-((6-(trifluoromethyl)pyridin-3-yl)methyl)-[1,2,4]triazolo[4,3-b]pyridazin-3(2H)-one as a TFA salt. This compound was taken in 2 mL methanol in a filtration column attached with a stopcock and polystyrene based carbonate resin, PL-CO3 MP-resin, (100 mg, loading 2.4 mmol/g) was added. Contents were shaken for 2 h and methanol solution was filtered and evaporated under reduced pressure to give the title compound 8-(2-methoxypyrimidin-5-yl)-7-p-tolyl-2-((6-(trifluoromethyl)pyridin-3-yl)methyl)-[1,2,4]triazolo[4,3-b]pyridazin-3(2H)-one in a freebase form (7.6 mg, 31% yield), as a yellow crystalline solid. MS (M+H)=494. ¹H NMR (CD₃OD): δ 8.79 (1H, s), 8.39 (1H, s), 8.07 (1H, d, J=8.2 Hz), 7.84 (1H, s), 7.64-7.69 (2H, m), 7.24 (4H, m), 5.4 (2H, s), 3.81 (3H, s). Analytical HPLC purity: 99% at 2.13 min (retention time), (Xterra MS-C18, 4.6×50 mm); Eluted with 30% to 100% B, 4.5 min gradient, (A=water+0.1% TFA and B=acetonitrile+0.1% TFA); Flow rate at 2.5 mL/min. UV detection at 220 nm.

Example 370

Preparation of 2-(4-(Trifluoromethyl)benzyl)-7-(4-chlorophenyl)-8-(pyridin-3-yloxy)-[1,2,4]triazolo[4,3-b]pyridazin-3(2H)-one

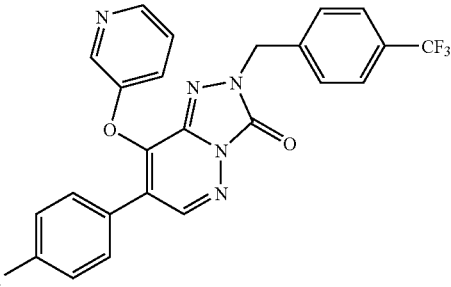

8-Chloro-7-(4-chlorophenyl)-[1,2,4]triazolo[4,3-b]pyridazin-3(2H)-one (20 mg, 47 μmol), prepared as described in Example 361F in 1-methylpyrrolidone (1 mL) in a 1 dram vial was added 3-hydroxypyridine (9.5 mg, 100 μmol), and anhydrous potassium carbonate (21 mg, 150 μmol). The reaction vessel was capped and heated at 80° C. for 16 h in a turbo coil heater with shaking. Reaction mixture was filtered through a Whatman 0.45 μm syringe filter and the crude product is purified using preparative HPLC (Xterra MS-C18, 30×50 mm); Eluted with 10% to 100% B, 8 min gradient, (A=water+0.1% TFA and B=acetonitrile+0.1% TFA); Flow rate at 30 mL/min. UV detection at 220 nm) to give the title compound 2-(4-(trifluoromethyl)benzyl)-7-(4-chlorophenyl)-8-(pyridin-3-yloxy)-[1,2,4]triazolo[4,3-b]pyridazin-3(2H)-one as a TFA salt. This compound was taken in 2 mL methanol in a filtration column attached with a stopcock and polystyrene based carbonate resin, PL-CO3 MP-resin, (100 mg, loading 2.4 mmol/g) was added. Contents were shaken for 2 h and methanol solution was filtered and evaporated under reduced pressure to give the title-compound 2-(4-(trifluoromethyl)benzyl)-7-(4-chlorophenyl)-8-(pyridin-3-yloxy)-[1,2,4]triazolo[4,3-b]pyridazin-3(2H)-one in a freebase form (5.7 mg, 16% yield), as a yellow crystalline solid. MS (M+H)=498; ¹H NMR (CD₃OD): δ 8.34 (1H, s), 8.30 (1H, s), 8.29 (1H, s), 7.51-7.53 (3H, m), 7.37 (2H, m), 7.31-7.32 (2H, m), 7.23-7.24 (2H, m), 7.22 (1H, s), 5.07 (2H, s). Analytical HPLC purity: 99% at 2.07 min (retention time) (Xterra MS-C18, 4.6×50 mm); Eluted with 10% to 100% B, 4.5 min gradient, (A=water+0.1% TFA and B=acetonitrile+0.1% TFA); Flow rate at 2.5 mL/min. UV detection at 220 nm.

Example 371

Preparation of 2-(4-(Trifluoromethyl)benzyl)-7-(4-chlorophenyl)-8-(3-hydroxypyrrolidin-1-yl)-[1,2,4]triazolo[4,3-b]pyridazin-3(2H)-one

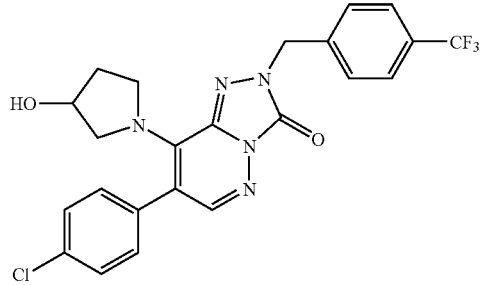

To a solution of 2-(4-(trifluoromethyl)benzyl)-8-chloro-7-(4-chlorophenyl)-[1,2,4]triazolo[4,3-b]pyridazin-3(2H)- one (20 mg, 46 μmol), prepared as described in Example 361, in 1-methylpyrrolidone (1 mL) in a 1 dram vial was added 3-pyrrolidinol (8.7 mg, 100 μmol). The reaction vessel was capped and heated at 80° C. for 16 h in a turbo coil heater with shaking. Reaction mixture was filtered through a Whatman 0.45 μm syringe filter and the crude product was purified using preparative HPLC (Xterra MS-C18, 30×50 mm); Eluted with 10% to 100% B, 8 min gradient, (A=water+0.1% TFA and B=acetonitrile+0.1% TFA); Flow rate at 30 mL/min. UV detection at 220 nm) to give the title compound, 2-(4-(trifluoromethyl)benzyl)-7-(4-chlorophenyl)-8-(3-hydroxypyrrolidin-1-yl)-[1,2,4]triazolo[4,3-b]pyridazin-3(2H)-one TFA salt, (18.5 mg, 52% yield), as a yellow crystalline solid. MS (M+H)=498; $^1$H NMR (CD$_3$OD): 7.79 (1H, s), 7.7-7.78 (2H, m), 7.58-7.60 (2H, m), 7.44-7.45 (2H, m), 7.35-7.37 (2H, m), 5.36 (2H, s), 3.73 (m, 2H), 3.55 (m, 1H), 3.52 (2H, m), 1.88 (2H, m). Analytical HPLC purity: 99% at 2.06 min (retention time), (Xterra MS-C18 (4.6×50 mm); Eluted with 10% to 100% B, 4.5 min gradient, (A=water+0.1% TFA and B=acetonitrile+0.1% TFA); Flow rate at 2.5 mL/min. UV detection at 220 nm.

Example 372

Preparation of 2-(4-(Trifluoromethyl)benzyl)-7-(4-chlorophenyl)-8-(1H-imidazol-1-yl)-[1,2,4]triazolo[4,3-b]pyridazin-3(2H)-one

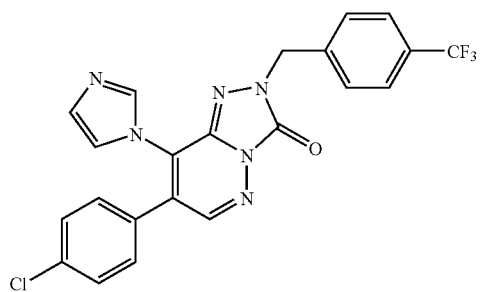

To a solution of 2-(4-(trifluoromethyl)benzyl)-8-chloro-7-(4-chlorophenyl)-[1,2,4]triazolo[4,3-b]pyridazin-3(2H)-one (20 mg, 46 μmol), prepared as described in Example 361, in 1-methylpyrrolidone (1 mL) in a 1 dram vial was added imidazole (6.8 mg, 100 μmol). The reaction vessel was capped and heated at 80° C. for 16 h in a turbo coil heater with shaking. The Reaction mixture was filtered through a Whatman 0.45 μm syringe filter and the crude product was purified using preparative HPLC (Xterra MS-C18, 30×50 mm); Eluted with 10% to 100% B, 8 min gradient, (A=water+0.1% TFA and B=acetonitrile+0.1% TFA); Flow rate at 30 mL/min. UV detection at 220 nm) to give the title compound 2-(4-(trifluoromethyl)benzyl)-7-(4-chlorophenyl)-8-(1H-imidazol-1-yl)-[1,2,4]triazolo[4,3-b]pyridazin-3(2H)-one as a TFA salt. This compound was taken in 2 mL methanol in a filtration column attached with a stopcock and polystyrene based carbonate resin, PL-CO3 MP-resin, (100 mg, loading 2.4 mmol/g) was added. Contents were shaken for 2 h and methanol solution was filtered and evaporated under reduced pressure to give the title compound 2-(4-(trifluoromethyl)benzyl)-7-(4-chlorophenyl)-8-(1H-imidazol-1-yl)-[1,2,4]triazolo[4,3-b]pyridazin-3 (2H)-one in a freebase form (18.5 mg, 52% yield), as a yellow crystalline solid. MS (M+H)=471; $^1$H NMR (CD$_3$OD): δ 8.42 (1H, s), 7.83 (1H, s), 7.65-7.66 (2H, m), 7.57 (2H, m), 7.45-7.47 (2H, m), 7.28-7.29 (2H, m), 7.14 (1H, s), 7.07 (1H, s), 5.33 (2H, s). Analytical HPLC purity: 99% at 2.06 min (retention time), (Xterra MS-C18, 4.6×50 mm); Eluted with 10% to 100% B, 4.5 min gradient, (A=water+0.1% TFA and B=acetonitrile+0.1% TFA); Flow rate at 2.5 mL/min. UV detection at 220 nm.

Example 373

Preparation of 2-(4-(Trifluoromethyl)benzyl)-8-(benzyloxy)-7-(4-chlorophenyl)-[1,2,4]triazolo[4,3-b]pyridazin-3(2H)-one

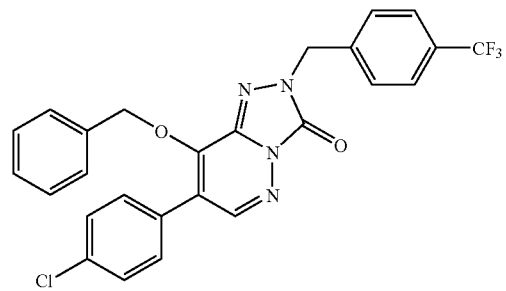

To a solution of 2-(4-(trifluoromethyl)benzyl)-8-chloro-7-(4-chlorophenyl)-[1,2,4]triazolo[4,3-b]pyridazin-3(2H)-one (20 mg, 46 μmol), prepared as described in Example 361, in 1-methylpyrrolidone (1 mL) in a 1 dram vial was added benzyl alcohol (10.8 mg, 100 μmol), and 1M solution of potassium t-butoxide in THF (100 uL). The reaction vessel was capped and stirred at room temperature for 16 h. Reaction mixture was quenched with 100 uL of methanol, filtered through a Whatman 0.45 μm syringe filter and the crude product was purified using preparative HPLC (Xterra MS-C18, 30×50 mm); Eluted with 10% to 100% B, 8 min gradient, (A=water+0.1% TFA and B=acetonitrile+0.1% TFA); Flow rate at 30 mL/min. UV detection at 220 nm) to give the title compound 2-(4-(Trifluoromethyl)benzyl)-8-(benzyloxy)-7-(4-chlorophenyl)-[1,2,4]triazolo[4,3-b]pyridazin-3(2H)-one. (4.9 mg, 16% yield), as a yellow crystalline solid. MS (M+H)=511; $^1$H NMR MeOD: δ 8.25 (1H, s), 7.60-7.7 (4H, m), 7.47-7.55 (4H, m), 7.13-7.31 (5H, m), 5.81 (2H, s), 5.39 (2H, s). Analytical HPLC purity: 99% at 2.31 min (retention time), (Xterra MS-C18, 4.6×50 mm); Eluted with 10% to 100% B, 4.5 min gradient, (A=water+0.1% TFA and B=acetonitrile+0.1% TFA); Flow rate at 2.5 mL/min. UV detection at 220 nm.

Examples 374 to 468

The following Examples were prepared according to methods and procedures above:

| Example Number | Structure | HPLC Retention Time (min) | Mass Specs Observed (M + H) |
|---|---|---|---|
| 374 | 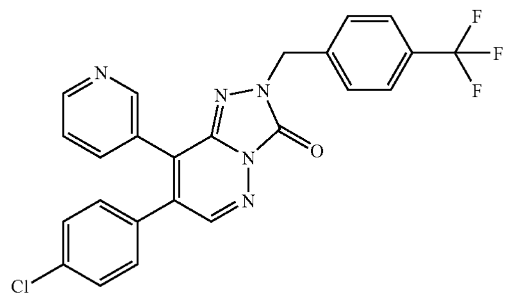 | 3.42 | 482 |
| 375 | 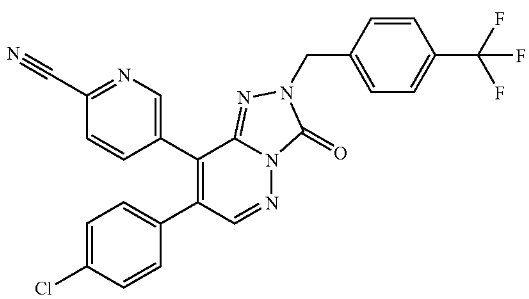 | 3.72 | 506 |
| 376 | 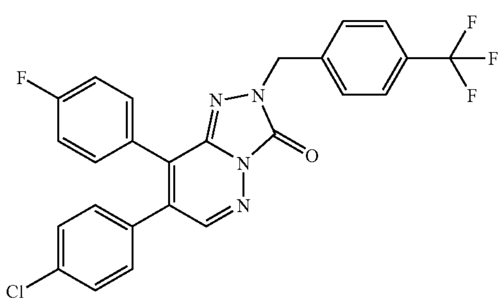 | 3.97 | 499 |
| 377 | 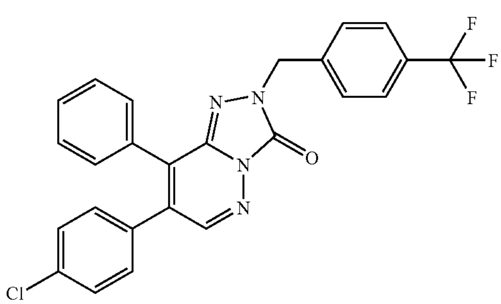 | 3.96 | 481 |
| 378 | 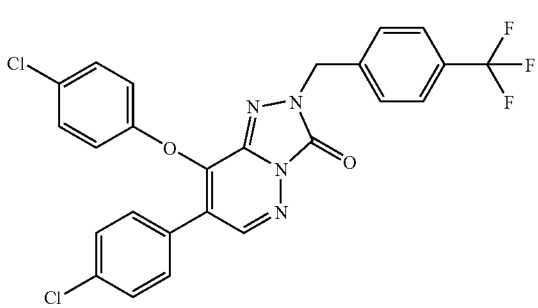 | 4.15 | 531 |

| Example Number | Structure | HPLC Retention Time (min) | Mass Specs Observed (M + H) |
|---|---|---|---|
| 379 | 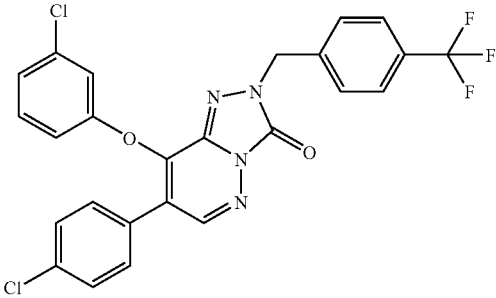 | 4.16 | 531 |
| 380 | 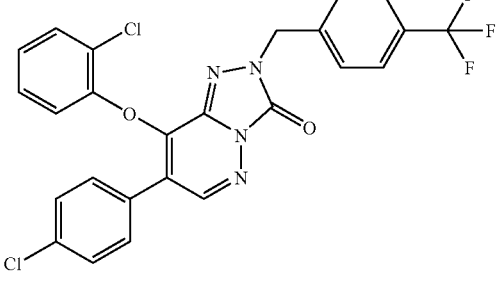 | 4.14 | 531 |
| 381 | 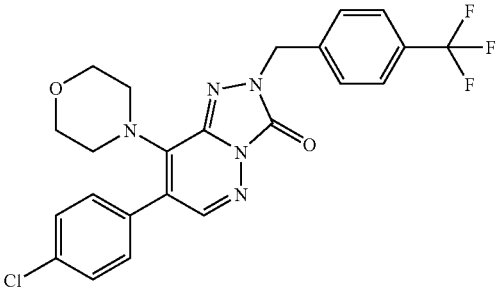 | 3.76 | 489 |
| 382 | 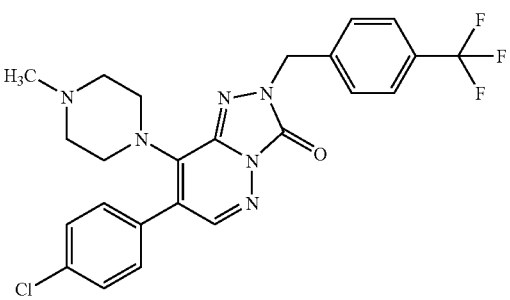 | 2.67 | 503 |
| 383 | 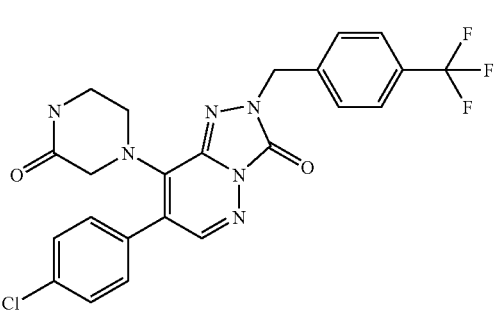 | 3.34 | 503 |

-continued

| Example Number | Structure | HPLC Retention Time (min) | Mass Specs Observed (M + H) |
|---|---|---|---|
| 384 | 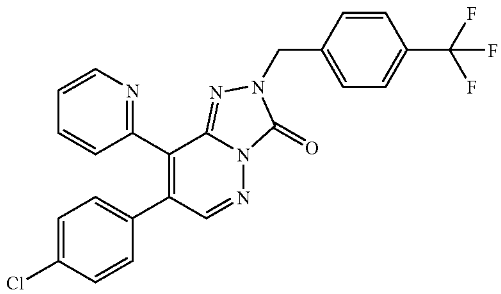 | 3.45 | 482 |
| 385 | 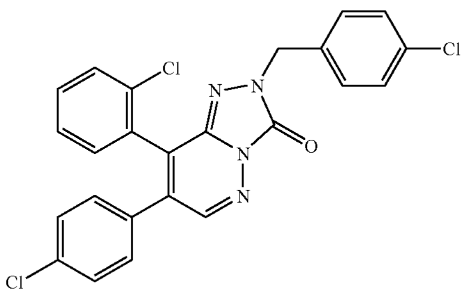 | 4.01 | 481 |
| 386 | 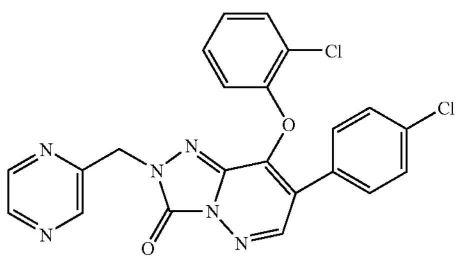 | 1.96ᶜ | 465 |
| 387 | 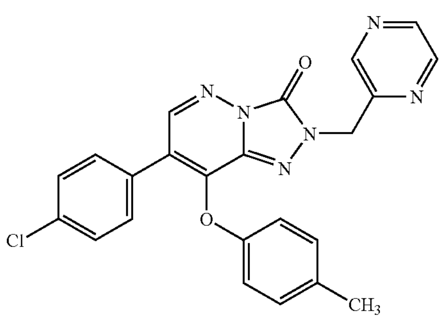 | 1.97ᶜ | 445 |
| 388 | 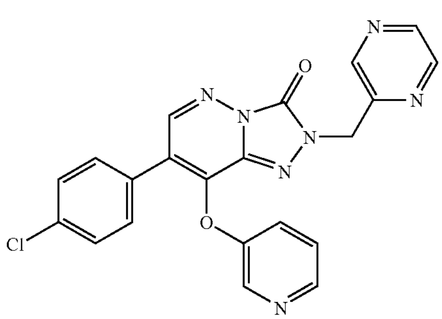 | 1.45ᶜ | 432 |

-continued

| Example Number | Structure | HPLC Retention Time (min) | Mass Specs Observed (M + H) |
|---|---|---|---|
| 389 | 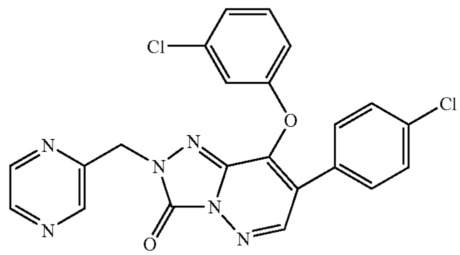 | 1.99[c] | 465 |
| 390 | 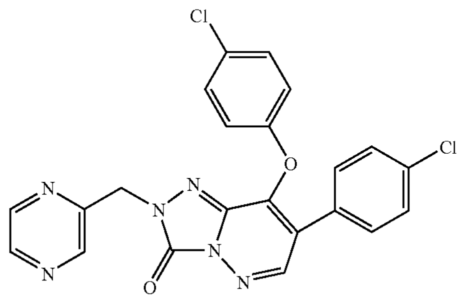 | 1.97[c] | 465 |
| 391 | 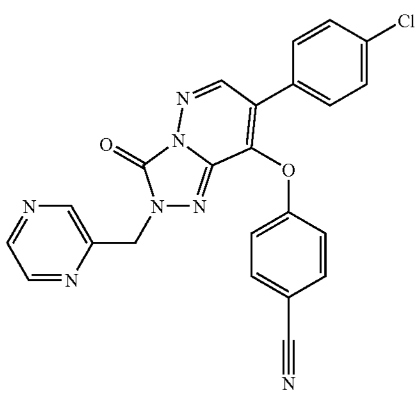 | 1.72[c] | 456 |
| 392 | 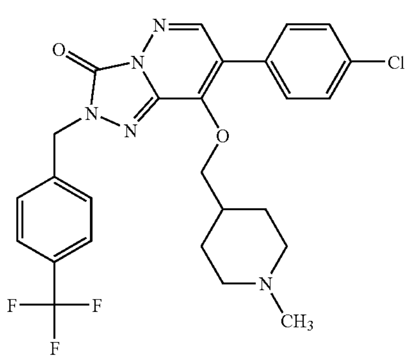 | 1.69[c] | 532 |

-continued

| Example Number | Structure | HPLC Retention Time (min) | Mass Specs Observed (M + H) |
|---|---|---|---|
| 393 | 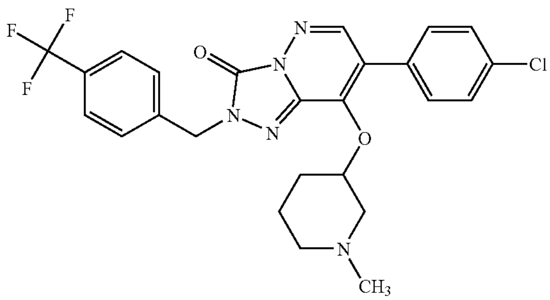 | 1.63<sup>c</sup> | 518 |
| 394 | 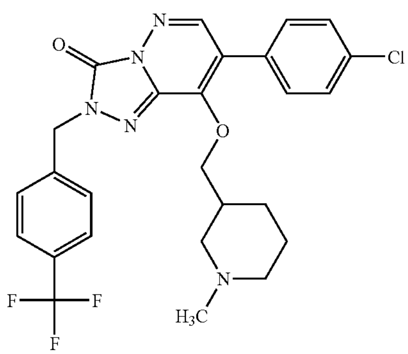 | 1.69<sup>c</sup> | 532 |
| 395 | 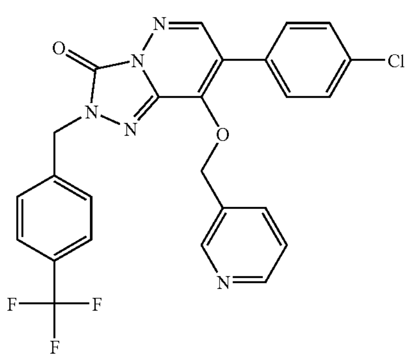 | 1.91<sup>c</sup> | 512 |
| 396 | 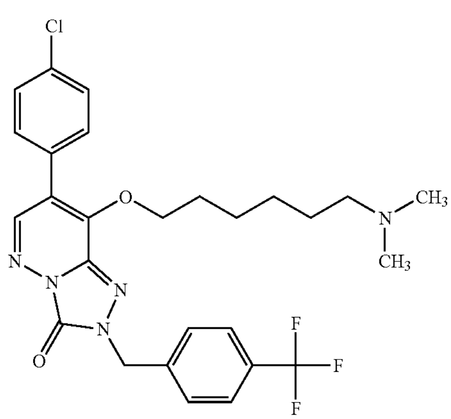 | 1.84<sup>c</sup> | 548 |

-continued
| Example Number | Structure | HPLC Retention Time (min) | Mass Specs Observed (M + H) |
|---|---|---|---|
| 397 | 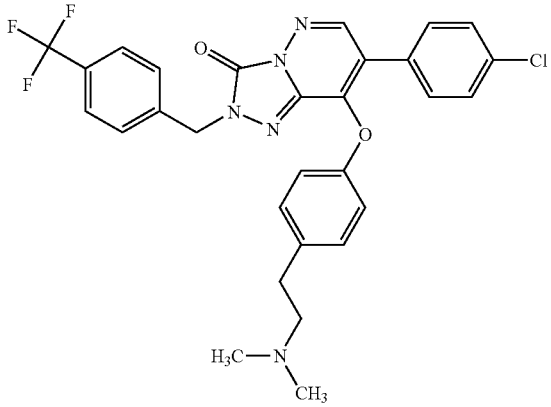 | 1.8<sup>c</sup> | 568 |
| 398 | 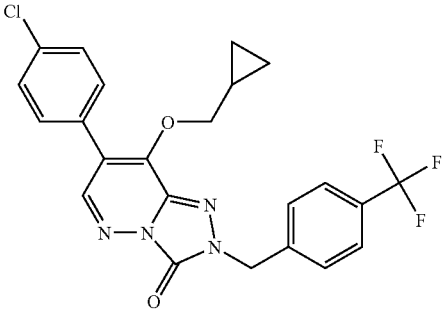 | 2.28<sup>c</sup> | 475 |
| 399 | 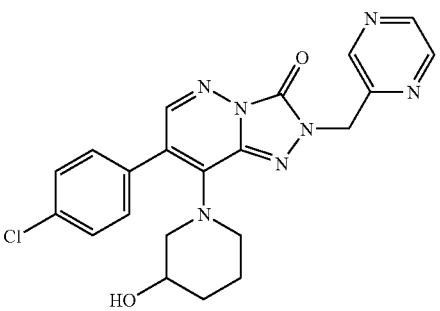 | 1.64<sup>c</sup> | 438 |
| 400 | 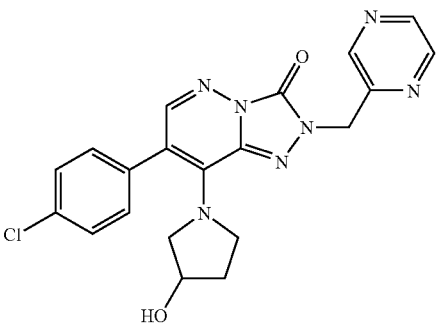 | 1.54<sup>c</sup> | 424 |

-continued

| Example Number | Structure | HPLC Retention Time (min) | Mass Specs Observed (M + H) |
|---|---|---|---|
| 401 | 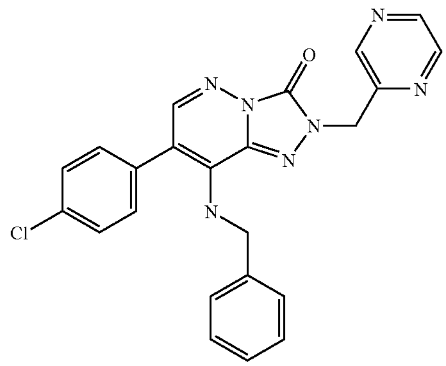 | 1.89ᶜ | 444 |
| 402 | 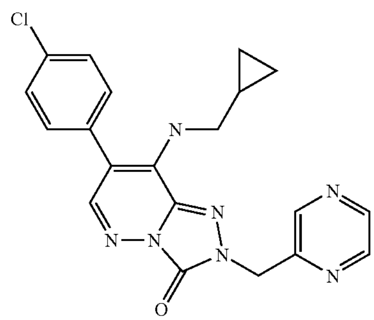 | 1.82ᶜ | 408 |
| 403 | 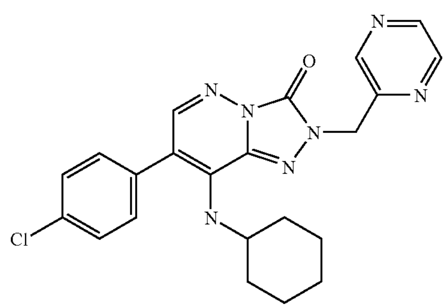 | 2.03ᶜ | 436 |
| 404 | 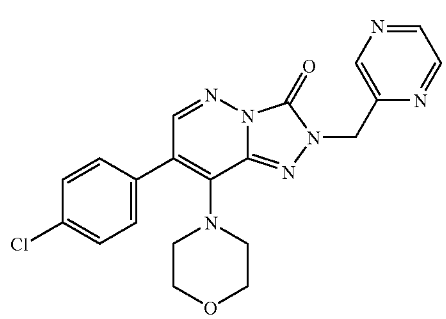 | 1.64ᶜ | 424 |

| Example Number | Structure | HPLC Retention Time (min) | Mass Specs Observed (M + H) |
|---|---|---|---|
| 405 | 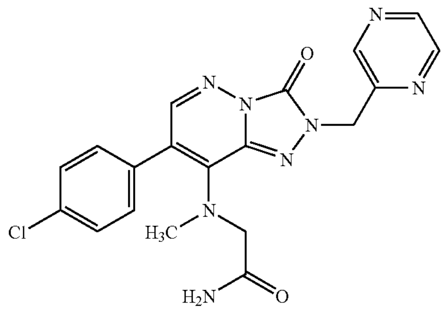 | 1.36$^c$ | 425 |
| 406 | 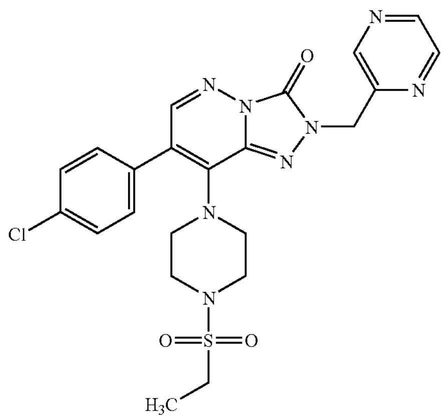 | 1.62$^c$ | 515 |
| 407 | 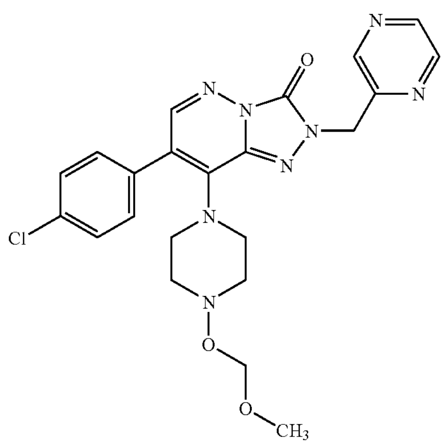 | 1.84$^c$ | 482 |
| 408 | 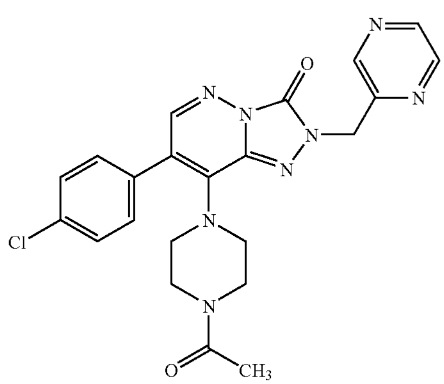 | 1.5$^c$ | 465 |

-continued

| Example Number | Structure | HPLC Retention Time (min) | Mass Specs Observed (M + H) |
|---|---|---|---|
| 409 | 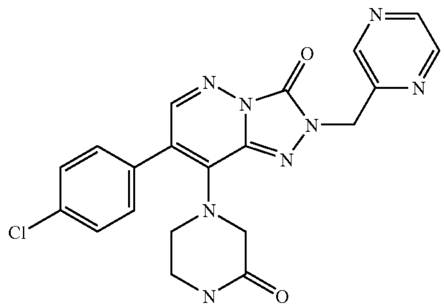 | 1.33ᵉ | 437 |
| 410 | Chiral | 1.63ᵉ | 436 |
| 411 | 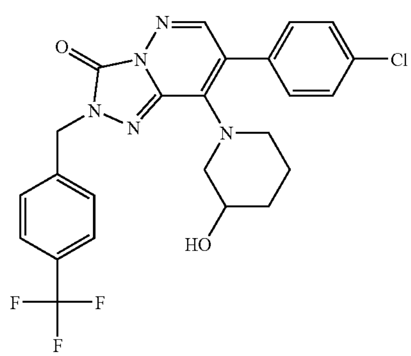 | 2.11ᵉ | 504 |
| 412 | 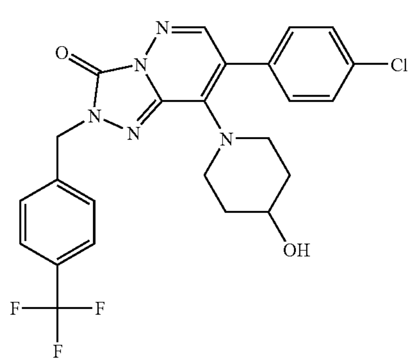 | 2.04ᵉ | 504 |

-continued

| Example Number | Structure | HPLC Retention Time (min) | Mass Specs Observed (M + H) |
|---|---|---|---|
| 413 | 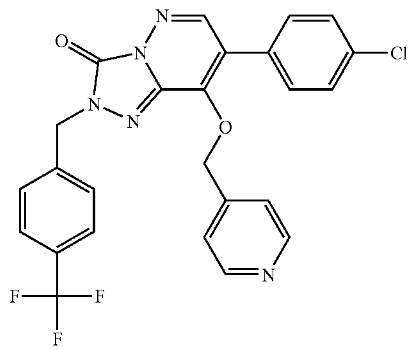 | 1.61c | 511 |
| 414 | 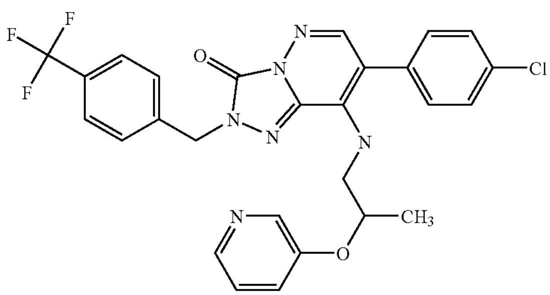 | 1.88c | 555 |
| 415 | 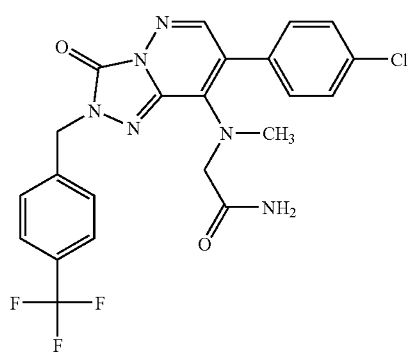 | 1.9c | 491 |
| 416 | 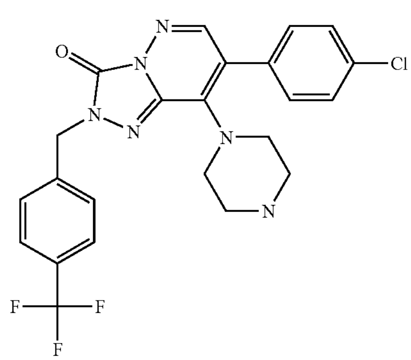 | 1.59c | 489 |

-continued

| Example Number | Structure | HPLC Retention Time (min) | Mass Specs Observed (M + H) |
|---|---|---|---|
| 417 | 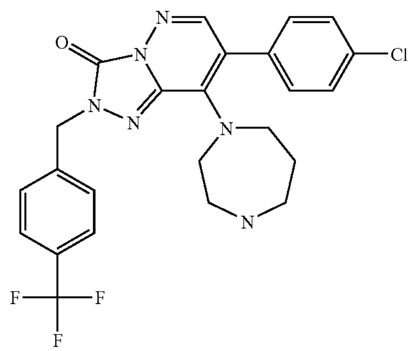 | 1.63[c] | 503 |
| 418 | 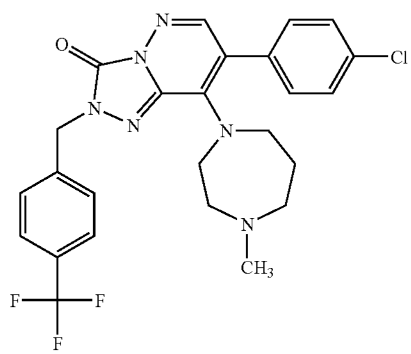 | 1.6[c] | 517 |
| 419 | 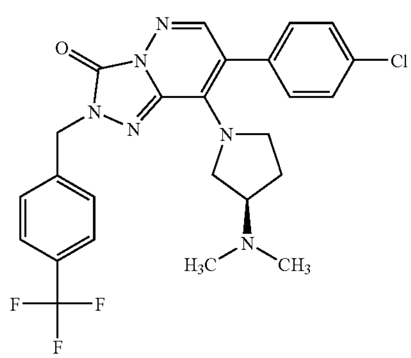 | 1.57[c] | 517 |
| 420 | 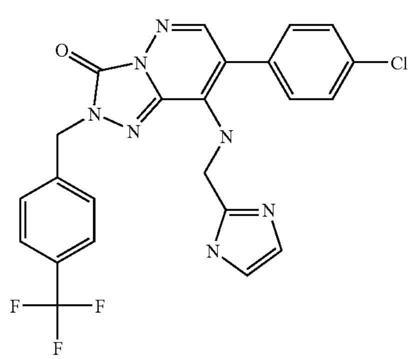 | 1.53[c] | 500 |

-continued

| Example Number | Structure | HPLC Retention Time (min) | Mass Specs Observed (M + H) |
|---|---|---|---|
| 421 | 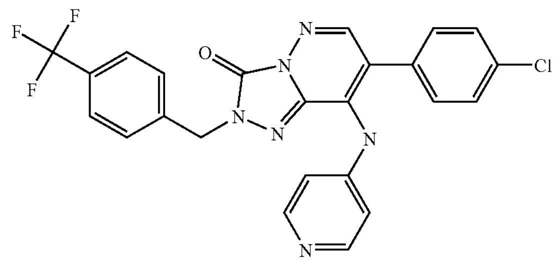 | 1.49c | 497 |
| 422 | 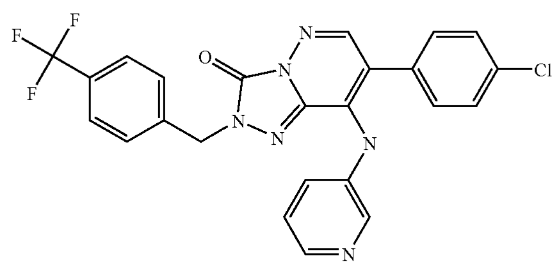 | 1.7c | 497 |
| 423 | 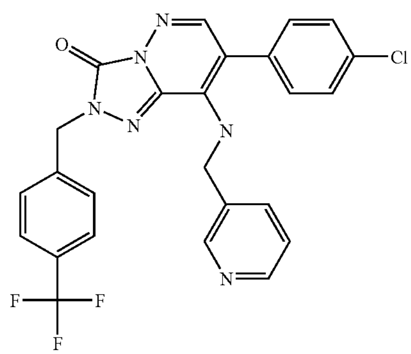 | 1.68c | 511 |
| 424 | 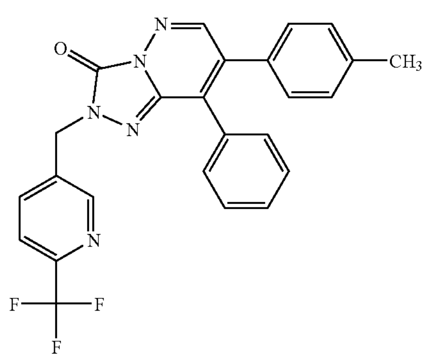 | 3.06c | 462 |
| 425 | 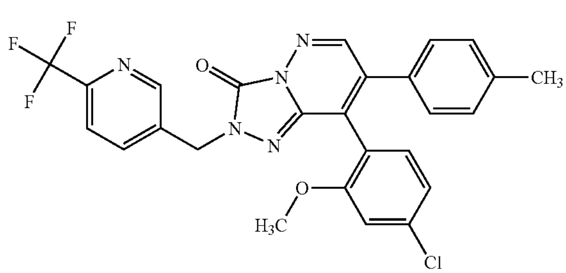 | 3.26c | 526 |

-continued

| Example Number | Structure | HPLC Retention Time (min) | Mass Specs Observed (M + H) |
|---|---|---|---|
| 426 | 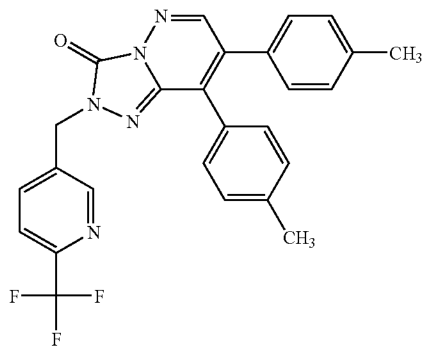 | 3.25ᶜ | 476 |
| 427 | 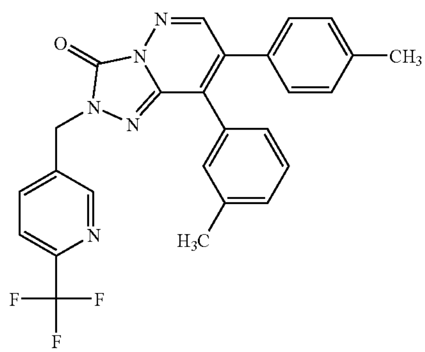 | 3.21ᶜ | 476 |
| 428 | 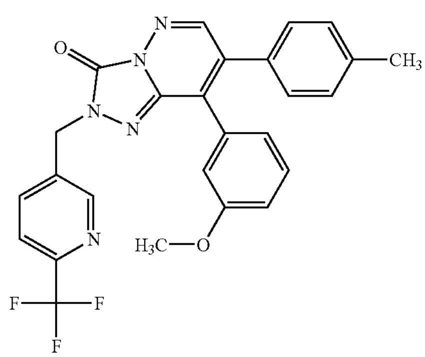 | 3.04ᶜ | 492 |
| 429 | 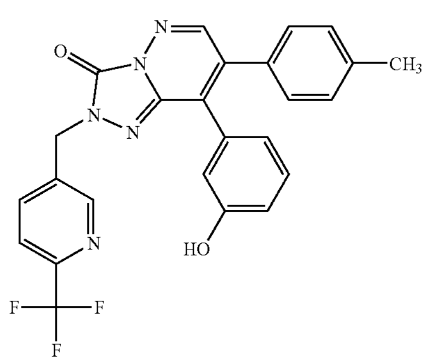 | 2.56ᶜ | 478 |

-continued

| Example Number | Structure | HPLC Retention Time (min) | Mass Specs Observed (M + H) |
|---|---|---|---|
| 430 | 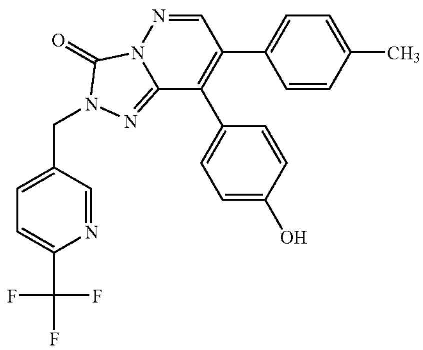 | 2.53ᶜ | 478 |
| 431 | 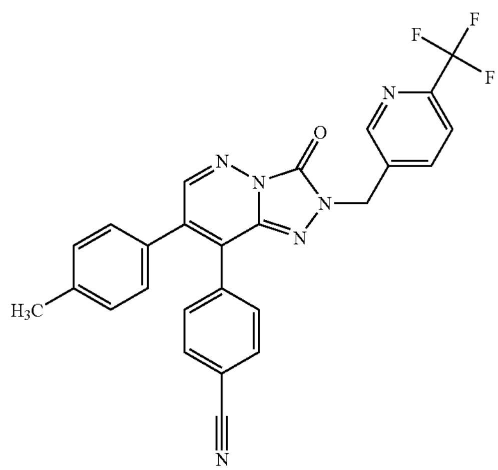 | 2.86ᶜ | 487 |
| 432 | 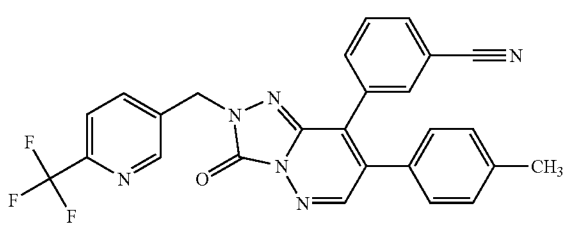 | 2.85ᶜ | 487 |
| 433 | 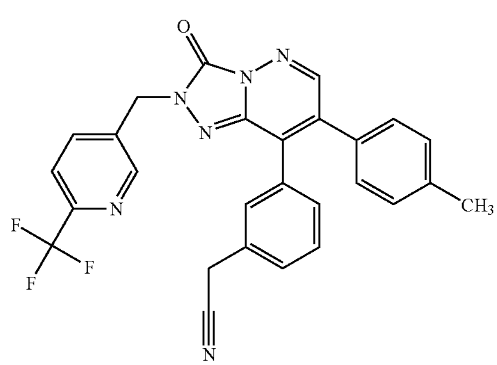 | 2.78ᶜ | 501 |

-continued

| Example Number | Structure | HPLC Retention Time (min) | Mass Specs Observed (M + H) |
|---|---|---|---|
| 434 | 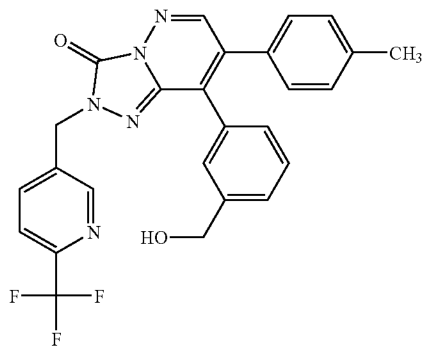 | 2.47c | 492 |
| 435 | 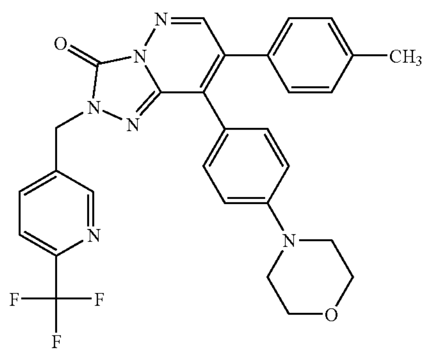 | 2.86c | 547 |
| 436 | 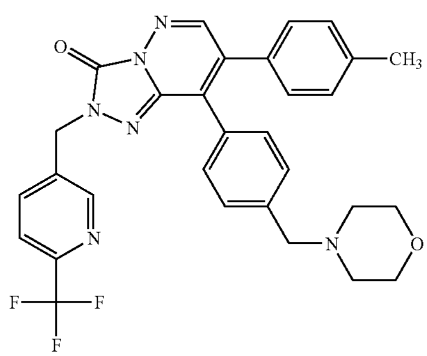 | 1.92c | 561 |
| 437 | 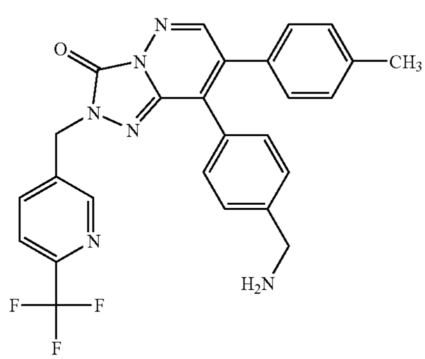 | 1.88c | 491 |

-continued

| Example Number | Structure | HPLC Retention Time (min) | Mass Specs Observed (M + H) |
|---|---|---|---|
| 438 | 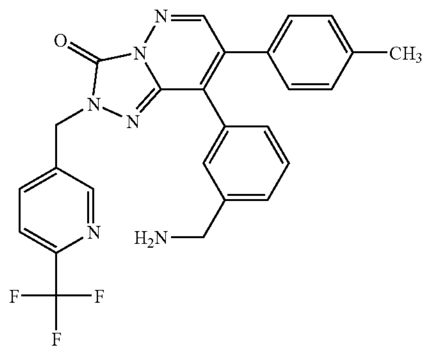 | 1.88c | 491 |
| 439 | 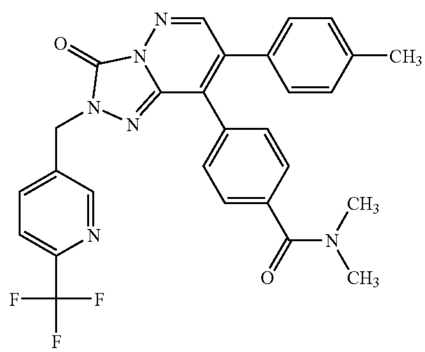 | 2.39c | 533 |
| 440 | 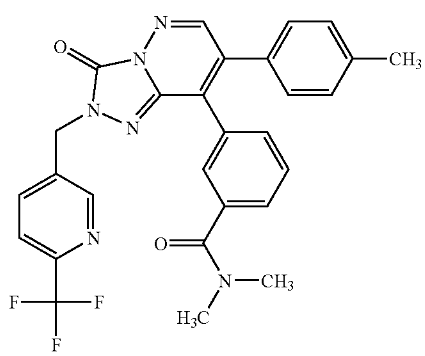 | 2.43c | 533 |
| 441 | 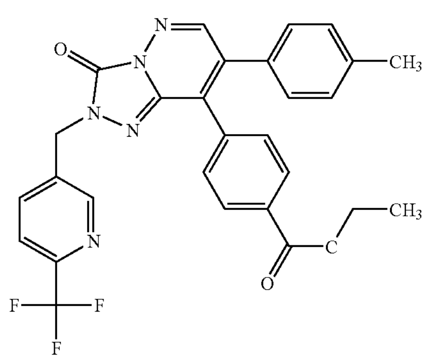 | 3.19c | 534 |

-continued

| Example Number | Structure | HPLC Retention Time (min) | Mass Specs Observed (M + H) |
|---|---|---|---|
| 442 | 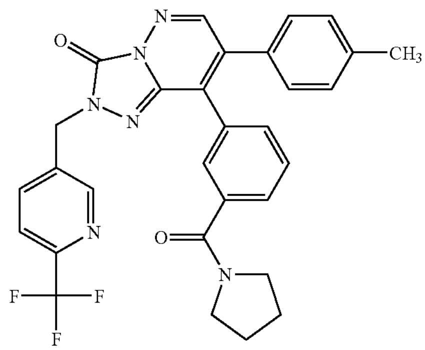 | 2.55<sup>c</sup> | 559 |
| 443 | 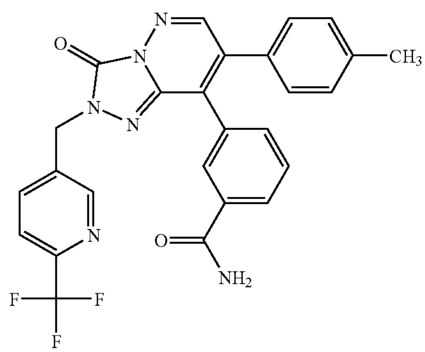 | 2.19<sup>c</sup> | 505 |
| 444 | 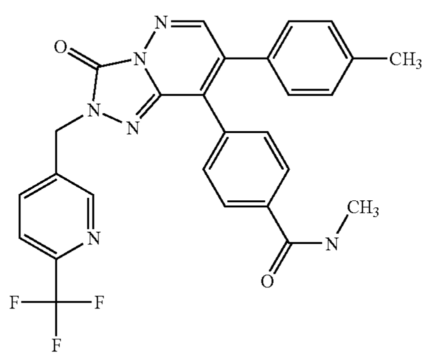 | 2.27<sup>c</sup> | 519 |
| 445 | 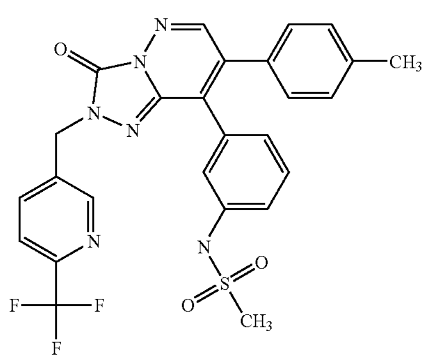 | 2.53<sup>c</sup> | 555 |

-continued

| Example Number | Structure | HPLC Retention Time (min) | Mass Specs Observed (M + H) |
|---|---|---|---|
| 446 | 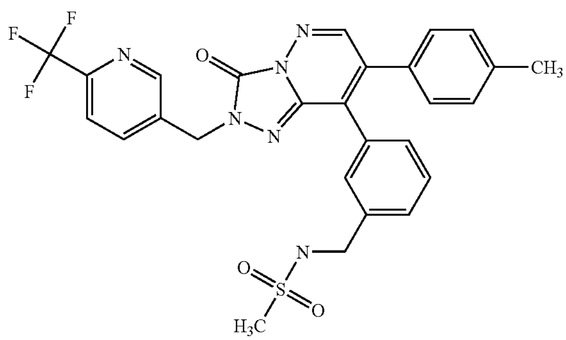 | 2.53ᶜ | 569 |
| 447 | 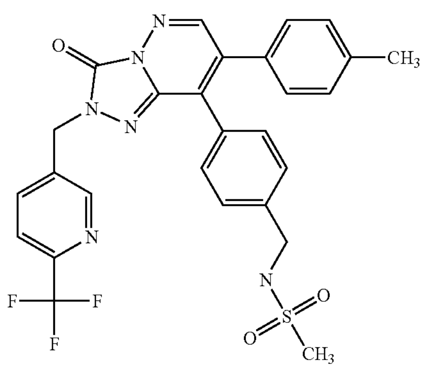 | 2.47ᶜ | 569 |
| 448 | 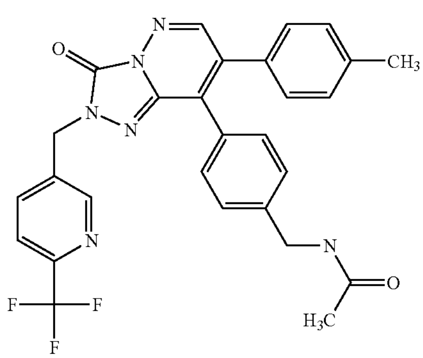 | 2.26ᶜ | 533 |
| 449 | 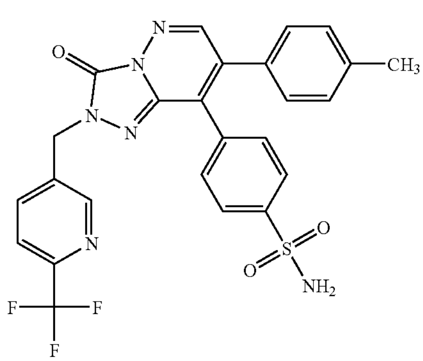 | 2.35ᶜ | 541 |

-continued

| Example Number | Structure | HPLC Retention Time (min) | Mass Specs Observed (M + H) |
|---|---|---|---|
| 450 | 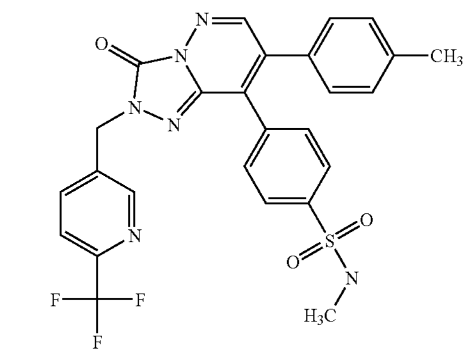 | 2.55<sup>c</sup> | 555 |
| 451 | 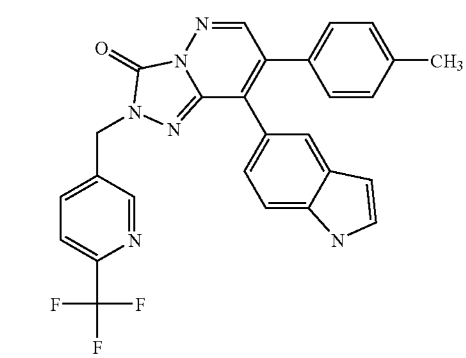 | 2.79<sup>c</sup> | 501 |
| 452 | 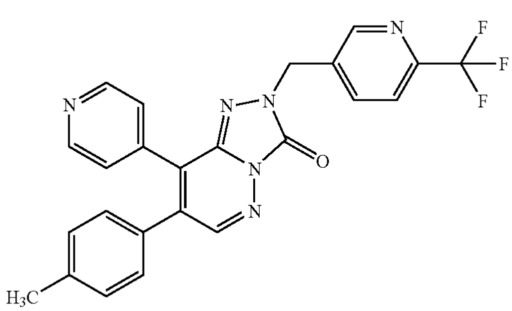 | 2.65 | 463 |
| 453 | 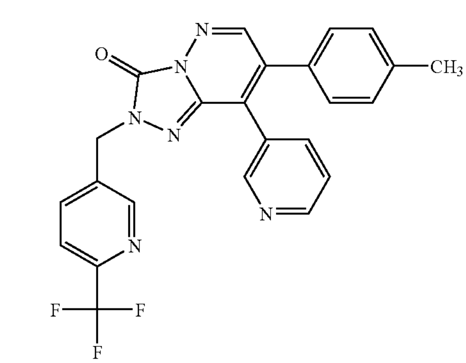 | 1.61<sup>c</sup> | 463 |

-continued
| Example Number | Structure | HPLC Retention Time (min) | Mass Specs Observed (M + H) |
|---|---|---|---|
| 454 | 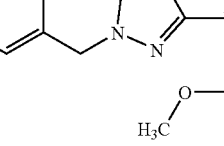 | 1.75[c] | 493 |
| 455 | 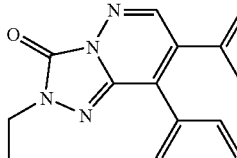 | 2.36[c] | 493 |
| 456 | 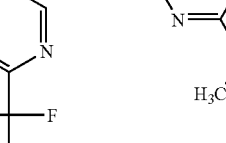 | 2.3[c] | 493 |
| 457 | 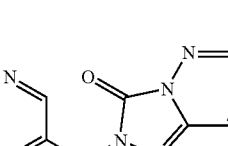 | 1.83[c] | 493 |
| 458 | 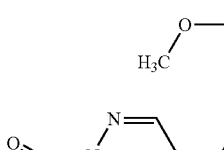 | 2.56[c] | 523 |

-continued

| Example Number | Structure | HPLC Retention Time (min) | Mass Specs Observed (M + H) |
|---|---|---|---|
| 459 | 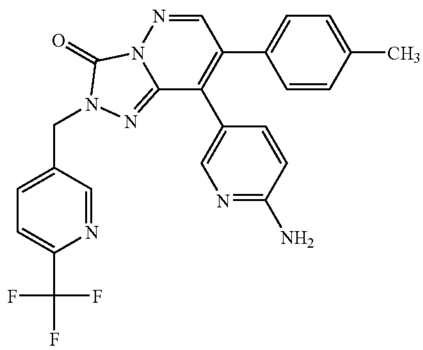 | 1.42c | 478 |
| 460 | 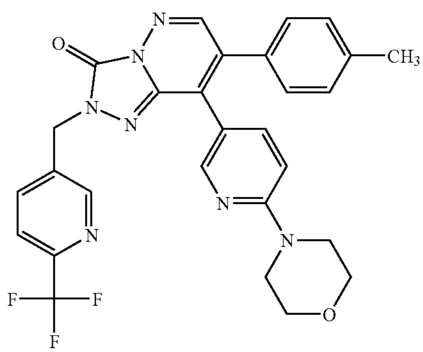 | 1.74c | 548 |
| 461 | 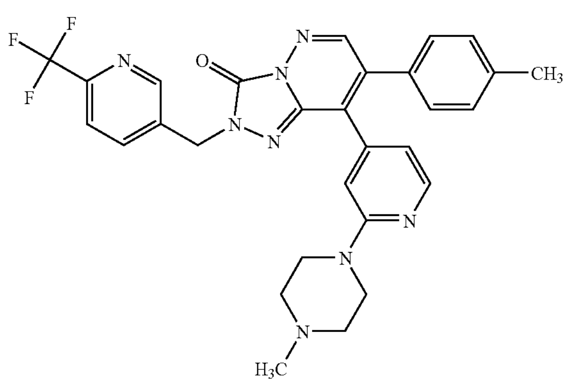 | 1.49c | 561 |
| 462 | 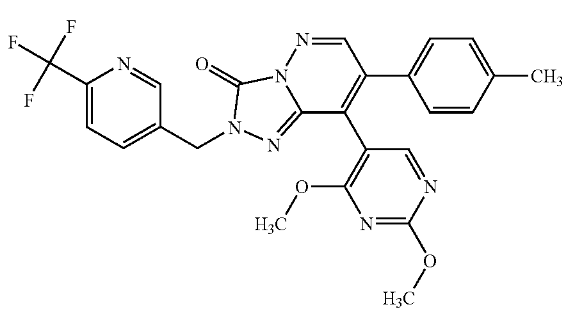 | 2.21c | 524 |

-continued

| Example Number | Structure | HPLC Retention Time (min) | Mass Specs Observed (M + H) |
|---|---|---|---|
| 463 | 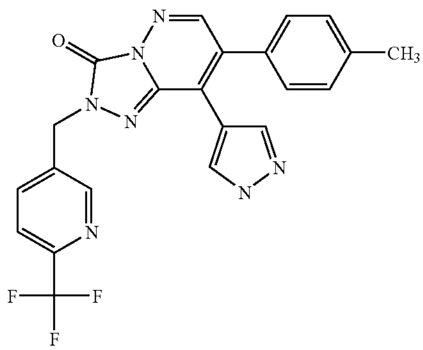 | 1.85$^c$ | 452 |
| 464 | 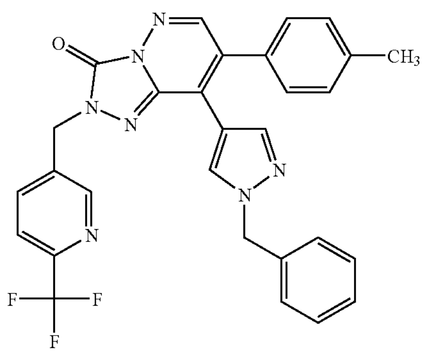 | 2.51$^c$ | 542 |
| 465 | 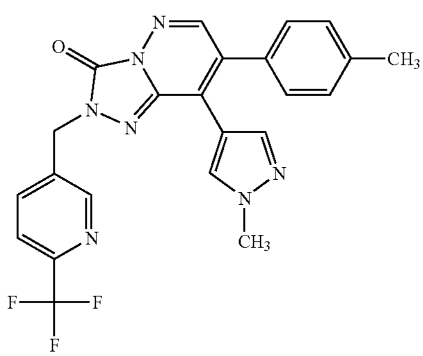 | 2.09$^c$ | 466 |
| 466 | 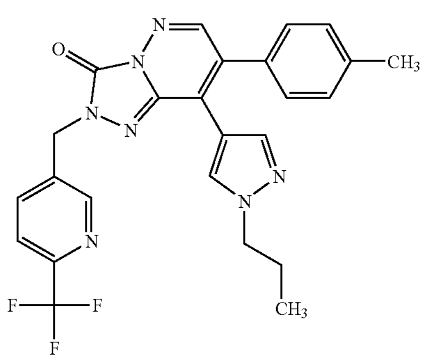 | 2.39$^c$ | 494 |

-continued

| Example Number | Structure | HPLC Retention Time (min) | Mass Specs Observed (M + H) |
|---|---|---|---|
| 467 | 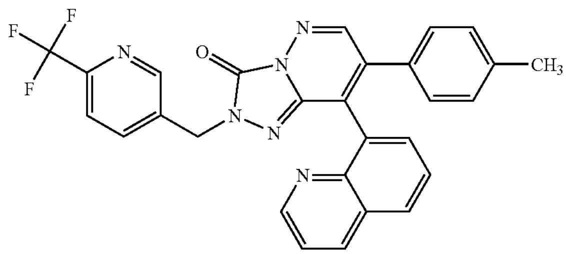 | 1.99$^c$ | 513 |
| 468 | 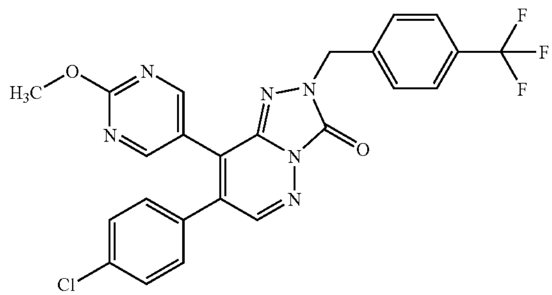 | 3.7 | 513 |

Example 469

Preparation of 2-(4-(Trifluoromethyl)benzyl)-7,8-bis(4-chlorophenyl)-6-methyl-5,6-dihydro-[1,2,4]triazolo[4,3-b]pyridazin-3(2H)-one

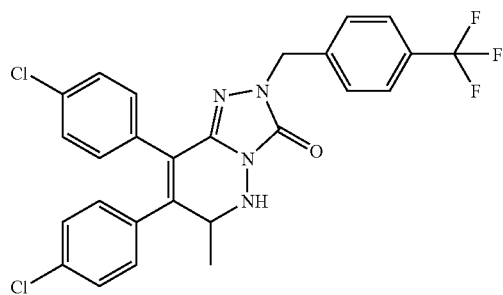

To a solution of 2-(4-(trifluoromethyl)benzyl)-7,8-bis(4-chlorophenyl)-[1,2,4]triazolo[4,3-b]pyridazin-3(2H)-one, (250 mg, 0.485 mmol), prepared as described in Example 17, in THF (4 mL) at −20° C. was added methyl magnesium bromide (0.81 mL, 2.43 mmol, 3.0 M in Et$_2$O). The reaction was stirred at −20° C. for 30 min. LC-MS showed that the reaction was complete. To the reaction mixture was added 20 mL of MeOH to quench the reaction. The reaction was allowed to warm to RT and the solvent was evaporated. The residue was diluted with EtOAc (100 mL), washed with H$_2$O (10 mL) and saturated aqueous NaCl (5 mL×2). The organic layer was dried (MgSO$_4$), filtered and concentrated under reduced pressure. The crude product was purified by silica gel column chromatography using an automated system, eluting with a gradient of (0% to 80% EtOAc for 40 min. and holds at 80% for 10 min.) to give the title compound, 2-(4-(Trifluoromethyl)benzyl)-7,8-bis(4-chlorophenyl)-6-methyl-5,6-dihydro-[1,2,4]triazolo[4,3-b]pyridazin-3(2H)-one (254 mg), as a beige solid in 98% yield. HPLC retention time: 4.23 min; MS [M+H]$^+$: found 531. $^1$HNMR (CDCl$_3$, 400 MHz) δ7.52 (d, 2H), 7.38 (d, 2H), 7.17-7.11 (m, 4H), 7.05 (dd, 2H), 6.94 (dd, 2H), 4.94 (s, 2H), 4.16 (q, 1H), 1.24 (d, 3H).

Example 470

Preparation of (R)-2-(4-(Trifluoromethyl)benzyl)-7,8-bis(4-chlorophenyl)-6-methyl-5,6-dihydro-[1,2,4]triazolo[4,3-b]pyridazin-3(2H)-one and (S)-2-(4-(Trifluoromethyl)benzyl)-7,8-bis(4-chlorophenyl)-6-methyl-5,6-dihydro-[1,2,4]triazolo[4,3-b]pyridazin-3(2H)-one

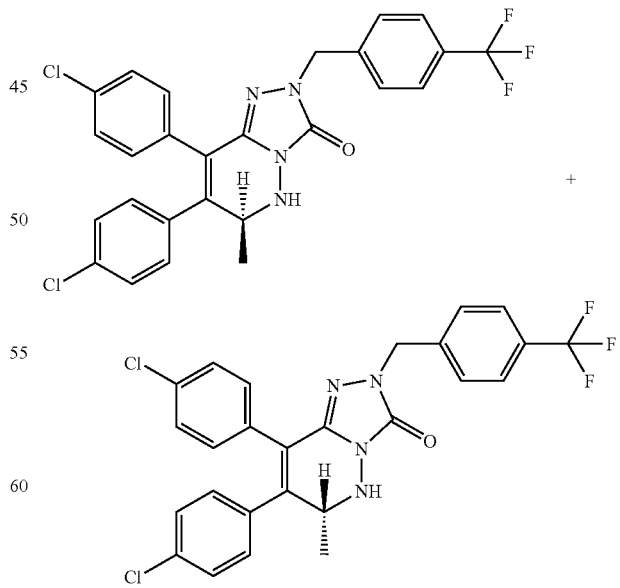

(R,S)-2-(4-(Trifluoromethyl)benzyl)-7,8-bis(4-chlorophenyl)-6-methyl-5,6-dihydro-[1,2,4]triazolo[4,3-b]pyridazin-3(2H)-one, prepared as described in 466, was separated into individual stereoiomers using the following chiral HPLC conditions: Chiral HPLC separation conditions: chiral OJ 4.6×250 mm; solvent A: heptane and solvent B: 0.1% DEA in MeOH:EtOH (1:1); 15% isocratic B; flow rate: 1 mL/min.; injection volume: 10 μL; UV wavelength: 254 nm. Isomer A: HPLC: 6.81 min.; MS [M+H]⁺: found 531. Isomer B: HPLC: 11.45 min.; MS [M+H]⁺: found 531.

Example 471

Preparation of 2-(4-(Trifluoromethyl)benzyl)-7,8-bis (4-chlorophenyl)-6-methyl-[1,2,4]triazolo[4,3-b] pyridazin-3(2H)-one

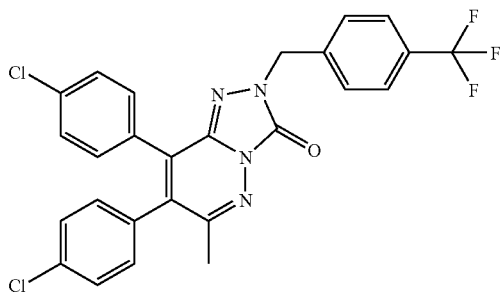

To a solution of 2-(4-(trifluoromethyl)benzyl)-7,8-bis(4-chlorophenyl)-6-methyl-5,6-dihydro-[1,2,4]triazolo[4,3-b]pyridazin-3(2H)-one (28 mg, 0.053 mmol), prepared as described in Example 469 in CH₂Cl₂ (0.5 mL) at RT was added DDQ (15 mg, 0.064 mmol). The reaction was stirred at RT for 1 h. LC-MS showed the completion of the reaction. The reaction mixture was concentrated under reduced pressure. The resulting residue was purified by using silica gel column chromatography using an automated system eluting with a gradient of (0% to 80% EtOAc for 20 min.) to give the title compound, 2-(4-(trifluoromethyl)benzyl)-7,8-bis(4-chlorophenyl)-6-methyl-[1,2,4]triazolo[4,3-b]pyridazin-3 (2H)-one (23 mg, 84% yield) as a yellow solid in 84% yield. HPLC retention time: 4.18 min; MS [M+H]⁺: found 529. ¹H NMR (CDCl₃, 400 MHz) δ 7.61 (d, 2H), 7.52 (d, 2H), 7.35 (dd, 2H), 7.27 (dd, 2H), 7.16 (dd, 2H), 7.02 (dd, 2H), 5.28 (s, 2H), 2.29 (s, 3H).

Example 472

Preparation of 2-(4-(Trifluoromethyl)benzyl)-5-acetyl-7,8-bis(4-chlorophenyl)-6-methyl-5,6-dihydro-[1,2,4]triazolo[4,3-b]pyridazin-3(2H)-one

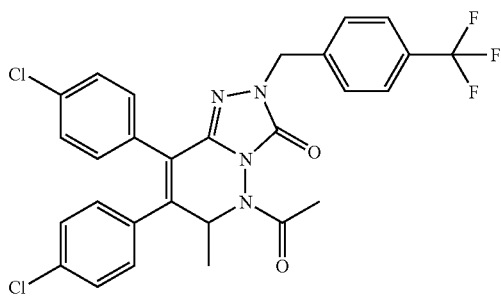

To a solution of 2-(4-(trifluoromethyl)benzyl)-7,8-bis(4-chlorophenyl)-6-methyl-5,6-dihydro-[1,2,4]triazolo[4,3-b]pyridazin-3(2H)-one (8 mg, 0.015 mmol), prepared as described in Example 469 in CH₂Cl₂ (0.2 mL) at RT was added diisopropyl ethyl amine (5.8 mg, 0.045 mmol), followed by acetyl chloride (2.4 mg, 0.030 mmol). The reaction was stirred at RT for 2 h. LC-MS showed the completion of the reaction. The solvent was evaporated and the residue was purified using reverse phase HPLC to give the title compound, 2-(4-(Trifluoromethyl)benzyl)-5-acetyl-7,8-bis(4-chlorophenyl)-6-methyl-5,6-dihydro-[1,2,4]triazolo[4,3-b]pyridazin-3(2H)-one, (6 mg, 70%) as a white solid. HPLC retention time: 4.23 min; MS [M+H]⁺: found 573. ¹H NMR (CDCl₃, 400 MHz) δ 7.65 (d, 2H), 7.51 (d, 2H), 7.30-7.22 (m, 4H), 7.17 (dd, 2H), 7.06 (dd, 2H), 5.70 (q, 1H), 5.14-5.11 (m, 2H), 2.28 (s, 3H), 1.28 (s, 3H).

Example 473

Preparation of 2-(4-(Trifluoromethyl)benzyl)-5-benzyl-7,8-bis(4-chlorophenyl)-6-methyl-5,6-dihydro-[1,2,4]triazolo[4,3-b]pyridazin-3(2H)-one

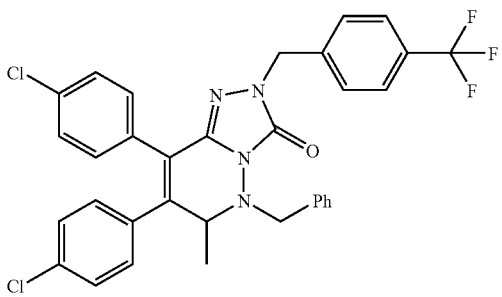

To a solution of 2-(4-(trifluoromethyl)benzyl)-7,8-bis(4-chlorophenyl)-6-methyl-5,6-dihydro-[1,2,4]triazolo[4,3-b]pyridazin-3(2H)-one (15 mg, 0.028 mmol) prepared as described in Example 469 in DMF (0.5 mL) at RT was added K₂CO₃ (11.6 mg, 0.084 mmol), followed by benzyl bromide (9.6 mg, 0.056 mmol). The reaction was heated at 80° C. for overnight. The reaction was filtered. The collected solution was concentrated under educed pressure. The crude product was purified using reverse phase HPLC to give the title compound, 2-(4-(Trifluoromethyl)benzyl)-5-benzyl-7,8-bis (4-chlorophenyl)-6-methyl-5,6-dihydro-[1,2,4]triazolo[4,3-b]pyridazin-3(2H)-one, (2 mg, 11%) as a white solid. HPLC retention time: 4.44 min; MS [M+H]⁺: found 621. ¹H NMR (CDCl₃, 400 MHz) δ 7.60 (d, 2H), 7.45 (d, 2H), 7.33-7.29 (m, 5H), 7.23-7.13 (m, 4H), 7.05-7.00 (m, 2H), 6.87-6.81 (m, 2H), 5.04 (s, 2H), 4.26-4.15 (m, 2H), 3.98-3.93 (q, 1H), 1.30 (d, 3H).

Example 474

Preparation of 7,8-Bis(4-chlorophenyl)-2-methyl-[1,2,4]triazolo[4,3-b]pyridazin-3(2H)-one

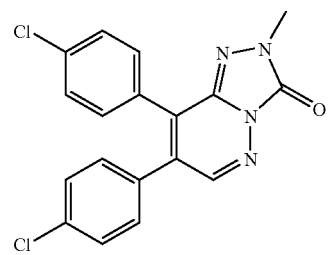

To a solution of the 7,8-bis(4-chlorophenyl)-[1,2,4]triazolo[4,3-b]pyridazin-3(2H)-one (100 mg, 0.28 mmol), prepared as described in Example 1, in DMF (3 mL) at RT was added K₂CO₃ (116 mg, 0.84 mmol), followed by iodomethane (79 mg, 0.56 mmol). The reaction was heated at 60° C. for overnight. The reaction was diluted with EtOAc (20 mL), washed with saturated aqueous NaCl (20 mL×3). The organic layer was dried (MgSO$_4$), filtered and concentrated under reduced pressure to give the title compound, 7,8-bis(4-chlorophenyl)-2-methyl-[1,2,4]triazolo[4,3-b]pyridazin-3(2H)-one, (104 mg, 100%) as a yellow oil. HPLC retention time: 3.67 min; MS [M+H]$^+$: found 371.

Example 475

Preparation of 6-Benzyl-7,8-bis(4-chlorophenyl)-2-methyl-5,6-dihydro-[1,2,4]triazolo[4,3-b]pyridazin-3(2H)-one

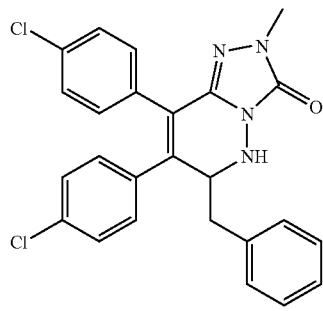

To a solution of 7,8-bis(4-chlorophenyl)-2-methyl-[1,2,4]triazolo[4,3-b]pyridazin-3(2H)-one (50 mg, 0.135 mmol), prepared as described in Example 474, in THF (1 mL) at −20° C. was added benzyl magnesium bromide (0.34 mL, 0.675 mmol, 2.0 M in THF). The reaction was stirred at −20° C. for 30 min. After this time MeOH (5 mL) was added to quench the reaction. The reaction was allowed to warm to RT and the reaction mixture was concentrated under reduced pressure. The residue was purified by silica gel column chromatography using an automated system eluting with a gradient of (0% to 80% EtOAc for 20 min. and holds at 80% for 20 min.) to give the title compound, 6-benzyl-7,8-bis(4-chlorophenyl)-2-methyl-5,6-dihydro-[1,2,4]triazolo[4,3-b]pyridazin-3(2H)-one (29 mg, 46%) as a beige solid. HPLC retention time: 4.10 min; MS [M+H]$^+$: found 463. $^1$H NMR (CDCl$_3$, 400 MHz) δ 7.30-6.90 (m, 13H), 4.22 (t, 1H), 3.36 (s, 3H), 2.90-2.75 (m, 2H).

Examples 476 to 487

The following Examples were prepared according to the methods and procedues desrcribed above:

| Example Number | Structure | HPLC Retention Time (min) | Mass Specs Observed (M + H) |
|---|---|---|---|
| 476 | 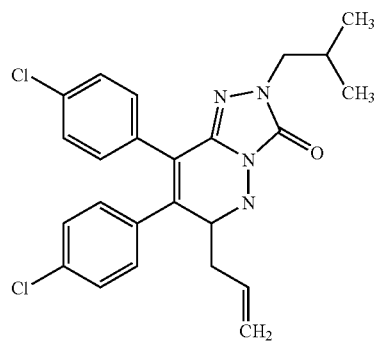 | 4.26 | 455 |
| 477 | 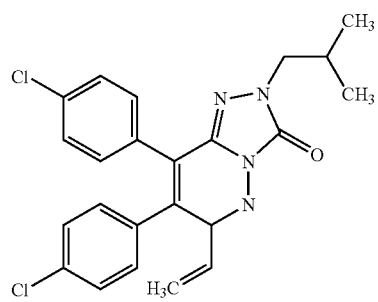 | 4.12 | 441 |

-continued

| Example Number | Structure | HPLC Retention Time (min) | Mass Specs Observed (M + H) |
|---|---|---|---|
| 478 | 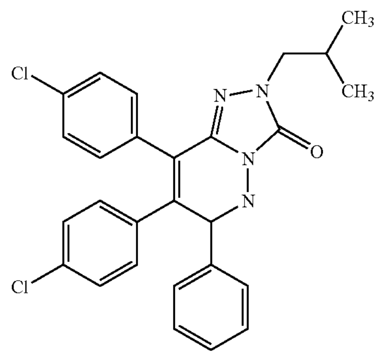 | 4.23 | 491 |
| 479 | 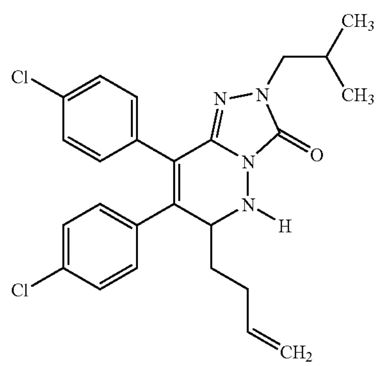 | 4.35 | 469 |
| 480 | 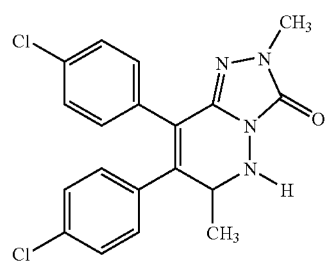 | 3.73 | 387 |
| 481 | 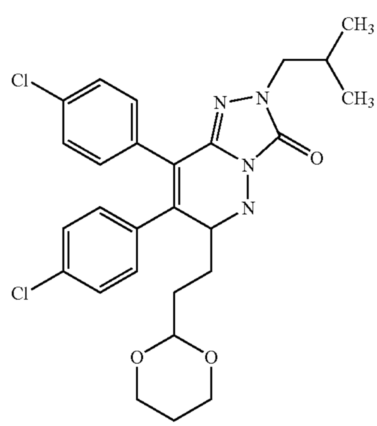 | 3.96 | 529 |

-continued

| Example Number | Structure | HPLC Retention Time (min) | Mass Specs Observed (M + H) |
|---|---|---|---|
| 482 | 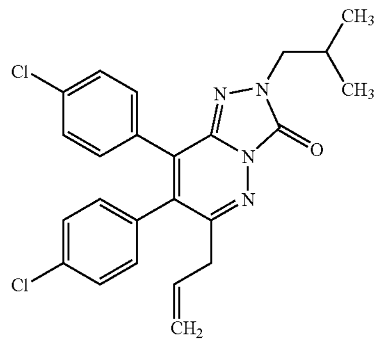 | 4.19 | 453 |
| 483 | 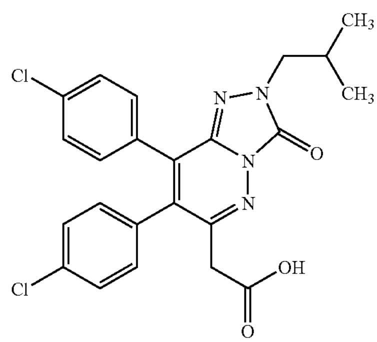 | 3.82 | 471 |
| 484 | 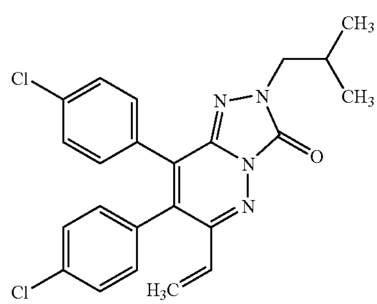 | 4.19 | 439 |
| 485 | 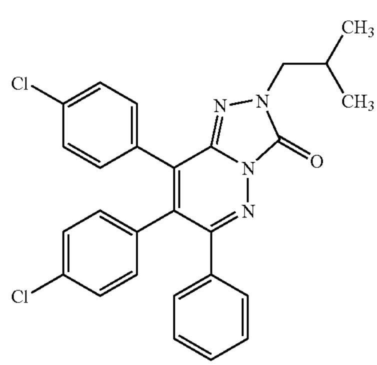 | 4.21 | 489 |

| Example Number | Structure | HPLC Retention Time (min) | Mass Specs Observed (M + H) |
|---|---|---|---|
| 486 | 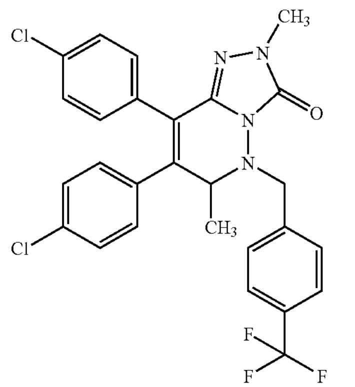 | 4.24 | 545 |
| 487 | 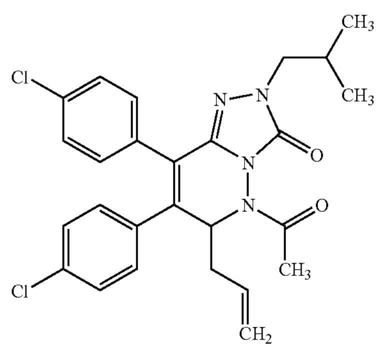 | 4.28 | 497 |

The compounds of Set A below, in which R[1] varies, R[2] is 4-chlorophenyl, R[3] is 2-(trifluoromethyl)pyridin-5-ylmethyl, R[6] is hydrogen, R[7] is absent, and n is a double bond, may be prepared by one skilled in the art by the methods described above. The compounds of Set A are meant to further illustrate the scope of the invention without being limiting in any way.

Set A:

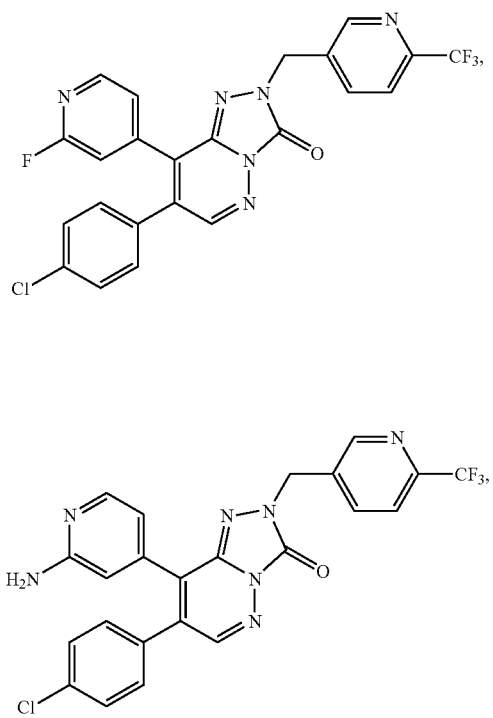

-continued
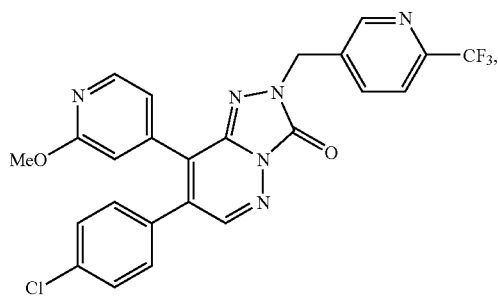
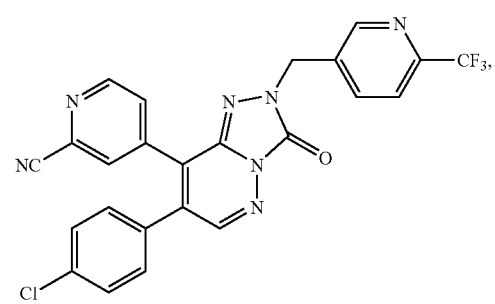
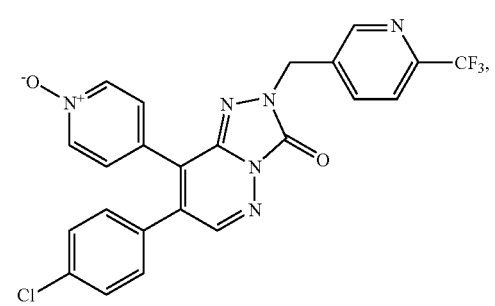
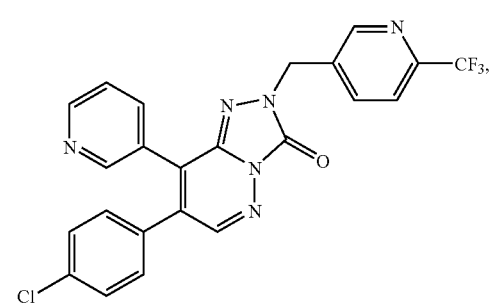
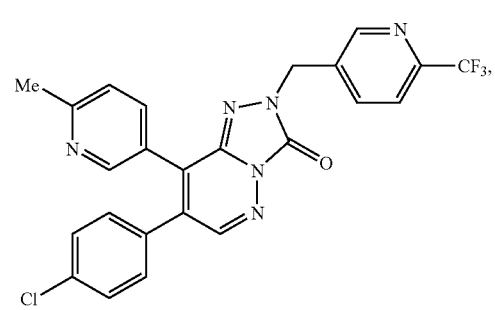
-continued
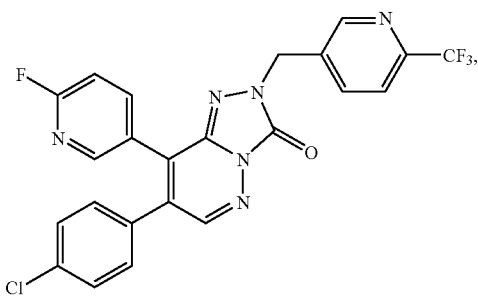
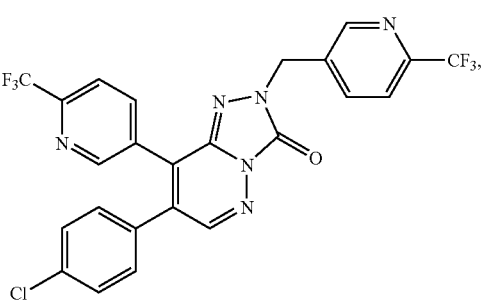
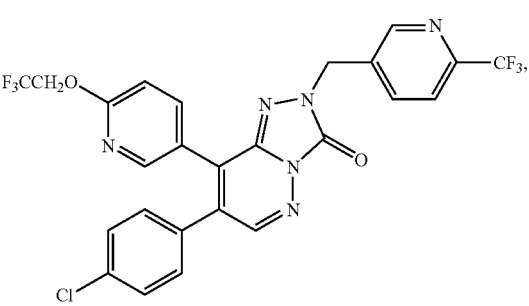
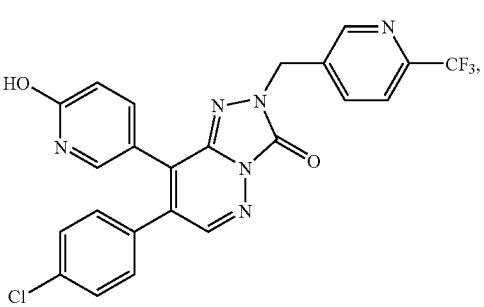
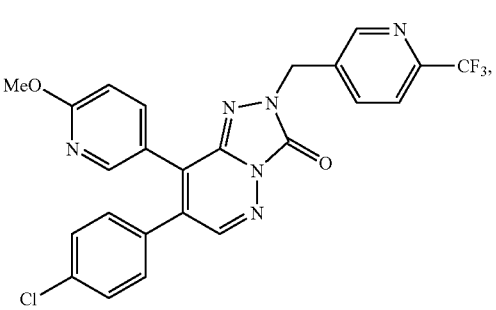

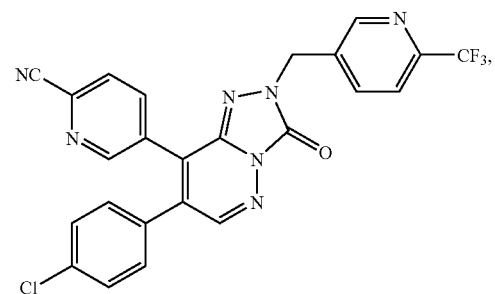
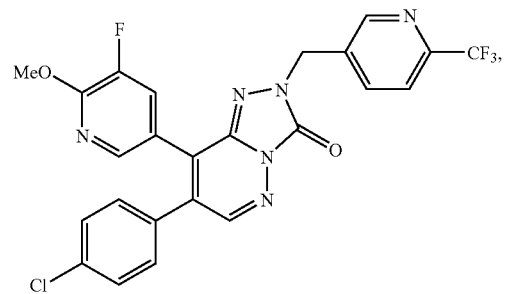
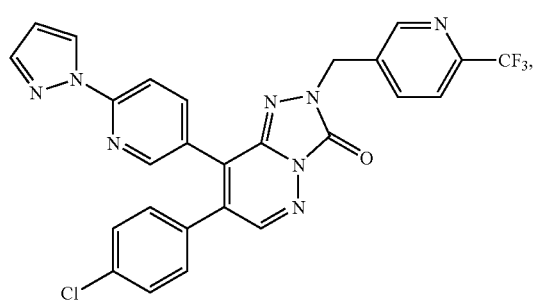
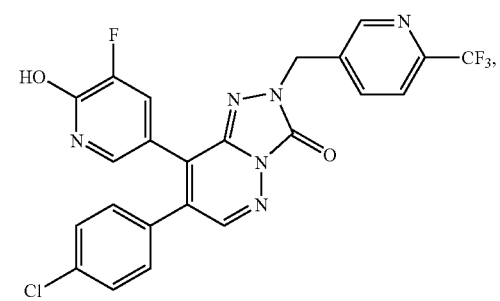
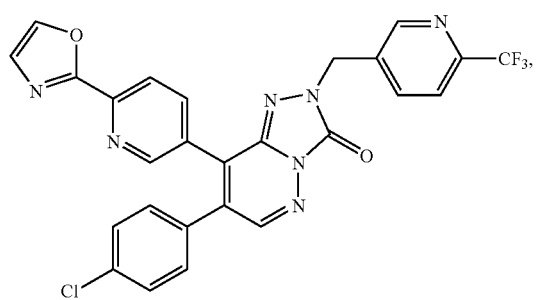
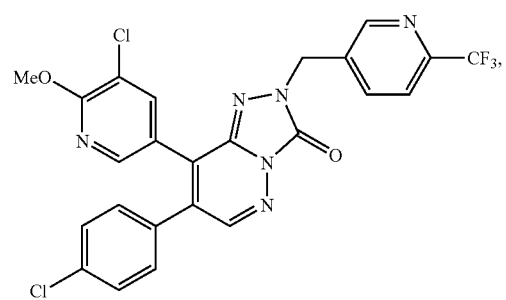
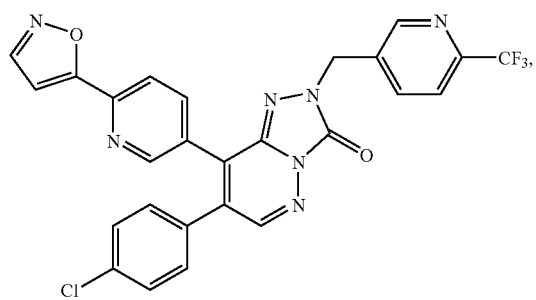
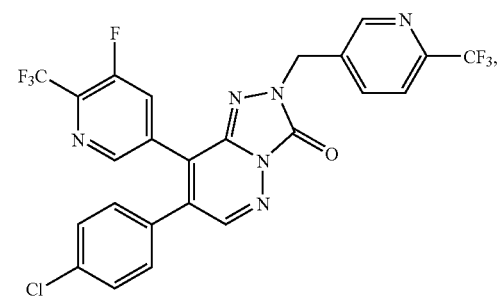
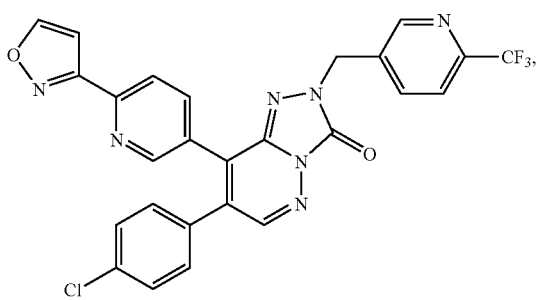
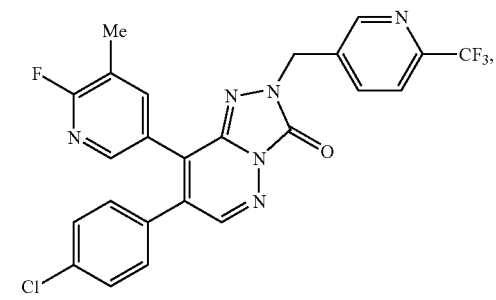

-continued
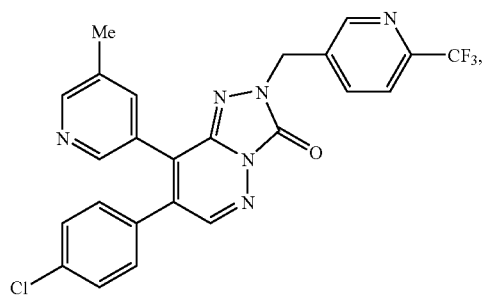
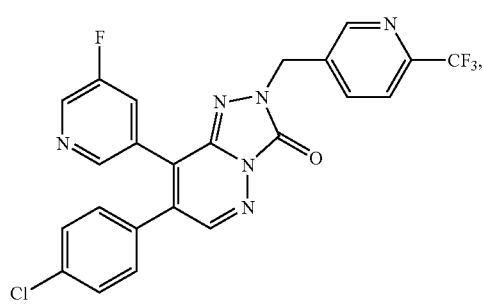
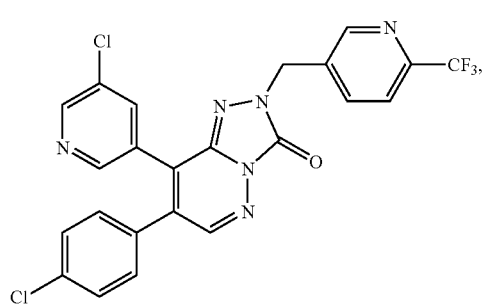
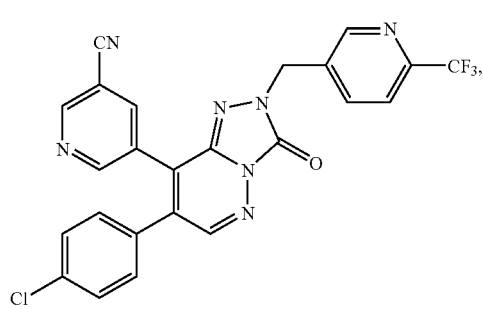
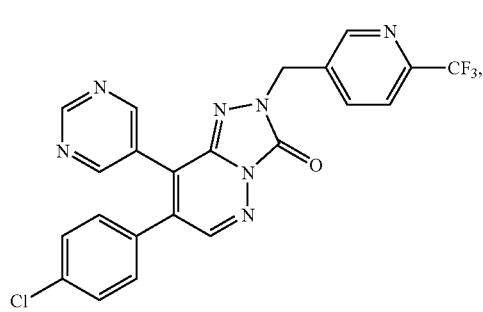
-continued
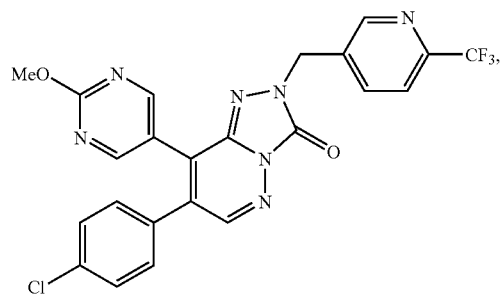
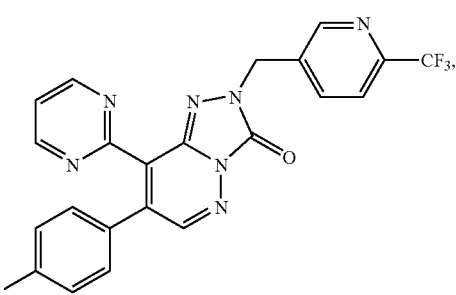
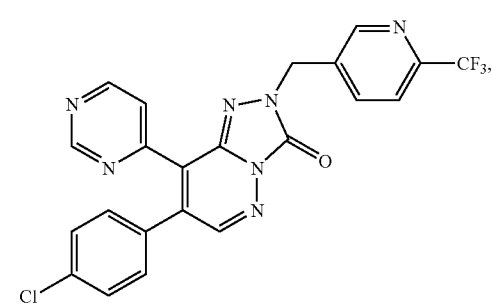
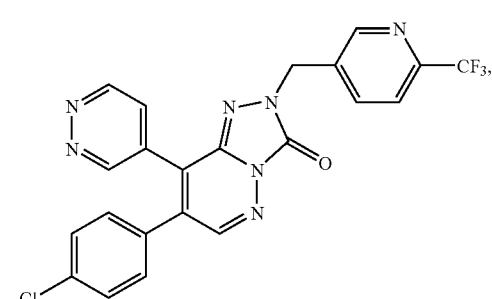
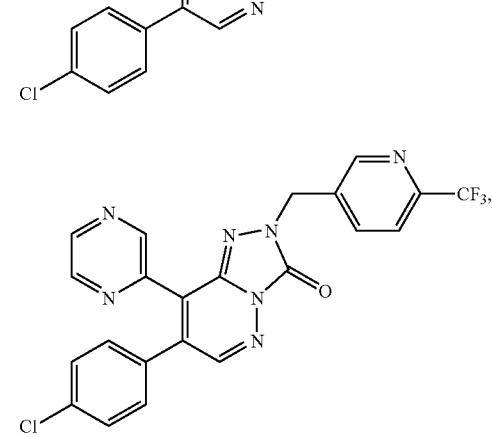

-continued
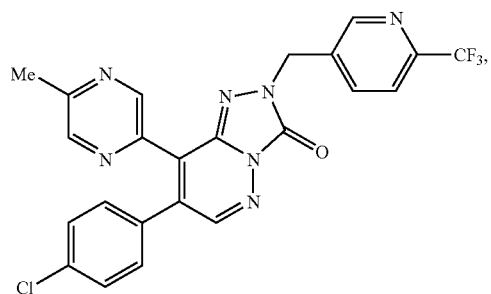
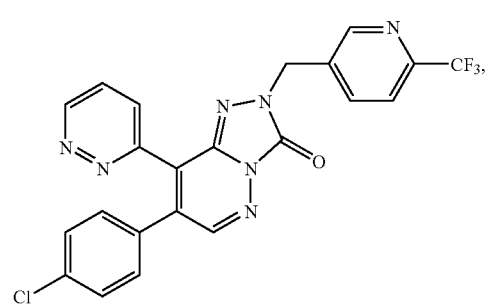
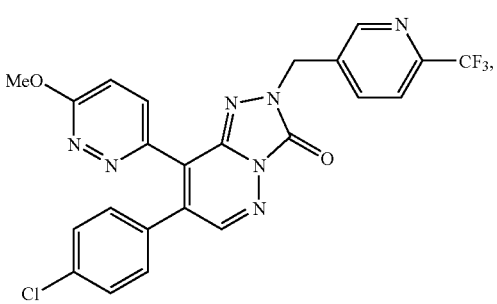
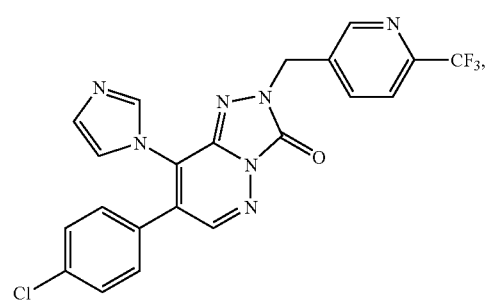
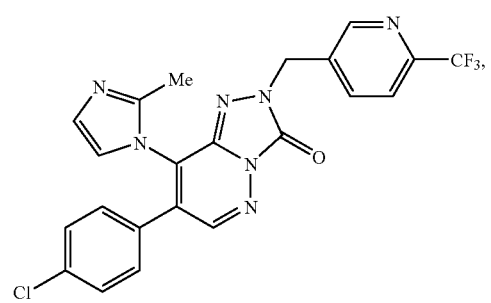
-continued
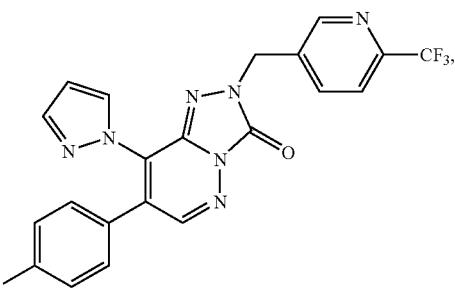
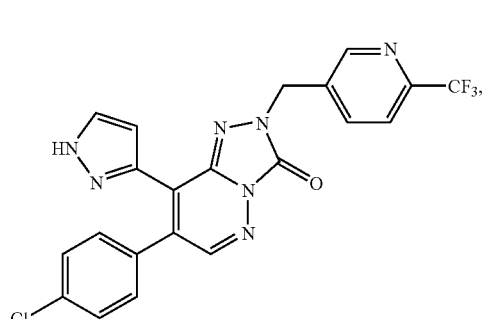
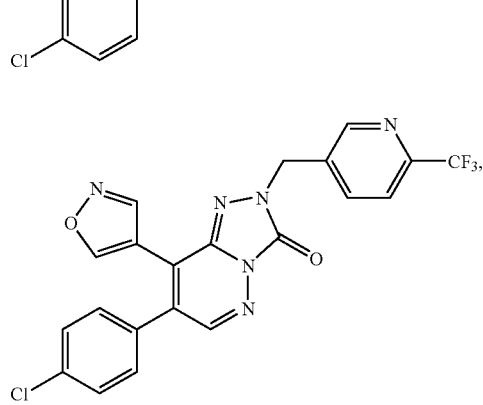
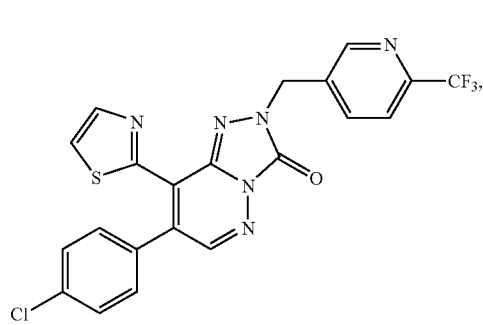
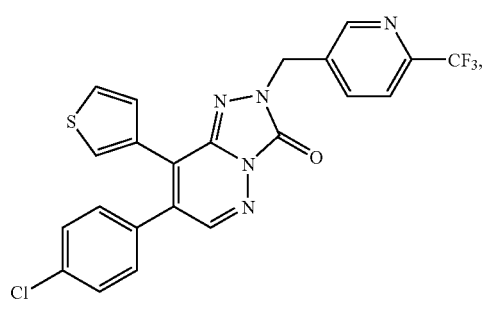

299
-continued
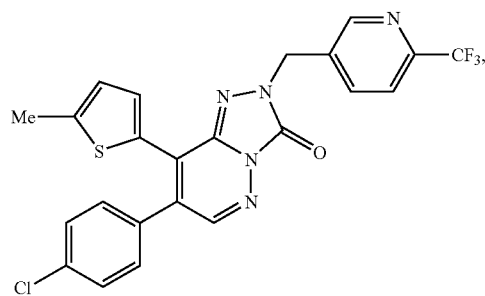
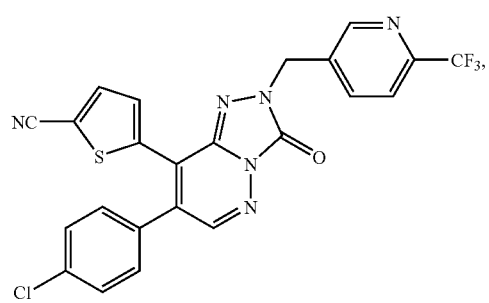
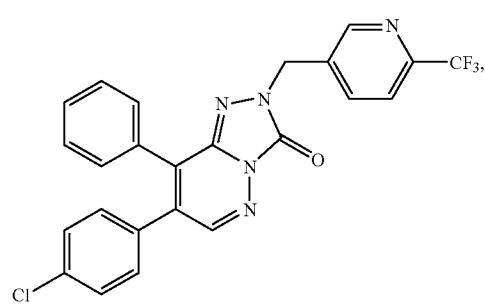
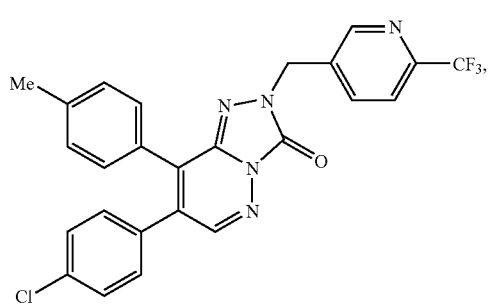
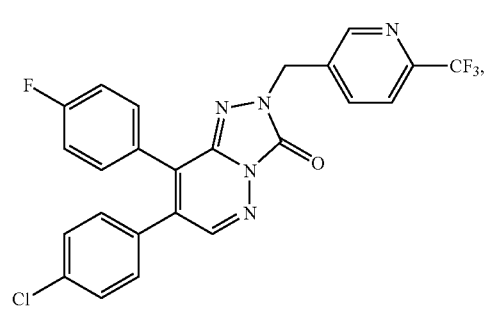
300
-continued
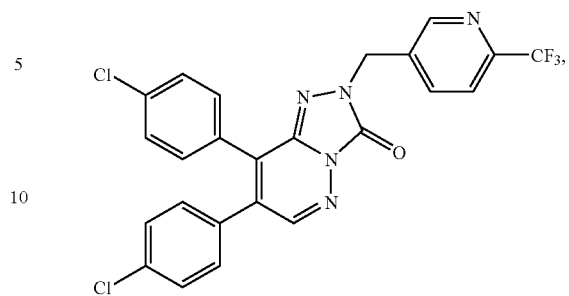
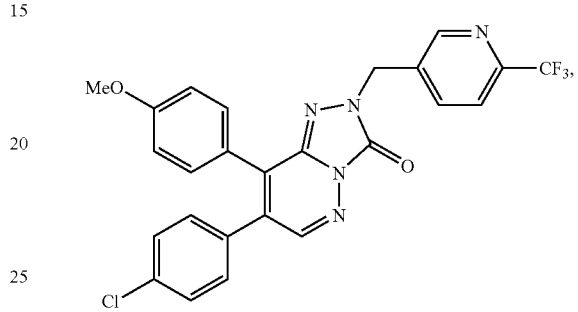
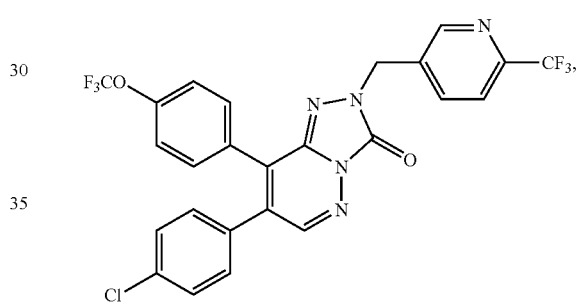
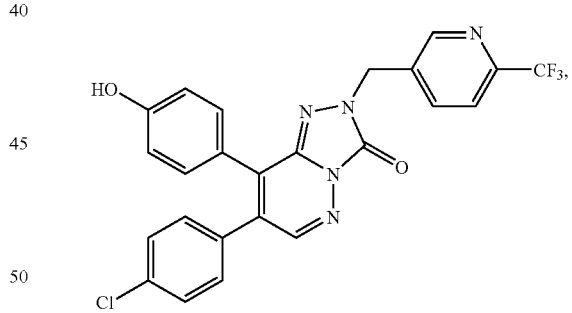
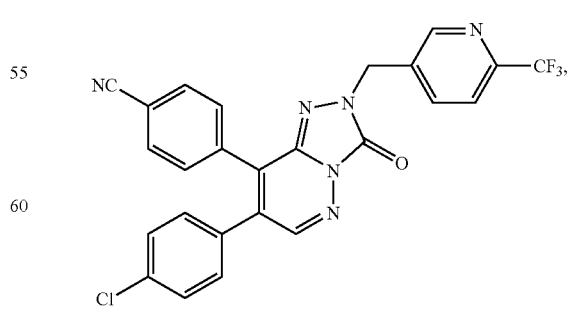

-continued
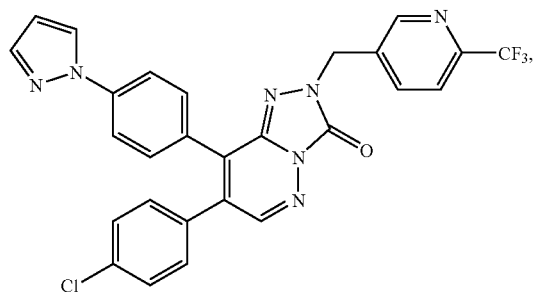
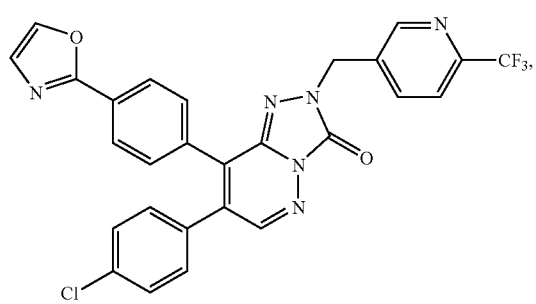
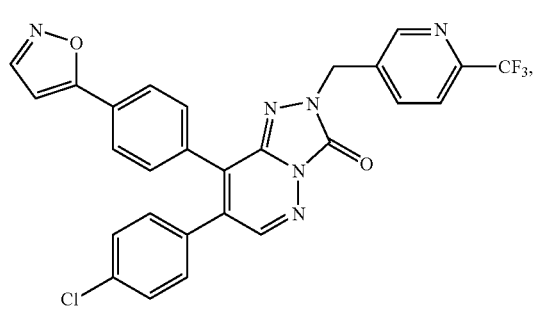
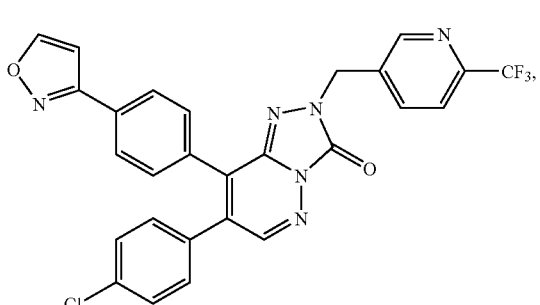
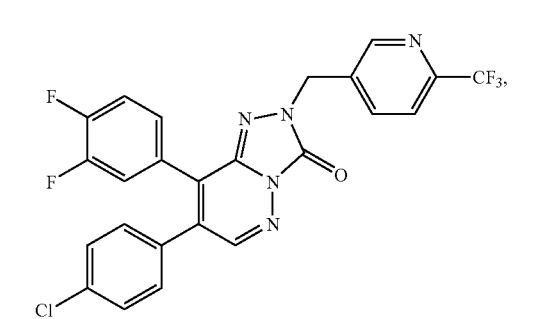
-continued
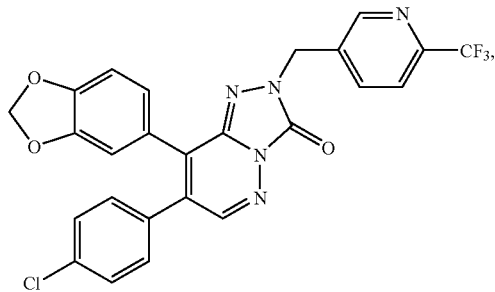
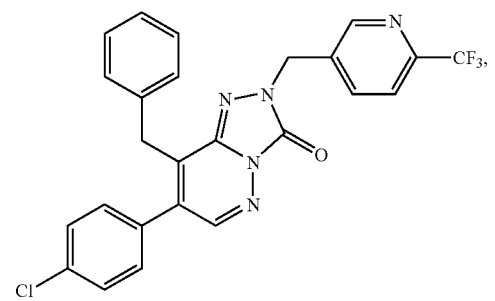
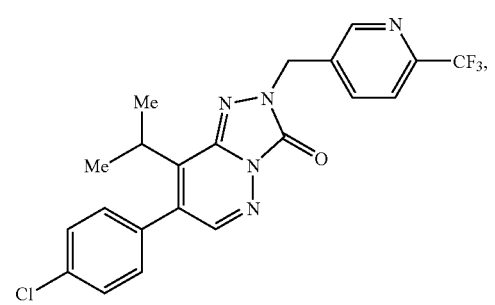
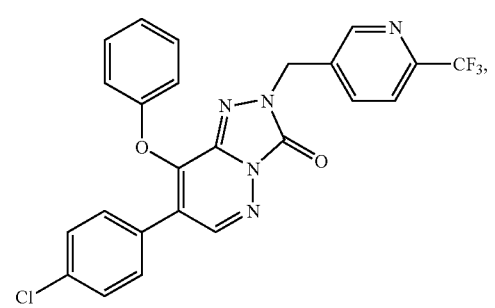
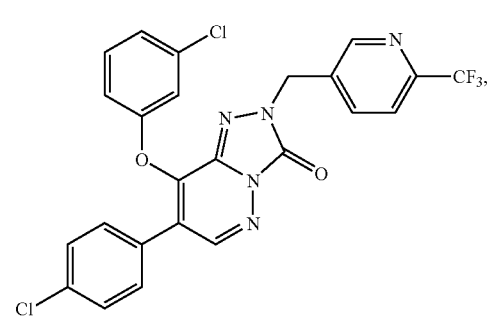

-continued
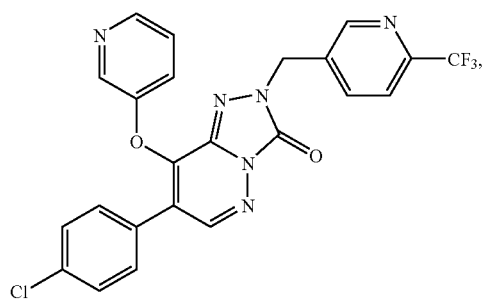
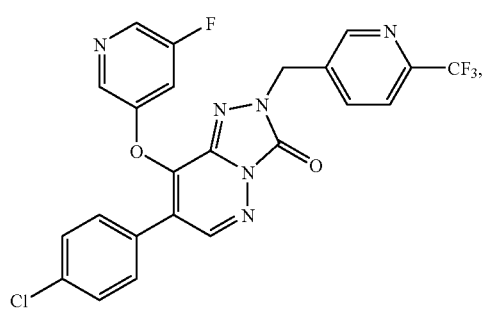
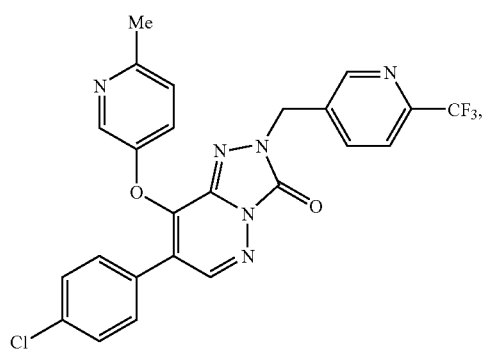
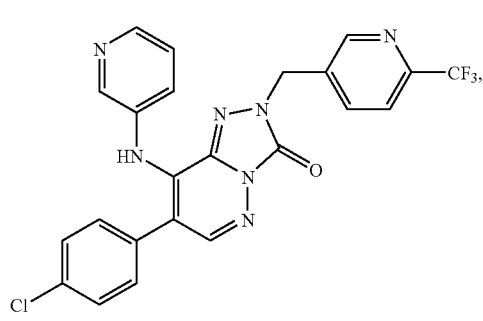
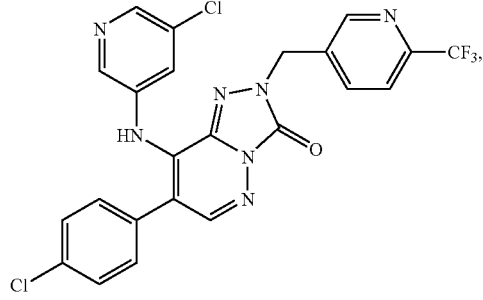
-continued
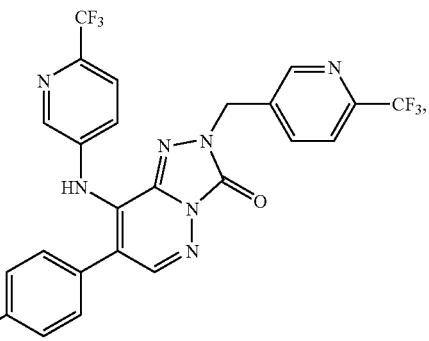
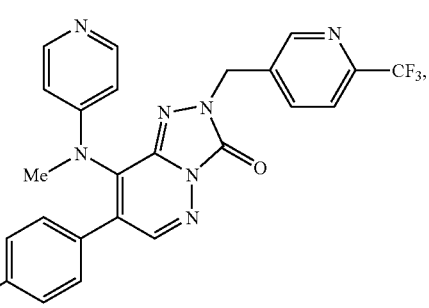
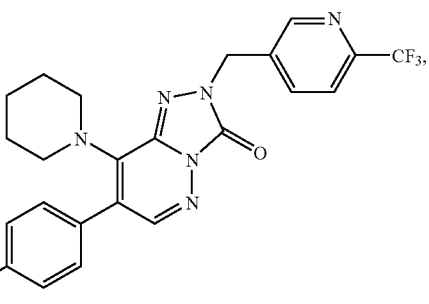
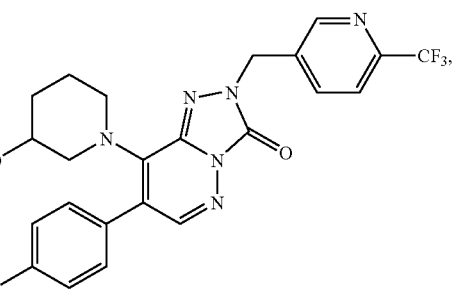
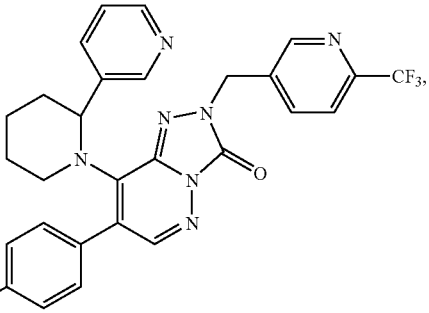

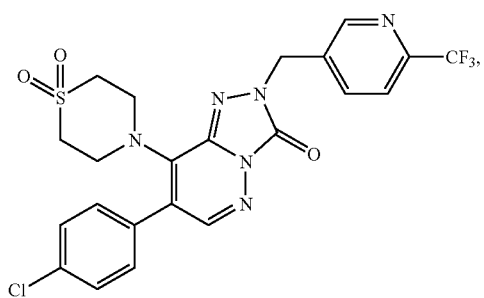

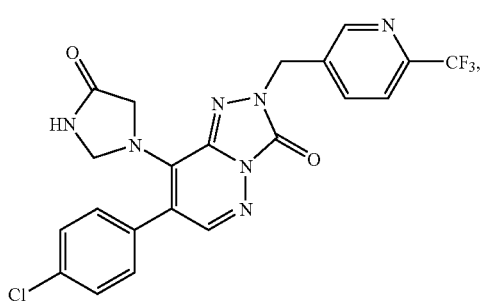

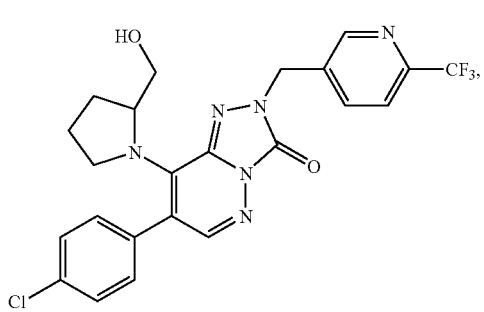

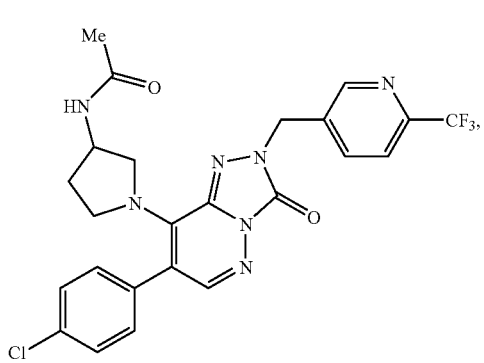

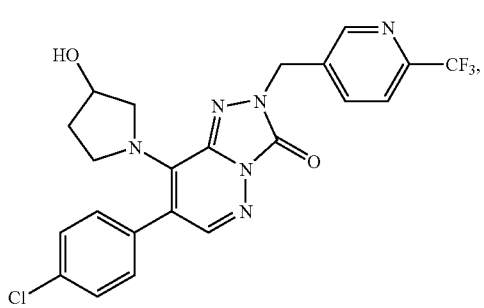

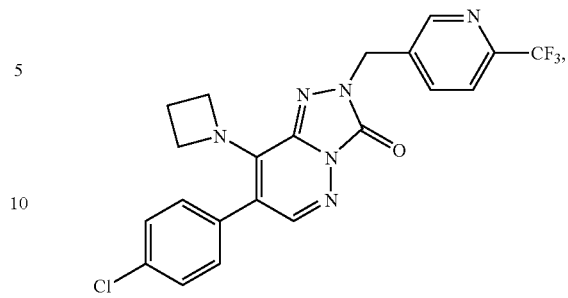

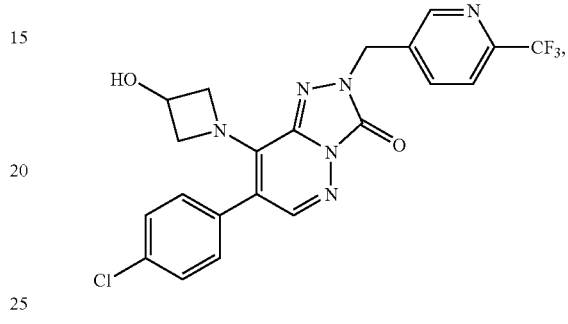

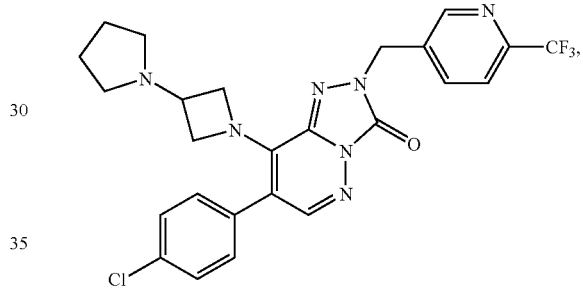

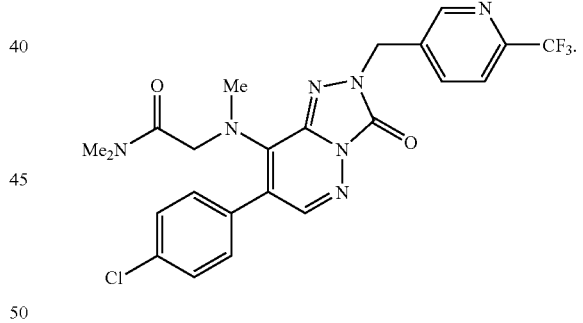

As noted above, Set A consists of compounds that differ from one another only in the identity of $R^1$ with $R^2$ fixed as 4-chlorophenyl. Set A may be considered a one dimensional library of example compounds. Were one to vary both $R^1$ and $R^2$, a two dimensional library of example compounds would result. Set B is the two dimensional library that consists of all permutations of all of the variants of $R^1$ represented in Set A and a set of $R^2$ variants listed below. In Set B, $R^3$ is 2-(trifluoromethyl)pyridin-5-ylmethyl, $R^6$ is hydrogen, $R^7$ is absent, and n is a double bond. The compounds of Set B may be prepared by one skilled in the art by the methods described above. The compounds of Set B are meant to further illustrate the scope of the invention without being limiting in any way.

R² Variants of Set B:
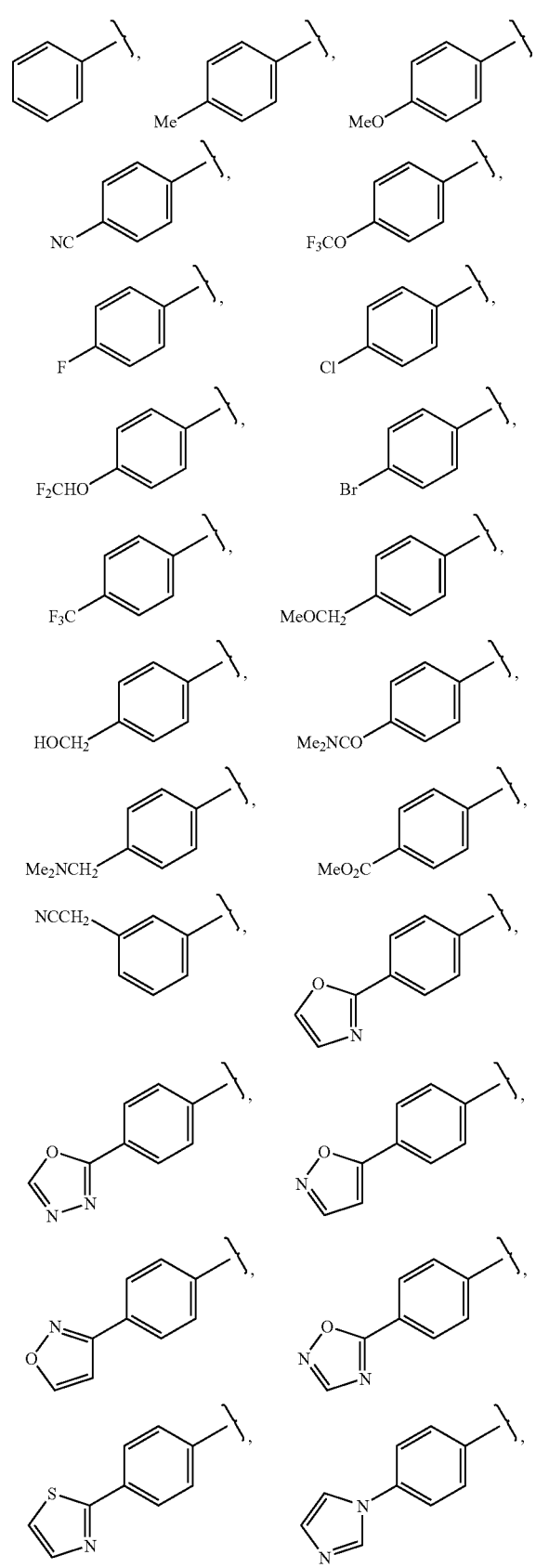
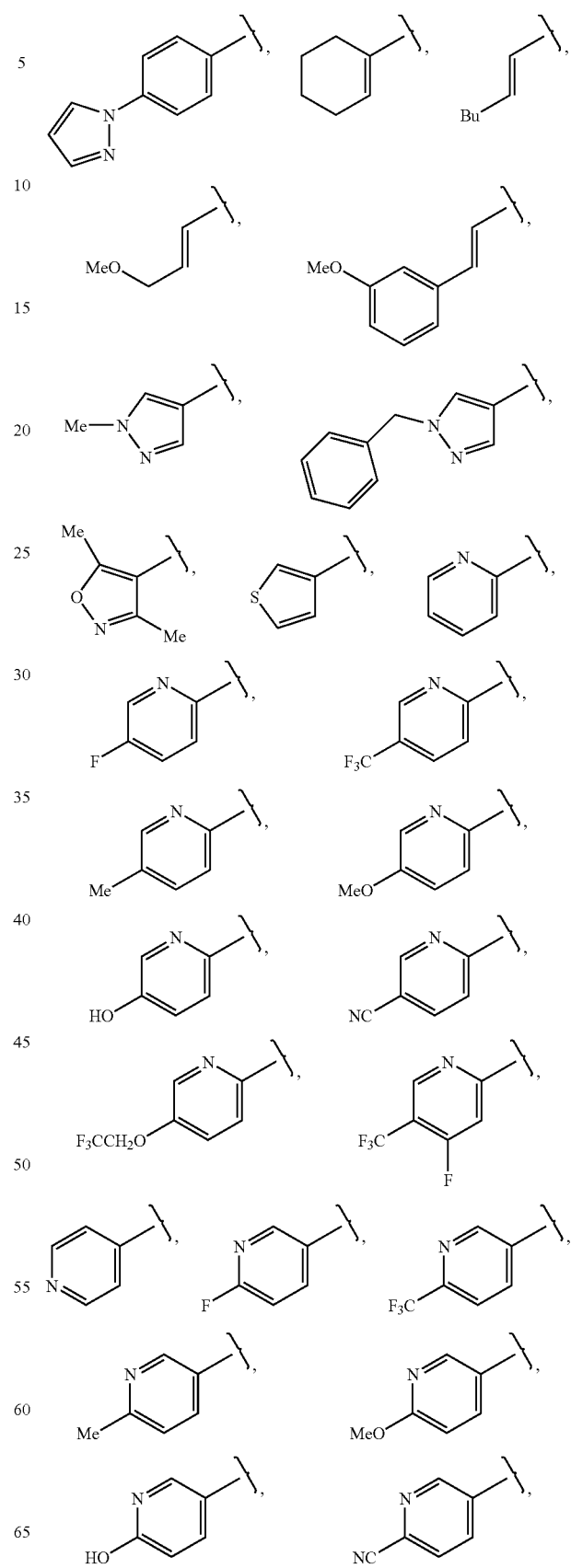

-continued

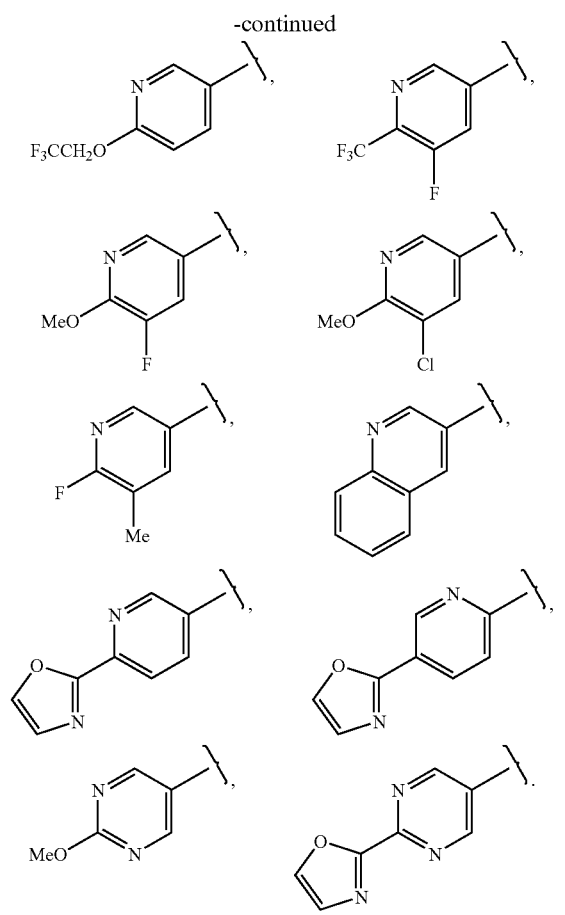

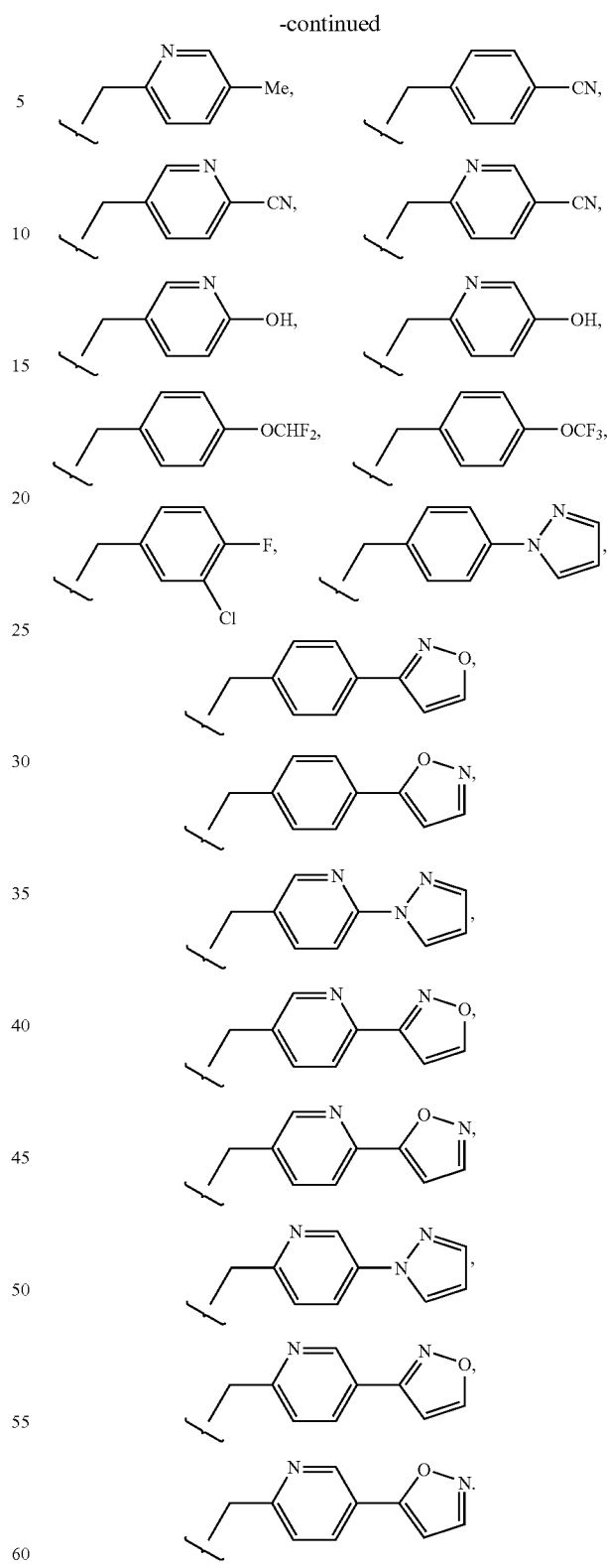

Further, as noted above, Set B is the two dimensional library that consists of all permutations of all of the variants of $R^1$ represented in Set A and a set of $R^2$ variants listed above with $R^3$ fixed as 2-(trifluoromethyl)pyridin-5-ylmethyl. Were one to vary $R^1$ and $R^2$ and $R^3$, a three dimensional library of example compounds would result. Set C is the three dimensional library that consists of all permutations of all of the variants of $R^1$ represented in Set A, all of the $R^2$ variants listed above for Set B, and a set of $R^3$ variants listed below. In Set C, $R^6$ is hydrogen, $R^7$ is absent, and n is a double bond. The compounds of Set C may be prepared by one skilled in the art by the methods described above. The compounds of Set C are meant to further illustrate the scope of the invention without being limiting in any way.

$R^3$ Variants of Set C:

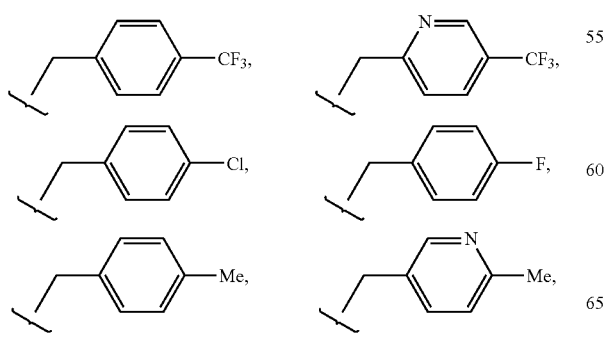

As a further illustration of the meaning of Set C, listed below are three representative structures from Set C with explanations of how they fall within the scope of Set C above. These representative structures are meant to be illustrative without being limiting in any way.

When R¹ is chosen from the first listed member of Set A, R² is chosen to be the first listed R² variant of Set B, and R³ is chosen to be the first listed R³ variant of Set C, the following structure results:

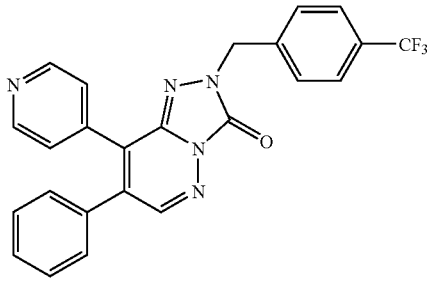

When R¹ is chosen from the last listed member of Set A, R² is chosen to be the last listed R² variant of Set B, and R³ is chosen to be the last listed R³ variant of Set C, the following structure results:

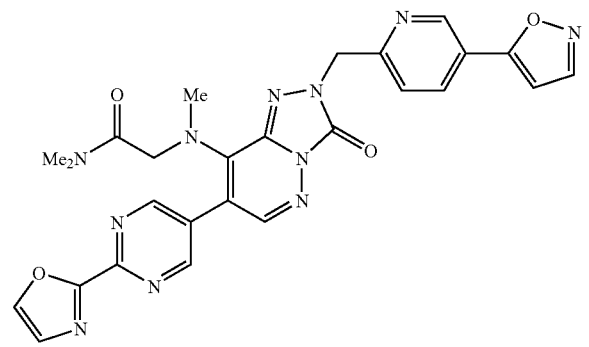

When R¹ is chosen from a randomly selected member of Set A, R² is chosen to be a randomly selected R² variant of Set B, and R³ is chosen to be a randomly selected R³ variant of Set C, the following structure results:

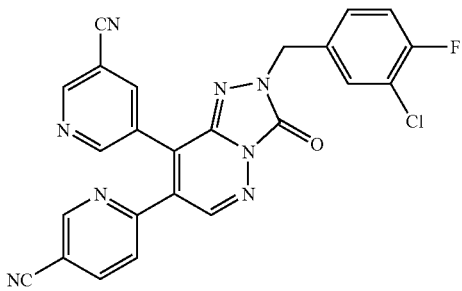

Additional non-limiting example compounds that may be prepared by one skilled in the art by the methods described above are the following:

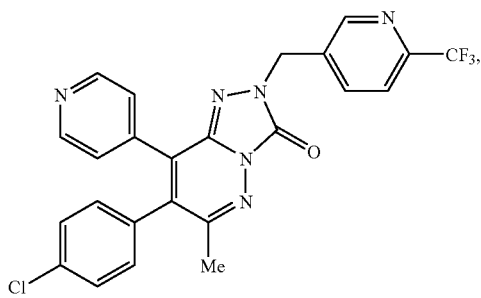

-continued

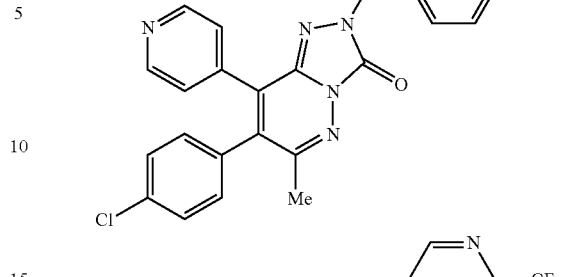

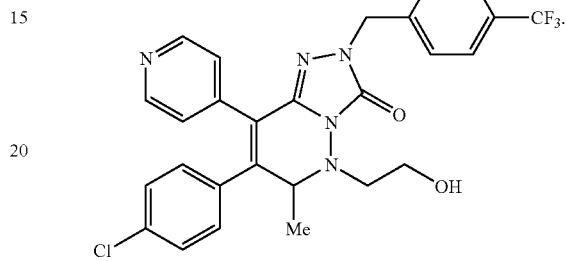

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 µl. 5 µg of membranes were brought up to a final volume of 95 µl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final ³H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25× PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding $K_i$ values of working Examples 1-63 fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to preincubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., Am. J. Physiol. Endocrinol. Metab., 284: E966-E971 (2003)), AZ-242 (tesaglitazar; Astra-Zeneca; as described in B. Ljung, et. al., J. Lipid Res., 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., J. Med. Chem., 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano, et al., J. Med. Chem., 20, 243-249 (1977), the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future, 24, 9-15 (1999), (Avasimibe); "The ACAT inhibitor, Cl-1011 is effective in the prevention and regression of aortic fatty streak area in hamsters", Nicolosi et al., Atherosclerosis (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Lett,* 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B 12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein" *New England J. of Medicine,* 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound of formula I

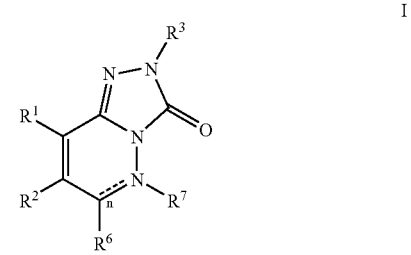

all pharmaceutically acceptable salts and stereoisomers thereof,
wherein:
n is a single bond or a double bond;
$R^1$ is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —$NR^8R^9$, —$CO_2R^8$, —$CONR^8R^9$, —$OR^8$, —$NR^8COR^9$, —$NR^8CONR^8R^9$, —$NR^8CO_2R^9$, —$OCONR^8R^9$, —$NR^8S(O)_mR^9$, —$NR^8S(O)_mNR^8R^9$, —$NR^8S(O)_mOR^9$ and —$OS(O)_mNR^8R^9$; provided that $R^1$ is not $C_1$-$C_6$ alkyl when $R^2$ and $R^3$ are $C_1$-$C_6$ alkyl and $R^6$ is a substituted phenyl;
$R^2$ is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —$NR^8R^9$, —$CO_2R^8$, —$CONR^8R^9$, —$OR^8$, —$NR^8COR^9$, —$NR^8CONR^8R^9$, —$NR^8CO_2R^9$, —$OCONR^8R^9$, —$NR^8S(O)_mR^9$, —$NR^8S(O)_mNR^8R^9$, —$NR^8S(O)_mOR^9$ and —$OS(O)_mNR^8R^9$;
$R^3$ is selected from the group consisting of optionally substituted alkyl, optionally substituted alkenyl, optionally substituted alkynyl, optionally substituted cycloalkyl, optionally substituted cycloalkylalkyl, optionally substituted heterocyclylalkyl, optionally substituted arylalkyl and optionally substituted heteroarylalkyl;
$R^6$ is selected group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl and optionally substituted heteroarylalkyl,
wherein the $R^6$ group has a molecular weight of less than 200 atomic mass units;

$R^7$ is absent when n is a double bond;

$R^7$ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl, optionally substituted heteroarylalkyl, —COR$^8$, —CO$_2$R$^8$, —CONR$^8$R$^9$ and —S(O)$_m$R$^8$ when n is a single bond;

$R^8$ and $R^9$ independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

$R^8$ and $R^9$ taken together can optionally form a 4, 5, 6, or 7 membered optionally substituted heterocyclyl ring or a 5 or 6 membered optionally substituted heteroaryl ring; and m is an integer of 1 or 2.

2. The compound according to claim 1, wherein:

$R^1$ is selected from the group consisting of optionally substituted alkyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$;

$R^2$ is selected from the group consisting of optionally substituted alkyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$;

$R^3$ is selected from the group consisting of optionally substituted alkyl, optionally substituted cycloalkyl, optionally substituted cycloalkylalkyl, optionally substituted heterocyclylalkyl, optionally substituted arylalkyl and optionally substituted heteroarylalkyl;

$R^6$ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl and optionally substituted heteroarylalkyl, wherein the $R^6$ group has a molecular weight of less than 200 atomic mass units;

$R^7$ is absent;

$R^8$ and $R^9$ are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

$R^8$ and $R^9$ taken together can optionally form a 5, 6, or 7 membered optionally substituted heterocyclyl ring or a 5 or 6 membered optionally substituted heteroaryl ring; and n is a double bond.

3. The compound according to claim 2, wherein:

$R^6$ is selected from the group consisting of H, optionally substituted alkyl, optionally substituted aryl, optionally substituted heteroaryl, optionally substituted arylalkyl and optionally substituted heteroarylalkyl, wherein the $R^6$ group has a molecular weight of less than 200 atomic mass units.

4. The compound according to claim 3, wherein:

$R^2$ is selected from the group consisting of optionally substituted alkyl, optionally substituted cycloalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$.

5. The compound according to claim 4, wherein:

$R^1$ is selected from the group consisting of optionally substituted alkyl, optionally substituted cycloalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$.

6. The compound according to claim 5, wherein:

$R^3$ is selected from the group consisting of optionally substituted alkyl, optionally substituted cycloalkyl, optionally substituted heterocyclylalkyl, optionally substituted arylalkyl and optionally substituted heteroarylalkyl.

7. The compound according to claim 1, wherein:

$R^1$ is selected from the group consisting of optionally substituted aryl, optionally substituted heteroaryl, optionally substituted aryloxy, optionally substituted heteroaryloxy, —OR$^8$ and —NR$^8$R$^9$;

$R^2$ is selected from the group consisting of optionally substituted heteroaryl, optionally substituted aryloxy, optionally substituted heteroaryloxy, —OR$^8$ and —NR$^8$R$^9$;

$R^3$ is selected from the group consisting of optionally substituted alkyl, optionally substituted heterocyclylalkyl, optionally substituted arylalkyl and optionally substituted heteroarylalkyl;

$R^6$ is selected from the group consisting of H, optionally substituted alkyl and optionally substituted heterocyclyl, wherein the $R^6$ group has a molecular weight of less than 200 atomic mass units;

$R^8$ and $R^9$ are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

$R^8$ and $R^9$ taken together can optionally form a 5, 6, or 7 membered optionally substituted heterocyclyl ring or a 5 or 6 membered optionally substituted heteroaryl ring; and n is a double bond.

8. The compound according to claim 7, wherein:
R$^6$ is selected from the group consisting of H, methyl, ethyl and isopropyl.

9. The compound according to claim 8, wherein:
R$^2$ is selected from the group consisting of aryl and heteroaryl wherein the aryl or heteroaryl group is optionally substituted with the group consisting of H, alkyl, haloalkyl, halogen, heterocyclyl, aryl, heteroaryl, —OR$^8$, —CO$_2$R$^8$, —CONR$^8$R$^9$, —SO$_2$R$^8$, and —SO$_2$NR$^8$R$^9$.

10. The compound according to claim 9, wherein:
R$^1$ is selected from the group consisting of heterocyclyl, aryl, heteroaryl, aryloxy, heteroaryloxy, —OR$^8$ and —NR$^8$R$^9$ wherein the heterocyclyl, aryl, heteroaryl, aryloxy or heteroaryloxy group is optionally substituted with the group consisting of H, cyano, haloalkyl, alkyl, halogen, heterocyclyl, aryl, heteroaryl, —OR$^8$, —CO$_2$R$^8$, CONR$^8$R$^9$, —SO$_2$R$^8$, and —SO$_2$NR$^8$R$^9$.

11. The compound according to claim 10, wherein:
R$^3$ is selected from the group consisting of alkyl, arylalkyl, heteroarylalkyl and heterocyclylalkyl, wherein the arylalkyl, heteroarylalkyl or heterocycloalkyl group is optionally substituted with the group consisting of hydrogen, cyano, haloalkyl, alkyl, cycloalkyl, halogen, hydroxyl, amino, —OR$^8$, —NR$^8$NR$^9$, —SO$_2$R$^8$, —SO$_2$NR$^8$R$^9$, heteroaryl, heterocyclyl, and aryl.

12. The compound according to claim 1, wherein:
R$^1$ is selected from the group consisting of optionally substituted alkyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$;
R$^2$ is selected from the group consisting of optionally substituted alkyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$;
R$^3$ is selected from the group consisting of optionally substituted alkyl, optionally substituted cycloalkyl, optionally substituted cycloalkylalkyl, optionally substituted heterocyclylalkyl, optionally substituted arylalkyl and optionally substituted heteroarylalkyl;
R$^6$ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl and optionally substituted heteroarylalkyl,
wherein the R$^6$ group has a molecular weight of less than 200 atomic mass units;
R$^7$ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted arylalkyl, optionally substituted heteroarylalkyl, —CONR$^8$R$^9$, —CO$_2$R$^8$, —COR$^8$ and —SO$_2$R$^8$;
R$^8$ and R$^9$ are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;
R$^8$ and R$^9$ taken together can optionally form a 5, 6, or 7 membered optionally substituted heterocyclyl ring or a 5 or 6 membered optionally substituted heteroaryl ring; and
n is a single bond.

13. The compound according to claim 12, wherein;
R$^6$ is selected from the group consisting of H, optionally substituted alkyl, optionally substituted aryl, optionally substituted heteroaryl, optionally substituted arylalkyl and optionally substituted heteroarylalkyl,
wherein the R$^6$ group has a molecular weight of less than 200 atomic mass units.

14. The compound according to claim 13, wherein;
R$^7$ is selected from the group consisting of H, optionally substituted alkyl, —COR$^8$, —CO$_2$R$^8$, —CONR$^8$R$^9$ and —SO$_2$R$^8$.

15. The compound according to claim 14, wherein:
R$^2$ is selected from the group consisting of optionally substituted alkyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$.

16. The compound according to claim 15, wherein:
R$^1$ is selected from the group consisting of optionally substituted alkyl, optionally substituted cycloalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —OR$^8$ and —NR$^8$R$^9$.

17. The compound according to claim 16, wherein:
R$^3$ is selected from the group consisting of optionally substituted alkyl, optionally substituted cycloalkyl, optionally substituted heterocyclylalkyl, optionally substituted arylalkyl and optionally substituted heteroarylalkyl.

18. The compound according to claim 1, wherein:
R$^1$ is selected from the group consisting of optionally substituted aryl, optionally substituted heteroaryl, optionally substituted aryloxy, optionally substituted heteroaryloxy, —OR$^8$ and —NR$^8$R$^9$;
R$^2$ is selected from the group consisting of optionally substituted aryl, optionally substituted heteroaryl, optionally substituted aryloxy, optionally substituted heteroaryloxy, —OR$^8$ and —NR$^8$R$^9$;
R$^3$ is selected from the group consisting of optionally substituted alkyl, optionally substituted heterocyclylalkyl, optionally substituted arylalkyl and optionally substituted heteroarylalkyl;
R$^6$ is selected from the group consisting of H, optionally substituted alkyl, optionally substituted arylalkyl and optionally substituted heteroarylalkyl,
wherein the R$^6$ group has a molecular weight of less than 200 atomic mass units;

R[7] selected from the group consisting of H, —COR[8], —CO$_2$R[8], —CONR[8]R[9] and —SO$_2$R[8];

R[8] and R[9] are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

R[8] and R[9] taken together can optionally form a 5, 6, or 7 membered optionally substituted heterocyclyl ring or a 5 or 6 membered optionally substituted heteroaryl ring; and n is a single bond.

19. The compound of claim 1 selected from:

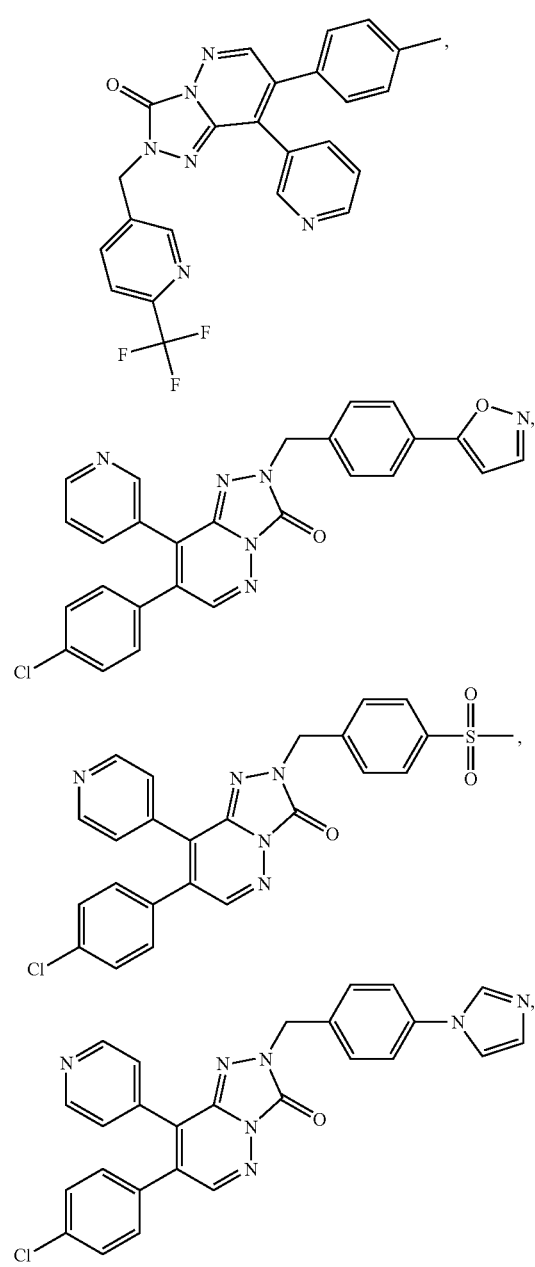

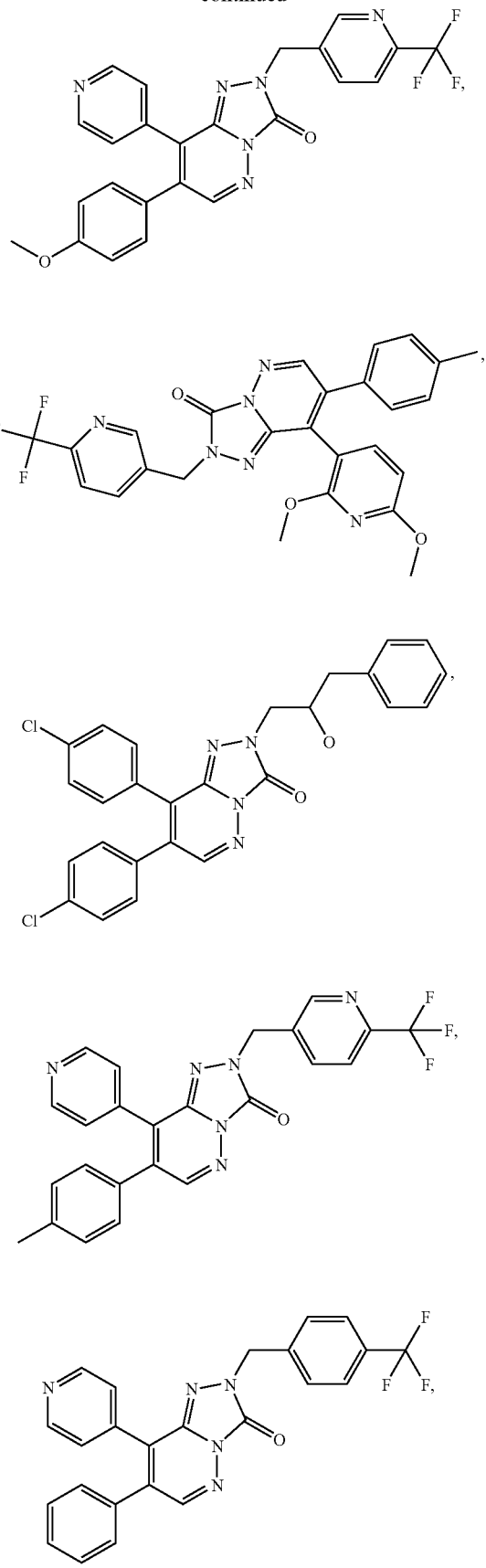

-continued
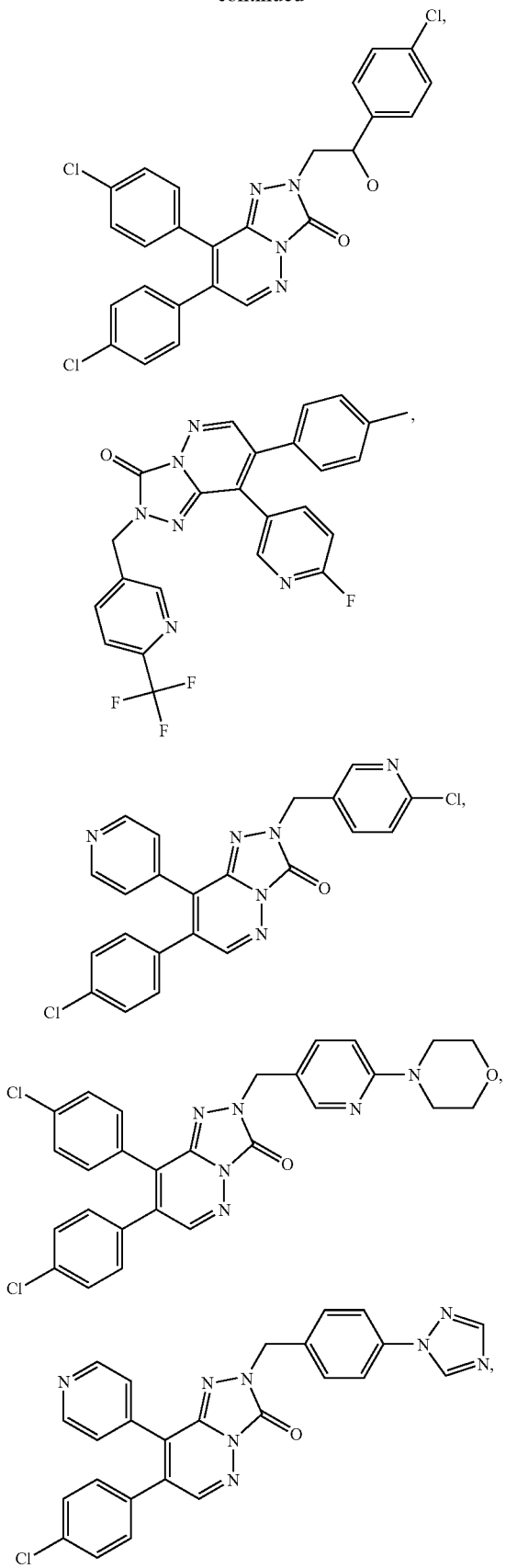
-continued
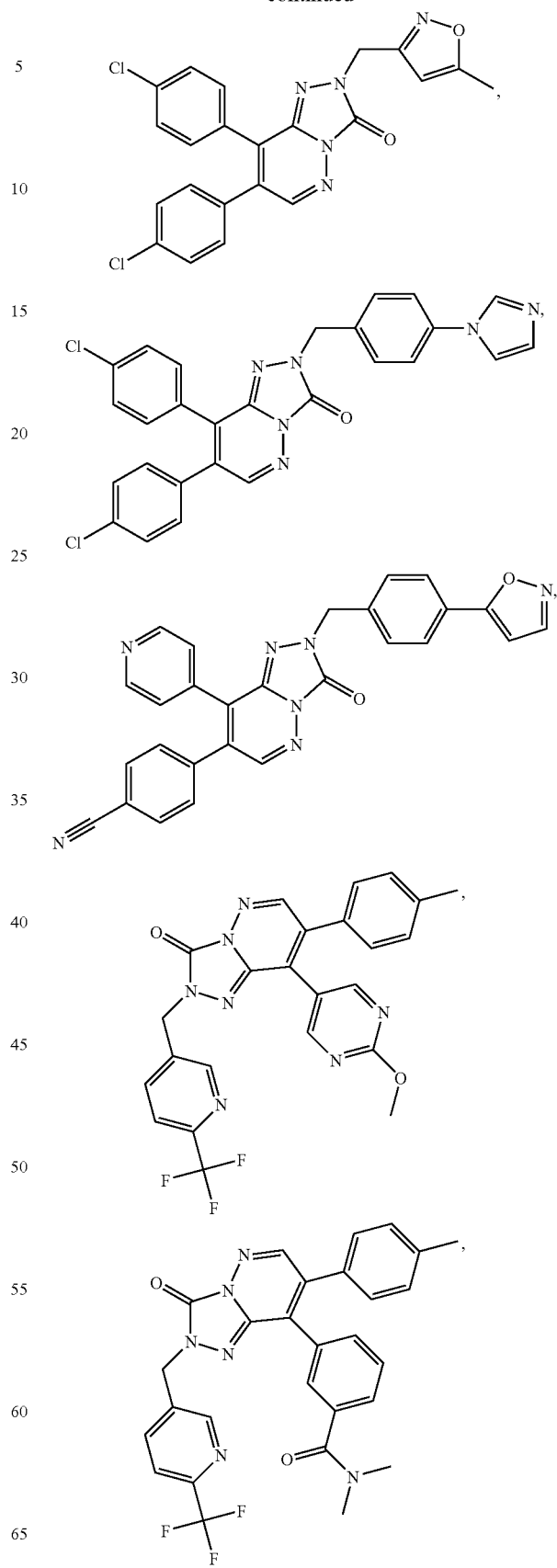

333
-continued
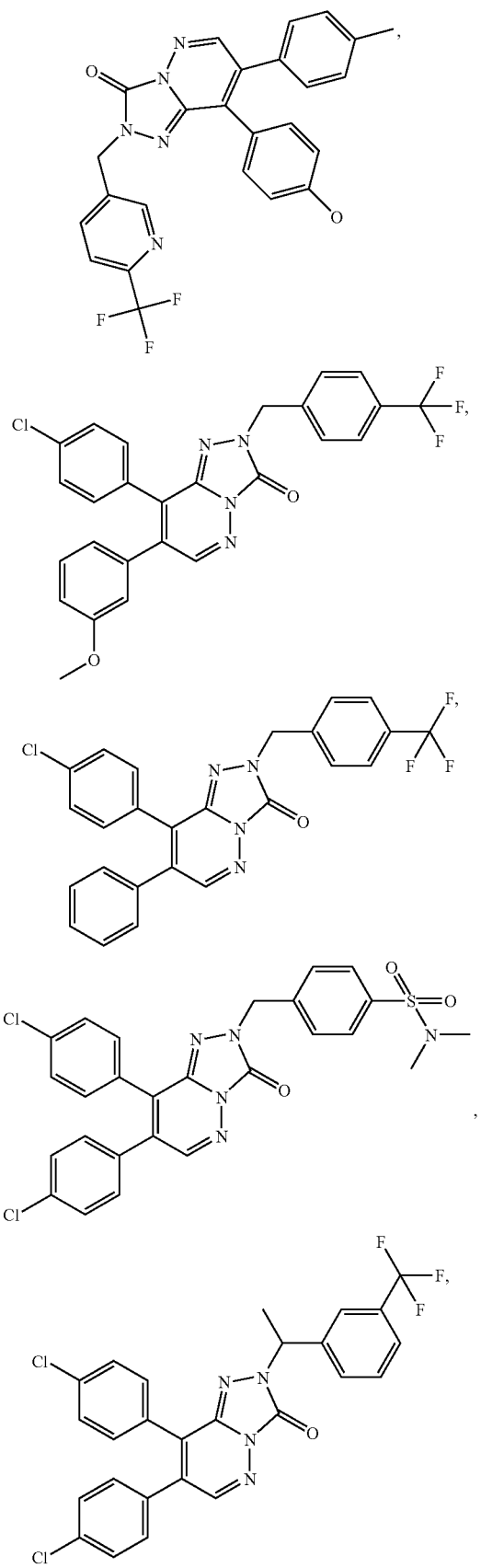
334
-continued
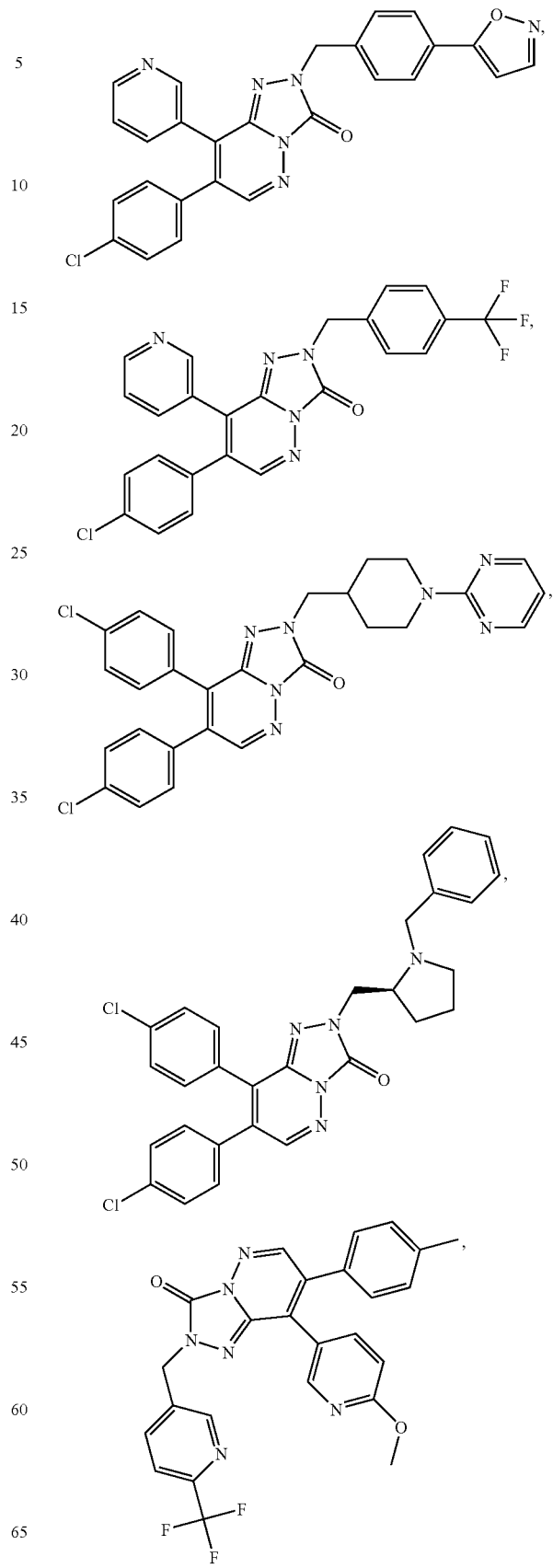

-continued
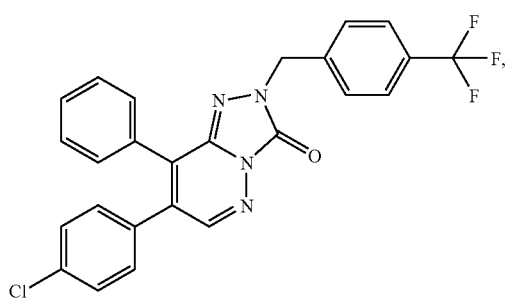
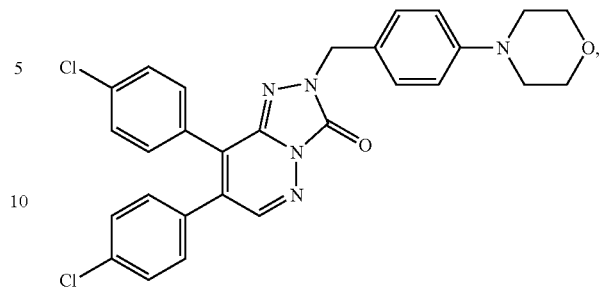
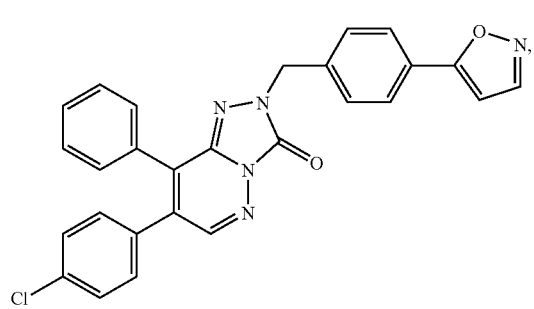
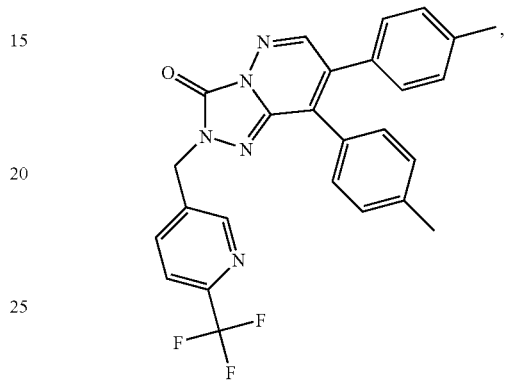
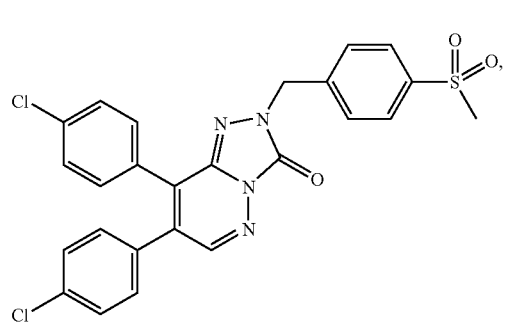
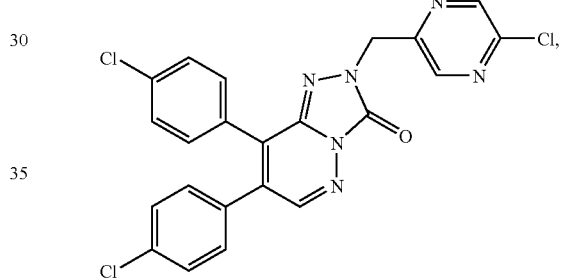
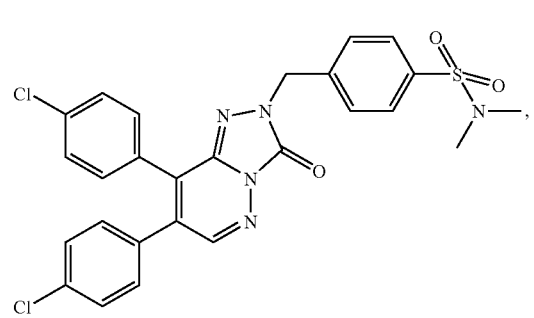
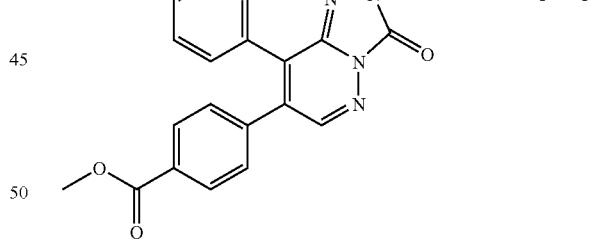
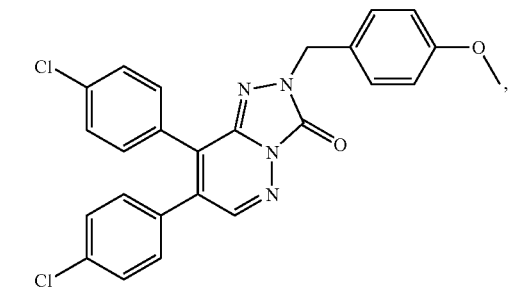
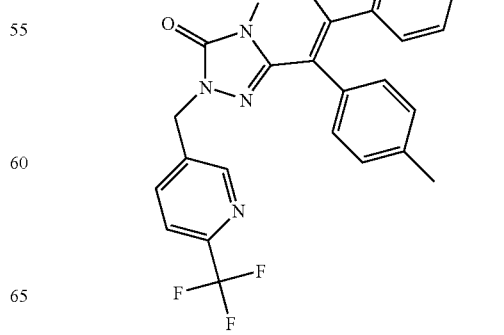

-continued
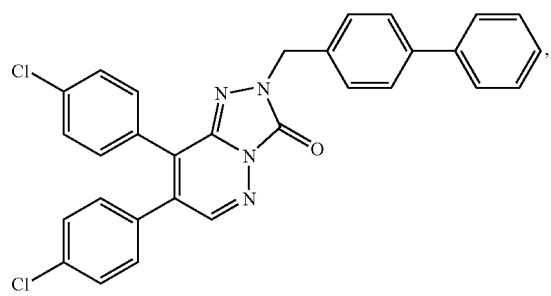
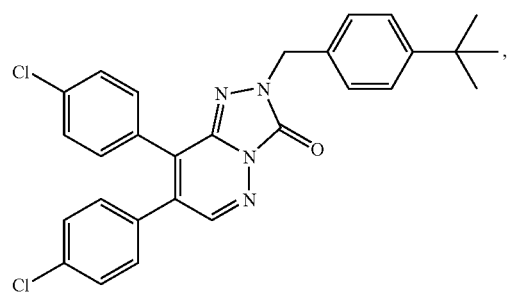
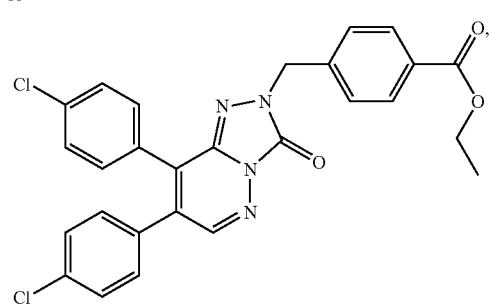
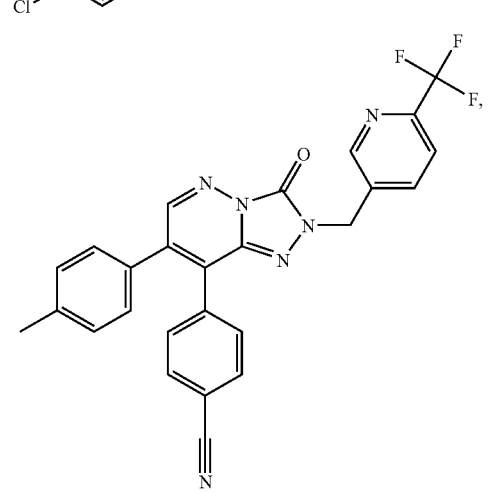
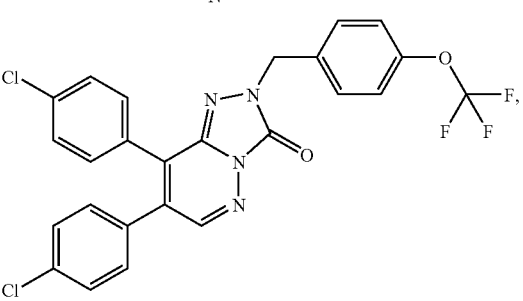
-continued
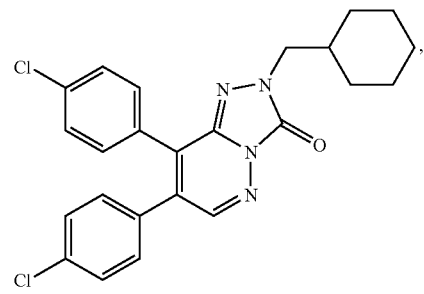
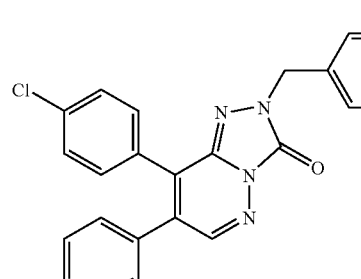
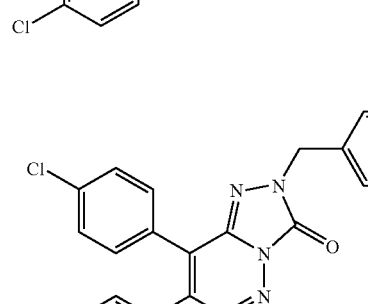
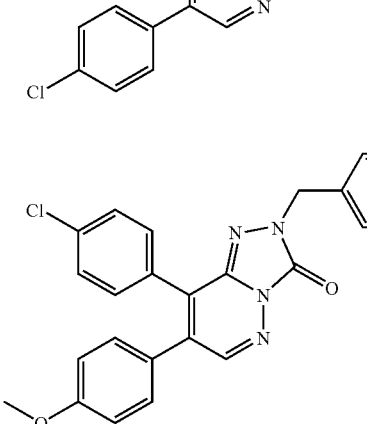
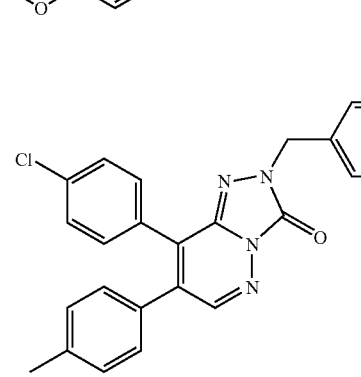

-continued
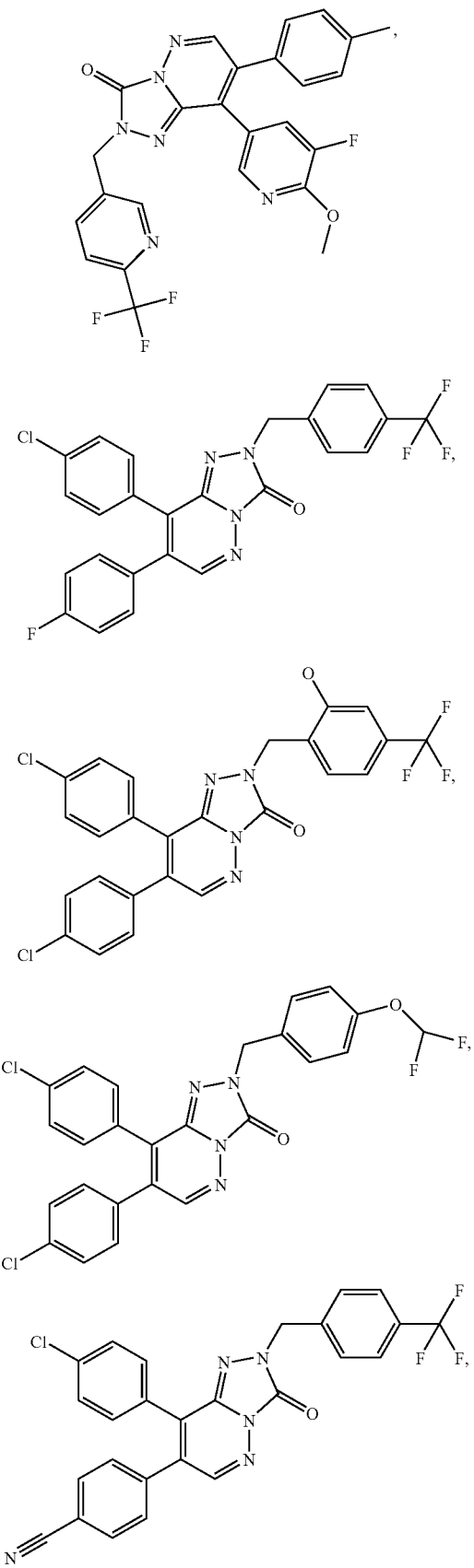
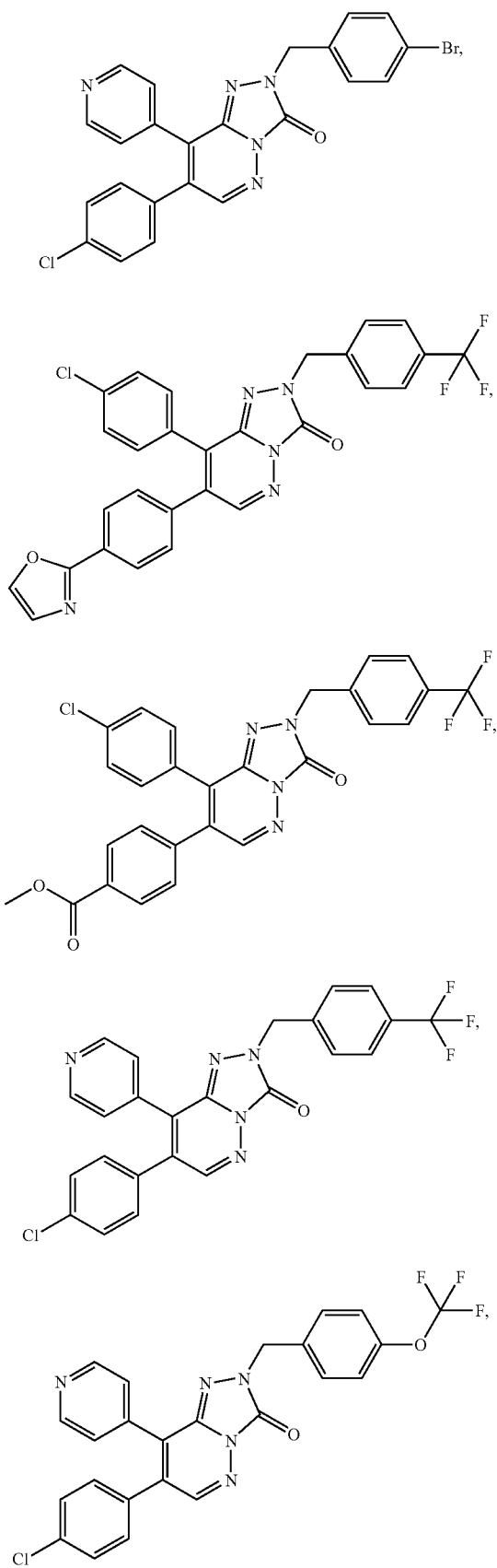

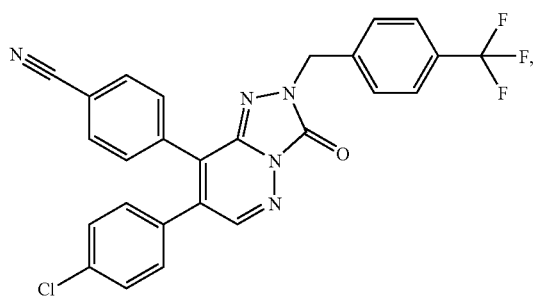

343
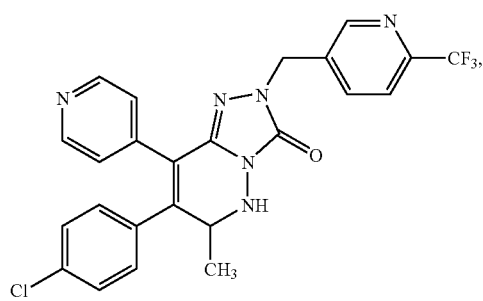
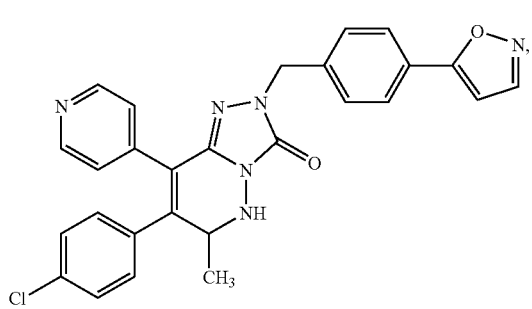
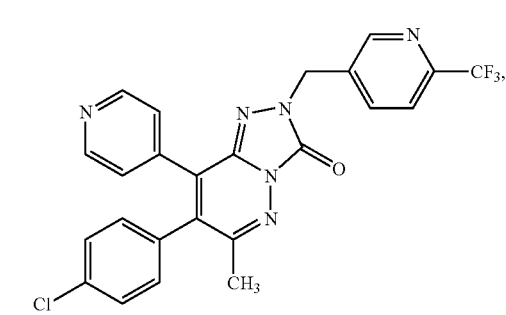
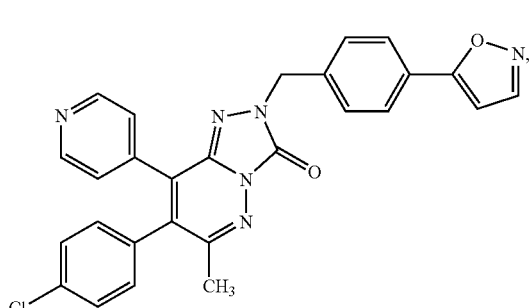
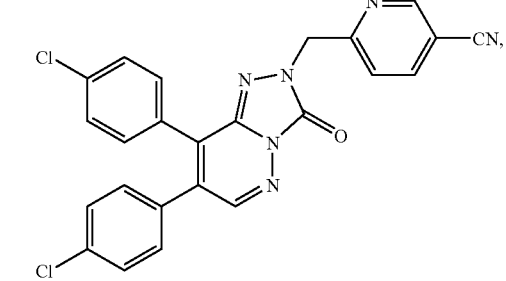
344
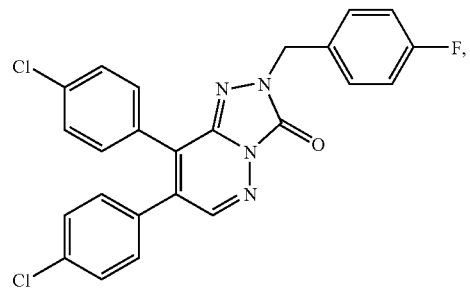
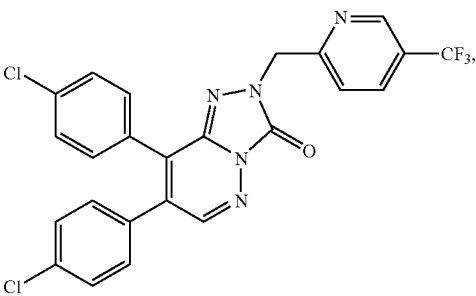
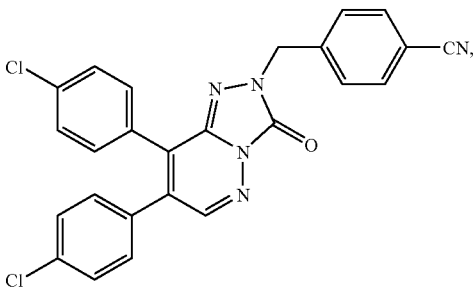
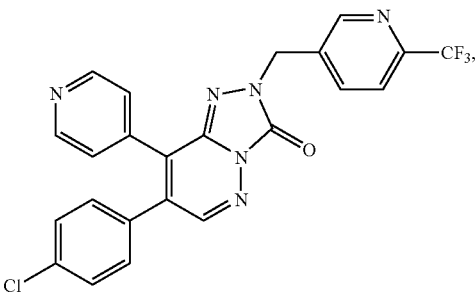
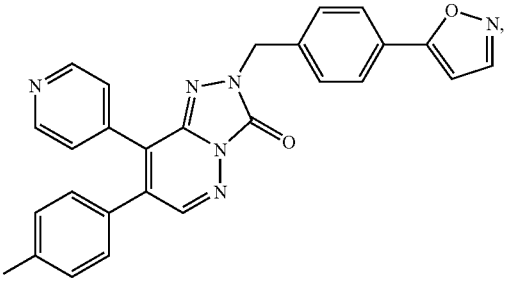

345
-continued
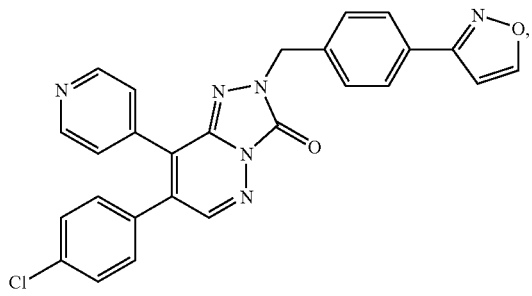
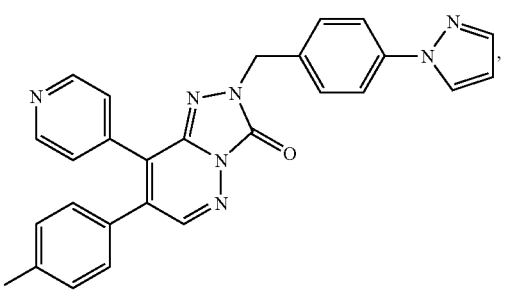
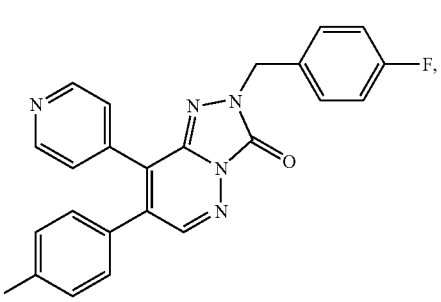
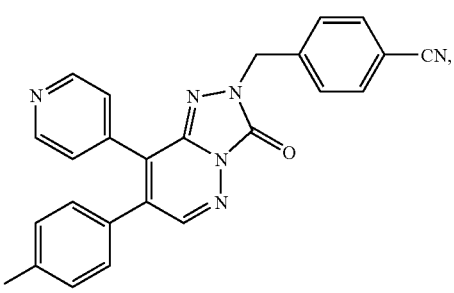
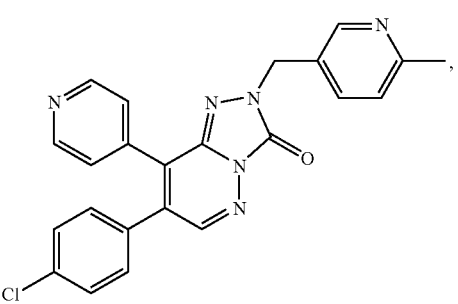
346
-continued
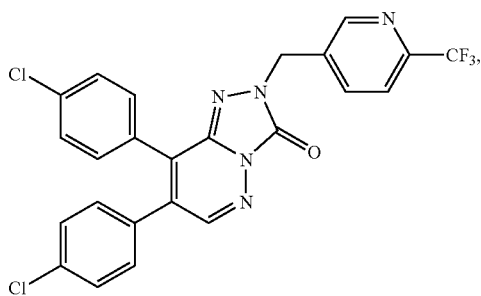

-continued
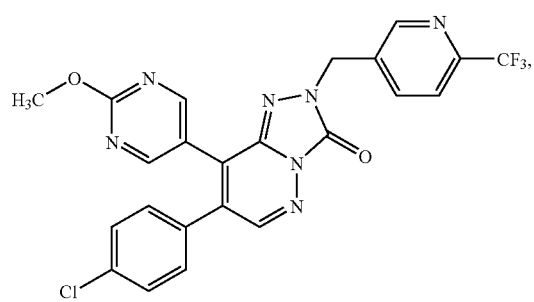
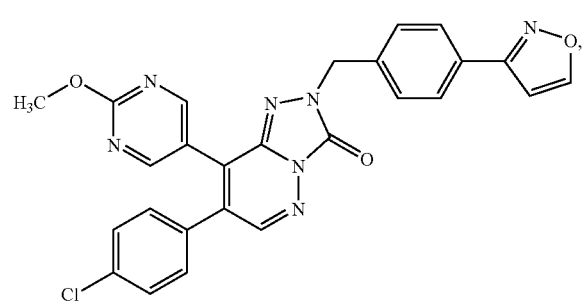
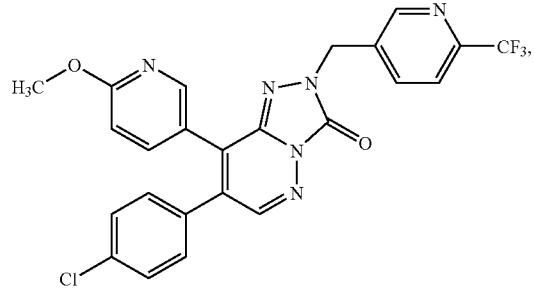
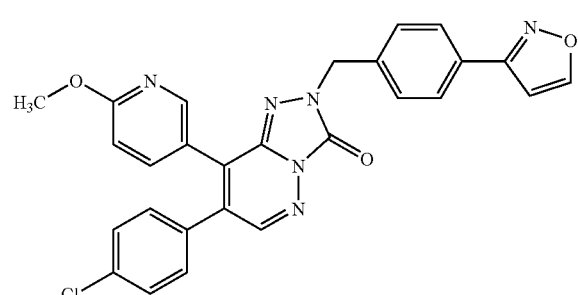
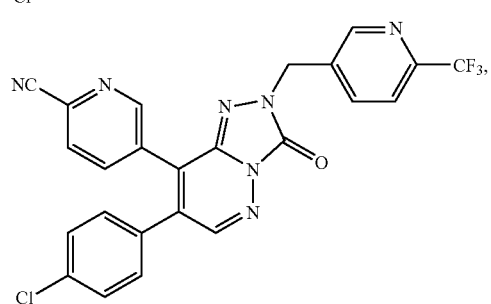
-continued
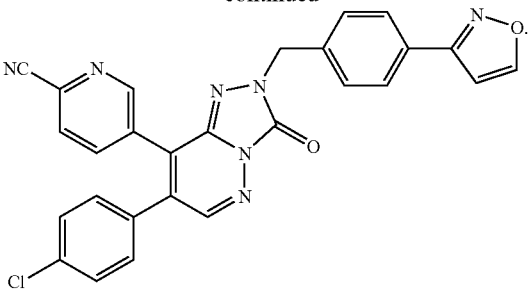
20. The compound of claim 1 selected from:
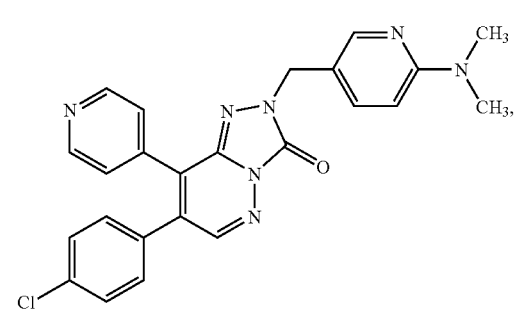
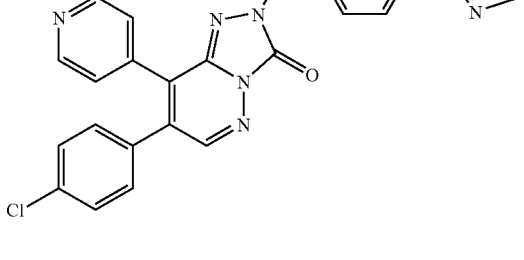
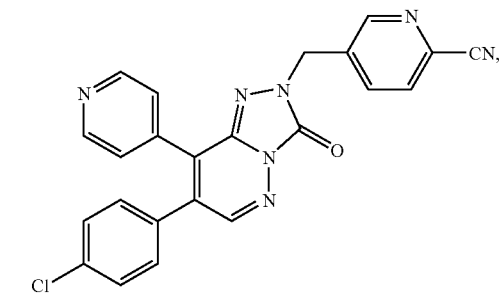
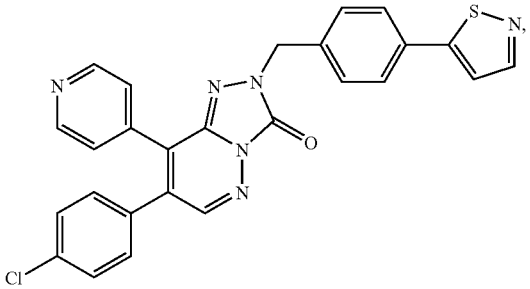

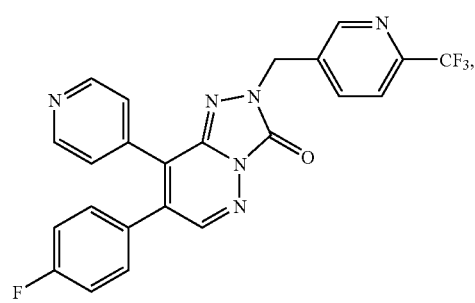
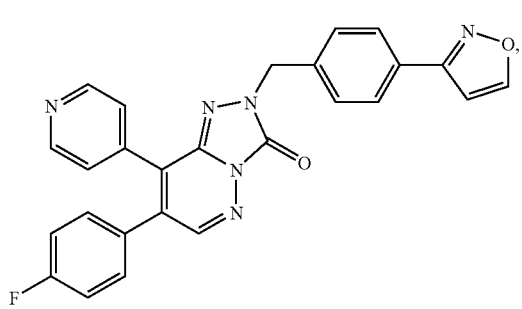
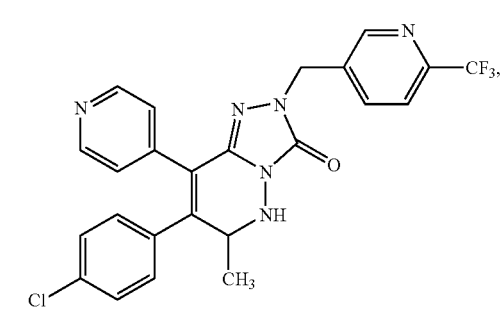
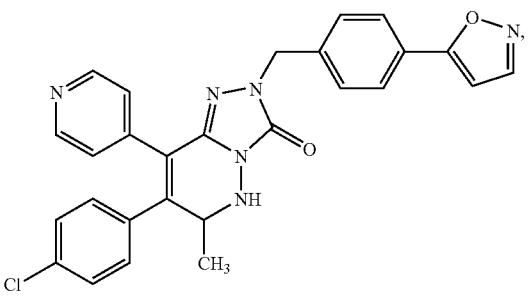
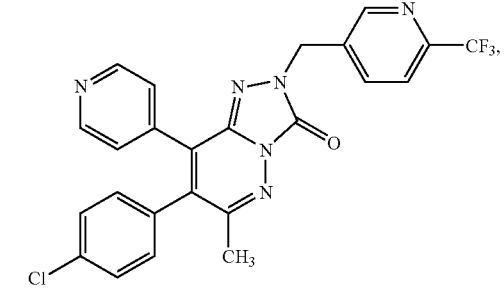
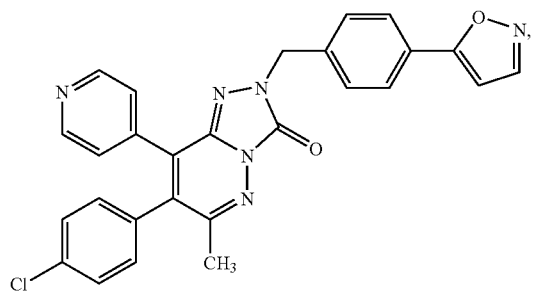
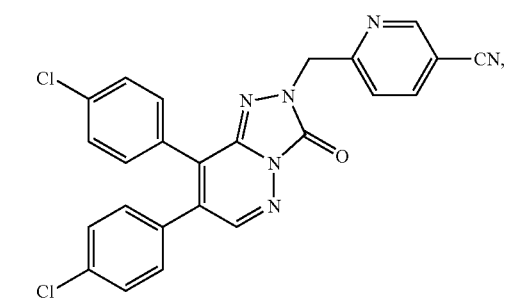
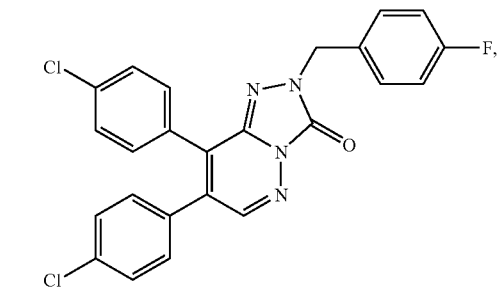
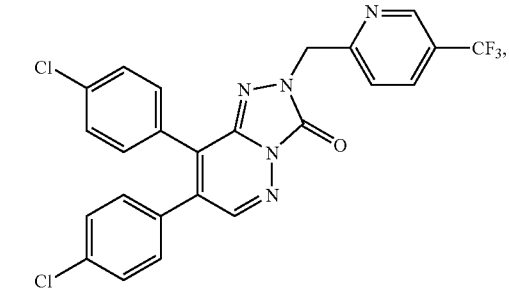
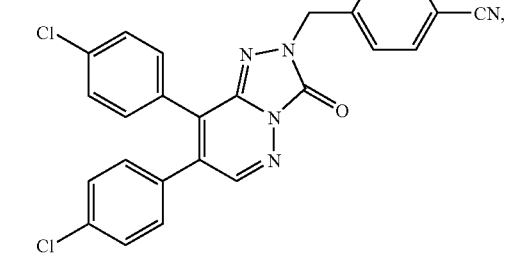

-continued
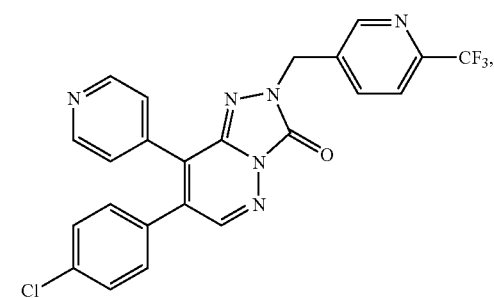
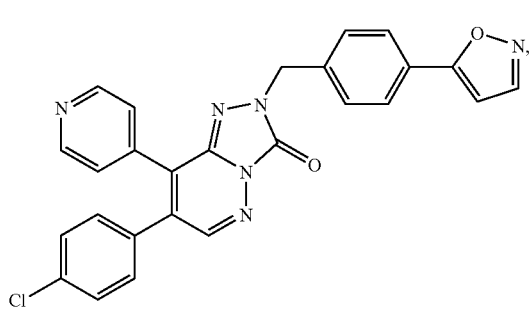
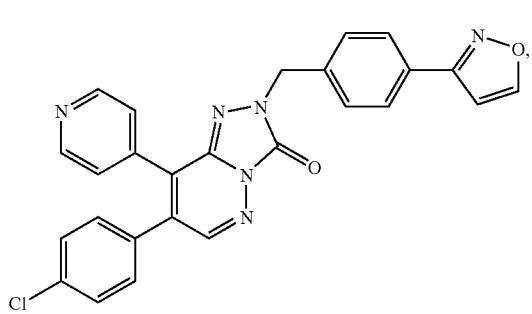
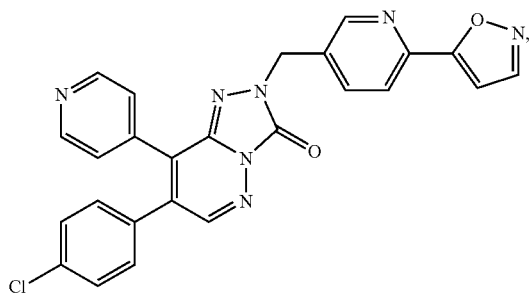
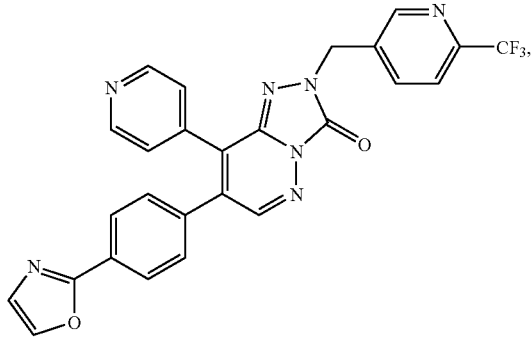
-continued
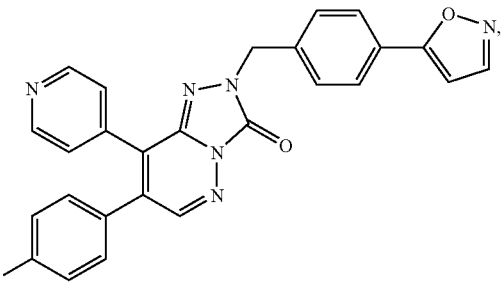
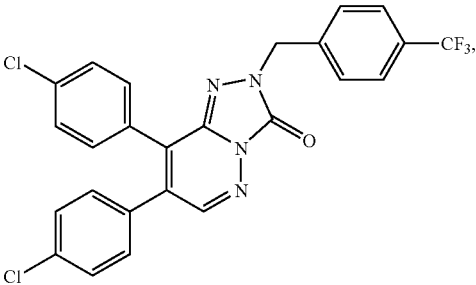
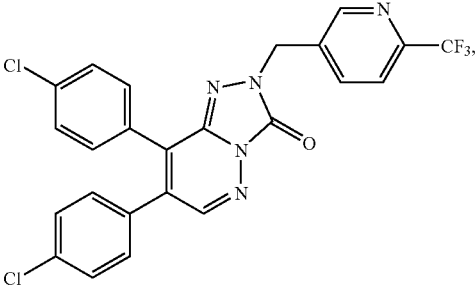
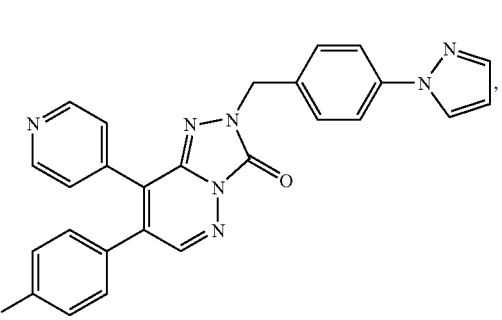
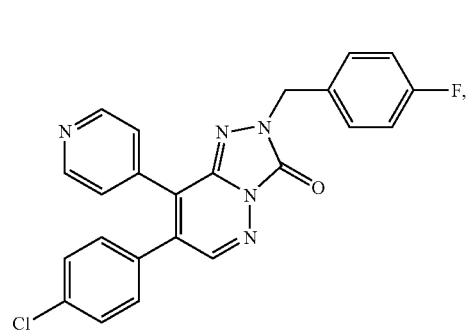

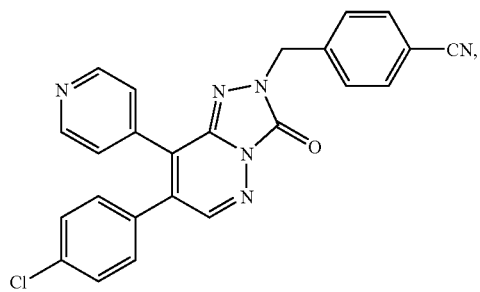
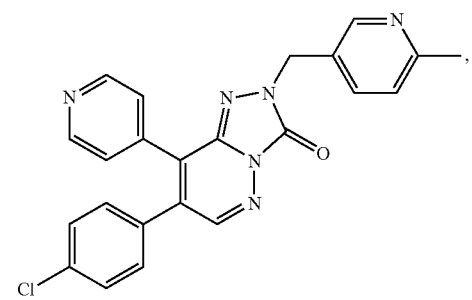
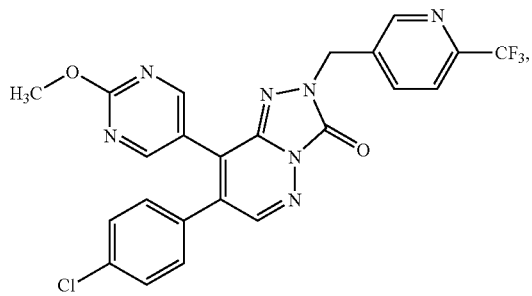
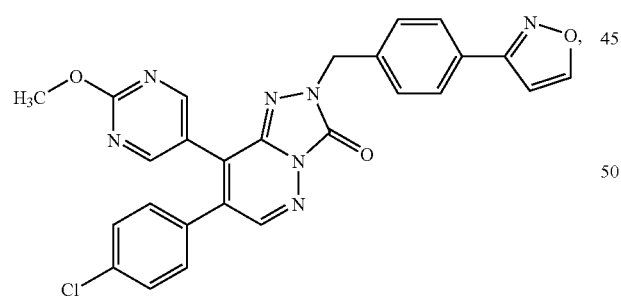
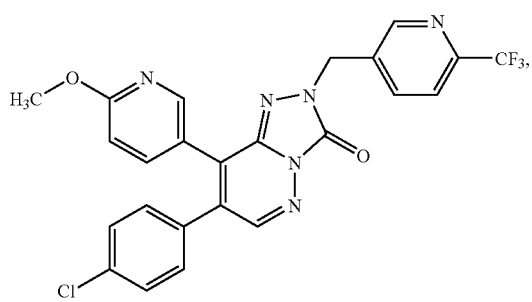
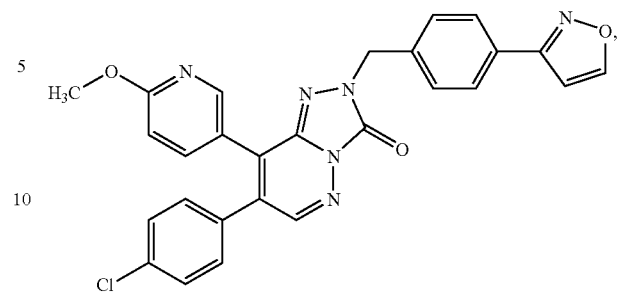
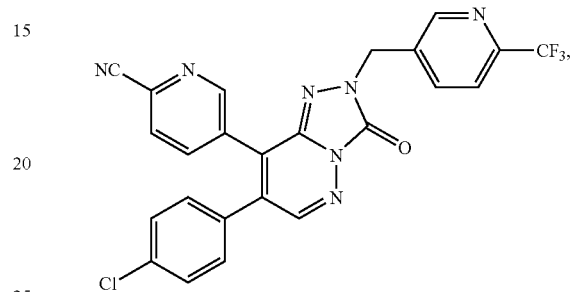
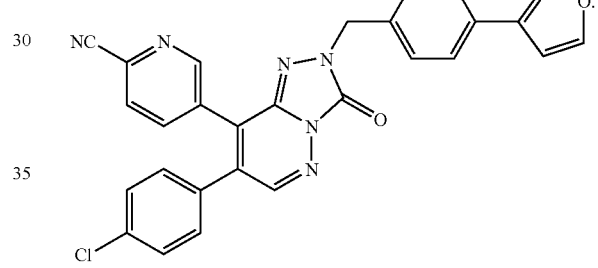
21. The compound of claim 1 selected from;
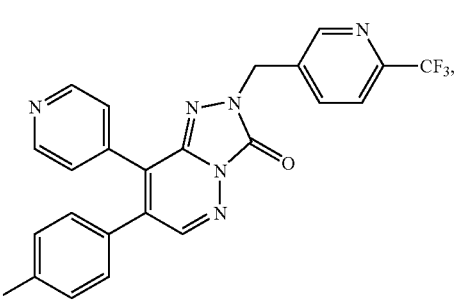
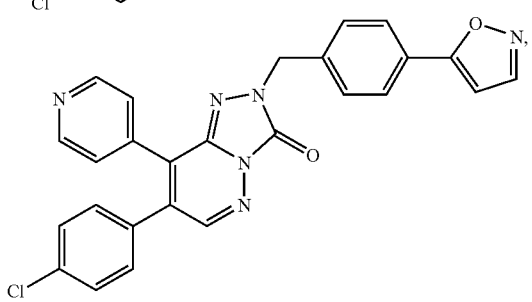

355
-continued
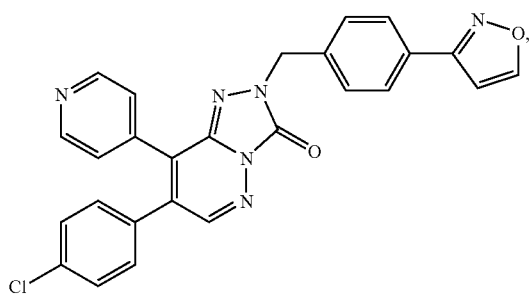
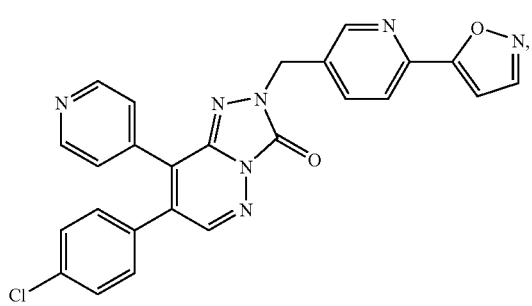
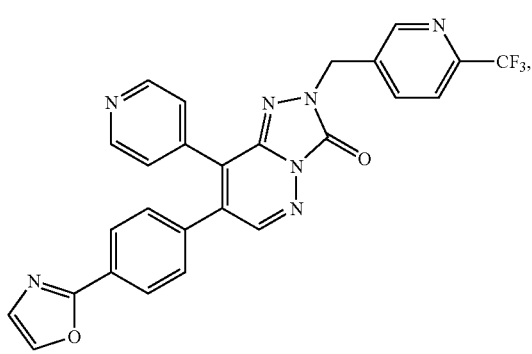
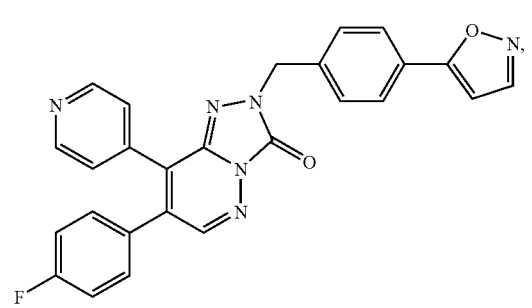
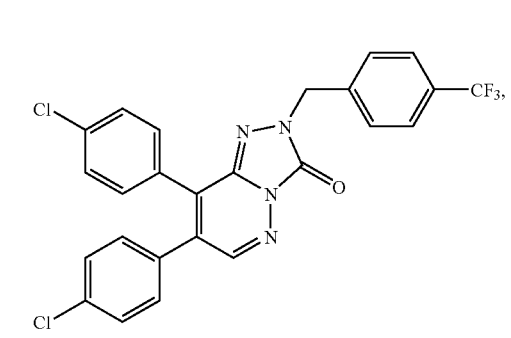
356
-continued
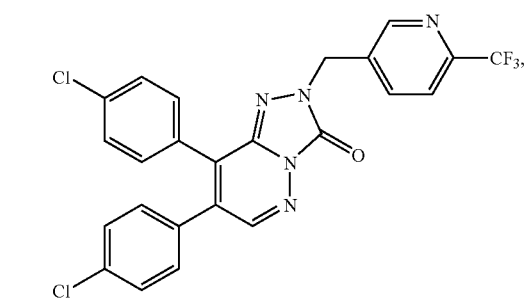
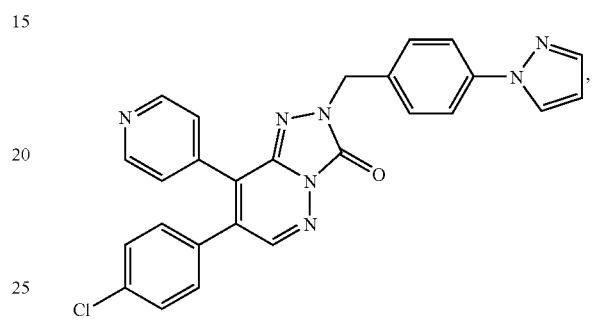
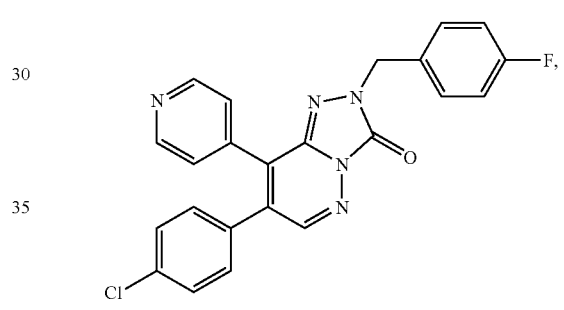
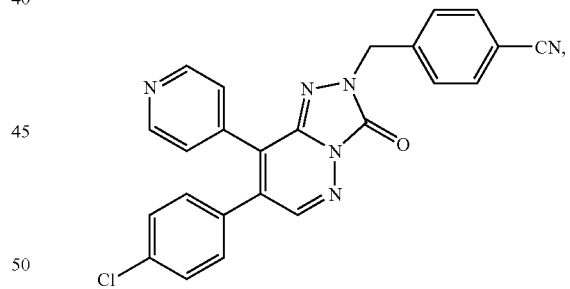
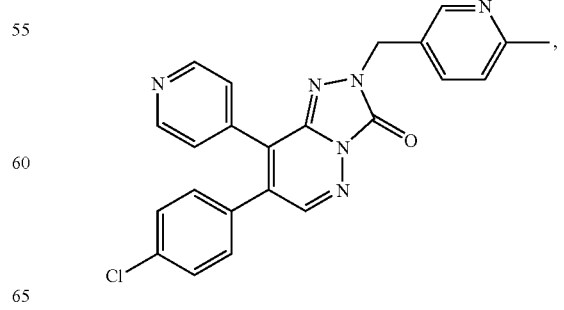

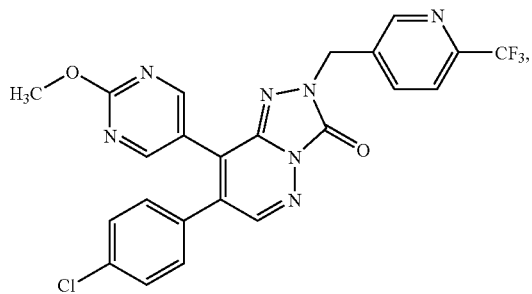

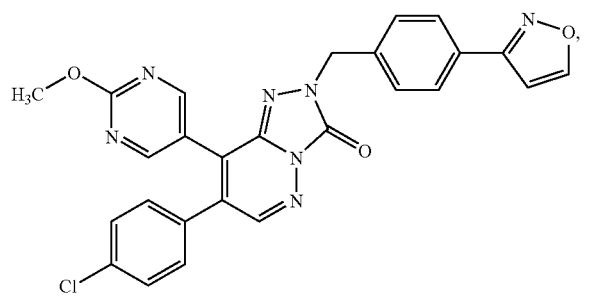

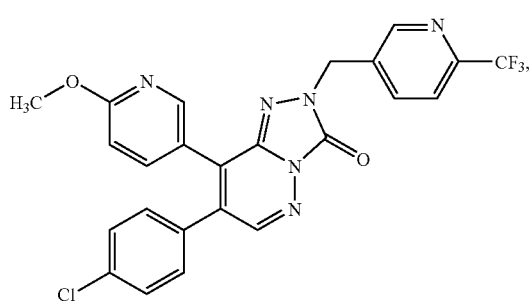

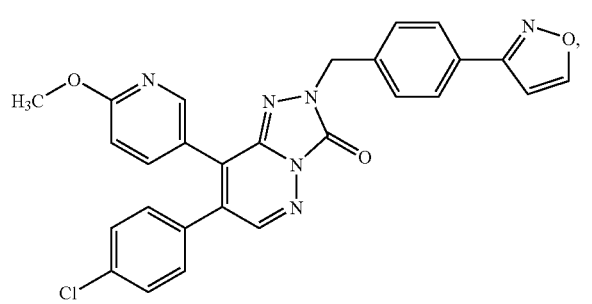

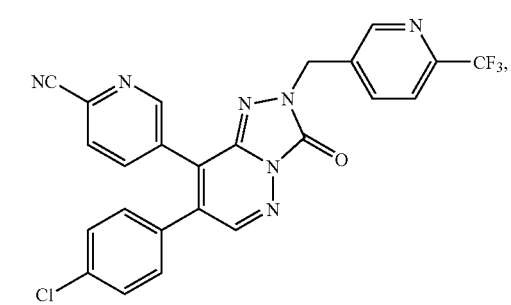

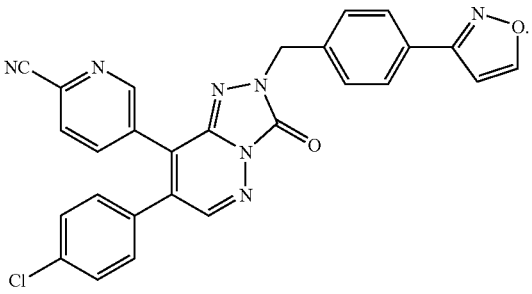

22. A pharmaceutical composition, comprising: one or more compound of Formula I

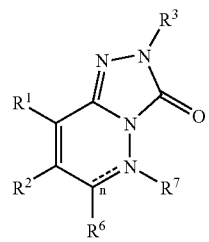

I all pharmaceutically acceptable salts and stereoisomers thereof, wherein:

n is a single bond or a double bond;

$R^1$ is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —$NR^8R^9$, —$CO_2R^8$, —$CONR^8R^9$, —$OR^8$, —$NR^8COR^9$, —$NR^8CONR^8R^9$, —$NR^8CO_2R^9$, —$OCONR^8R^9$, —$NR^8S(O)_mR^9$, —$NR^8S(O)_mNR^8R^9$, —$NR^8S(O)_mOR^9$ and —$OS(O)_mNR^8R^9$;

$R^2$ is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —$NR^8R^9$, —$CO_2R^8$, —$CONR^8R^9$, —$OR^8$, —$NR^8COR^9$, —$NR^8CONR^8R^9$, —$NR^8CO_2R^9$, —$OCONR^8R^9$, —$NR^8S(O)_mR^9$, —$NR^8S(O)_mNR^8R^9$, —$NR^8S(O)_mOR^9$ and —$OS(O)_mNR^8R^9$;

$R^3$ is selected from the group consisting of optionally substituted alkyl, optionally substituted alkenyl, optionally substituted alkynyl, optionally substituted cycloalkyl, optionally substituted cycloalkylalkyl, optionally substituted heterocyclyl, optionally substituted aryl, optionally substituted heteroaryl, optionally substituted heterocyclylalkyl, optionally substituted arylalkyl and optionally substituted heteroarylalkyl;

R⁶ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl and optionally substituted heteroarylalkyl, wherein the R⁶ group has a molecular weight of less than 200 atomic mass units;

R⁷ is absent when n is a double bond;

R⁷ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl, optionally substituted heteroarylalkyl, —COR⁸, —CO₂R⁸, —CONR⁸R⁹ and —S(O)ₘR⁸ when n is a single bond;

R⁸ and R⁹ are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

R⁸ and R⁹ taken together can optionally form a 4, 5, 6, or 7 membered optionally substituted heterocyclyl ring or a 5 or 6 membered optionally substituted heteroaryl ring; and m is an integer of 1 or 2; and at least one pharmaceutically acceptable diluent or carrier.

23. The pharmaceutical composition according to claim 22, further comprising: at least one other therapeutic agent.

24. A pharmaceutical combination comprising a pharmaceutical composition of claim 22 and a therapeutic agent selected from anti-obesity agents; appetite suppressants; and agents used to treat substance abuse and addictive disorders.

25. A pharmaceutical combination of claim 24 wherein the other therapeutic agent may be administered prior to, simultaneously with, or following the administration of the pharmaceutical composition of claim 22.

26. A pharmaceutical combination of claim 24 wherein the anti-obesity agent is selected from melanocortin receptor (MC4R) agonists; melanin-concentrating hormone receptor (MCHR) antagonists; growth hormone secretagogue receptor (GHSR) antagonists; galanin receptor modulators; orexin antagonists; CCK agonists; GLP-1 agonists and other pPreproglucagon-derived peptides; NPY1 or NPY5 antagonists; NPY2 and NPY4 modulators; corticotropin releasing factor agonists; histamine receptor-3 (H3) modulators; aP2 inhibitors; PPAR gamma modulators; PPAR delta modulators; acetyl-CoA carboxylase (ACC) inhibitors; 11-β-HSD-1 inhibitors; adiponectin receptor modulators; beta 3 adrenergic agonists, including AJ9677, L750355 and CP331648 or other known beta 3 agonists; thyroid receptor beta modulator; lipase inhibitors, including orlistat and ATL-962; serotonin receptor agonists, including BVT-933; monoamine reuptake inhibitors or releasing agents, including fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol; anorectic agents, including topiramate; ciliary neurotrophic factor, including Axokine; brain-derived neurotrophic factor; leptin and leptin receptor modulators and other cannabinoid-1 receptor antagonists, including SR-141716 and SLV-319.

27. A pharmaceutical combination of claim 24 wherein the agent used to treat substance abuse and addictive disorders is selected from selective serotonin reuptake inhibitors; methadone; buprenorphine; nicotine; and bupropion.

28. A method for treating substance abuse, a dependence disorder, bulimia, obesity or any disease resulting in the patient becoming overweight, comprising: administering to a patient in need of treatment a therapeutically effective amount of a compound according to formula I:

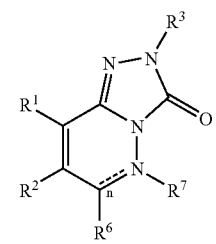

all pharmaceutically acceptable salts and stereoisomers thereof, wherein:

n is a single bond or a double bond;

R¹ is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —NR⁸R⁹, —CO₂R⁸, —CONR⁸R⁹, —OR⁸, —NR⁸COR⁹, —NR⁸CONR⁸R⁹, —NR⁸CO₂R⁹, —OCONR⁸R⁹, —NR⁸S(O)ₘR⁹, —NR⁸S(O)ₘNR⁸R⁹, —NR⁸S(O)ₘOR⁹ and —OS(O)ₘNR⁸R⁹;

R² is selected from the group consisting of halogen, cyano, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted arylalkyl, optionally substituted heteroaryl, optionally substituted heteroarylalkyl, optionally substituted aryloxy, optionally substituted heteroaryloxy, —NR⁸R⁹, —CO₂R⁸, —CONR⁸R⁹, —OR⁸, —NR⁸COR⁹, —NR⁸CONR⁸R⁹, —NR⁸CO₂R⁹, —OCONR⁸R⁹, —NR⁸S(O)ₘR⁹, —NR⁸S(O)ₘNR⁸R⁹, —NR⁸S(O)ₘOR⁹ and —OS(O)ₘNR⁸R⁹;

R³ is selected from the group consisting of optionally substituted alkyl, optionally substituted alkenyl, optionally substituted alkynyl, optionally substituted cycloalkyl, optionally substituted cycloalkylalkyl, optionally substituted heterocyclylalkyl, optionally substituted arylalkyl and optionally substituted heteroarylalkyl;

R⁶ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl and optionally substituted heteroarylalkyl,
wherein the $R^6$ group has a molecular weight of less than 200 atomic mass units;

$R^7$ is absent when n is a double bond;

$R^7$ is selected from the group consisting of H, optionally substituted alkyl, optionally substituted cycloalkyl, optionally substituted heterocyclyl, optionally substituted cycloalkylalkyl, optionally substituted heterocycloalkyl, optionally substituted aryl, optionally substituted heteroaryl, optionally substituted arylalkyl, optionally substituted heteroarylalkyl, —$COR^8$, —$CO_2R^8$, —$CONR^8R^9$ and —$S(O)_mR^8$ when n is a single bond;

$R^8$ and $R^9$ are independently selected from the group consisting of H, optionally substituted alkyl, optionally substituted aryl, optionally substituted arylalkyl, optionally substituted cycloalkyl, optionally substituted cycloalkylalkyl, optionally substituted heterocyclyl, optionally substituted heterocycloalkyl, optionally substituted heteroaryl and optionally substituted heteroarylalkyl;

$R^8$ and $R^9$ taken together can optionally form a 4, 5, 6, or 7 membered optionally substituted heterocyclyl ring or a 5 or 6 membered optionally substituted heteroaryl ring; and m is an integer of 1 or 2.

29. The method according to claim 28, wherein the obesity is due to genetic or environmental causes, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure.

30. The method according to claim 28 in which substances of abuse or dependence include alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines, other known or unknown substances, or combinations of the substances of abuse.

31. The method according to claim 30 wherein the substance abuse or dependence may occur without physiological dependence.

* * * * *

UNITED STATES PATENT AND TRADEMARK OFFICE
CERTIFICATE OF CORRECTION

PATENT NO. : 7,378,418 B2
APPLICATION NO. : 11/016135
DATED : May 27, 2008
INVENTOR(S) : Guixue Yu et al.

It is certified that error appears in the above-identified patent and that said Letters Patent is hereby corrected as shown below:

Column 324, line 59, after "selected", please insert -- from the --.

Column 330, lines 30 to 40, please delete " 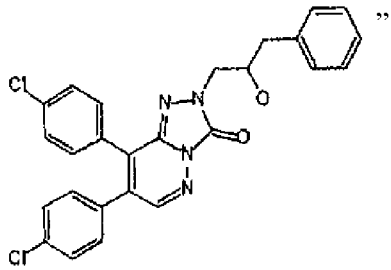 "

and insert -- 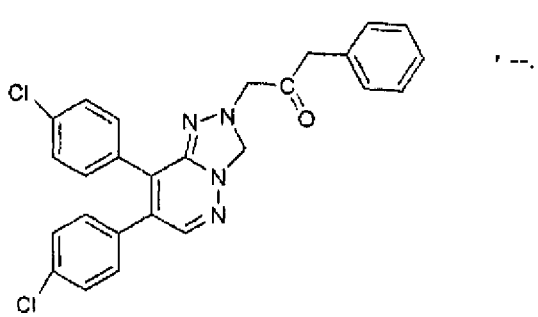 , --.

Column 331, lines 1 to 15, please delete " 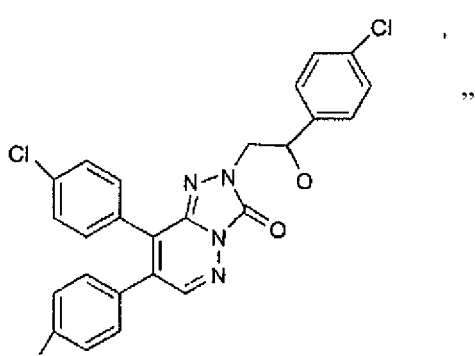 "

and insert -- 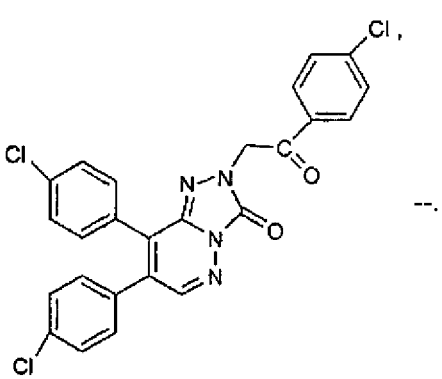 --.

UNITED STATES PATENT AND TRADEMARK OFFICE
CERTIFICATE OF CORRECTION

PATENT NO. : 7,378,418 B2
APPLICATION NO. : 11/016135
DATED : May 27, 2008
INVENTOR(S) : Guixue Yu et al.

It is certified that error appears in the above-identified patent and that said Letters Patent is hereby corrected as shown below:

Column 338, lines 15 to 27, please delete " 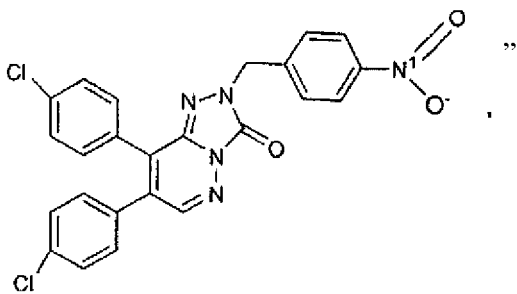 ", and insert -- 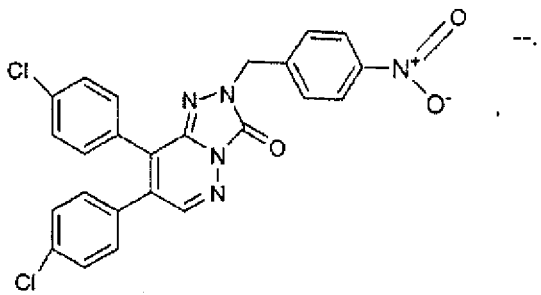 --.

Signed and Sealed this

Twenty-third Day of September, 2008

JON W. DUDAS
*Director of the United States Patent and Trademark Office*

UNITED STATES PATENT AND TRADEMARK OFFICE
CERTIFICATE OF CORRECTION

PATENT NO.      : 7,378,418 B2                              Page 1 of 1
APPLICATION NO. : 11/016135
DATED           : May 27, 2008
INVENTOR(S)     : Guixue Yu et al.

It is certified that error appears in the above-identified patent and that said Letters Patent is hereby corrected as shown below:

In the Claims:

Column 330, lines 30 to 40, please delete

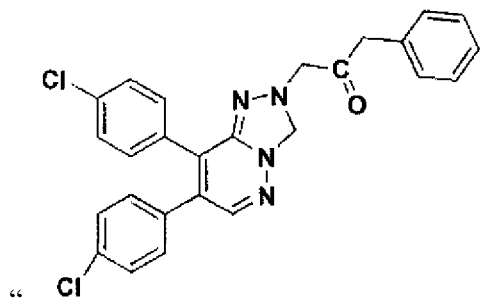

" and insert --

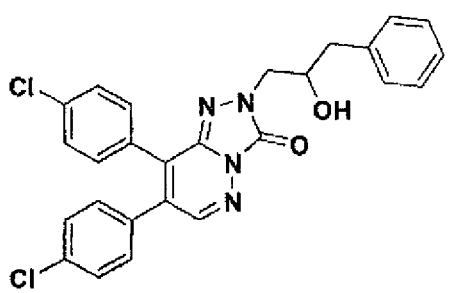

--.

Column 331, lines 1 to 15, please delete

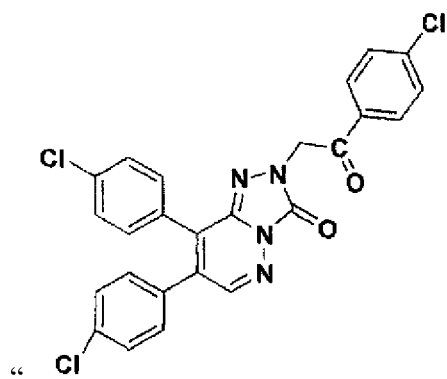

" and insert --

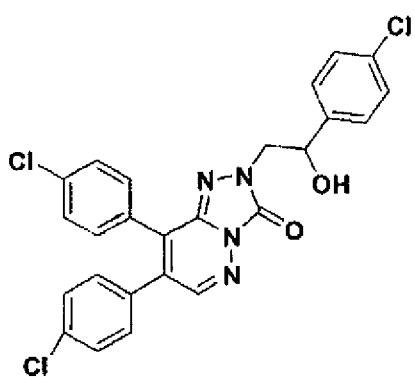

--.

Signed and Sealed this
First Day of May, 2012

David J. Kappos
*Director of the United States Patent and Trademark Office*